(12) United States Patent
Kley

(10) Patent No.: US 6,861,648 B2
(45) Date of Patent: Mar. 1, 2005

(54) SCANNING PROBE MICROSCOPY INSPECTION AND MODIFICATION SYSTEM

(75) Inventor: Victor B. Kley, Berkeley, CA (US)

(73) Assignee: General Nanotechnology LLC, Berkeley, CA (US)

( * ) Notice: Subject to any disclaimer, the term of this patent is extended or adjusted under 35 U.S.C. 154(b) by 59 days.

(21) Appl. No.: 09/919,780

(22) Filed: Jul. 31, 2001

(65) Prior Publication Data

US 2002/0117611 A1 Aug. 29, 2002

Related U.S. Application Data

(63) Continuation of application No. 09/355,072, filed as application No. PCT/US98/01528 on Jan. 21, 1998, now Pat. No. 6,337,479, which is a continuation-in-part of application No. 08/906,602, filed on Dec. 10, 1996, now Pat. No. 6,265,711, which is a continuation of application No. 08/281,883, filed on Jul. 28, 1994, now abandoned, said application No. PCT/US98/01528, is a continuation-in-part of application No. 08/885,014, filed on Jul. 1, 1997, now Pat. No. 6,144,028, which is a continuation of application No. 08/412,380, filed on Mar. 29, 1995, now abandoned, which is a continuation-in-part of application No. 08/281,883, said application No. PCT/US98/01528, is a continuation-in-part of application No. 08/776,361, filed as application No. PCT/US95/09553 on Jul. 28, 1995, now Pat. No. 6,339,217, which is a continuation-in-part of application No. 08/412,380, which is a continuation-in-part of application No. 08/281,883, said application No. PCT/US98/01528, is a continuation-in-part of application No. 08/613,982, filed on Mar. 4, 1996, now Pat. No. 5,756,997, and a continuation-in-part of application No. PCT/US96/12255, filed on Jul. 24, 1996, which is a continuation-in-part of application No. 08/506,516, filed on Jul. 24, 1995, now Pat. No. 5,751,683, said application No. PCT/US98/01528, is a continuation-in-part of application No. 08/786,623, filed on Jan. 21, 1997, now abandoned, which is a continuation-in-part of application No. 08/906,602, which is a continuation of application No. 08/281,883, said application No. 08/786,623, is a continuation-in-part of application No. PCT/US95/09553, which is a continuation-in-part of application No. 08/412,380, which is a continuation-in-part of application No. 08/281,883, said application No. 08/786,623, is a continuation-in-part of application No. 08/506,516, and a continuation-in-part of application No. 08/613,982, and a continuation-in-part of application No. PCT/US96/12255, which is a continuation-in-part of application No. 08/506,516, said application No. PCT/US98/01528, is a continuation-in-part of application No. 08/827,953, filed on Apr. 6, 1997, now abandoned, which is a continuation-in-part of application No. 08/906,602, which is a continuation-in-part of application No. 08/281,883, said application No. 08/827,953, filed on Apr. 6, 1997, now abandoned, is a continuation-in-part of application No. 08/412,380, which is a continuation-in-part of application No. 08/281,883, said application No. 08/827,953, is a continuation-in-part of application No. PCT/US95/09553, which is a continuation-in-part of application No. 08/412,380, which is a continuation-in-part of application No. 08/281,883, said application No. 08/827,953, is a continuation-in-part of application No. 08/506,516, and a continuation-in-part of application No. 08/613,982, and a continuation-in-part of application No. PCT/US96/12255, which is a continuation-in-part of application No. 08/506,516, said application No. 08/827,953, is a continuation-in-part of application No. 08/786,623, which is a continuation-in-part of application No. 08/906,602, and a continuation-in-part of application No. 08/506,516, and a continuation-in-part of application No. 08/613,982, and a continuation-in-part of application No. PCT/US95/09553, and application No. PCT/US96/12255, said application No. 08/827,953, is a continuation-in-part of application No. 08/906,602, which is a continuation of application No. 08/281,883.

(51) Int. Cl.[7] ........................ G01N 23/00; G01N 13/16; G01B 5/28

(52) U.S. Cl. ........................................ 250/306; 73/105

(58) Field of Search ................................ 250/306–307, 250/216, 234–235; 356/176

(56) References Cited

U.S. PATENT DOCUMENTS

| | | |
|---|---|---|
| 4,907,195 A | 3/1990 | Kazan et al. |
| 5,047,633 A | 9/1991 | Finlan et al. |
| 5,047,649 A | 9/1991 | Hodgson et al. |
| 5,072,116 A * | 12/1991 | Kawade et al. ............. 250/306 |
| 5,107,112 A | 4/1992 | Yanagisawa et al. |
| 5,166,520 A | 11/1992 | Prater et al. |
| 5,254,209 A | 10/1993 | Schmidt et al. |
| 5,283,437 A | 2/1994 | Greschner et al. |
| 5,308,974 A | 5/1994 | Elings et al. |
| 5,319,977 A | 6/1994 | Quate et al. |

| | | |
|---|---|---|
| 5,353,632 A | 10/1994 | Nakagawa |
| 5,357,109 A | 10/1994 | Kusumoto |
| 5,392,275 A | 2/1995 | Kawada et al. |
| 5,414,690 A | 5/1995 | Shido et al. |
| 5,416,331 A | 5/1995 | Ichikawa et al. |
| 5,418,363 A | 5/1995 | Elings et al. |
| 5,426,631 A | 6/1995 | Miyazaki et al. |
| 5,471,458 A | 11/1995 | Oguchi et al. |
| 5,472,881 A | 12/1995 | Beebe et al. |
| 5,490,132 A | 2/1996 | Yagi et al. |
| 5,519,686 A | 5/1996 | Yanagisawa et al. |
| 5,548,117 A | 8/1996 | Nakagawa |
| 5,559,328 A * | 9/1996 | Weiss et al. ............... 250/306 |
| 5,602,820 A | 2/1997 | Wickramasinghe et al. |
| 5,634,230 A | 6/1997 | Maurer |
| 5,679,952 A * | 10/1997 | Lutwyche et al. .......... 250/306 |
| 5,804,709 A | 9/1998 | Bourgoin et al. |
| 5,865,978 A | 2/1999 | Cohen |
| 5,922,214 A | 7/1999 | Liu et al. |
| 6,031,756 A | 2/2000 | Gimzewski et al. |
| 6,173,604 B1 | 1/2001 | Xiang et al. |
| 6,199,269 B1 | 3/2001 | Greco et al. |
| 6,229,607 B1 | 5/2001 | Shirai et al. |
| 6,239,426 B1 | 5/2001 | Muramatsu et al. |
| 6,337,479 B1 | 1/2002 | Kley |
| 6,353,219 B1 | 3/2002 | Kley |
| 6,614,227 B2 | 9/2003 | Ookubo |

FOREIGN PATENT DOCUMENTS

| | | |
|---|---|---|
| WO | WO 96/03641 A1 | 2/1996 |
| WO | WO 98/34092 A2 | 8/1998 |

OTHER PUBLICATIONS

Ager et al., "Multilayer hard carbon films with low wear rates," *Surface and Coatings Technology*, 91:91–94 (1997).

Jaschke et al. "Deposition of Organic Material by the Tip of a Scanning Force Microscope," Langmuir 11:1061–1064 (1995).

* cited by examiner

*Primary Examiner*—Nikita Wells
*Assistant Examiner*—Christopher M. Kalivoda
(74) *Attorney, Agent, or Firm*—Townsend and Townsend and Crew LLP

(57) ABSTRACT

A scanning probe microscopy (SPM) inspection and/or modification system which uses SPM technology and techniques. The system includes various types of microstructured SPM probes for inspection and/or modification of the object. The components of the SPM system include microstructured calibration structures. A probe may be defective because of wear or because of fabrication errors. Various types of reference measurements of the calibration structure are made with the probe or vice versa to calibrate it. The components of the SPM system further include one or more tip machining structures. At these structures, material of the tips of the SPM probes may be machined by abrasively lapping and chemically lapping the material of the tip with the tip machining structures.

26 Claims, 55 Drawing Sheets

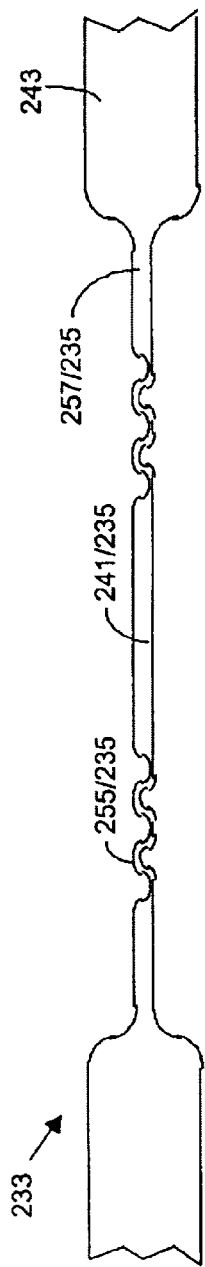
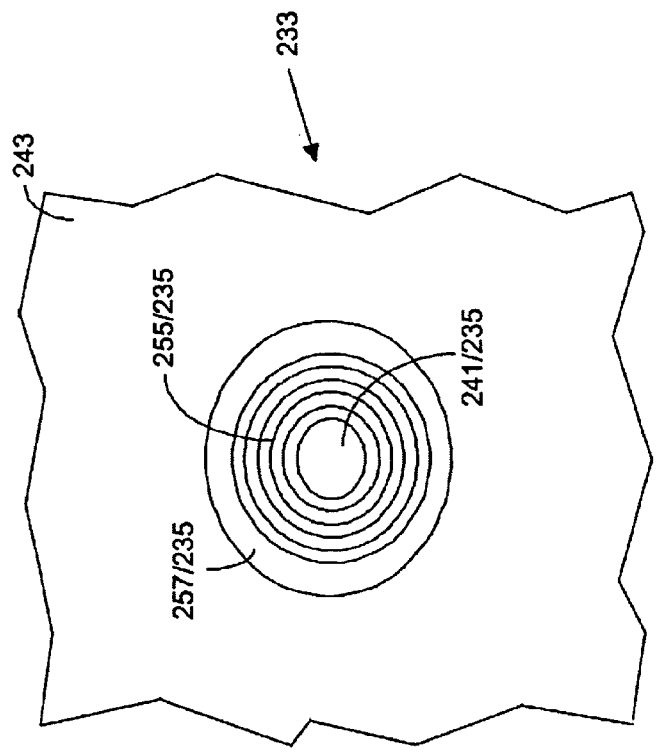
Figure 14
Figure 15

SCANNING PROBE MICROSCOPY INSPECTION AND MODIFICATION SYSTEM

CROSS REFERENCE TO RELATED APPLICATIONS

This application is a continuation of U.S. patent application Ser. No. 09/355,072, filed on Jul. 21, 1999 now U.S. Pat. No. 6,337,479, which is a National Phase filing of PCT Patent Application No. PCT/US98/01528, filed Jan. 21, 1998 (Pub. WO 98/34092).

PCT Patent Application No. PCT/US98/01528 is a continuation-in-part of U.S. patent application Ser. No. 08/906,602, filed Dec. 10, 1996, now U.S. Pat. No. 6,265,711, which is a file wrapper continuation of U.S. patent application Ser. No. 08/281,883, filed Jul. 28, 1994, now abandoned.

PCT Patent Application No. PCT/US98/01528 in a continuation-in-part of U.S. patent application Ser. No. 08/885,014, filed Jul. 1, 1997, now U.S. Pat. No. 6,144,028, which is a continuation of U.S. patent application Ser. No. 08/412,380, filed Mar. 29, 1995, now abandoned, which is continuation-in-part of U.S. patent application Ser. No. 08/281,883, filed Jul. 28, 1994, now abandoned.

PCT Patent Application No. PCT/US98/01528 is a continuation-in-part of U.S. patent application Ser. No. 08/776,361, filed May 16, 1997, now U.S. Pat. No. 6,339,217, which is a National Phase filing of PCT Application No. PCT/US95/09553, filed Jul. 28, 1995 (Pub. WO 96/03641), which is a cantinuation-in-part of U.S. patent application Ser. No. 08/412,380, filed Mar. 29, 1995, now abandoned, which is a continuation-in-part of U.S. patent application Ser. No. 08/281,883, filed Jul. 28, 1994, now abandoned.

PCT Patent Application No. PCT/US98/01528 is a continuation-in-part of U.S. patent application Ser. No. 08/506,516, filed Jul. 24, 1995, now U.S. Pat. No. 5,751,683.

PCT Patent Application No. PCT/US98/01528 is a continuation-in-part of U.S. patent application Ser. No. 08/613,982 filed Mar. 4, 1996, now U.S. Pat. No. 5,756,997.

PCT Patent Application No. PCT/US98/01528 is a continuation-in-part of PCT Patent Application No. PCT/US96/12255, filed Jul. 24, 1996 (Pub. WO 97/04449), which is a CIP of U.S. patent application Ser. No. 08/506,516, filed Jul. 24, 1995, now U.S. Pat. No. 5,751,683.

PCT Patent Application No. PCT/US98/01528 is a continuation-in-part of U.S. patent application Ser. No. 08/786,623, filed Jan. 21, 1997, now abandoned, which is a continuation in part of:

- U.S. patent application Ser. No. 08/906,602, filed Dec. 10, 1996, now U.S. Pat. No. 6,265,711, which is a file wrapper continuation of U.S. patent application Ser. No. 08/281,883, filed Jul. 28, 1994, now abandoned.
- PCT Patent Application No. PCT/US95/09553, filed Jul. 28, 1995 (Pub. WO 96/03641), which is a CIP of U.S. patent application Ser. No. 08/412,380, filed Mar. 29, 1995, now abandoned, which is a continuation-in-part of U.S. patent application Ser. No. 08/281,883, filed Jul. 28, 1994, now abandoned;
- U.S. patent application Ser. No. 08/506,516, filed Jul. 24, 1995, now U.S. Pat. No. 5,751,683;
- U.S. patent application Ser. No. 08/613,982, filed Mar. 4, 1996, now U.S. Pat. No. 5,756,997; and
- PCT Patent Application No. PCT/US96/12255, filed Jul. 24, 1996 (Pub. WO 97/04449), which is a CIP of U.S. patent application Ser. No. 08/506,516, filed Jul. 24, 1995, now U.S. Pat. No. 5,751,683.

PCT Patent Application No. PCT/US98/01528 is a continuation-in-pan of U.S. patent application Ser. No. 08/827,953, filed Apr. 6, 1997, now abandoned, which is a continuation in part of:

- U.S. patent application Ser. No. 08/906,602, filed Dec. 10, 1996, now U.S. Pat. No. 6,265,711, which is a file wrapper continuation of U.S. patent application Ser. No. 08/281,883, filed Jul. 28, 1994, now abandoned;
- U.S. patent application Ser. No. 08/412,380, filed Mar. 29, 1995, now abandoned, which is a continuation-in-part of U.S. patent application Ser. No. 08/281,883, filed Jul. 28, 1994, now abandoned;
- PCT Patent Application No. PCT/US95/09553, filed Jul. 28, 1995 (Pub. WO 96/03641), which is a CIP of U.S. Patent Application Ser. No, 08/412,380, filed Mar. 29, 1995, now abandoned, which is a continuation-in-part of U.S. patent application Ser. No, 08/281,883, filed Jul. 28, 1994, now abandoned;
- U.S. patent application Ser. No. 08/506,516, filed Jul. 24, 1995, now U.S. Pat. No. 5,751,683;
- U.S. patent application Ser. No. 08/613,982, filed Mar. 4, 1996, now U.S. Pat. No. 5,756,997;
- PCT Patent Application No. PCT/US96/12255, filed Jul. 24, 1996 (Pub. WO 97/04449), which is a CIP of U.S. patent application Ser. No. 08/506,516, filed Jul. 24, 1995, now U.S. Pat. No. 5,751,683; and
- U.S. patent application Ser. No. 08/786,623, filed Jan. 21, 1997, now abandoned, which is a continuation in part of U.S. patent application Ser. Nos. 08/906,602, 08/506,516, and 08/613,982, and PCT Patent Application Nos. PCT/US95/09553 and PCT/US96/12255 with priorities as set forth above.

All of the identified and cross-referenced applications are hereby incorporated by reference in their entirety.

FIELD OF THE INVENTION

The present invention relates generally to systems and methods for modifying and/or inspecting an object. In particular, it pertains to a system and method for using nanostructured and nanopositioned probes to remove material from or add material to an object, chemically change the material of an object, and/or analyze the material of an object.

BACKGROUND OF THE INVENTION

Common microfabrication techniques such as e-beam, laser beam, and standard photolithography are used to directly make or modify semiconductor wafers or fabrication masks. However, these techniques suffer from limitations in the size and energy which may to be used to create, modify, and inspect structures on the wafers or masks. Specifically, it is desirable that techniques be available to create, modify, and inspect structures in the range of a single molecule (approximately 1 Angstrom or less). However, the current techniques are unable to create, modify, and inspect structures at and below 100 nanometers.

For example, in conventional semiconductor fabrication mask repair systems, a finely focused laser beam is used to remove or chemically activate for removal material deposited in a pattern on a mask Similarly, the laser beam is used to deposit material on the mask by locally heating sites on the mask while the mask is in a gaseous environment.

However, these techniques can only be used to create desired changes of no smaller then 500 nanometers. Moreover, these semiconductor fabrication mask repair systems cannot insure that the changes made to a modified mask will produce the desired pattern on a target wafer.

SUMMARY OF THE INVENTION

In summary the present invention is a SPM (scanning probe microscopy) inspection and/or modification system which uses SPM technology and techniques in new and novel ways to inspect and/or modify an object. The system includes various types of microstructured SPM (scanning probe microscopy) probes for inspection and/or modification of the object.

The components of the SPM system also include microstructured calibration structures. A probe may be defective because of wear or because of fabrication errors. Various types of reference measurements of the calibration structure are made with the probe or vice versa to calibrate it.

In addition, the components of the SPM system may include one or more tip machining structures. At these structures, material of the tips of the SPM probes may be machined by abrasively lapping and chemically lapping the material of the tips. This is done by rubbing the material of the tips against the tip machining structures.

The SPM probes include probes with which the object may be inspected in a number of ways using SPM technology and techniques. This inspection is performed with various components of the SPM system for making SPM measurements with the probes. All of the SPM measurements are processed and inspection data (or results) for the object is generated. This inspection data may include an image and/or analysis of the object. The analysis may be of the electrical, optical, chemical, (including catalytic), and/or biological (including morphological) properties, operation, and/or characteristics of the object.

The SPM probes also include probes with which the object may be modified in a number of ways using SPM technology and techniques. Some of these probes may also be used to inspect the object, as just discussed. A user may request that a modification be made to the object based on the inspection data just described or on inspection data generated by some of the other components of the system without using any probes.

The generated inspection data is then compared with target data (or parameters). This target data may include a target image and/or analysis of the object which is/are compared with the generated image and/or analysis. If they do not match within a predefined tolerance level, then modification data is generated that identifies the types of modifications that need to be made to the object to fall within the tolerance level. These modifications may be simply to remove particle contaminants on the object or more importantly to structurally and/or chemically modify the material of the object by removing, deforming, and/or chemically changing a portion of it or adding other material to it. Then, one or more of the modification probes are used to make these desired modifications.

The process just described can be iteratively repeated until the generated inspection data converges to the target data so as to be within the predefined tolerance level. This process is particularly useful in fabrication and/or repair of semiconductor wafers and fabrication masks, lithographic structures, and thin film magnetic read/write heads.

BRIEF DESCRIPTION OF DRAWINGS

FIGS. 12 to 15 show different views of a nanostructured force balance of the SPM system of FIG. 1.

DETAILED DESCRIPTION OF THE INVENTION

Figure 1:
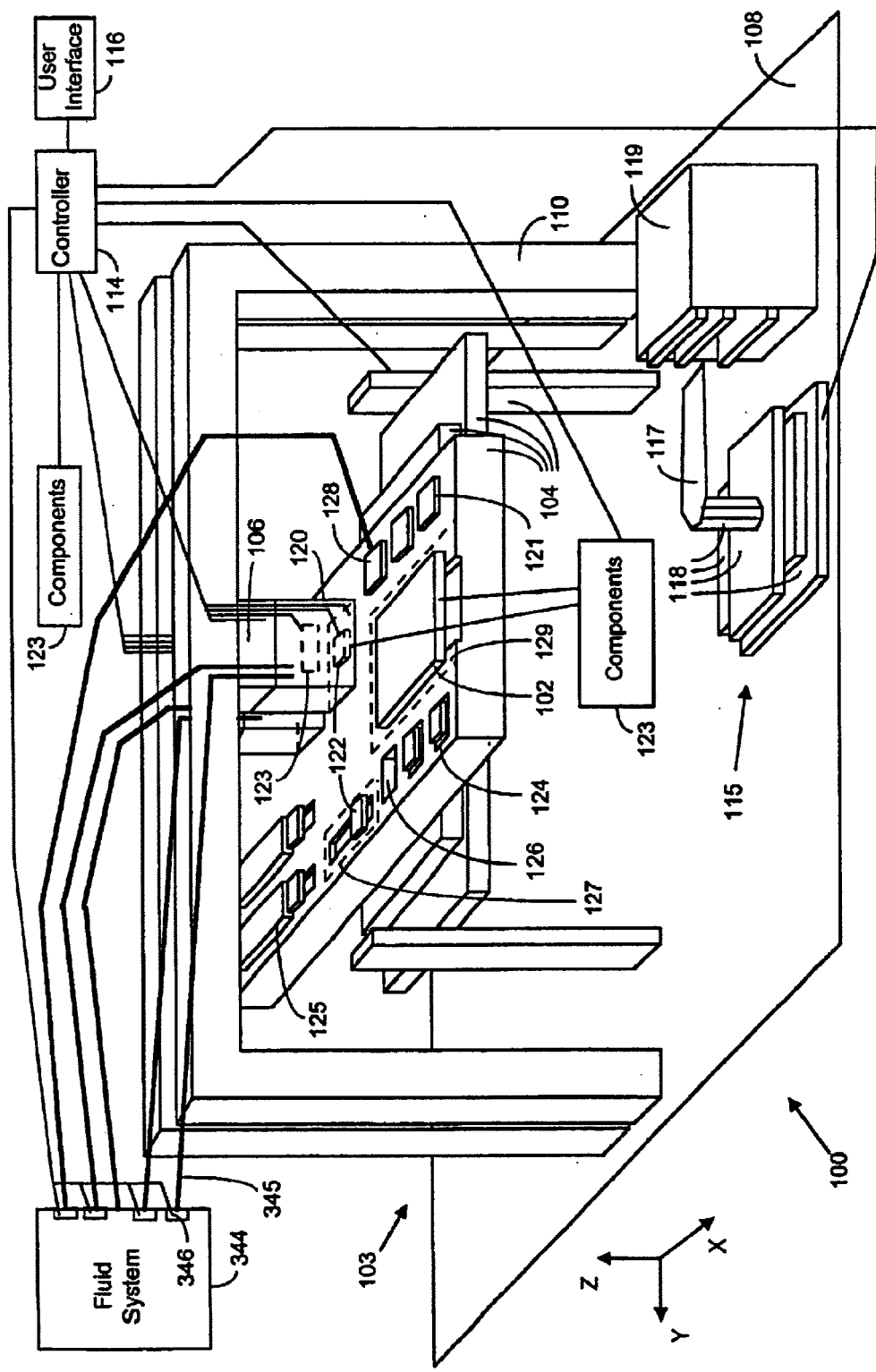
FIG. 1 shows an SPM inspection and/or modification system for inspecting and/or modifying an object.

Referring to FIG. 1, there is shown an exemplary embodiment of an SPM (scanning probe microscopy) object inspection and/or modification system 100 which uses SPM technology and techniques in new and novel ways to inspect and/or modify an object 102. For example, as will be discussed throughout this document, the system can be used to perform tests, fabrication (i.e., manufacturing) steps, and/or repairs on semiconductor wafers and fabrication masks, lithographic structures (i.e., masters), and thin film magnetic read/write heads. Additionally, as will also be discussed throughout this document, the SPM system can also be used to analyze and/or alter biological or chemical samples.

The components of the SPM system 100 include a positioning system 103 that comprises a rough positioning apparatus 104, fine positioning apparatuses 106, a support table 108, and scanning head support structures 110. The rough positioning apparatus comprises a rough 3-D (i.e., three dimensions) translator, such as a mechanical ball screw mechanism. The rough positioning apparatus is fixed to the support table. Each fine positioning apparatus comprises a fine 3-D translator, such as a piezoelectric translator with or without linear position feedback. Each fine positioning apparatus is fixed to a corresponding scanning head support structure. Each scanning support structure is fixed to the support table.

The components of the SPM system 100 also include one or more scanning heads 120. Each scanning head is fixed to a corresponding fine positioning apparatus 106 and is roughly and finely positioned in 3-D (i.e., X, Y, and Z dimensions) with the rough positioning apparatus 104 and the corresponding fine positioning apparatus. This positioning may be done in order to load and unload various types of microstructured SPM (scanning probe microscopy) probes 122 of the SPM system to and from the scanning heads and position the loaded probes for calibration and inspection and/or modification of the object. This positioning is done with respect to the object 102, calibration structures 128, probe suppliers 124 and 125, a probe disposal 126, a probe storage site 127, and other components 123 of the SPM system.

The components of the SPM system 100 also include a programmed controller 114 that includes a user interface 116. It also includes an object loader 115 that comprises a load arm 117, a positioning system 118 connected to the load arm, and an object storage unit 119. When it is desired to inspect and/or modify the object 102, a user of the system uses the user interface to request that the controller have the object loaded by the object loader for inspection and/or modification. The controller controls the object loader's load arm and positioning system so as to load the object 102 from the object loader's storage unit onto the object loading site 129. The object loading site is also one of the SPM system's components and is located on the upper surface of the rough positioning apparatus 104. In loading the object onto the object loading site, the object is removed from the storage unit with the load arm. The load arm is then lowered into the recess of the object loading site so that the object rests on the object loading site and no longer on the load arm. The load arm is then slid out of the recess. Similarly, when the inspection and/or modification of the object is over, the user requests with the user interface that the controller have the object unloaded. In response, the controller controls the load arm to unload the object from the object loading site and place it back in the storage unit. This is done by sliding the load arm into the recess and raising it so that the object rests on the load arm and no longer on the object loading site. The load arm is then used to place the object back in the storage unit. The object loader may be a conventional semiconductor wafer or fabrication mask loader used in fabrication of wafers or masks.

As alluded to earlier, the components of the SPM system 100 further include SPM probes 122, vertical and horizontal probe suppliers 124 and 125, and a probe storage site 127. The probes can be loaded onto each scanning head 120 from the vertical and horizontal probe suppliers or from the probe storage site 127. The probe storage site and the probe suppliers are located on the rough positioning apparatus 104. Each probe supplier may supply a different type of probe than any other probe supplier and comprises a stacking mechanism for stacking the same type of probe. This may be a spring, air, gravity, electromechanical, or vacuum driven stacking mechanism.

Moreover, when the user wishes to use a particular SPM probe 122 for inspecting and/or modifying the object 102, the user instructs the controller 114 with the user interface 116 to load this probe onto one of the scanning heads 120. If a probe of this type has already been used before and has been stored at the probe storage site 127, the controller controls the positioning system 103 to position the scanning head over this site and lower it onto the probe. The controller then controls the scanning head so that the probe is loaded onto it. But, if a new probe of this type is required because one has not been used or the previously used one has become defective, the controller controls the positioning system to position the scanning head over the probe supplier 124 or 125 that supplies the desired type of probe and lower it onto the probe that is currently at the top of the stack of the probe supplier. The controller then causes the probe to be popped off of the stack and loaded onto the scanning head. In addition, in the instances described later where active mechanical, electrical, electromagnetic, vacuum, hydraulic, pneumatic, fluids, magnetic, or other mechanisms are integrated into the probe, provision is made on the probe and in the scanning head for control connections (i.e., electrical, optical, mechanical, vacuum, etc.). As a result, the scanning head may sense optical, mechanical or electrical variations which tell the controller which type of probe has been loaded. Thus, different types of probes may be loaded through the same probe supplier. The different types of probes and probe suppliers and the specific ways in which the probes may be loaded onto the scanning heads will be discussed later.

However, when the user wishes to use another one of the SPM probes 122 for inspecting and/or modifying the object 102 with the same scanning head 120, the user instructs the controller 114 with the user interface 116 to unload the currently loaded probe. In response, the controller controls the positioning system 103 to position the scanning head so that the probe that is currently loaded is lowered to the probe storage site 127 on the rough positioning apparatus. Then, the controller causes the probe to be unloaded from the scanning head onto this site.

In order to calibrate an SPM probe 122 that is loaded onto one of the scanning heads 120 and determine whether it is defective, the components of the SPM system 100 include microstructured calibration structures 128 located on the rough positioning apparatus 104. A probe may be defective because of wear or because of fabrication errors. For each type of probe, the controller 114 stores one or more reference parameters each associated with a corresponding calibration structure 128. Thus, the controller controls the positioning system 103, the probe, and some of the other components 123 of the SPM system 100 so that various types of reference measurements of the calibration structure 128 are made with the probe or vice versa. These reference measurements are then compared with the reference parameters. If they do not match within a predefined tolerance level stored by the controller and set by the user with the user interface 116, then the probe is considered to be defective. Otherwise, the controller uses the reference measurements to calibrate the probe in the ways described later. The specific types of calibrations that can be made for the probes are described later.

In addition, the components of the SPM system 100 may include one or more tip machining structures 121. At these structures, material of the tips of the SPM probes 122 may be machined by abrasively lapped and chemically lapped. This is done by rubbing the material of the tip against the tip machining structures.

The components of the SPM system 100 also include a probe disposal 126 which is used to dispose of (or discard) SPM probes 122 that are defective. In the case of a probe that is determined to be defective in the manner just described, the user can instruct the controller 114 with the user interface 116 to have the defective probe discarded. In response, the controller controls the positioning system 103 to position the scanning head 120 over the probe disposal and lower it to the probe disposal. Then, the controller controls the scanning head to unload the currently loaded probe into the probe disposal.

In an alternative embodiment, each scanning head 120 could be fixed to a corresponding rough positioning subsystem 104 and a corresponding fine positioning subsystem 106. The probe suppliers 124 and 125, probe disposal 126, and the calibration structures 128 would then be located on the support table 108. In this way, each scanning head could be independently positioned with respect to the probe suppliers and probe disposal for loading, unloading, and disposal of SPM probes 122 and independently positioned for positioning a probe with respect to the object 102 for inspection and/or modification of the object and the reference structures for calibration and examination of the probes. Moreover, in such an embodiment, there would be a corresponding scanning head, a corresponding rough positioning subsystem, and a corresponding fine positioning subsystem for inspection and for modification.

The SPM probes 122 include probes with which the object 102 may be inspected in a number of ways using SPM technology and techniques. This inspection is performed with various components of the SPM system including the controller 114, the user interface 116, the positioning system 103, the scanning heads 120, those of the calibration structures 128 used to calibrate the probes, and those of the other components 123 of the SPM system that are used for making SPM measurements with the probes. In doing so, the user requests that an inspection be made with the user interface. When this occurs, one or more of the probes are selectively loaded, calibrated, and unloaded in the manner discussed earlier for making SPM measurements of the object. Moreover, for each probe that is used to make certain SPM measurements of the object, the controller controls the positioning system, any of the other components of the SPM system used to make these SPM measurements, and the loaded probe so that these SPM measurements are made with the probe. The controller then processes all of the SPM measurements and generates inspection data (or results) for the object. This inspection data may include an image and/or analysis of the object. The analysis may be of the electrical, optical, chemical, (including catalytic), and/or biological (including morphological) properties, operation, and/or characteristics of the object. The various types of probes used to inspect the object and the corresponding kinds of inspections they are used to make will be described in greater detail later.

Although it may be desired to simply inspect the object 102, certain components of the SPM system 100 are used to modify the object based on the inspection data generated by the inspection subsystem. Thus, the SPM probes 122 also include probes with which the object 102 may be modified in a number of ways using SPM technology and techniques. Some of these probes may also be used to inspect the object, as just discussed. The components of the SPM system used for this purpose include the controller 114, the user interface 116, the positioning system 103, the scanning heads 120, those of the calibration structures 128 used to calibrate the modification probes, and those of the other components 123 of the SPM system that are used in making modifications to the object with the probes. With the user interface, the user requests that a modification be made to the object based on the inspection data just described or on inspection data generated by some of the other components 123 of the system without using any probes.

The controller 114 can compare the generated inspection data with target data (or parameters). This target data may include a target image and/or analysis of the object which is/are compared with the generated image and/or analysis. If they do not match within a predefined tolerance level stored by the controller and specified by the user with the user interface 116, the controller generates modification data that identifies the types of modifications that need to be made to the object to fall within the tolerance level. These modifications may be simply to remove particle contaminants on the object or more importantly to structurally and/or chemically modify the material of the object by removing, deforming, and/or chemically changing a portion of it or adding other material to it. Then, one or more of the modification probes are selectively loaded, calibrated, and unloaded in the manner described earlier to make these desired modifications. Furthermore, for each modification probe used to make certain desired modifications to the object, the controller controls the positioning system, any of the other components of the SPM system used in making these modifications, and, if needed, the modification probe so that these modifications are made. The various types of SPM probes used to modify the object and the corresponding kinds of modifications they make will be described in greater detail later.

The process just described can be iteratively repeated until the generated inspection data converges to the target data so as to be within the predefined tolerance level. This process is particularly useful in fabrication and/or repair of semiconductor wafers and fabrication masks, lithographic structures, and thin film magnetic read/write heads.

Repair and/or Fabrication of Masks and/or Wafers

Specifically, the SPM system 100 may be used to perform precision repairs of a completed mask or wafer after fabrication. In fact, the SPM system may even be used to perform precision repairs and/or fabrication steps of a partially completed mask or wafer during fabrication. These repairs and/or fabrication steps comprise structurally and/or chemically modifying to the material of the mask or wafer by removing, deforming, and/or chemically changing a portion of it or adding other material to it.

For example, the SPM system 100 may be provided with repair and/or fabrication data for a mask or wafer that was previously inspected by a conventional mask or wafer inspection system. The provided repair and/or fabrication data identifies where a repair and/or a fabrication step is to be performed on the mask or wafer. Using one or more of the SPM probes 122 and/or some of the other components 123 of the SPM system, the controller 114 locates a reference point on the wafer or mask. Then, using the reference point and the provided repair and/or fabrication data, the controller may cause an inspection of the wafer or mask to be made where the repair and/or fabrication step is to be performed. This is done with one or more of the probes in the manner briefly described earlier and will described in greater detail later. As a result, inspection data is generated which comprises an image and/or analysis of the mask or wafer. By comparing the generated inspection data with target data stored by the controller, repair and/or fabrication (i.e., modification) data is generated by the controller. Then, based on the repair and/or fabrication data, the controller causes the repair and/or fabrication step to be performed on material of the object with one or more of the probes and under the direction of the user. This is done in the manner described briefly earlier and will be described in greater detail later.

Then, the controller 114 causes another inspection of the mask or wafer to be made after the repair and/or fabrication step. This inspection may be done with or without any of the SPM probes 122 in the manner described earlier. Furthermore, this may be done in such a way that the mask or wafer is inspected so as to simulate or emulate its use in the environment in which it is normally used.

For example, in the case of a mask, some of the other components 123 of the SPM system and/or one of the SPM probes 122 would cause radiation to be directed at the mask. Such radiation may comprise electromagnetic energy, such as radio frequency waves, gamma rays, x-rays, ultraviolet light, infrared light, visible light, and/or charged particles, such as protons, electrons, alpha particles, or ions. The resulting radiation that would be projected by the mask onto a wafer or that would be reflected and/or emitted by the mask would then be detected by some of the other components of the SPM system and/or one of the SPM probes. From the detected radiation, the controller generates and displays a patterned image of the detected radiation so as to emulate the way in which the mask would expose a wafer to radiation during actual fabrication of the wafer.

Alternatively, one or more of the SPM probes 122 may be used to make SPM measurements of the mask which are used by the controller 114 to produce a structural image of the mask in response. From this produced structural image, the controller 114 would simulate the detection of resulting radiation that would be projected by it or reflected and/or emitted by it in response to radiation directed at it. From this simulation, a patterned image of the detected radiation is generated.

In either case, the controller 114 compares the generated patterned image with a recorded target patterned image or criteria to generate repair and/or fabrication data that identifies any further repair and/or fabrication step to be performed on the mask. The controller 114 then causes the entire process to be repeated until the generated patterned image has converged to the target patterned image or criteria within the specified tolerance level.

Furthermore, in the case of a wafer, one or more of the SPM probes 122 may be used to make SPM measurements of the wafer. These SPM measurements may be used by the controller 114 to generate an analysis of the properties, operation, and/or characteristics of the wafer and/or a structural image of the wafer. This generated analysis and/or image is then compared with a target analysis or image to generate repair and/or fabrication data that identifies that identifies any further repair and/or fabrication step to be performed on the wafer. The controller 114 then causes the entire process to be repeated until the generated analysis and/or image converges to the target analysis or image within the specified tolerance level.

Removal of Particle Contaminants from Masks and/or Wafers

In addition to performing repairs and/or fabrication steps on a mask or wafer, the SPM system 100 could also be used to remove a particle contaminant on a mask or wafer. This would be done in a similar manner to that just described. Specifically, the SPM system would be provided with inspection data from a conventional contaminant inspection system that indicates where the particle contaminant is located on the mask or wafer. Then, one or more of the SPM probes 122 would be used to remove the particle contaminant without modifying the material of the mask or wafer based on the inspection data. In order to confirm that the particle contaminant has been removed, one or more of the SPM probes could be used to inspect the mask or wafer to determine whether this is the case. This may also be done in the manner described earlier by inspecting the mask or wafer so as to simulate or emulate its use in the environment in which it is normally used. Thus, this process may be repeated until the particle contaminant is removed.

Lithographic Structure Fabrication and/or Repair

Since the SPM system 100 may be used to perform precision repairs and/or fabrication steps of a partially completed or fully completed semiconductor fabrication mask, it may be also be used more generally for performing a repair or fabrication step on a lithographic structure. Such a lithographic structure may be a semiconductor mask as just described or other lithographic master used to fabricate replicable structures. Such replicable structures include optical structures (including x-ray and UV phase and diffraction optics), precision measuring scales, micro-machines, biochemical patterns, phosphors, fluorescent structures, biological structures (including DNA, RNA, proteins, catalysts, and enzymes). This process would be performed in the same manner just described for a semiconductor fabrication mask, except that the inspection or measurement imaging may include nanospectrophotometry, chemical analysis, and x-ray analysis.

Thin Film Read/Write Head Fabrication and/or Repair

The process just described can also be used to perform precision repairs and/or fabrication steps of a thin film magnetic read/write head or other magnetic structure. In particular, gaps (or grooves) in and between the write and read poles of the thin film magnetic material can be precisely created and/or repaired. In addition, such gaps may be magnetically characterized and then refined to optimize its magnetic field properties using the SPM probes. More generally, a gap (or groove) between magnetic elements of a magnetic microstructure can be created and/or repaired and characterized using this process. Specifically, a magnetically sensitive SPM probe may be used to map the magnetic field of the magnetic microstructure at varying drive energies and then other SPM probes may be used to modify the gap or apply additional magnetic material to obtain the desired field distribution for any given magnetic microstructure design.

Probe Fabrication and/or Repair

The SPM system 100 may also be used to perform precision repairs and/or fabrication steps when the object 102 itself is an SPM probe, such as one of the SPM probes 122 disclosed herein. Specifically, material could be added and/or removed to and from the probe using the SPM probes disclosed herein in order to create a desired shape or function for the probe.

Structure of SPM Probe 122-1

Figure 2:
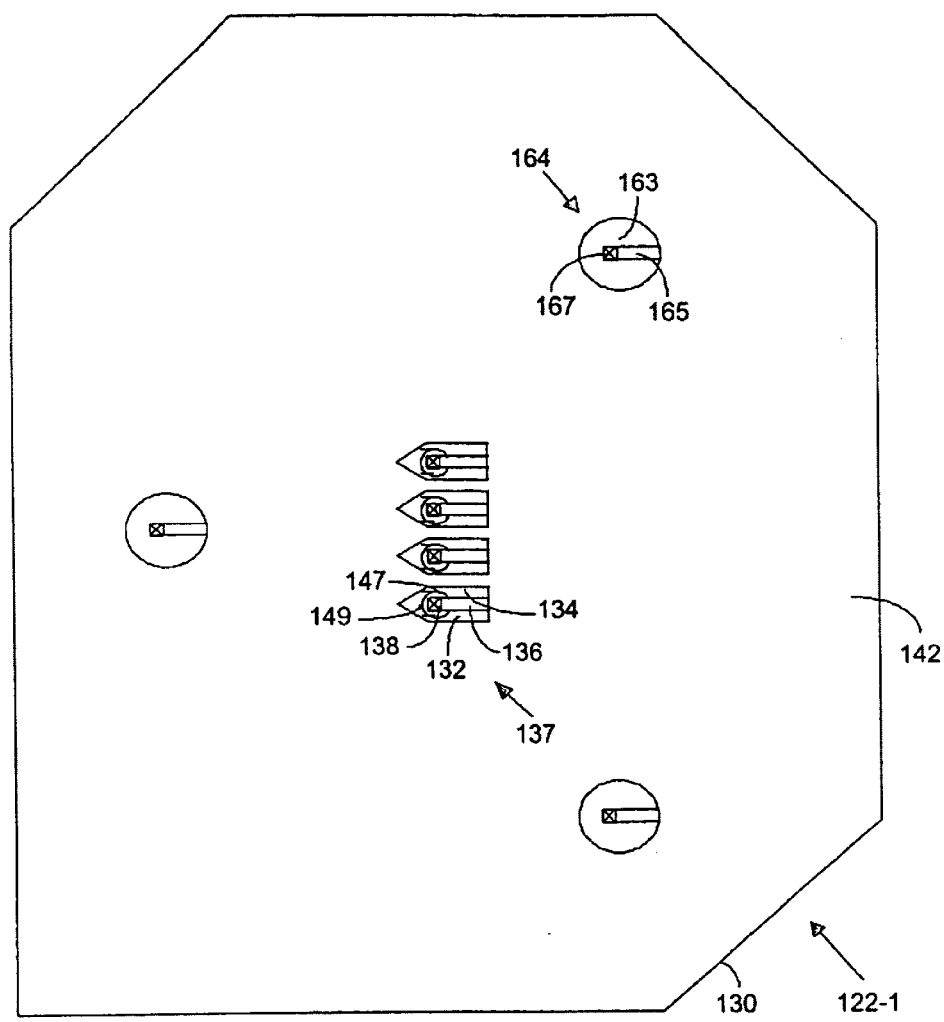
FIGS. 2 to 4 show different views of a first SPM probe of the SPM system of FIG. 1.

Referring now to FIG. 2, there is shown a microstructured SPM (scanning probe microscopy) probe 122-1 for use in inspecting the object 102 by making SPM measurements of the object, such as AFM (atomic force microscopy), STM (scanning tunneling microscopy), and/or radiation measurements, such as NSOM (near-field scanning optical microscopy) measurements and/or far-field radiation measurements. This probe may also be used to modify the object.

The SPM probe 122-1 has a base 130 and apertures (or openings) 132 that define corresponding inner perimeter surfaces 134 of the base. The probe also has several cantilevers 136 each connected to the base and extending into a corresponding aperture. On each cantilever is a corresponding tip 138. Each cantilever and corresponding tip form a corresponding SPM tool 137 that is used in making the SPM measurements and is attached to the base, disposed in the corresponding aperture, and framed (or surrounded) by the corresponding inner surface of the base.

Figure 3:
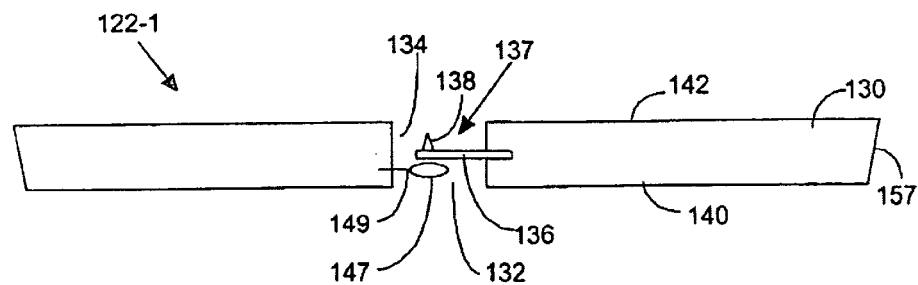

As shown in FIG. 3, when not engaged for inspecting the object 102, each SPM tool 137 of the SPM probe 122-1 is normally kept in the corresponding aperture 132 between the upper and lower surfaces 140 and 142 of the base 130 so that the tool, and in particular the tip 138, is protected from being damaged during loading onto and unloading from one of the scanning heads 120. Moreover, referring to FIG. 1, the probe may be supplied by one of the probe suppliers 124 that has a vertical stacking mechanism and extends vertically up through the rough positioning subsystem 104. In such a probe supplier, the probe can be vertically stacked on top of other probes of this type without damaging the tools of the probe.

Figure 4:
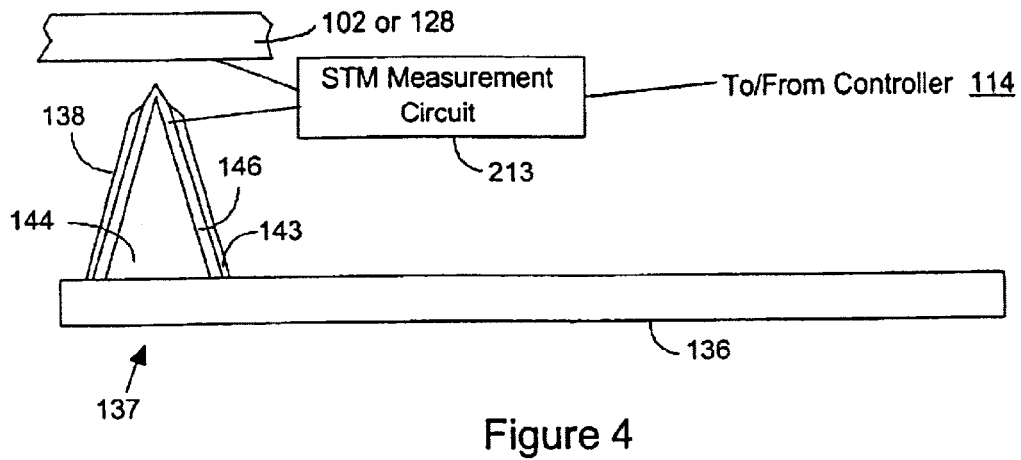

Referring to FIG. 4, the tip 138 and cantilever 136 of each SPM tool 137 of the SPM probe 122-1 have a core material 144 that comprises a conductive or semiconductive material, such as silicon or silicon nitride. Referring back to FIG. 3, the base 130 of the probe and the tip and cantilever of each tool of the probe may be integrally formed together from this core material. Alternatively, the base of the probe may be formed on and around each tool. In either case, this is done using conventional semiconductor manufacturing techniques.

As alluded to earlier, each SPM tool 137 of the SPM probe 122-1 can be used to make AFM measurements in order to inspect the object 102. Thus, in order to be resistant to frictional wear when being used in this manner, the tip 138 of each tool may include an obdurate coating 146 over the core material 144 at least at the sharp end of the tip, as shown in FIG. 4. This coating may comprise diamond, silicon carbide, carbon nitride, diamond like carbon, or some other obdurate material, and may have a thickness in the range of approximately 1 Angstroms to 10 micrometers.

In the case where the obdurate coating 146 comprises diamond like carbon, a mask may be placed over each tool so that only the tips 138 are exposed. Then, carbon is vacuum arc deposited on the core material 144 to form the carbon coating. This may be done in the manner described in Ager, J. W. et al., "Multilayer Hard Carbon Films with Low Wear Rates", Surface and Coatings Technology, submitted Mar. 26, 1996, Anders, S. et al., "Properties of Vacuum Arc Deposited Amorphous Hard Carbon Films", Applications of Diamond Films and Related Materials, Third International Conference, 1995, and Pharr, G. M. et al., "Hardness, Elastic Modules, and Structure of Very Hard Carbon Films Produced by Cathodic Arc Deposition with Substrate Pulse Biasing.

But, in the case where the obdurate coating 146 comprises diamond, carbon is deposited on the exposed surface of the core material 144 of the tips in the same manner as just described. In this case however, the carbon forms seed sites for growing diamond crystals. Alternatively, seed sites may be formed by pushing or rubbing each tip on a surface containing fine grain diamond (such as a lap or polycrystalline diamond coated surface). The probe is then placed in a methane and hydrogen or methane and argon atmosphere for chemical vapor deposition (CVD) of diamond on the exposed surfaces. As a result of the seed sites, a polycrystalline diamond coating is grown on the exposed surfaces with the diamond crystals being grown normal to the exposed surfaces. The use of a methane and argon atmosphere has several advantages over the use of a methane and hydrogen atmosphere. Specifically, a methane and argon atmosphere is safer because it is less volatile. And, in a methane and argon atmosphere, the rate of growth and size of the diamond crystals is smaller. This is desirable for fabrication of the tips 138 of the microstructured SPM probe 122-1.

Moreover, during the deposition process, a bias voltage may be applied to the core material 144 of the probe 122-1. This voltage should be sufficient to create an electrical field at the sharp end of the tips 138 of the probe which is large enough so that the diamond crystals grown at the sharp end of the tips are symmetrically aligned but small enough so that the diamond crystals grown below the sharp end of the tips are not symmetrically aligned. The advantage of this is to obtain a consistent orientation and tip behavior at the sharp end without sacrificing the durability and stability of the obdurate coating 146 below the sharp end.

And, when the obdurate coating 146 comprises carbon nitride, the same seeding processes as was just described for diamond growth may be used. Then, the probe 122-1 is placed in an atmosphere of monatomic nitrogen. The monatomic nitrogen is obtained by passing nitrogen gas through a hollow tungsten heater consisting of a hollow tungsten structure through which an electric current is passed. The tungsten heater is maintained at a temperature of 2100 to 3000° C. In one embodiment, the tungsten heater also includes a quantity of carbon sufficient to combine chemically to form a carbon nitride layer on the carbon seed sites at the cool exposed surfaces (800° C.) of the core material 144 of the tips. In another embodiment, the process begins without introducing nitrogen gas. After a few atoms of carbon are deposited, the nitrogen gas is introduced into the tungsten electrode and deposition and growth of the polycrystalline carbon nitride coating is initiated.

In addition, the tools 137 of the probe 122-1 can be used to make STM measurements in order to inspect the object 102. Thus, so that each tip 138 can be used in this manner, the obdurate coating 146 of each tip can be made to be conductive. This is done by doping the diamond, silicon carbide, carbon nitride, diamond like carbon, or other material which comprises the obdurate coating with a suitable impurity, such as boron. In the case of diamond like carbon, this is not necessary since it is conductive but may be done anyway to improve conductivity.

Formation of conductive diamond, silicon carbide, and carbon nitride crystals on SPM tips is further described in U.S. patent application Ser. No. 08/906,602, PCT Application No. PCT/US95/09553, U.S. patent application Ser. No. 08/506,516, and PCT Application No. PCT/US96/12255 referenced earlier. And, growth of diamond and silicon crystals is further described in "Deposition, Characterization, and Device Development in Diamond, Silicon Carbide, and Gallium Nitride Thin Films", by Robert F. Davis, Journal of Vacuum Science and Technology, volume A 11 (4) (July/August 1993), which is hereby incorporated by reference. Furthermore, growth of diamond crystals on field emissive tips is described in E. I. Givargizov et al., "Growth of Diamond Particles on Sharpened Silicon Tips for Field Emission", Diamond and Related Materials 5 (1996), pp. 938–942, E. I. Givargizov et al., "Growth of Diamond Particles on Sharpened Silicon Tips", Materials Letters 18 (1993), pp. 61–63, K. Okano et al., "Mold Growth of Polycrystalline Pyramidal-Shape Diamond for Field Emitters", Diamond and Related Materials 5 (1996), pp. 19–24, which are also hereby incorporated by reference in their entirety.

Furthermore, referring to FIG. 3, the tools 137 of the probe 122-1 can be used to make radiation measurements in order to inspect the object 102. Thus, for each tool of the probe, the probe includes a corresponding lens 147 and lens support 149 that supports the lens. As with the tip and cantilever of each tool, the lens and lens support for each tool may be integrally formed together with the base 130 or the base may be formed on and around the lens support. This is also done using conventional semiconductor manufacturing techniques.

In order to make these radiation measurements, the each tip 138 of the probe 122-1 has a reflective coating 143 that reflects light so as to contain within the tip any light that propagates in the tip. This coating may comprise a light reflective material, such as aluminum, tungsten, or gold. It may be formed over the obdurate coating 146 using conventional techniques and have a thickness in the range of approximately 1 Angstrom to 1 micron. A small portion of the reflective coating 143 is removed or rubbed off at the sharp end of each tip 138 using conventional techniques to at least the point where the reflective coating is no longer opaque to light propagating through the tip. Furthermore, the reflective coating is removed or rubbed off only so that it ends approximately 5 to 10 nm from the point of the sharp end. As a result, an aperture having a diameter in the range of approximately 5 to 100 nm is formed at the sharp end. Moreover, in the case where the light reflective coating 143 is conductive, it can also be used to make the STM measurements. In this case, the obdurate coating 146 need not be made conductive.

As an additional note, the formation of the tips 138 and cantilevers 138 of the probe 122-1 are similarly described in U.S. Patent Application No., PCT Application No. PCT/US95/09553, U.S. patent application Ser. No. 08/506,516, and PCT Application No. PCT/US96/12255 referenced earlier.

Referring again to FIG. 2, and as mentioned earlier, the probe 122-1 has multiple tools 137 each comprising a cantilever 136 and a tip 138 on the cantilever. Thus, when the tip of one of the probe's tools is determined to be defective in the manner to be described later, then another one of the probe's tools with a tip determined not to be defective can be used for inspecting the object 102 without having to load another probe of this type.

Probe Loading and Unloading

Figure 6:
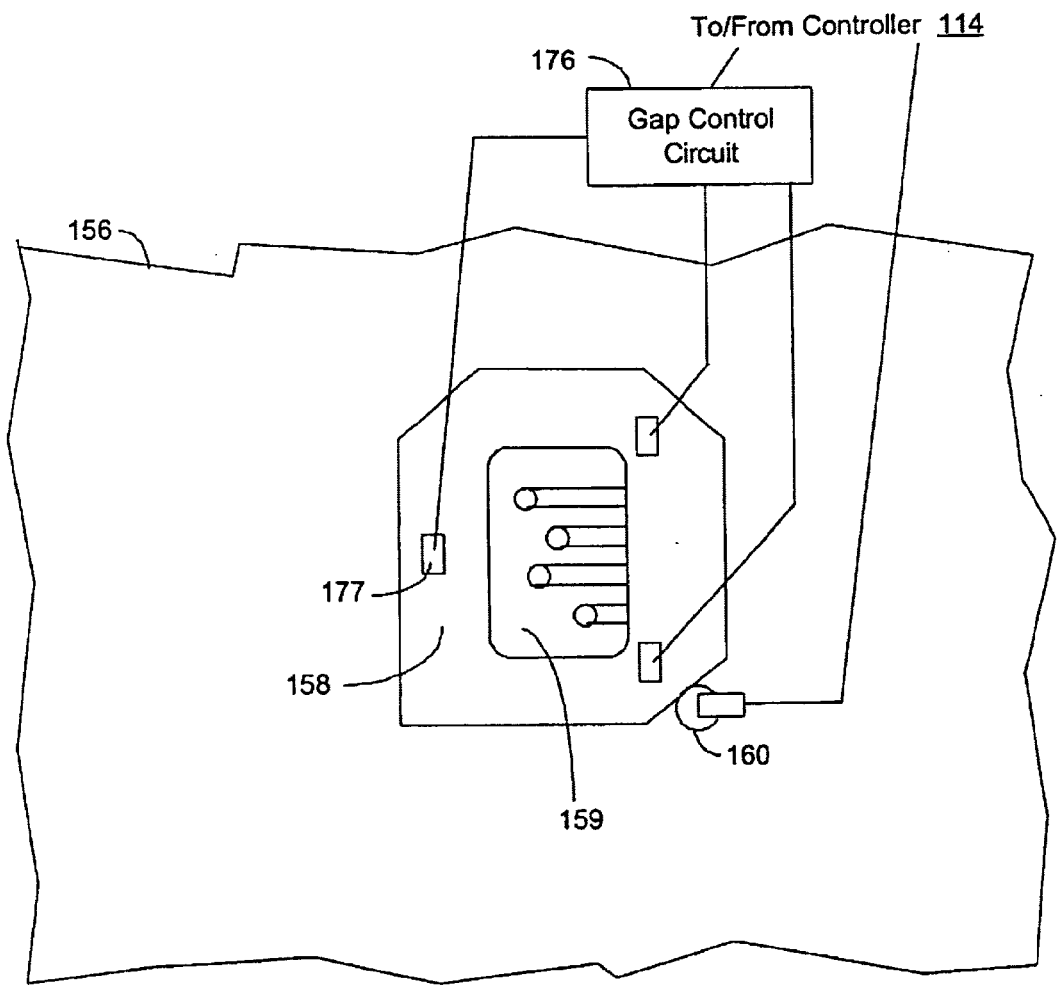
FIGS. 5 to 8 show different views of a scanning head of the SPM system of FIG. 1.
Figure 5:
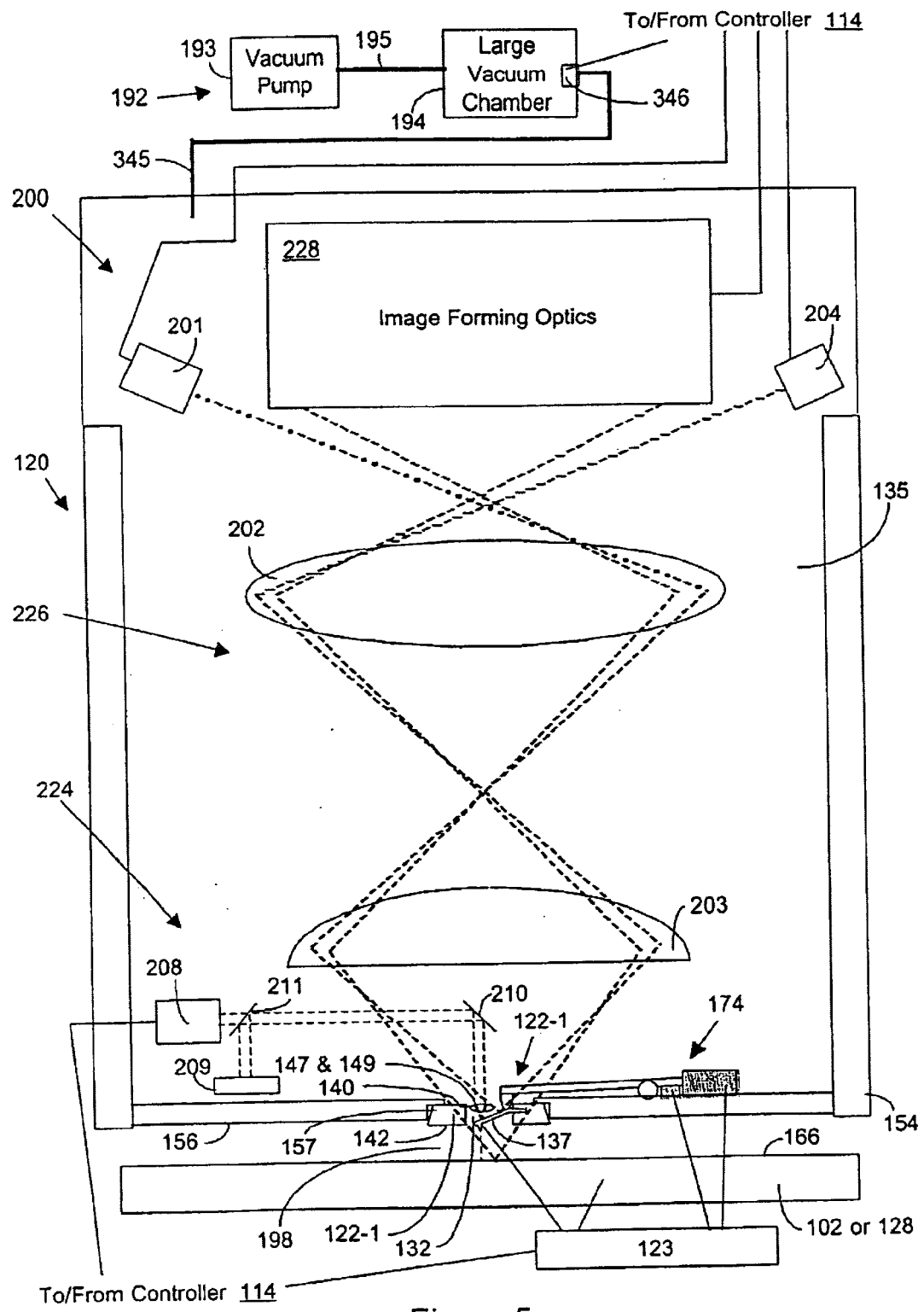

FIG. 5 shows the way in which the probe 122-1 is loaded onto one of the scanning heads 120. The scanning head includes a housing 154 with a probe holding plate 156. As shown in FIG. 6, the probe holding plate includes a seat 158 formed by a recess in the probe holding plate that is in the shape of the base of the probe and seats (or holds) the probe. And, the other components 123 of the SPM system 100 include a rotary cam assembly 160 that is formed in the probe holding plate. Thus, when the probe is being loaded onto the scanning head in the manner described earlier, the controller 114 controls the rotary cam assembly so that its rotary cam rotates and presses against the probe and locks it into place in the seat of the probe holding plate. In this way, the probe is loaded onto the scanning head. Similarly, when the probe is being unloaded from the scanning head in the manner described earlier, the controller controls the rotary cam assembly so that the rotary cam rotates and no longer presses against the probe and unlocks it from the seat of the probe holding plate.

Furthermore, as shown in FIG. 3, the base 130 of the SPM probe 122-1 has a tapered outer perimeter surface 157 so that the bottom surface 142 has an area larger than that of the top surface 140. In addition, referring to FIG. 6, the bottom surface has an area larger than that of the recess that forms the seat 158 in the probe holding plate 156. Thus, as shown in FIG. 5, when the probe is loaded onto one of the scanning heads 120, the base of the probe is wedged into the recess so that the probe is properly seated in the seat of the scanning head's probe holder 156 with no movement between the probe and the probe holding plate.

Tip Activation and Deactivation

Figure 7:
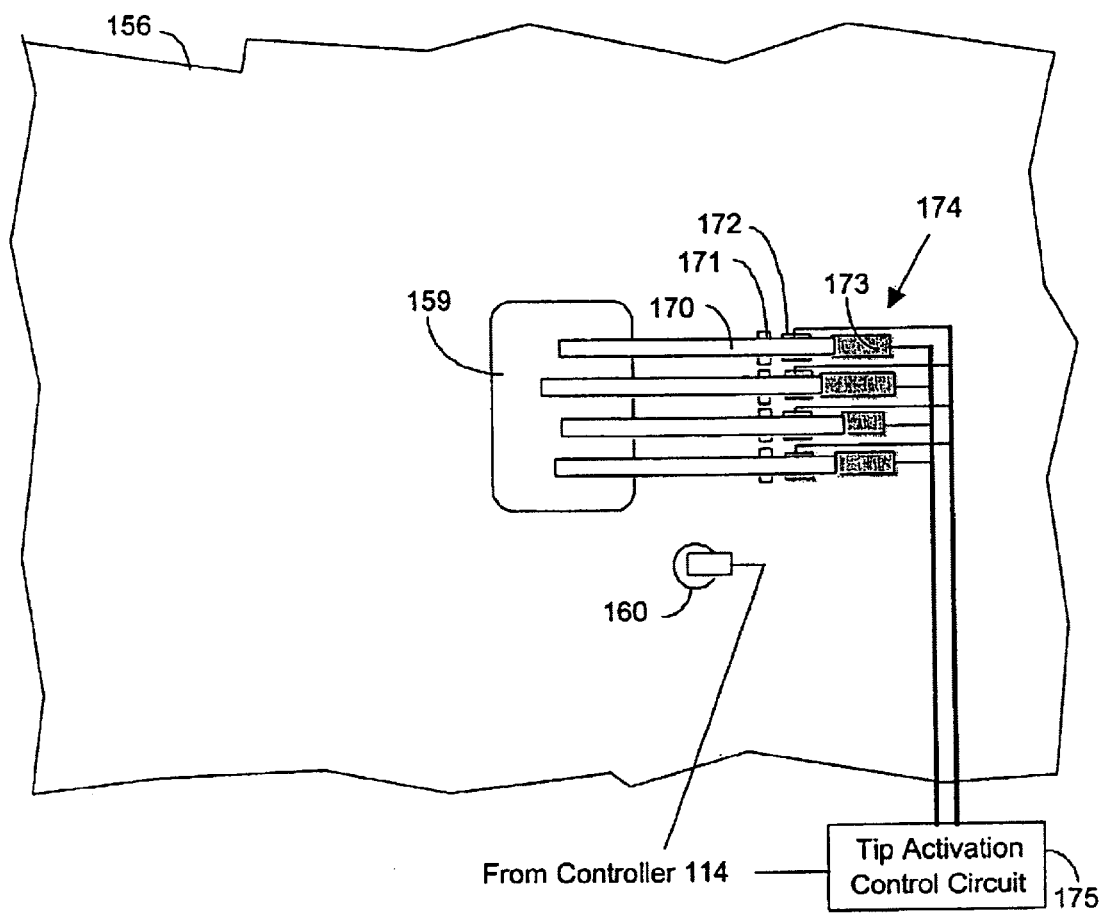

Referring now to FIGS. 5 and 7, fixed to the probe holding plate 156 are tip actuators 174 that are each used to selectively activate and deactivate a corresponding tip 138 of the SPM probe 122-1 for use in inspecting the object 102. Each tip actuator includes an L-shaped lever arm 170, a pivot 171, an engagement transducer 172, and an adjustment transducer 173. The L-shaped lever arm has one end fixed to the engagement and adjustment transducers and a rounded end that extends into an aperture 159 in the seat 158 of the probe holding plate 156. The engagement and adjustment transducers may each comprise a material, such as a piezoelectric material or a resistive metal (e.g., Nickel Chromium alloy), which change dimensions when a voltage or current signal is applied to it. Alternatively, electromagnetic or electrostatic transducers or actuators could be used.

Figure 8:
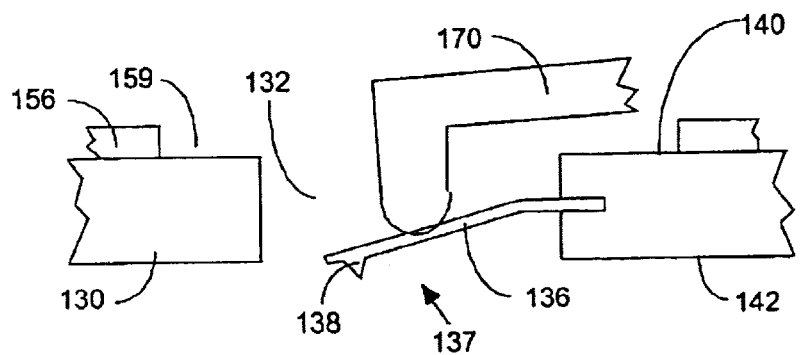

The other components 123 of the SPM system 100 also include a tip actuator control circuit 175. In selectively activating the tip 136 of one of the SPM tools 137 of the SPM probe 122-1, the controller 114 causes the control circuit to control the change in dimension of the engagement transducer 172 of the corresponding tip actuator 174 so that it pushes up on the end of the lever arm 170 to which it is fixed. In response, the lever arm pivots on the pivot 171 and, as shown in FIG. 8, the rounded end of the lever arm extends down through the aperture 159 in the seat 158 of the holding plate 156 and into the corresponding aperture 132 of the probe. In doing so, the rounded end engages and presses against the corresponding cantilever 136 so as to push down on it. As a result, the cantilever bends so that the tip 138 on the cantilever is moved below the lower surface 142 of the base 130 of the probe and is activated for operation in inspecting the object 102. Similarly, the tip is selectively deactivated when the controller controls the change in dimension of the engagement transducer 172 of the corresponding tip actuator so that it pulls down on the end of the lever arm to which it is fixed. In response, the lever arm pivots on the pivot and the rounded end of the lever arm extends up so that the cantilever bends up until the tip is located above the lower surface of the base. As a result, and tip is then protected against being damaged.

Figure 18:
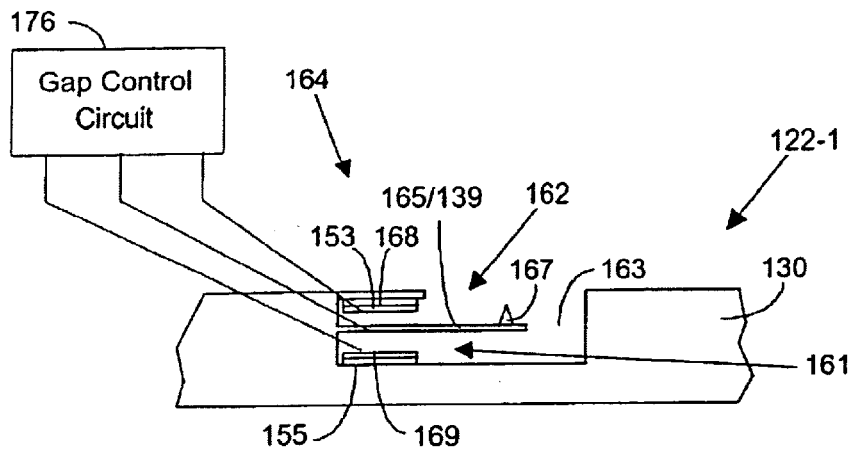
FIGS. 18 and 19 show different embodiments for the gap sensors of the first SPM probe to sense the width of the gap in which the differential pressure chamber is formed.

In alternative embodiment, each tool 137 of the probe 122-1 may include an electrostatic (i.e., capacitive) tip actuator. Such a tip actuator would be configured and operate like the electrostatic tip actuators 162 of the gap sensors 164 of the probe, as shown in FIG. 18 and described later.

Calibration with AFM Measurements

Figure 9:
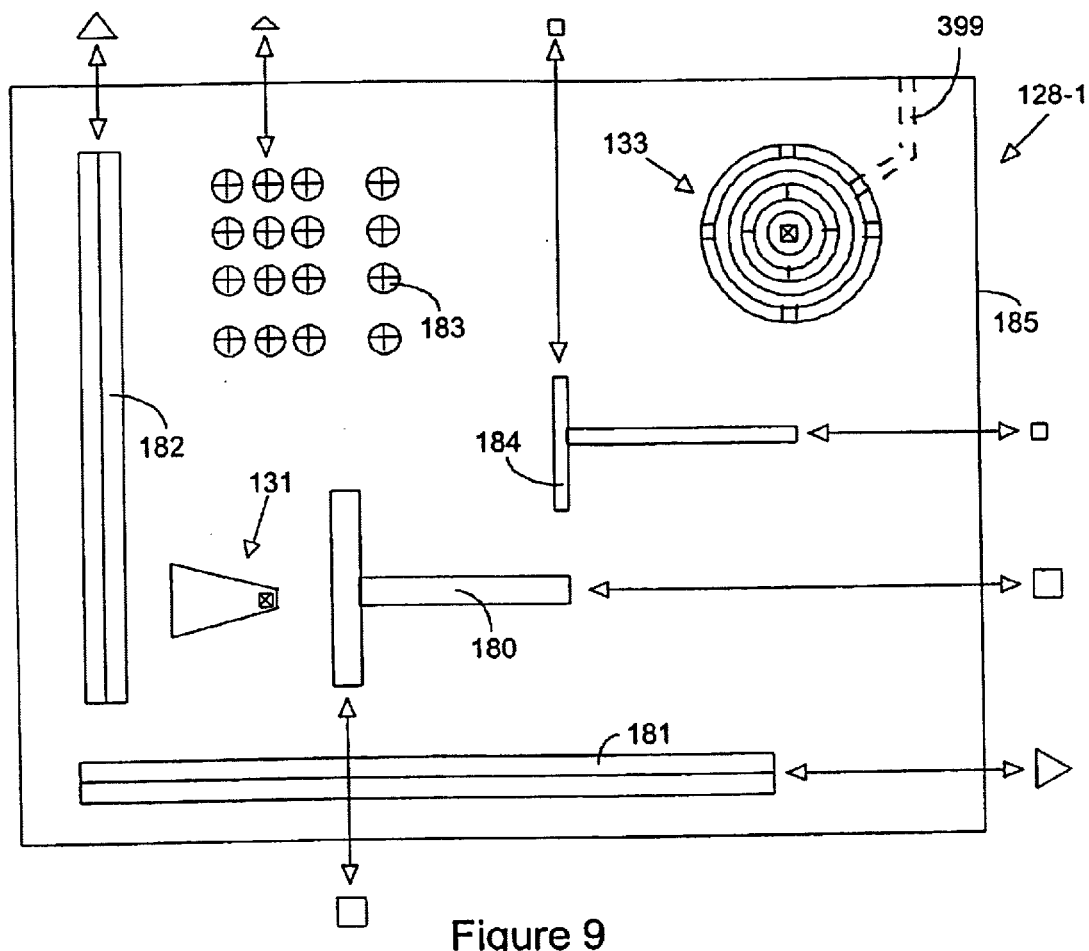
FIGS. 9, 10, and 87 show different views of a calibration structure of the SPM system of FIG. 1.

Turning now to FIG. 9, the calibration structures 128 include a first calibration structure 128-1 that, referring to FIG. 1, may be located on the rough positioning subsystem 104. And, it may be used to calibrate and examine an activated tip 138 of the SPM probe 122-1 by calibrating its position and examining its profile (or shape) to determine whether it is defective. So that this may be done, the calibration structure includes various reference substructures 180 to 184 on its base 185. These reference substructures have different shapes, sizes, orientations, and positions with respect to a precisely known reference location in the SPM system 100.

Turning again to FIG. 1, when the tip 138 of one of the SPM tools 137 of the SPM probe 122-1 is to be used to inspect the object 102, the user uses the user interface 116 to instruct the controller 114 to first have the positioning of the activated tip calibrated and its profile examined. In response, the controller controls loading of the probe onto the scanning head 120 and activation of the tip in the manner just discussed. Referring back to FIG. 9, the controller then calibrates positioning of the activated tip by controlling the positioning system 103 to scan (or position) the activated tip over the reference substructures 180 to 184 of the calibration structure 128-1. As this is done, an AFM measurement of the deflection of the cantilever 136 on which the activated tip is located is made at each scan point.

Referring to FIG. 5, in order to make these AFM measurements, the other components 123 of the SPM system 100 may include in each of the scanning heads 120 a cantilever deflection measurement system 200. The cantilever deflection measurement system has optics that comprise a light source 201, lenses 202 and 203, and a photodetector 204. As is well known to those skilled in the art, the optics 201 to 204 are used as an interferometer to optically detect and measure the deflection of the cantilever 136. This kind of arrangement may be configured in the manner described in U.S. patent application Ser. No. 08/613,982 referenced earlier where the light source and photodetector are located externally from the scanning head. Alternatively, the cantilever deflection measurement system may comprise components to electrostatically (i.e., capacitively) detect and measure the cantilever deflection.

The AFM measurements of the deflection of the cantilever 136 are used by the controller 114 to calibrate the activated tip 138 of the SPM probe 122-1 for precise positioning of the tip with respect to the reference location and to examine its profile. This is done by producing an image of the calibration structure 128-1 from these measurements. This produced image is then compared with a stored reference image of the calibration structure which was produced similarly using a reference tip that was precisely scanned (or positioned) over the calibration structure with respect to the reference location and has a precisely known reference profile. The images are compared to determine the positional offset between them. Based on the determined positional offset, precise positioning of the tip with respect to the reference location is then calibrated. Moreover, by comparing the resolution of the images, it can be determined if the tip is defective from wear or malformation. If the tip is defective, then the tip of another tool of the probe may be activated, have its position calibrated, and be examined to determine if it is defective in the manner just described. But, if all of the tips of the tools of the probe are defective, then the probe must be discarded and another probe will have to be loaded onto the scanning head 120 from one of the probe suppliers 124. Otherwise, if the activated tip is not defective, it can then be used to inspect the object 102.

Additionally, the position calibration technique just described may be used in combination with any of the other position calibrations described herein. This would be done to provide a particular optimal reference process in which a more precise position calibration is determined or in which the position calibration is derived in a shorter time.

Calibration using Reference SPM Probe 131

Figure 10:
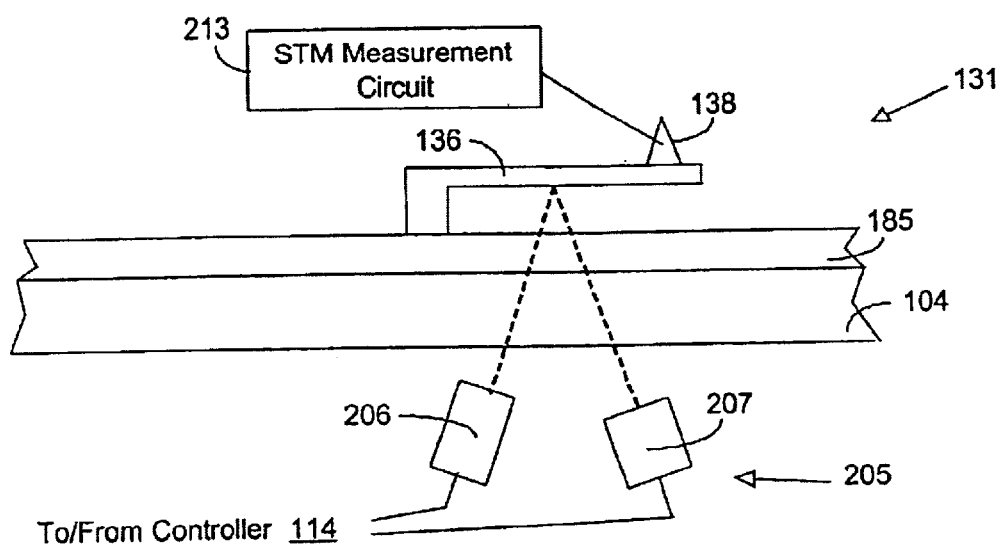

Furthermore, as shown in FIG. 10, in order to calibrate and examine the activated tip 138 of the selected SPM tool 137, the calibration structure 128-1 may also include a reference SPM probe 131. The reference SPM probe comprises a reference cantilever 136 connected to and suspended over the base 185 of the calibration structure and a reference tip 138 on the cantilever. The reference tip and cantilever may be constructed like the activated tip and cantilever of the selected SPM tool. The other components 123 of the SPM system 100 will then include another cantilever deflection measurement system 205 that comprises optics used in conjunction with the reference tip and reference cantilever. The optics comprise a light source 206 and a photodetector 207. Like the optics 201 to 204 In each scanning head 120, these optics are used as an interferometer to optically detect and measure the deflection of the reference cantilever 136 of the calibration structure. In order that the light provided by the light source be reflected by the cantilever, the light may be transparent to the rough positioning apparatus and the base of the reference structure but not transparent to the cantilever. Alternatively, if the light Is also transparent to the cantilever, the optics would include a reflective material on the cantilever that reflects the light. And, in an alternative embodiment, the cantilever deflection measurement system may comprise components to electrostatically (i.e., capacitively) detect and measure the deflection of the reference cantilever in the manner described later for the electrostatic deflection sensors 161 shown in FIG. 18 and described later.

Turning again to FIG. 1, in this case, the controller 114 calibrates the position of the activated tip 138 of the SPM probe 122-1 by controlling the positioning system 103 to scan the activated tip over the reference tip 138 of the calibration structure 128-1. Referring to FIG. 10, as this occurs, the deflection of the reference cantilever 136 is measured by the cantilever deflection measurement system 205 at each scan point as just described. Since the reference tip is at a precisely known position with respect to the reference location, the AFM measurements of the deflection of the reference cantilever are used to calibrate the precise position of the activated tip of the probe with respect to the reference location and to examine the tip's profile. Specifically, the AFM measurements are used to produce an image of the activated tip. From the produced image, the positional offset of the activated tip at the known position of the reference tip can be determined. Based on this positional offset, the precise positioning of the tip with respect to the reference location is then calibrated. Moreover, from the produced image, it can be determined whether or not the activated tip is defective.

Furthermore, the reference tip 138 can be made conductive in the same manner was described earlier for the activated tip 138 of the SPM probe 122-1. In this case, the position of the activated tip can be calibrated and its profile examined using STM measurements. This would be done in the same manner was just described for making AFM measurements, except that STM measurements of the tunneling current between the reference tip and the activated tip would be made to produce an image of the activated tip. This would be done using the STM measurement circuit 213 in the manner described later.

Additionally, the position calibration technique just described may be used in combination with any of the other position calibrations described herein. This would be done to provide a particular optimal reference process in which a more precise position calibration is determined or in which the position calibration is derived in a shorter time.

Calibration Using SPM Probe 133

Turning now to FIG. 9, the calibration structure 128-1 may include a reference SPM probe 133 for calibrating the position of and examining the profile of the activated tip 138 of the SPM probe 122-1. This is done by generating a particle beam that strikes the activated tip and collecting the secondary particles that result. The SPM probe 133 is formed in the base 185 of the calibration structure and is located at a precisely known location with respect to the reference location discussed earlier.

Figure 87:
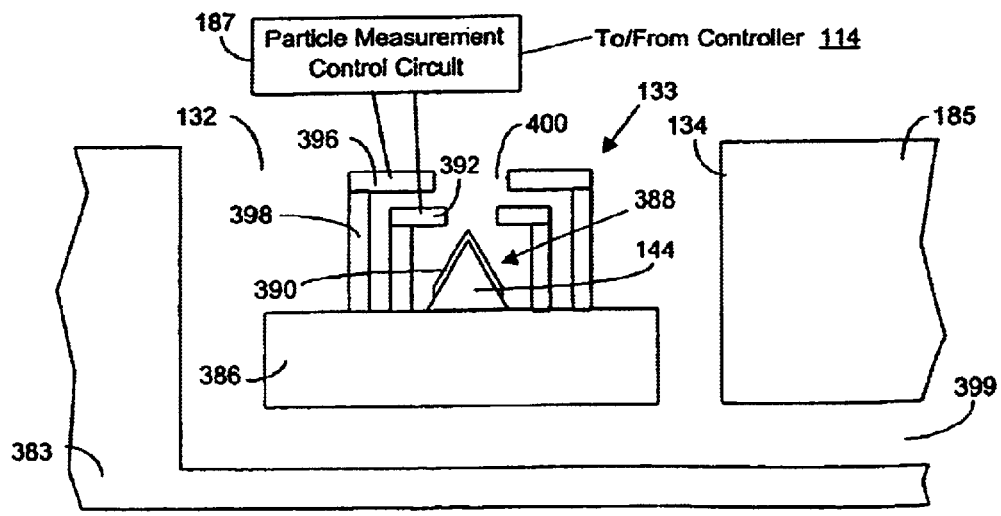

For example, the reference SPM probe 133 may be constructed like the e-beam tool 382 of the eighth SPM probe 122-8 discussed later, except that it has a duct 399 formed in the base 185 of the calibration structure. The duct is connected to the aperture 132 of the reference SPM probe, as shown in FIG. 87. Referring to FIG. 1, the duct is also connected to a corresponding flexible tube 345. Thus, when the controller 114 calibrates the position of the activated tip 138 of the first SPM probe 122-1, it causes the valve 346 to be opened so that the vacuum source 192 is in fluid communication with the aperture 132 of the SPM probe 133. As a result, a microvacuum chamber (i.e., zone or space) is created in the gap between the SPM probe 122-1 and the base 185. This is done in a similar way to that described in more detail for establishing a gap between the first SPM probe 122-1 and the object 102 using the apertures 132 in the first probe.

Then, referring to FIG. 9, the controller 114 controls the positioning system 103 to scan the activated tip 138 over the reference SPM probe 133. The other components 123 of the SPM system 100 further include a particle measurement control circuit 187, as shown in FIG. 87. The controller controls the particle measurement control circuit to cause the SPM probe to produce an e-beam and detect any secondary electrons in the manner discussed later for the e-beam tool 382 of the SPM probe 122-8. The particle measurement control circuit makes a particle measurement of the detected electrons and provides it to the controller. The controller collects the particle measurements and produces an image of the activated tip in the same manner as a conventional particle microscope, such as an electron microscope. From the produced image, the positional offset of the tip at the known position of the SPM probe can be determined. Based on this positional offset, the precise positioning of the tip with respect to the reference location is then calibrated. Moreover, from the produced image, it can be determined whether or not the tip is defective.

Similarly, the reference SPM probe 133 could be constructed like each of the ion beam tools 450 of the eleventh SPM probe 122-11 discussed later. Here, the position of the activated tip 138 would be done in a similar manner to that just described. But, in this case, an ion beam would be produced and secondary ions would be collected by such a reference SPM probe in the manner discussed later for the eleventh probe.

Additionally, the position calibration technique just described may be used in combination with any of the other position calibrations described herein. This would be done to provide a particular optimal reference process in which a more precise position calibration is determined or in which the position calibration is derived in a shorter time.

Calibration with Radiation Measurements

Figure 11:
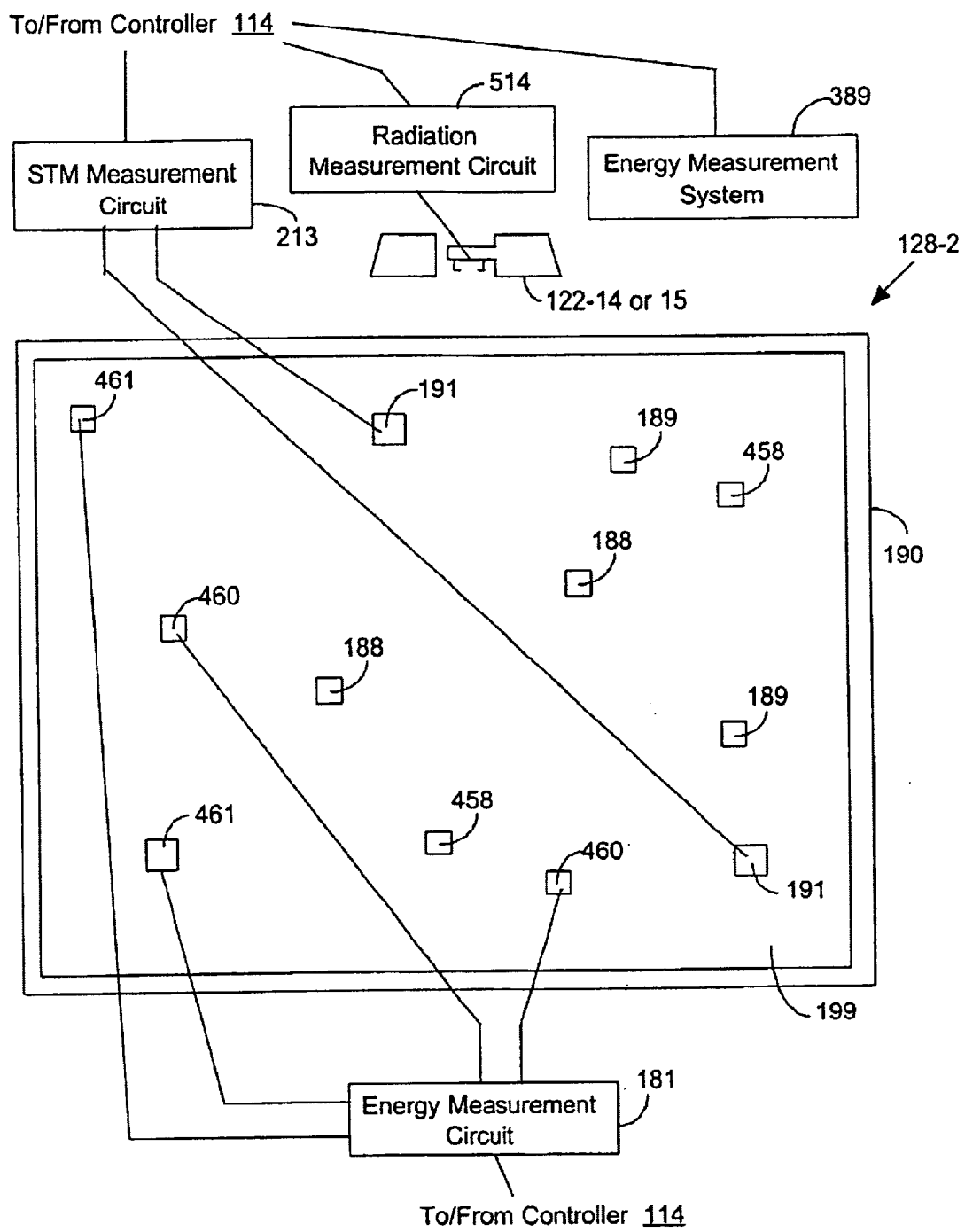
FIGS. 11 and 52 show different views of another calibration structure of the SPM system of FIG. 1.

The position of the activated tip 138 of the SPM probe 122-1 may also be calibrated in another way. In order to do this, the SPM system 100 includes another calibration structure 128-2 that, like the first calibration structure 128-1, may be located on the rough positioning subsystem 104. As shown in FIG. 11, this calibration structure may include one or more reference materials 189 on an insulating material 199 on the base 190 of the reference structure. Each reference material has a precisely known position with respect to the reference location. And, each reference material may comprise a material that has known radiation properties when light interacts with it. For example, this may be a material with known light absorption properties or known light reflection properties. Furthermore, this may be a material with known light frequency altering properties. For example, such a material may be a frequency doubling material, such as gallium arsenide or gallium nitride. Or this material could be a fluorescing material or a material which produces second harmonic or Raman characteristics when light interacts with it.

Referring to FIG. 5, as alluded to earlier, the probe 122-1 is used for making radiation measurements and includes a lens 147 over each tip 138 for doing so. In addition, in order to make radiation measurements, the measurement components include measurement optics 224 comprising a light source 208, a photodetector 209, and mirrors 210 and 211 which are all located in the scanning head 120 and optically coupled together. But, these optics and the lens over an activated tip may also be used to calibrate the position of the tip.

Turning again to FIG. 1, in this case, the controller 114 calibrates the position of the activated tip 138 by controlling the positioning system 103 to attempt to position the tip over one of the reference materials 189 of the calibration structure 128-2. Then, referring to FIG. 5, the controller controls the light source 208 to provide radiation in the form of a narrow beam of light with a desired wavelength (i.e., frequency) spectrum. The narrow beam of light is directed to the lens 147 of the probe 122-1 by the mirror 210. The lens focuses the narrow beam of light within the activated tip 138. The tip acts as an antenna or waveguide and the focused light propagates through the tip until it is emitted by the tip's aperture, which was described earlier. The emitted light then optically interacts with the reference material. The resulting light from the optical interaction is captured by the tip's aperture and propagates back through the tip to the lens. The lens then directs the resulting light to the mirror 210 which re-directs it to the other mirror 211. This mirror then directs the resulting light to the photodetector 209 which detects it and makes NSOM measurements of its constituent wavelengths. These NSOM measurements are further described in U.S. patent application Ser. No. 08/906,602, U.S. patent application Ser. No. 08/412,380, and PCT Application No. PCT/US95/09553 referenced earlier.

And, referring to FIG. 11, in an alternative embodiment, the other components 123 of the SPM system 100 may include a radiation measurement system 389 which is used instead of the photodetector 209 to detect the resulting light from the optical interaction of the light emitted by the tip and the reference material. Or, the resulting light may be detected using one of the SPM probes 122-14, 122-15, or 122-16 in the manner described later. In this case, the narrow beam of light may be chopped or modulated in a characteristic way by the light source 208. Then, this chopping or modulation is reproduced in the radiation measurement system 389 or the radiation measurement circuit 514 used with the SPM probes 122-14, 122-15, or 122-16 so that the excitation and/or resulting radiation can easily be distinguished from the background or noise radiation by the radiation measurement system.

Furthermore, in another embodiment, rather than using the mirrors 210 and 211, a fiber optic guide may be used to deliver the light to the activated tip 138 and direct the resulting light back to the photodetector. Additionally, a fresnel lens integrated in the cantilever over the tip could be used rather than the refractive lens 147 to focus the narrow beam of light within the tip and direct the resulting light from the optical interaction with the reference material back to the fiber optic guide. Such a configuration is described in U.S. patent application Ser. No. 08/281,883, U.S. patent application Ser. No. 08/412,380, and PCT Application No. PCT/US95/09553 referenced earlier.

From the radiation measurements made by either the photodetector 209, the radiation measurement system 389, or one of the SPM probes 122-14, 122-15 or 122-16, the controller 114 generates a spectrum of the measured wavelengths (i.e., frequency spectrum) and compares the generated spectrum and its intensity (i.e., amplitude) with a stored known reference spectrum of wavelengths for radiation that results when light with the same wavelength spectrum as the narrow beam of light optically interacts with the reference material 189. If they match and the intensity is maximized, this means that activated tip 138 was positioned directly over the reference material. Thus, in a closed feedback loop, the tip is positioned, the light is emitted from the tip, the wavelengths and the intensity of the resulting radiation are measured, and the generated and reference spectrums are compared in the manner just described until it is determined by the controller that the tip is in fact positioned over the reference material. Since the tip will be positioned in very small motions about the reference material 189, the use of the chopped or modulated narrow beam of light is very helpful in this process because the resulting radiation and its intensity can be easily measured independent of noise.

Once it is determined by the controller that the tip 138 is positioned over the reference material 189, the positional offset of the activated tip at the known position of the reference material is determined. Based on this positional offset, the precise positioning of the tip with respect to the reference location is then calibrated.

Since there may be more then one reference material 189, the process just described may be repeated for each of these reference materials. In this way, the results of the calibrations computed for all of the reference materials may be combined to provide a weighted or averaged calibration of the position of the activated tip 138.

The second calibration structure 128-2 may additionally include one or more reference radiation detection devices 460 formed on the insulating material 199 of the base 190 of the calibration structure. Each radiation detection device has a precisely known position with respect to the reference location. More specifically, referring to FIG. 52, each radiation detection device includes an aperture structure 466 and a semiconductor radiation detector 463 formed on the insulating material. The aperture structure blocks (or absorbs) extraneous radiation from contacting the radiation detector and is grounded by the radiation measurement circuit 181. But, it also allows radiation that is directed to the radiation detector to pass through the aperture 467 in the aperture structure and contact the radiation detector. The radiation detector may comprise a radiation sensitive semiconductor junction diode or junction transistor, such as a photodiode or phototransistor, that is formed in the manner well known to those skilled in the art and in the manner described in "Radiation Detection and Measurement", by Glenn F. Knoll, Wiley, New York, 1979, Ch. 11, pp. 359–413, Ch. 2, pp. 39–78. The radiation detector may be suitably doped and constructed to detect a wide spectrum of radiation or selected kinds of radiation. Here, the radiation detector detects radiation in the form of light that passes through the aperture.

Turning again to FIG. 1, in this case, the controller 114 calibrates the position of the activated tip 138 in a similar way to that just described. Here, however, the controller controls the positioning system 103 to attempt to position the tip over one of the radiation detection devices 460. Then, referring to FIG. 5, the controller causes light to be emitted from the tip's aperture in the manner just discussed. The radiation detector then provides a signal representing the light it detects to a radiation measurement circuit 181. The radiation measurement circuit is one of the other components 123 of the SPM system 100 and makes a measurement of the detected light. It then provides this measurement to the controller 114 which analyses the measurement to determine if the radiation detector detected the light emitted by the tip. Thus, in a closed feedback loop, the tip is positioned, the light is emitted by the tip, and the measurement from the radiation measurement circuit is analyzed in the manner just described until it is determined by the controller that the tip is in fact positioned over the reference material. Once this occurs, a positional offset is computed and the precise positioning of the tip with respect to the reference location is then calibrated based on the positional offset in the manner just described.

If there are multiple radiation detection devices 460 for detecting light, the results of the calibrations computed for all of the radiation detection devices may be combined to provide a weighted or averaged calibration of the position of the activated tip. Or, the controller 114 compares the relative intensities or time of flights of the radiation detected by the radiation detection devices to determine which one is close to the tip.

Additionally, the position calibration technique just described may be used in combination with any of the other position calibrations described herein. This would be done to provide a particular optimal reference process in which a more precise position calibration is determined or in which the position calibration is derived in a shorter time.

Calibration with STM Measurements

Referring to FIG. 11 again, the second calibration structure 128-2 also includes one or more other reference structures 191 that may be used to calibrate the position of the activated tip 138. These reference structures are formed on an insulating material 199 on the base 190 of the calibration structure. The reference structures may each comprise a conductive tip at a precisely known position with respect to the reference location. Each conductive tip is coated with a conductive material with known conductive properties and is connected to an STM measurement circuit 213. The STM measurement circuit is one of the other components 123 of the SPM system 100.

As discussed earlier, the SPM probe 122-1 may be used to make STM measurements. As shown in FIG. 4, depending on which is conductive, the obdurate coating 146 or the reflective coating 143 of each tip of the probe 122-1 is coupled to the STM measurement circuit 213. Thus, an activated tip 138 of the probe may have its position calibrated by using it to make STM measurements with the reference structures 191 on the calibration structure 128-2.

Specifically, referring again to FIG. 1, the controller 114 calibrates the position of the activated tip 138 of the SPM probe 122-1 by controlling the positioning system 103 to attempt to position the activated tip over one of the reference structures 191 of the calibration structure 128-2. Then, referring to FIG. 10, the controller controls the STM measurement circuit 213 to apply a specific voltage across whichever of the obdurate coating 146 and the reflective coating 143 of the tip is conductive and the reference structure so as to generate and measure a tunneling current between them. The controller compares the generated STM measurement with a stored precisely known reference measurement of a tunneling current between the reference structure and a reference tip caused by the same voltage. If they match, this means that activated tip 138 was positioned directly over the reference material. Thus, in a dosed feedback loop, the tip is positioned and the generated and reference STM measurements are compared in the manner just described until it is determined that the tip is in fact positioned over the reference structure. Once this occurs, the positional offset of the activated tip at the known position of the reference structure is determined. Based on this positional offset, the precise positioning of the tip with respect to the reference location is then calibrated.

Also, since there may be more then one reference structure 191, the process just described may be repeated for each of these reference structures. Thus, as with the reference materials 189, the results of the calibrations computed for all of the reference structures 191 may be combined to provide a weighted or averaged calibration of the position of the activated tip 138.

Additionally, the reference structures 191 may also be used to calibrate the activated tip 138 of the SPM probe 122-1 for making STM measurements. Specifically, the controller 114 controls the generating of an STM measurement of the tunneling current between the activated tip and one of the reference structures 191 in the manner just described. Then, the controller compares this generated STM measurement with the reference measurement described earlier to determine the offset between them. Based on this offset, the precise tunneling current between the activated tip and the object 102 can be calibrated for making STM measurements. And, this process may be repeated for each of the reference structures. Thus, similar to the position calibration using these reference structures, the results of the STM measurement calibrations computed for all of these reference structures may be combined to provide a weighted or averaged STM measurement calibration for the activated tip.

Additionally, the position calibration technique just described may be used in combination with any of the other position calibrations described herein. This would be done to provide a particular optimal reference process in which a more precise position calibration is determined or in which the position calibration is derived in a shorter time.

Tip Machining Structures

Figure 84:
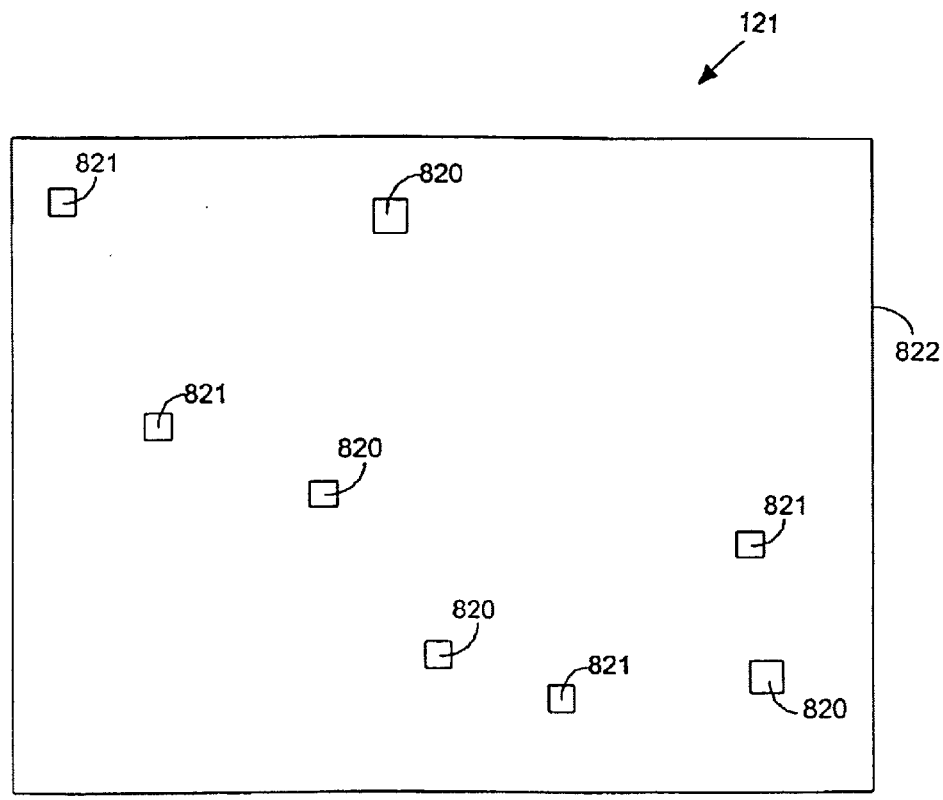
FIGS. 84 and 85 show different views of a tip machining structure of the SPM system of FIG. 1.

As mentioned earlier, the components of the SPM system 100 may include one or more tip machining structures 121. As shown in FIG. 84, such a tip machining structure includes abrasive and chemical lapping microstructures 820 and 821 on a base 822 of the structure. These lapping structures may be used to machine the activated tip 138 of the SPM probe 122-1 to sharpen and/or shape it.

Figure 85:
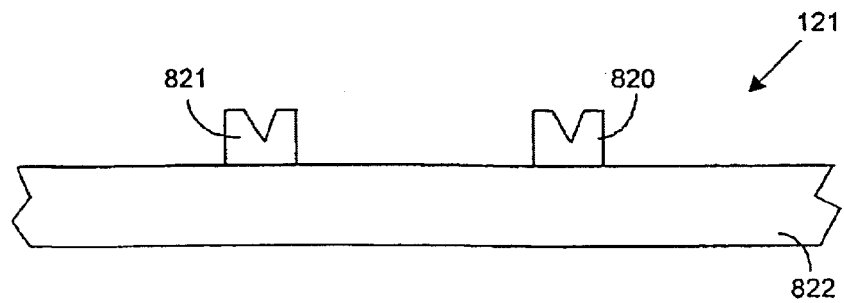

The abrasive lapping microstructures 820 may be used to abrasively remove (or lap) material from the activated tip 138. For example, as shown in FIG. 85, such a lapping microstructure may be shaped like the tip. Then, the controller 114 controls the positioning system 103 to move the tip so that it rubs against the lapping microstructure. This abrasively shapes and/or sharpens the tip. For example, the abrasive lapping microstructure may comprise silicon and be used to shape and/or sharpen the obdurate coating 146 of the tip.

Similarly, the chemical lapping microstructures 821 may be used to chemically remove (or lap) material from the activated tip 138. As shown in FIG. 85, such a lapping microstructure may also be shaped like the tip. Similar to the abrasive lapping microstructure 820, the controller 114 controls the positioning system 103 to move the tip so that it rubs against the chemical lapping microstructure. This chemically shapes and/or sharpens the tip. For example, the chemical lapping microstructure may comprise iron and be used to shape and/or sharpen the diamond coating 146 of the tip by chemically dissolving it.

As those skilled in the art will recognize, this may be done similarly for the tips 138, 238, 242, and 320 of any of the SPM probes 122-1 to 122-7, 122-17, and 122-18 described herein.

Calibration with Force Balance 128-3

Figure 12:
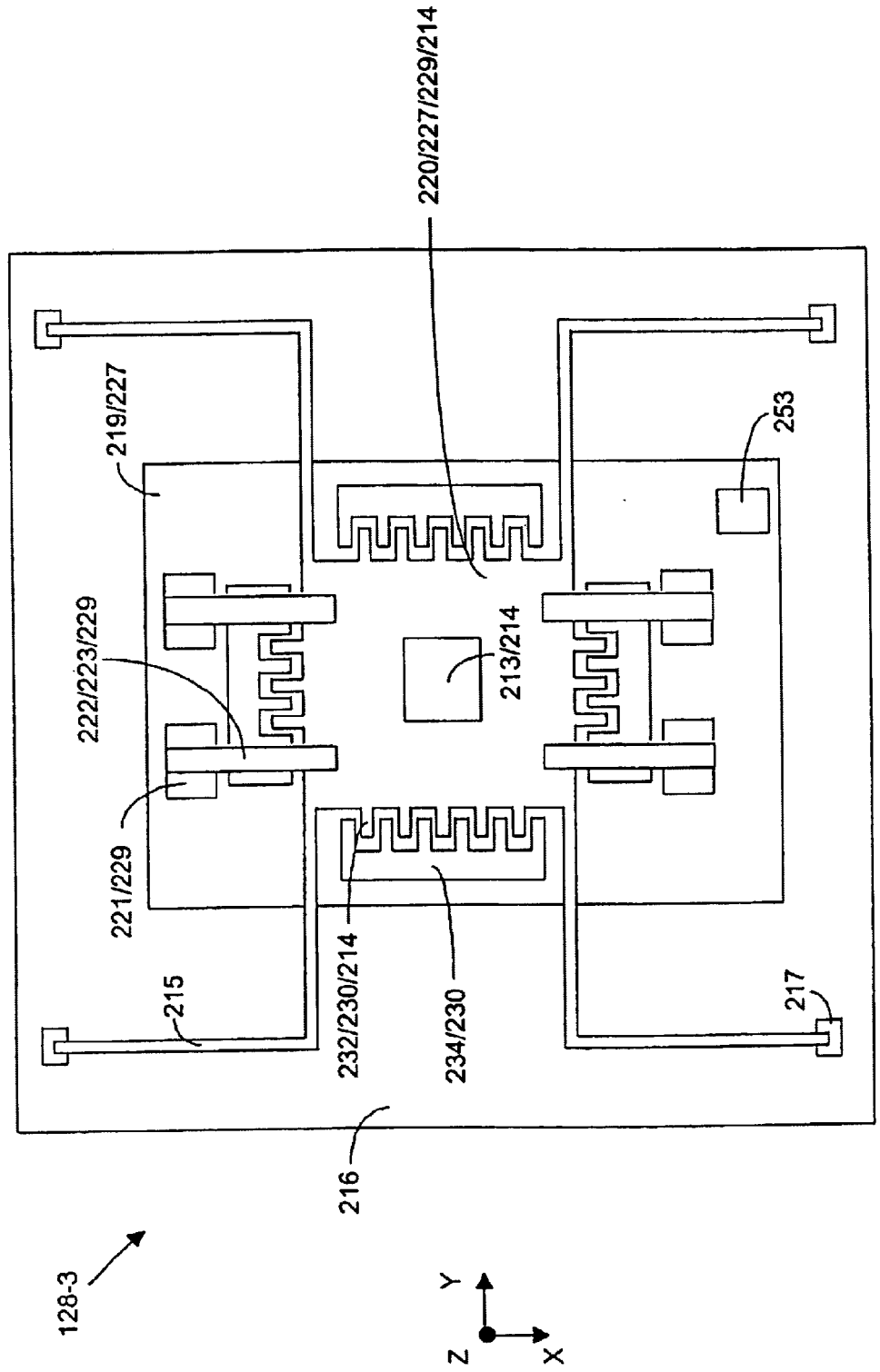
Figure 13:
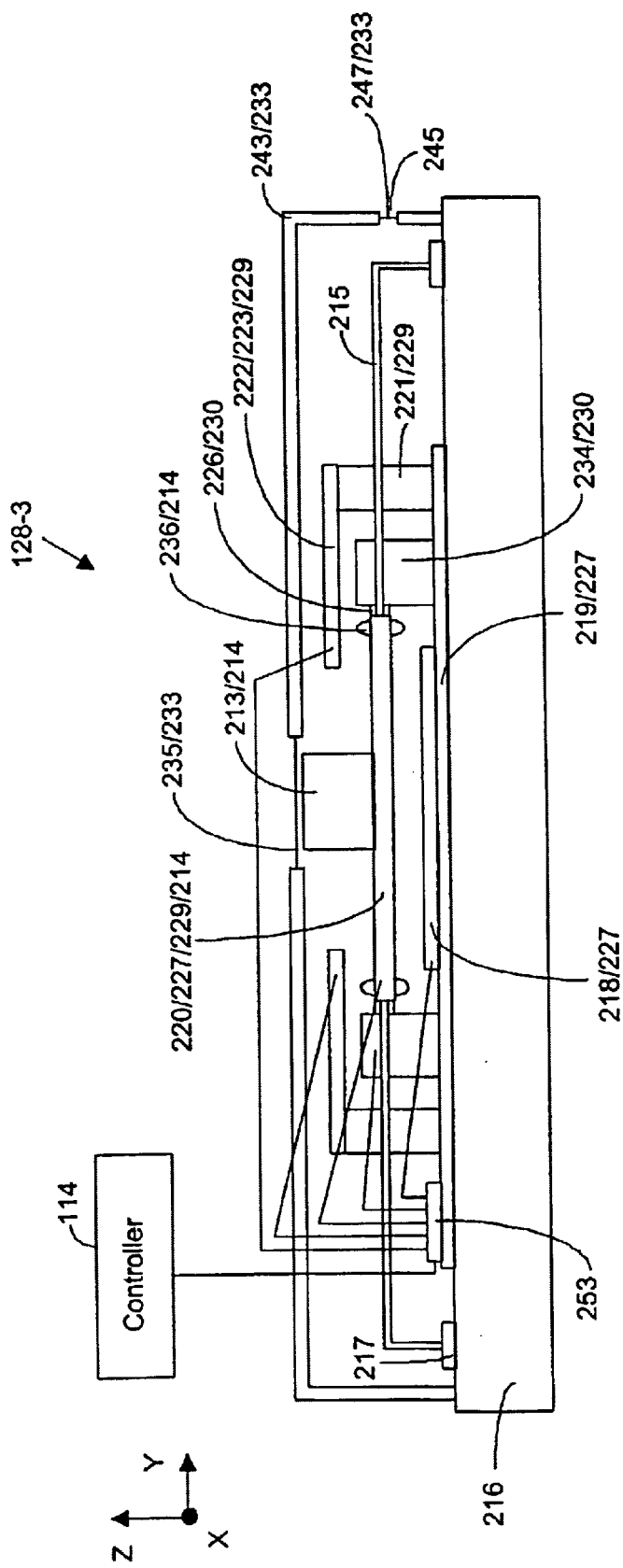

Referring to FIG. 12, the calibration structures 128 include a nanostructured force balance (or sensor) 128-3 for calibrating the activated tip and the cantilever 136 on which it is located for AFM operation. The force balance includes an electrostatically (i.e., capacitively) and mechanically displacible (i.e., moveable) balance platform 214. It also includes a suspension system 225 that comprises spring arms (or crab legs) 215. Each spring arm has one end coupled to the balance platform. As shown in FIG. 13, the force balance also includes a base 216 and anchors 217. The other end of each spring arm is coupled (i.e., anchored) to the base with a corresponding anchor. As a result, the spring arms displacibly (i.e., moveably) suspend the balance platform over the base so that it can be displaced.

Referring still to FIG. 13, the force balance 128-3 includes a Z dimension lower displacement actuator/sensor 227 that comprises a stationary lower plate electrode 218 and a displaceable plate electrode 220 that is also part of the balance platform 214. The lower plate electrode is formed on an insulating plate 219 on the base 216 and is thereby connected to the base. The lower plate electrode and the displaceable plate electrode together form a capacitor.

The force balance 128-3 also includes a Z dimension upper displacement actuator/sensor 229 that comprises insulating support anchors 221, a stationary upper plate electrode 223, and the displaceable plate electrode 220 just mentioned. The support anchors are anchored to the base and fixedly support the cantilevered electrodes 222 that form the stationary upper plate electrode. As a result, they connect the cantilevered electrodes to the base and suspend the cantilever electrodes over the balance platform. The upper plate electrode and the displaceable plate electrode together form a capacitor.

The upper displacement actuator/sensor 229 may be used to displace (or move) the balance platform 214 in the Z dimension in a direction up away from the base 216 and may be used to sense displacement (or movement) of the balance platform in this direction. Similarly, the lower displacement actuator/sensor 227 may be used to displace the balance platform 214 in the opposite direction in the Z dimension down toward the base 216 and may also be used to sense displacement of the balance platform in this direction.

Specifically, in the case of the displacement actuator/ sensor 227, when a differential voltage is applied between the displaceable plate electrode 220 and the stationary plate electrode 218 in a displacement actuating mode, a corresponding electrostatic force is caused which electrostatically (i.e., capacitively) displaces the balance platform 214 down toward the stationary lower plate electrode in the Z dimension. Alternatively, in a displacement sensing mode, the change in the voltage between the displaceable plate electrode and the stationary lower plate electrode can be electrostatically (i.e., capacitively) sensed to measure the displacement of the balance platform in the Z dimension. Similarly, in the case of the displacement actuator/sensor 229, an electrostatic force is caused which electrostatically (i.e., capacitively) displaces the balance platform up toward the cantilevered electrodes 222 in the Z dimension when a corresponding differential voltage is applied between the displaceable plate electrode and the cantilevered electrodes in a displacement actuating mode. And, in a displacement sensing mode, the displacement of the balance platform in the Z dimension can be electrostatically (i.e., capacitively) sensed by measuring the change in the voltage between the displaceable plate electrode and the cantilevered electrodes.

Turning back to FIG. 12, the force balance 128-3 also includes X and Y dimension displacement actuators/sensors 230. The X dimension actuators/sensors may be used to cause and sense displacement of the balance platform 214 in opposite directions in the X dimension. Similarly, the Y dimension actuators/sensors may be used to cause and sense displacement of the balance platform in opposite directions in the Y dimension.

Each of the displacement actuators/sensors 230 includes a displaceable comb structure 232 that is part of and fixed to the balance platform and a corresponding stationary comb structure 234 that is formed on the insulating plate 219. The fingers of each of the displaceable comb structures are interdigitized with (i.e., aligned between) the fingers of the corresponding stationary comb structure.

Each pair of corresponding displaceable and stationary comb structures 232 and 234 forms an electrostatic (i.e., capacitive) comb drive of the type described in "Electrostatic Comb Drive for Resonant Sensor and Actuator Applications", University of California at Berkeley Doctoral Dissertation, by William Chi-Keung Tang Nov. 21, 1990, which is hereby explicitly incorporated by reference. This type of electrostatic comb drive is also described in U.S. patent application Ser. No. 08/506,516 and PCT Application No. PCT/US96/12255 referenced earlier. In particular, the stationary and displaceable comb structures are made to be conductive. Thus, when a differential voltage is applied across a pair of corresponding stationary and displaceable comb structures in a displacement actuating mode, their comb fingers interact electrostatically (i.e., capacitively) with each other and cause an electrostatic force. This force causes the displaceable comb structure to move in a linear direction toward the stationary comb structure in the corresponding X or Y dimension. Alternatively, in a displacement sensing mode, the differential voltages across a pair of corresponding stationary and displaceable comb structures can be electrostatically (i.e., capacitively) sensed to measure the displacement of the balance platform in the corresponding X or Y dimension. Since the displaceable comb structures are fixed to each side of the balance platform, displacement of the balance platform can be electrostatically (i.e., capacitively) caused or sensed in both directions in the X dimension and in both directions in the Y dimension.

The force balance 128-3 also includes a balance control circuit 253. In response to control signals from the controller 14, the balance control circuit controls the voltages (i.e., the electrostatic forces) applied to the balance platform 214 by any of the displacement actuators/sensors 227, 229, and 230. Additionally, the balance control circuit measures any displacements of the balance platform in the X, Y, and Z dimensions from the changes in voltages sensed by these displacement actuators/sensors. In response, the balance control circuit generates displacement measurement signals that are provided to the controller and represent these measured displacements. The control circuit is preferably located on the base 216 of the force balance to minimize the amount of stray capacitances which may affect the operation of the control circuit.

In alternative embodiments, the Z dimension lower and upper displacement actuators/sensors 227 and 229 may each comprise a comb drive with displaceable and stationary comb structures like those of the X and Y dimension displacement actuators/sensors 230. Conversely, the X and Y dimension displacement actuators/sensors may comprise displaceable and stationary plate electrodes like those of the Z dimension lower and upper displacement actuators/ sensors. In other embodiments, piezoresistors or piezoelectric bimorphs could be used as displacement actuators in the X, Y, and Z dimensions to cause displacements in the X, Y, and Z directions.

Furthermore, referring to FIG. 13, the balance platform 214 may include insulating bushings (or dimples) 236 that extend out from the displaceable electrode plate 220. The bushings that extend out from the upper surface of the displaceable plate electrode prevent it from contacting the stationary plate electrode 218 when it is pulled down toward the stationary plate electrode so as not to cause a short circuit. Similarly, the bushings that extend out from the lower surface of the displaceable plate electrode prevent it from contacting the cantilevered electrodes 222 and thereby not causing a short circuit this way.

The displaceable electrode plate 220 and the displaceable comb structures 232 may be formed from the same semiconductor material, such as polysilicon, which is conductive. In this way, the displaceable electrode plate and the displaceable comb structures are electrically connected together. In this way, the same voltage (preferably ground) can be applied to the displaceable plate electrode and the moveable comb structures so that differential voltages can be conveniently applied and measured across these structures and the stationary plate electrode 218, the cantilevered electrodes 222, and the stationary comb structures 234. Moreover, the stationary plate electrode and the cantilevered electrodes may also be formed from a conductive material, such as polysilicon made or tungsten, while the stationary comb structures would be formed from the same conductive material as the moveable comb structures. The insulating plate 219, the insulating support anchors 221, the spring arm support anchors 217, and the insulating bushings 236 may be formed from an insulating material, such as silicon dioxide.

Additionally, in order to prevent particles from effecting the operation of the force balance 128-3, it includes an enclosure 233. The enclosure is connected to the base 216 and prevents entry of particles into the force balance.

In order to enable the force balance to operate properly, the enclosure 233 includes a flexible membrane (or diaphragm) 235 that is flexible in the X, Y, and Z dimensions. In this way, contact can be made with the contact platform 214 via the membrane so that displacement of the balance platform in the X, Y, and Z dimensions due to the contact will not be impeded. Specifically, the flexible membrane includes a connector portion 257, a spring portion 255, and a contact portion 241, as shown in FIG. 14. The contact portion is the portion of the membrane to which contact is made in order to cause displacement of the balance platform 214. The connector portion is connected to the main body 243 of the enclosure. The spring portion is connected between the connector and contact portions. The spring portion is corrugated and acts as a spring in the X and Y dimensions. This makes the membrane flexible through a very limited range all of the X, Y, and Z dimensions. Referring to FIG. 15, the connector, spring, and contact portions of the membrane are annular.

Referring back to FIG. 13, the enclosure 233 has an opening 245 to maintain a constant pressure within the enclosure during operation of the force balance 128-3. The enclosure further includes a filter 247 that extends across the opening and prevents any particles from entering into the enclosure through the opening.

In order to enable the contact platform 214 to be contacted through the enclosure 233 via the membrane 235, the contact platform 214 further comprises a contact portion 238 that protrudes out from the displaceable plate electrode 220 passed the cantilevered electrodes 222. In order to prevent wear of the balance platform 214, the contact portion may comprise an obdurate material, such as diamond, silicon carbide, carbon nitride, or diamond like carbon. In this case, the contact portion is formed on the plate electrode in a similar manner to that discussed earlier for the obdurate coating 146 of the tips 138 of the probe 122-1.

Turning again to FIG. 1, the user may use the user interface 116 to instruct the controller 114 to calibrate the first SPM probe 122-1 for the forces that are imparted by its activated tip 138 in response to corresponding positioning displacements in the position of the probe. This may be done in order to calibrate the probe for making SPM measurements, in particular AFM measurements, and SPM modifications, as will be explained later.

Referring back to FIGS. 5 and 12, the controller calibrates these forces by selectively controlling the positioning system 103 and the X, Y, and Z dimension displacement actuators/sensors 227, 229, and 230 to selectively apply opposing contact and actuator forces to the balance platform 214 of the force balance 128-3 while the activated tip is in contact with the balance platform. The contact forces are caused by positioning displacements in the position of the probe made with the positioning system. The actuator forces are electrostatic forces applied by the X, Y, and Z dimension displacement actuators/sensors 227, 229, and 230. The cantilever deflection measurement system 200 or the X, Y, and Z displacement actuators/sensors may be used to monitor the contact and actuator displacements of the balance platform due to the applied contact and actuator forces. As those skilled in the art will recognize, this calibration may be done in a number of ways.

For example, this can be done in a first DC mode. Specifically, the SPM system 100 is operated in a simple closed feedback loop using the positioning system 103, the cantilever deflection measurement system 200, and the X, Y, and Z dimension actuators/sensors 227, 229, and 230. The controller 114 initially controls the positioning system 103 to position the SPM probe 122-1 at a reference position where the activated tip 138 just contacts the balance platform 214 (via the membrane 235) without any bending of the cantilever 136 being measured by the cantilever deflection measurement system. Then, the controller 114 causes a known value of actuator force in the Z dimension to be applied to the balance platform by the upper Z dimension actuator/sensor 229. This causes an actuator displacement of the balance platform up toward the cantilevered electrodes 222 in the Z dimension. The contact displacement of the balance platform can be measured with the cantilever deflection measurement system by measuring the corresponding displacement of the tip. Alternatively, this displacement can be sensed by the lower Z dimension displacement actuator/sensor 227 and measured by the balance control circuit 253. In response to the measured displacement, the positioning system causes a positioning displacement in the position of the probe so that the cantilever 136 bends and the activated tip applies an opposing contact force to the balance platform. This causes an opposing contact displacement of the balance platform which is measured in the same way as the actuator displacement. The controller monitors the measured contact and actuator displacements for the point as they are nulled out by each other. The actuator force and the positioning displacement of the probe are recorded at this null point. Since the contact and actuator forces are also nulled out by each other, the value of the actuator force at this point is a measure of the contact force that is normal to the balance platform. This process is then repeated for other known values of the actuator force so that a force calibration table of contact forces in the Z direction and corresponding positioning displacements is recorded.

This process is done in a similar manner in the X and Y dimensions using the X and Y dimension displacement actuators/sensors 230. In this case, one of the X dimension displacement actuators/sensors is used as an actuator to cause actuator displacement of the balance platform in the X dimension while the other one is used to sense the actuator and contact displacements of the balance platform in the X dimension. Similarly, in the Y dimension, one of the Y dimension displacement actuators/sensors is used as an actuator to cause actuator displacement of the balance platform in the Y dimension while the other one is used to sense the actuator and contact displacements of the balance platform in the Y dimension. Here, the recorded contact forces are lateral forces. For example, these forces may include a cutting force when a tip 138, 238, and 320 of one of the SPM probes 122-1 to 122-7 is used to make a cut in or mill the contact portion 238 of the contact platform 214 in the manner described herein. These forces could also be stiction and friction forces.

As a result, a complete force calibration table of contact forces and corresponding positioning displacements can be compiled in this way. In other words, each contact force for a corresponding positioning displacement has normal and lateral components in the X, Y, and Z direction. For example, this complete force calibration table may identify the machining characteristics for the tip 138,238, and 320 of one of the SPM probes 122-1 to 122-7 discussed herein.

In a second DC mode, the SPM probe 122-1 is positioned initially at the reference position as in the first DC mode just discussed. Then, the controller 114 causes the positioning system 103 to cause a known positioning displacement in the position of the probe. As a result, the cantilever 136 bends and the activated tip applies a contact force to the balance platform which causes a contact displacement of the balance platform in the X, Y, and Z dimensions. This contact displacement is measured in the manner discussed earlier. In response to the measured contact displacement, the controller causes an opposing actuator force in the X, Y, and Z dimensions to be applied to the balance platform by the upper Z dimension actuator/sensor 229. This causes an opposing actuator displacement of the balance platform in the X, Y, and Z dimensions which is measured in the manner discussed earlier. As in the first DC mode, the controller then records the value of the actuator force and the positioning displacement of the probe at the point where the measured contact and actuator displacements are nulled out by each other. This process is then repeated for other known displacements of the probe so that a complete force calibration table of contact forces in the X, Y, and Z dimensions and corresponding positioning displacements is recorded.

In the DC modes just described, the lower Z dimension displacement actuator/sensor 227 is not needed and the force balance 128-3 could be constructed without them. But, in variations of the DC modes just described, the lower Z dimension displacement actuator/sensor 227 can be used to perform these modes at a biased reference position. In these modes, the SPM probe 122-1 is positioned at a reference position where the activated tip 138 does contact the balance platform 214 with bending of the cantilever 136. Then, the controller 114 causes the lower Z dimension displacement actuator/sensor to apply an actuator force to the balance platform. This causes an actuator displacement of the balance platform down toward the base 216. The controller monitors the deflection of the cantilever measured by the cantilever deflection measurement system. Then, at the point where no more bending of the cantilever is detected by the controller, the above DC modes are performed.

An AC mode may also be used to calibrate the activated tip 138. In this mode, the controller 114 first causes the lower Z dimension displacement actuator/sensor 227 to apply a reference actuator force with a known value to the balance platform 214 while the activated tip is not in contact with the balance platform. This causes the balance platform to be displaced in the Z dimension down toward the base 216. Then, while this force is still being applied without contact by the tip, the controller causes the balance platform to oscillate up and down in the Z dimension. This is done by causing the lower and upper Z dimension displacement actuators/sensors 227 and 229 to alternately apply actuator forces in the Z dimension to the balance platform. The frequency at which these forces are alternately applied is varied until the resonant frequency of oscillation is found. The known value of the reference actuator force and the resonant frequency are then recorded. This process is then repeated for other known values of the reference actuator force so that a Z dimension reference table of actuator forces in the Z dimension and corresponding resonant frequencies is recorded.

This process is similarly performed in the X and Y dimensions to obtain X and Y dimension reference tables of reference actuator forces in the X and Y dimensions for corresponding resonant frequencies. However, in the X dimension, the X dimension displacement actuators/sensors are used to cause actuator displacements of the balance platform in the X dimension. Similarly, the Y dimension displacement actuators/sensors are used to cause actuator displacements of the balance platform in the Y dimension.

Then, the SPM probe 122-1 is positioned initially at a reference position as described earlier without bending of the cantilever 136. The controller 114 then causes the positioning system 103 to cause a known positioning displacement in the position of the probe from the reference position. As described earlier, this causes the cantilever 136 to bend and the activated tip applies a contact force to the balance platform which causes a contact displacement of the balance platform in the X, Y, and Z dimensions. The controller then causes the balance platform to be oscillated in the X, Y, and Z dimensions in the manner just described. The frequencies at which the actuator forces are alternately applied in the X, Y, and Z dimensions are varied until the resonant frequencies of oscillation in the X, Y, and Z dimensions are found. The reference actuator forces in the X, Y, and Z dimension reference tables that correspond to these resonant frequencies are measures of the components in the X, Y, and Z dimensions of the contact force applied to the contact platform. These components are recorded as the contact force for the corresponding positioning displacement of the probe. This process is then repeated for other known positioning displacements to obtain a complete force calibration table of contact forces and corresponding positioning displacements.

The forces calibrated with the force balance 128-3 in the manner just described are at the micro, nano, pico, and femto Newton level. Thus, as those skilled in the art will recognize, the SPM system 100 can be used with the force balance 128-3 as a force measurement system to measure a contact force applied by an object to the balance platform 214 of the force balance 128-3. The controller 114 then causes the resulting contact and actuator displacements of the balance platform to be nulled in the manner described earlier. The value of the actuator force applied to cause this nulling effect is a measure of the contact force. Thus, this process could be used to simply measure the weight of an object at the micro, nano, pico, and femto Newton level which is placed on the balance platform. Or, it can be used in an inertial sensor to measure an inertial input that causes a corresponding displacement of an element of the inertial sensor that contacts the balance platform.

Furthermore, a similar procedure can be used to calibrate the force balance 128-3. Specifically, a contact force with a known value can be applied to the balance platform 214 to cause the contact displacement. The controller 114 then causes the resulting contact and actuator displacements of the balance platform to be nulled in the manner described earlier using the lower Z dimension displacement actuator/sensor 227. The value of the voltage applied to the lower Z dimension displacement actuator/sensor in order to cause the actuator force corresponding to the actuator displacement is recorded along with the known value of the contact force. The known value of the contact force is a measure of the value of the actuator force. This process is repeated for other contact forces with known values to create a calibration table of voltage values and corresponding actuator force values. This calibration table is then used in the above DC and AC modes to apply actuator forces with known values. This process is repeated for the other displacement actuators/sensors 229 and 230.

The force balance 128-3 was described previously for use in measuring or calibrating forces in the X, Y, and Z dimensions. However, as those skilled in the art will recognize, the force balance 128-3 can be used to measure or calibrate forces in only one or two dimensions as well. In this case, the force balance could be constructed without those of the displacement actuators/sensors 227, 229, and 230 for the corresponding dimension(s) not needed.

Additionally, the force balance 128-3 was described for use in calibrating the contact forces applied by the tip 138 of an SPM probe 122-1. However, it may be more generally used to calibrate the contact forces applied by any object which has a contact portion (e.g., the tip of the probe) and a positionable portion (e.g., the base 130 or the probe) and a spring portion (e.g., the cantilever) that connects the contact and positionable portions. More specifically, it could be used to calibrate the contact forces applied by the contact portion of the object with respect to positioned displacements of the positionable portion of the object.

Imaging Optics

Referring to FIG. 5, each scanning head 120 has imaging optics 226. The imaging optics are used to make an optical image of the object for properly inspecting the object 102 with the probe 122-1. These optics include image forming optics 228 and the lenses 202 and 203. The image forming optics may be conventional or confocal image forming optics as found in a conventional or confocal microscope. This kind of arrangement may be configured in the manner described in U.S. patent application Ser. No. 08/613,982 referenced earlier where the image forming optics are located externally from the scanning head.

The imaging optics 226 may be used to produce a low magnification optical image of the object 102 or a calibration structure 128. Specifically, the controller 114 causes the positioning system to scan the object 102 or a calibration structure 128 with the scanning head 120. At each scan point, the image forming optics 228 causes light to be directed to the lenses 202 and 203 which focus the light on the object or calibration structure. The resulting light reflected by the object or calibration structure is directed back to the image forming optics by the lenses. The image forming optics detects this resulting light and in response forms an optical image of the object or calibration structure. This optical image is then provided to the controller.

The optical images produced by the imaging optics 226 may be used by the controller 114 in various ways. They may be used in conjunction with SPM measurements to inspect the object in the manner described in U.S. patent application Ser. Nos. 08/906,602, 08/885,014, 08/776,361, and 08/613,982. Or, they may be used to produce complete images of the modifications being made to the object or the calibrations being made to the probe 122-1. Specifically, the image optics may be used to find reference points and/or specific (optically) resolvable structures to be modified and/or inspected.

SPM Inspections with SPM Probe 122-1

Referring again to FIG. 1, after calibrating the activated tip 138 of the probe 122-1 for making SPM measurements, it may be used to inspect the object 102 by performing SPM measurements of the object. Thus, when the user instructs the controller 114 with the user interface to use the activated tip to perform SPM measurements, the controller controls the positioning subsystem 103, the corresponding components 123 of the SPM system 100, and, as needed, the probe in inspecting the object 102. This is done by causing the probe to be scanned over the object and the desired SPM measurements of the object to be made at selected scan points.

For example, turning to FIG. 5, the SPM measurements may include AFM measurements made by scanning the activated tip 138 over the surface 166 of the object 102 and measuring the deflection of the cantilever 136 on which the tip is located at selected scan points. This is done with the cantilever deflection measurement system 200 in the same way as described earlier for calibrating the positioning of the tip 138. Moreover, this may be done using the force calibration table generated during calibration and described earlier.

Furthermore, the SPM measurements may also include STM measurements made by scanning the activated tip 138 over the surface 166 of the object 102 and causing and measuring a tunneling current between the activated tip and the object at selected scan points. This is done with the STM measurement circuit 213 in the same way as described earlier for calibrating the positioning of the tip 138.

The SPM measurements may also include radiation measurements made by scanning the activated tip 138 over the surface 166 of the object 102 and causing optical interaction between the tip and the object 102 at selected scan points. This may done in the manner discussed earlier for calibrating the position of the tip.

The SPM measurements just described may be combined together or used separately by the controller 114 to generate the inspection data for the object 102. As described earlier, this may include an image of the object and/or various analysis of the object and may be done in the manner described in U.S. patent application Ser. Nos. 08/906,602, 08/885,014, 08/776,361, and 08/613,982 referenced earlier.

For example, the AFM, STM, and radiation measurements may be combined to generate an image of the object with the AFM measurements being used to produce the basic image and the STM and radiation measurements being used to supplement the basic image. The AFM measurements would provide information about the heights of the surface at the various scan points. The STM measurements would provide information on the electrical properties of the object with which to supplement the basic image and the radiation measurements would provide information on the composition of the object (from the measured wavelength spectrum) with which to supplement the basic image. In addition, if the narrow beam of light used in producing the radiation measurements is rotationally polarized, as described in the patent applications just referenced, then the radiation measurements can be used to identify deep surface features, such as a pit, wall, or projection, and supplement the basic image with this information. Additionally, the STM measurements could simply be used by themselves to generate an electrical map or analysis of the object's conductivity and electrical properties according to the positioning of the tip in making the STM measurements. And, the radiation measurements could be used to generate a compositional analysis on the composition of the object mapped according to the positioning of the tip in making the radiation measurements. The AFM, STM, and radiation measurements can be made simultaneously during the surface scan using an activated tip 138 of the SPM probe 122-1.

Furthermore, as discussed earlier, the inspection data may be used to modify the object 102. In doing so, the controller 114 may compare the generated inspection data with target data that it stores. The target data may include a target image and/or analysis of the object which are compared with the generated image and/or analysis of the object. The resulting modification data from this comparison indicates where and how the object needs to be modified in order to fall within a predefined tolerance level of the reference parameters. Then, based on the modification data, the controller controls modification of the object 102 using the probe 122-1 or one or more of the other SPM probes described herein.

SPM Modifications with SPM Probe 122-1

The tip 138 of each SPM tool 137 of the SPM probe 122-1 has an obdurate coating 146, as mentioned earlier. As a result, an activated tip of the probe can also be used to make SPM modifications of the object 102 by making cuts in and/or deforming the material of the object. The manner in which this is done is described in greater detail in the discussion regarding the fifth SPM probe 122-5.

Operation with Vacuum

As an additional feature, the accuracy of the calibrations, examinations, inspections, and modifications just described can be Improved by operating the probe 122-1 in a vacuum. Specifically, by doing so, the AFM, STM, and radiation measurements and the SPM modifications of the object that were described earlier will be more accurate.

Referring to FIG. 1, in order to operate the probe 122-1 in a vacuum, the components of the SPM system 100 include a fluid system 344. Referring to FIG. 5, the fluid system includes a vacuum source 192 and a corresponding flexible tube 345 for each scanning head 120. The vacuum source comprises a vacuum pump 193, a large vacuum chamber 194, and a connector tube 195. The large vacuum chamber includes a valve 346 for each flexible tube. The connector tube enables the vacuum pump and the vacuum chamber to be in fluid communication with each other. As a result, the vacuum pump produces a vacuum in the large vacuum chamber. The large vacuum chamber is connected to each scanning head with a corresponding flexible tube. Each valve of the vacuum chamber can be individually controlled by the controller 114.

Referring to FIG. 5, the large vacuum chamber 194 is connected to the internal chamber 135 of the housing 154 of each scanning head 120 with a corresponding flexible tube 345. This means that a vacuum is also produced in the internal chamber when the corresponding valve 346 of the large vacuum chamber is opened by the controller 114. As shown in FIG. 2, the probe 122-1 has an aperture 132 for each tool 137 of the probe. Thus, turning back to FIG. 5, the vacuum source is in fluid communication with the apertures of the probe so that a microvacuum chamber (i.e., zone or space) can be created in the gap (or spacing) 198 between the probe 122-1 and the object 102 or calibration structure 128 in the space around these apertures when making SPM measurements. Furthermore, since the base 130 of the probe is wedged into the seat 158 as described earlier, a good vacuum seal is formed. Alternatively, the aperture may be directly connected to the vacuum chamber via one or more tubes.

To show that such a microvacuum chamber can be created under these circumstances, it will be assumed that the apertures 132 in the probe 122-1 approximate a single square aperture with 1 mm sides. It will also be assumed that base 130 of the probe approximates a circular plate with 10 mm diameter and has a lower surface 142 that is flat to within ±1 $\mu$m (i.e., 1 $\mu$m rms surface roughness) and that the surface 166 of the object is also flat to within ±1 $\mu$m. This will be assumed for a gap 198 between the object and the base with a width between 20 nm and 10 $\mu$m.

The gap 198 between the object and the base defines a duct where ambient gas may leak into the microvacuum chamber. The flow characteristics for this flow of gas are largely viscous with the given external pressure assumed to be 1.1 Atmospheres. The Knudsen number for the flow is given by $K=(\eta\sigma L)^{-1}$, where L is the width of the gap. For 1.1 Atmospheres, the particle density $\eta \approx 3.0 \times 10^{19}$ cm$^{-3}$. The molecular momentum exchange cross section a can be gleaned from the known viscosity $\mu$. This is done using $\mu$=m $<v>\sigma^1$, where m is the mass and v is the velocity across the cross section, so that the cross section $\sigma$ is on the order of $7.5 \times 10^{-15}$ cm$^2$. Thus the limiting width L is 0.04 $\mu$m, which is less than the rms roughness of the mating surfaces. Thus, K<1 until the gas pressure reduces to less than 0.04 Atmospheres and the rate-limiting step is viscous transport.

Adding a zone of Knudsen flow to the calculations will not affect the result obtained from the viscous calculation by a significant amount. Moreover, the viscous regime will increase to almost the entire leak path zone as the gap 198 is widened to several $\mu$m. As we shall see, the gas leak rate is a function of the radial aspect ratio only logarithmically, so that the addition of a molecular flow zone is not a large effect.

The problem geometry can be approximated by turning the outside square geometry with sides of 10 mm into an equivalent circle with radius of 5 mm. The gas leak rate in the actual square geometry can be bounded by the gas leak rate for the circular geometry just described and a circular geometry with the outer diameter set to the diagonal length of the square 5$\sqrt{2}$ mm.

Therefore, the result for the gas leak rate for a constant viscosity $\mu$ independent of gas pressure (accurate to first order) is given by first solving for the flux $\lceil$ using the equation of continuity $\nabla \cdot \lceil =0$. This gives $\lceil = -\nabla \phi$, where $\nabla^2 \phi=0$ and the solution for the circular geometry is $\phi = C_1 \log r + C_2$. Since the flow is viscous, we have that $\lceil = -k\nabla p^2$. In other words, the flow is proportional to the pressure gradient times the pressure (where isothermal flow conditions are assumed). The velocity profile in the duct is given by $v_r(z)=V(r)(1-4Z^2/L^2)$, where Z is taken to extend form $-L/2$ to $+L/2$. Substituting into the momentum equation $\partial p/\partial r = \mu \nabla^2 v_r$, we have that $V(r)=L^2/(8\mu)\partial p/\partial r$. The appropriate boundary conditions give $p(r)=p_o(\log(r/a)\log(b/a))^{0.5}$, where b is the outer radius and a is the inner radius. Differentiating this to obtain the pressure gradient $\partial p/\partial r$ at the outer edge, we have the complete expression for the gas leak rate:

$$Q = \frac{\Pi p^2 <L> <L^2>}{12kT\mu \log(b/a)}$$

where T is the temperature and k is Boltzman's constant. For the parameters given, b/a=10, $\mu$=1.8×10$^{-4}$ g cm s$^{-1}$, and <L> varies between 20 nm and 10 $\mu$m. The value of <L$^2$>, the rms channel width, also appears in the formula. Here, it is most appropriate to use <L$^2$>=$\delta^2$+L$^2_{rms}$, where L$_{rms}$ is the rms surface roughness and $\delta$ is the nominal spacing. We see that the surface roughness dominates for small $\delta$. For the curves in FIGS. 16 and 17, which will be described shortly, the parameter <L> was taken as $\sqrt{<L^2>}$.

Another question of interest is the outlet gas density in the microvacuum chamber. This can be found by using the free-streaming formula $Q=A\eta<v>/4$, where A is the area of the aperture. A calculation of the average velocity $v_r$ at the atmospheric side was also done to verify that the flow is dominantly subsonic.

Figure 16:
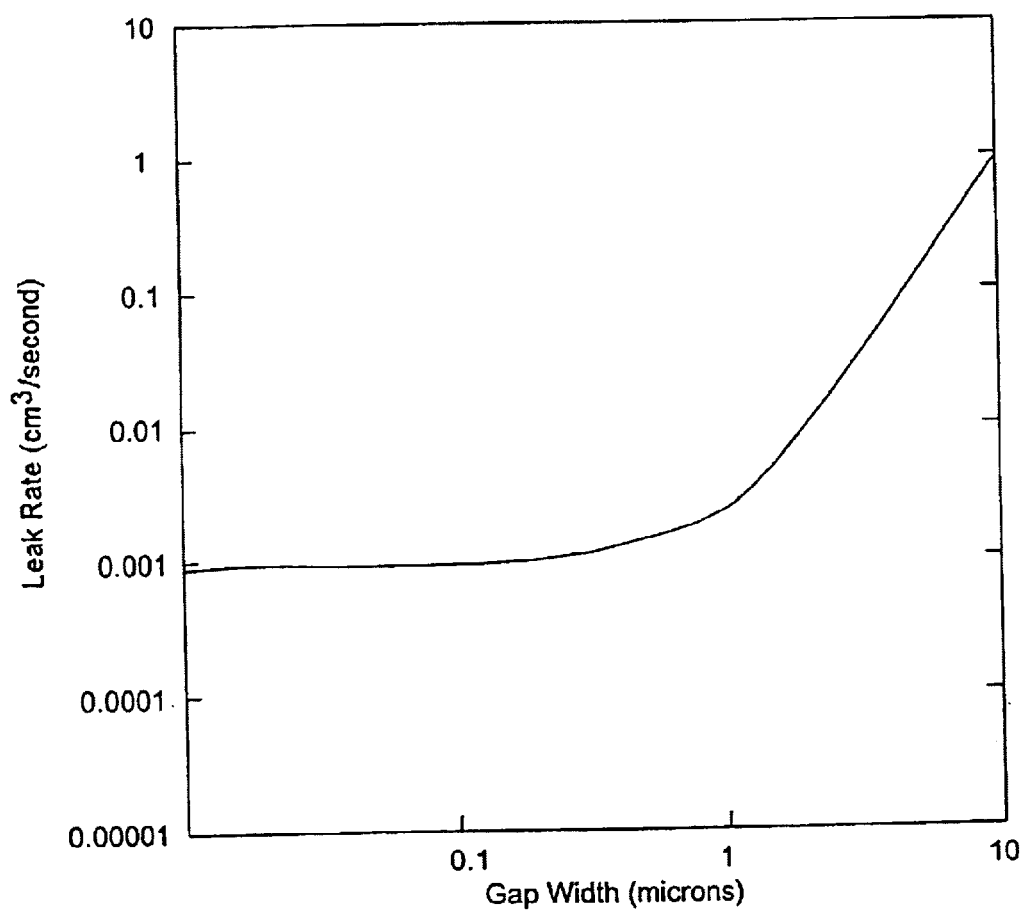
FIG. 16 and 17 show curves for a differential pressure chamber formed with the SPM system of FIG. 1 in the gap between the first SPM probe and the object.
Figure 17:
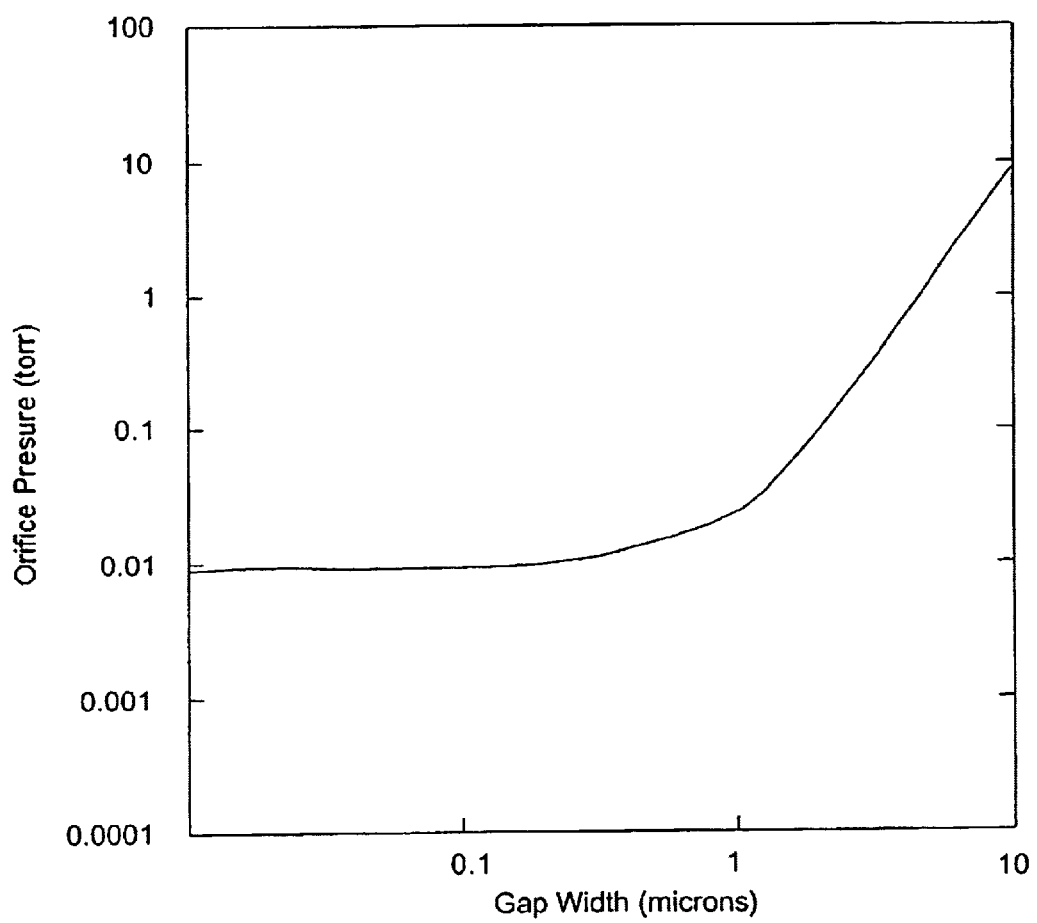

For the various widths L, the curve in FIG. 16 shows the outlet gas density (expressed as an equivalent pressure in torr at 300 Kelvin). Similarly, the curve in FIG. 17 shows the gas leak rate in standard cm³ per second.

Furthermore, the ion mean free path in the microvacuum chamber can be obtained from the outlet gas pressure. Using an estimate of $10^{-16}$ cm² for a typical ion-neutral collision cross section, a 1.0-torr pressure ($\eta=3.5\times10^{16}$ cm$^{-3}$) gives a mean free path of about 3 mm. The mean free path depends not only upon the gas pressure but upon the energy and species of the ion. Thus, the above estimate is only a rough guide. Furthermore, since a large vacuum chamber 194 and a high capacity vacuum pump 193 are in fluid communication with internal chamber 135 of the housing 154 of the scanning head 120, the mean free path is actually much larger.

The approximation of circular geometry can now be used to examine the square geometry. The result for the square geometry will lie between the results for the two limiting circular cases. For b/a=10, these results differ by log 10 √2/log 10, or about fifteen percent.

As a final note, the analysis above was made for a single aperture that approximates the size of the apertures 132 of the probe 122-1. Thus, in alternative embodiment, the probe could have just one such aperture rather than multiple apertures.

As those skilled in the art will recognize, the principles discussed above can be more general thought of in terms of a micro differential pressure chamber being formed in the gap 198. In other words, the microvacuum pressure chamber is simply a specific case where the differential pressure formed in the gap was due to a vacuum created there. Moreover, as will be discussed later, a differential pressure chamber may also be created in the gap by introducing a gas through the apertures 132 or other outlets in the probe.

Gap Sensing for Vacuum Operation

Referring back to FIG. 6, the width of the gap (or spacing) 198 between the object 102 and the base 130 of the probe 122-1 must be properly set (or adjusted) so that a microvacuum chamber can be maintained in the gap around the area of the apertures 132 of the probe 122-1. Thus, each scanning head 120 includes displacement transducers 177 on the seat 158 of the holding plate 156 of the housing 154. Like the engagement and adjustment transducers 172 and 173 discussed earlier, the displacement transducers may each comprise a material, such as a piezoelectric material or a resistive metal (e.g., Nickel Chromium alloy), which change dimensions when a voltage or current signal is applied to it.

In doing so, the components of the SPM system 100 further include a gap control circuit 176 that is coupled to the controller 114 and the displacement transducers 177. As a result, the controller 114 selectively controls the gap control circuit to change the dimension of the displacement transducers so that the they selectively push down on the upper surface 140 of the base and displace the base in varying amounts at different points. Thus, the width of the gap 198 between the lower surface 142 of the base and the surface 166 of the object can be finely set in this manner.

Referring to FIG. 2, the probe 122-1 has a number of recesses 163 in the base 130. Formed in these recesses are cantilevered gap sensors 164. Each gap sensor comprises a corresponding cantilever 165 and a corresponding tip 167 on the cantilever. As shown in FIG. 18, the cantilever of each gap sensor is connected to the base so that it is suspended in the corresponding recess.

Still referring to FIG. 18, each gap sensor 164 also includes an electrostatic (i.e., capacitive) tip actuator 162 for activating the corresponding tip 167 for sensing the gap between the object 102 and the base 130 of the probe 122-1. This tip actuator comprises a moveable plate electrode 139, an insulating plate 153 on an outcropping of the base 130 that extends into the recess 163, and a stationary lower plate electrode 168 on the insulating plate. The lower plate electrode is therefore connected to the base 130 and disposed below the cantilever. In this embodiment, the cantilever comprises a semiconductor material, such as silicon or silicon nitride, that is made conductive using conventional techniques. As a result, the cantilever comprises the moveable plate electrode. Alternatively, the moveable plate electrode may be formed on an insulating plate of the tip actuator which is formed on the cantilever so that the moveable plate electrode is connected to the cantilever. In either case, the moveable plate electrode and the stationary lower plate electrode form a capacitor so that, when the controller 114 causes the gap control circuit 176 to apply a suitable voltage between the moveable plate electrode and the lower plate electrode, the cantilever is electrostatically (i.e., capacitively) deflected (i.e., bent) down toward the object 102. As a result, the tip is activated for sensing the gap between the object and the base.

Each gap sensor 164 further includes a electrostatic (i.e., capacitive) deflection sensor 161 that comprises the moveable plate electrode 139, an insulating plate 155 on the surface of the recess 163, and a stationary upper plate electrode 169 on the insulating plate. The stationary upper plate electrode is disposed over the cantilever and connected to the base. The moveable plate electrode and the stationary upper plate electrode form a capacitor. Thus, when the corresponding tip 167 is activated, the gap control circuit electrostatically (i.e., capacitively) senses changes in voltage across the moveable plate electrode and the upper plate electrode caused by the deflection of the cantilever. In response, it makes gap measurements of the width of the gap and provides them to the controller 114. The gap measurements are then monitored by the controller 114.

Figure 19:
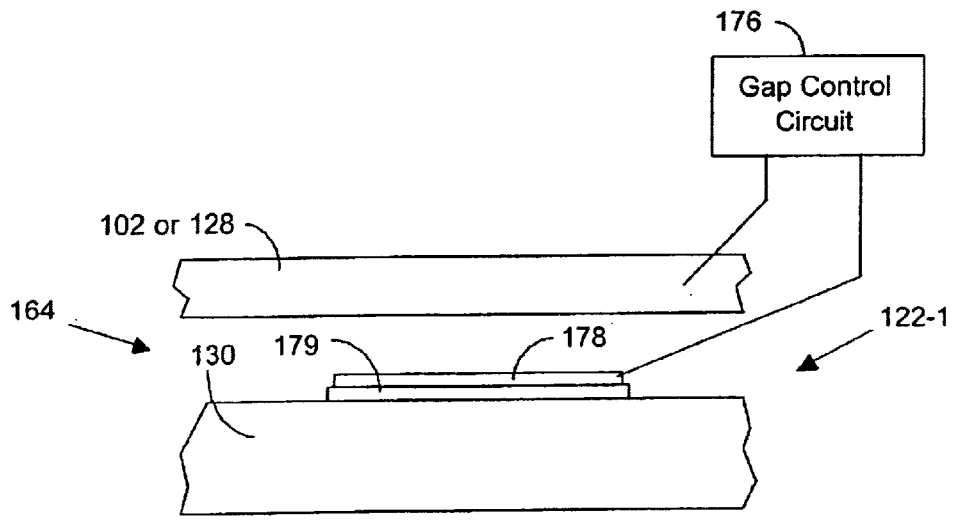

In alternative embodiment shown in FIG. 19, the gap sensors 164 could be electrostatic (i.e., capacitive) gap sensors when the object 102 is conductive. In this case, each gap sensor includes an insulating plate 178 on the base 130 of the SPM probe 122-1, a plate electrode 179 on the insulating plate, and the object. The plate electrode and the object form a capacitor. Thus, the change in voltage across the plate electrode and the object can be electrostatically (i.e., capacitively) sensed by the gap control circuit. In response, the gap control circuit 176 then generates a gap measurement signal that represents a measurement of the width of the gap between the object and the plate electrode.

Thus, in positioning the SPM probe 122-1 for making SPM measurements of the object 102, the controller 114 monitors the gap measurements made by the gap control circuit 176. Based on these gap measurements, the controller controls the positioning system 103 and gap control circuit 176 so as to provide the proper gap 198 between the upper surface 166 of the object 102 and the lower surface 142 of the probe. In this way, the entire gap can be set to have a uniform width between the upper surface of the object and the lower surface of the base so that the microvacuum chamber discussed earlier can be properly established and maintained. The above process is also used in establishing a gap between the lower surface of the probe and the upper surface of a calibration structure when the probe is being calibrated.

Referring to FIG. 1, as alluded to earlier, the vacuum source 192 of the SPM system includes a large vacuum chamber 194 for each flexible tube 345 connected to a scanning head 120. Thus, a vacuum can be maintained in the large vacuum chamber regardless of whether the corresponding valve of the large vacuum chamber is kept open or closed. And, since the volume of the internal chamber 135 of the housing 154 of the scanning head 120 is much smaller than the volume of the large vacuum chamber, the controller 114 can quickly establish a vacuum in the internal chamber and the microvacuum chamber in the gap 198 between the object 102 and the base 130 of the probe 122-1 by opening the valve. Similarly, the controller can end this vacuum by closing the valve.

Probe Loading and Unloading using Vacuum

Thus, referring to FIG. 5, not only can a vacuum between the object and the base of the probe 122-1 be easily established and ended in the manner just described, but the probe 122-1 itself can be loaded onto and unloaded from a scanning head 120. Specifically, turning to FIGS. 1 and 6, during the loading process, the controller 114 lowers the scanning head onto the probe so that the probe is within the seat 158. Then, referring back to FIGS. 1 and 5, the controller causes the corresponding valve 345 of the large vacuum chamber 194 to be opened so that a vacuum is created in the internal chamber 135 of the housing 154 of the scanning head. As a result, the probe will be locked onto the seat so that it is loaded onto the scanning head. Similarly, the probe can be unloaded by the controller by causing the valve to be closed and ending the vacuum in the internal chamber. Thus, this method of loading and unloading the probe onto and from the scanning head could be used instead of the rotary cam assembly 160 described earlier.

Structure of SPM Probe 122-2

Figure 20:
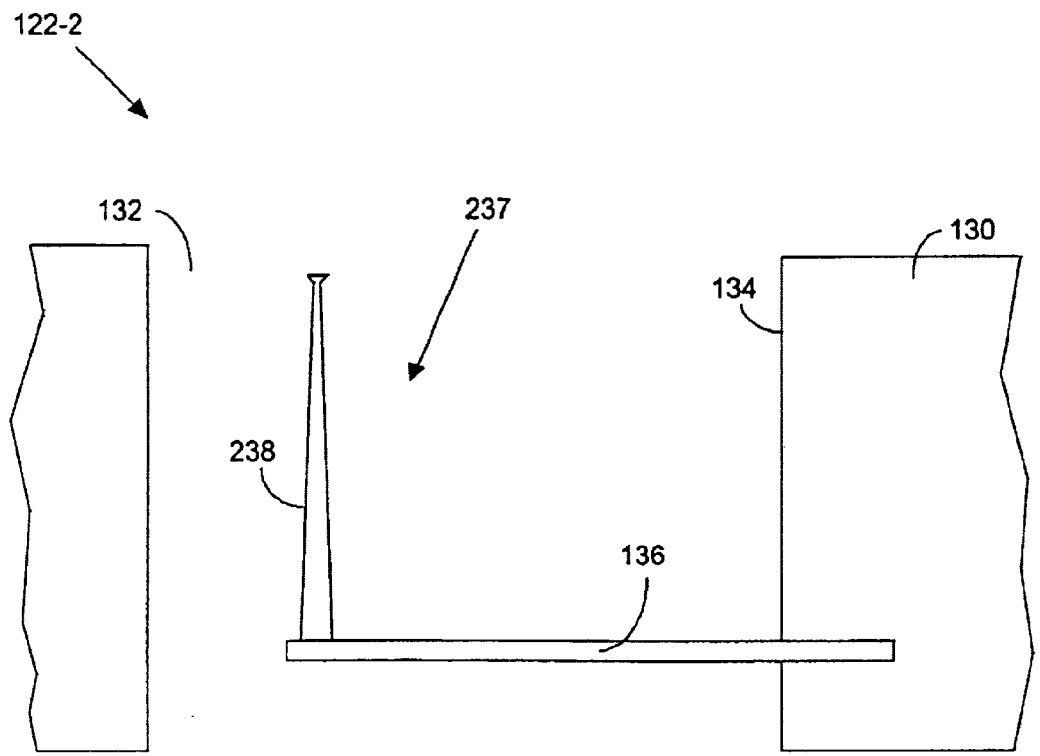

Turning now to FIG. 20, there is shown another microstrucured SPM probe 122-2 for use in inspecting the object 102 by making SPM measurements. It is constructed in the same manner as the first SPM probe 122-1, except that it has different tips 238 than the tips 138 of the first probe.

Figure 21:
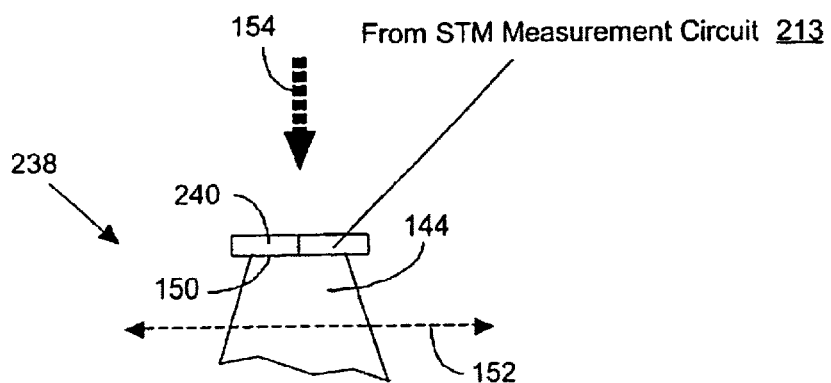
FIGS. 20 to 23 show different views and embodiments of a second SPM probe of the SPM system of FIG. 1.

In particular, in order to be resistant to frictional wear when being used to make AFM measurements, the tip 238 of each tool 237 of the SPM probe 122-2 may include and be coated with an obdurate plate 146 at the sharp end of the tip, as shown in FIG. 21. The tapered core material 144 of the tip may be shaped to have a flat portion at the sharp end of the tip on which the obdurate plate is formed. As with the first SPM probe 122-1, the obdurate plate may comprise diamond, diamond like carbon, silicon carbide, carbon nitride, or some other obdurate material and have a thickness in the range of approximately 1 Angstroms to 10 micrometers. The obdurate plate may be formed similar to the obdurate coating 146 described earlier for the first probe but with some modifications.

Figure 22:
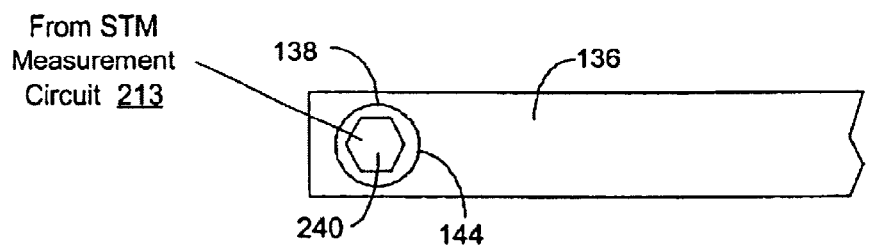
Figure 33:
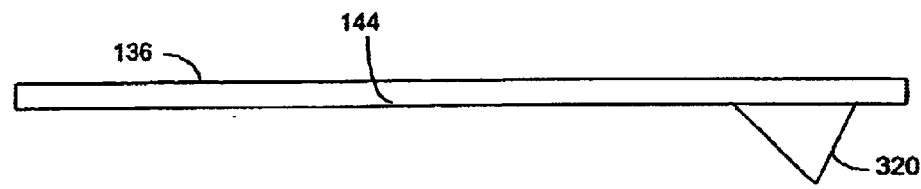

Specifically, the SPM probe 122-1 is formed so that the target surface 150 of each tip 138 of the probeon which the obdurate plate 240 is formed is oriented with respect to a particular crystal axis (or direction) 152 of the core material 144 with a desired orientations angle. Then, the obdurate plate comprises a crystal that is grown on the target surface of each tip with the crystal growth (or deposition) vector 154 being oriented with respect to the crystal axis of the core material with a desired crystal growth angle. Moreover, during crystal growth of the obdurate plate, a desired bias voltage can be applied to the core material to create an electrical field. By positioning the target surface in the bias electric field and/or a bias magnetic field in different ways about the axis of the crystal growth vector, different orientations (or alignments), of the grown crystal on the target surface can be formed, as shown in FIGS. 22 and 33. Thus, the orientations and crystal growth angles, the bias voltage, and the position of the target surface about the axis of the crystal growth vector, can be selected to produce a tip with an obdurate plate that has a desired crystal orientation on the target surface. And, it may be made conductive in the same way as was described earlier for the obdurate coating 146 so that it can be used with the STM measurement circuit 213 to make STM measurements.

For example, in the case where the core material 144 comprises silicon, the target surface 150 of each tip 138 of the probe 122-2 may be formed parallel to (or along) the [100] crystal axis of the silicon core material. Then, diamond like carbon could be formed on the target surface as the obdurate plate itself or as a seed site for actual diamond growth.

Figure 23:
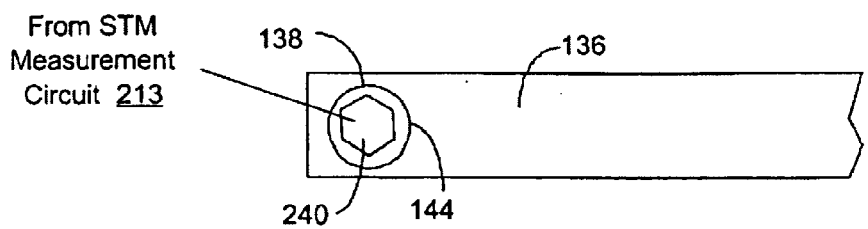

In the case where the diamond like carbon is used as a seed site, or where a seed site is formed by rubbing the tip in diamond as described earlier, a diamond crystal may be grown at the seed site in the manner described earlier for the diamond crystals of the obdurate coating 146. However, in this case, a hexagonal shaped diamond crystal is grown normal to the target surface to form the diamond plate when the crystal growth vector is perpendicular to the target surface. Growth of flattened hexagonal diamond crystals is described in Keiji Hirabayashi et al., "Synthesis and Growth of Flattened Diamond Crystals by Chemical Vapor Deposition, Diamond and Related Materials 5 (1996), pp. 48–52. And, referring back to FIGS. 22 and 23, a suitable bias voltage can be applied to the core material 144 to select the orientation of the diamond crystal on the target surface, as suggested earlier. It may then be doped with an impurity, such as boron, or grown with Boron in the growth plasma so that it is made conductive.

Similarly, the obdurate plate 250 may be formed with a silicon carbide or carbon nitride crystal that has a desired crystal orientation on the target surface 150. In order to do so, the process described earlier for growth of silicon carbide and carbon nitride crystals in forming the obdurate coating 146 would be modified. This would be done in the same way that the earlier described process of growing diamond crystals to form the obdurate coating was modified to grow the diamond crystal that forms the obdurate plate 250.

The obdurate plate 250 was just described as being a single crystal grown on the target surface 150 of the core material 144. However, those skilled in the art will recognize that the obdurate plate could be formed by one or more crystals that are grown on the target surface. In this case, the application of the bias voltage to the core material would cause these crystals to be symetrically aligned.

Probe Loading and Unloading, Tip Activation and Deactivation, Calibration, Inspection and Modification Operation, and Vacuum Operation of SPM Probe 122-2

Referring back to FIG. 20, unlike the first SPM probe 122-1, the second SPM probe 122-2 does not include a lens over each tip 238. Thus, the second probe is not used to make radiation measurements in the same manner as the first probe. However, the second probe may be loaded onto and unloaded from one of the scanning heads 120 in the same ways as were described earlier for the first probe. In addition, the tip 238 of each tool of the second probe may be activated and deactivated, calibrated, and have its profile examined in the ways described earlier for the first probe, except that the positioning of the tip of the second probe would not be calibrated using radiation measurements in the same manner as the first probe. And, the activated tip of each tool of the second probe would be used to make SPM measurements and SPM modifications in the ways described earlier for the first probe, except that, as just mentioned, it would not be used to make radiations measurements in the same manner as the first probe. Furthermore, optical images would be produced by the imaging optics 226 in the manner discussed earlier during operation and/or calibration of the second probe. Finally, during operation and/or calibration, a microvacuum chamber in the gap 198 between the second probe and the object 102 or calibration structure 128 may be established in any of the ways described earlier for the first probe using gap sensors 164 in the second probe.

Structure of SPM Probe 122-3

Figure 24:
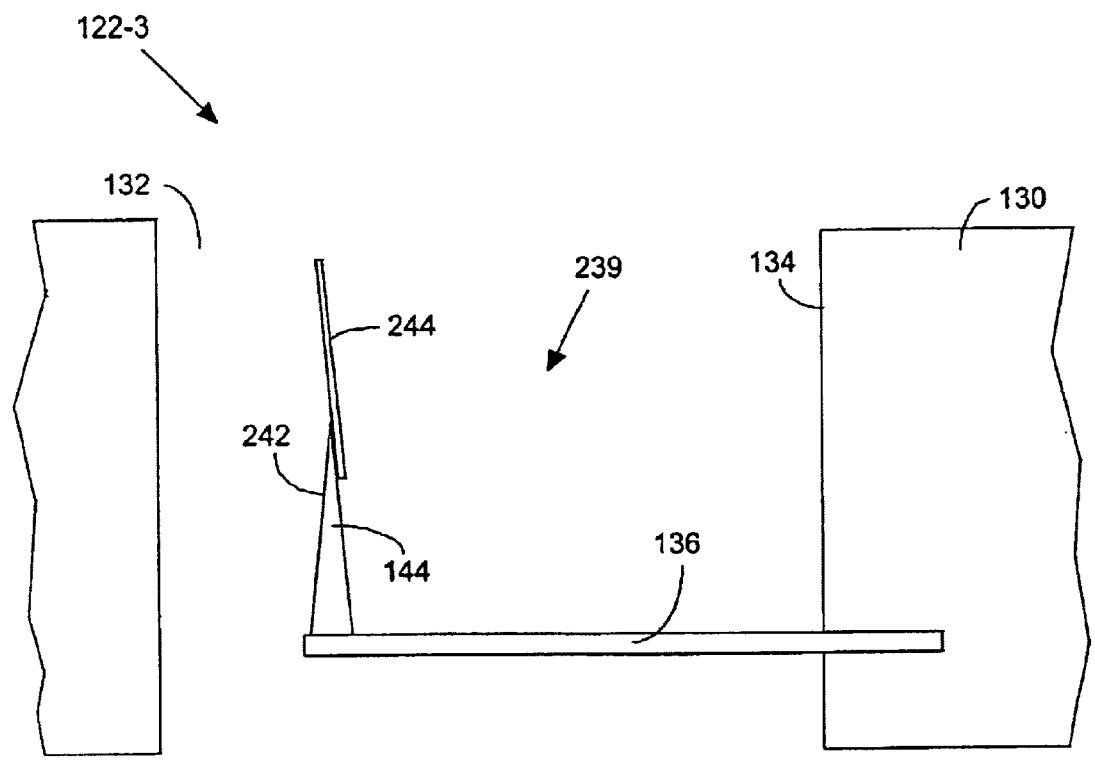
FIGS. 24 and 25 show different views of a third SPM probe of the SPM system of FIG. 1.

Turning now to FIG. 24, there is shown a third microstrucured SPM probe 122-3 for use in making SPM measurements. It is constructed like the first and second probes 122-1 and 122-2 except that it has different tips 242 than the tips 138 and 238 of the first and second probes.

The tip 242 of each SPM tool 239 of the SPM probe 122-3 includes a tapered core material 144 and a multiwalled nanotube (i.e., nanostructured tube) 244. The nanotube may comprise carbon or boron nitride and be formed in the manner described in S. Lijima, "Helical Microtubules of Graphitic Carbon," Nature (London) 354, 56 (1991) and A. Loiseau et al., "Boron Nitride Nanotubes with Reduced Number of Layers Synthesized by Arc Discharge," Physical Review Letters, vol. 76, no. 25 (June 1996), pp. 4737–4740, and Nasreen G. Chopra et al., "Boron Nitride Nanotubes," which are hereby explicitly incorporated by reference. Moreover, in the manner described in Honggjie Dai et al., "Nanotubes as Nanoprobes in Scanning Probe Microscopy," Nature, vol. 334 (November 1996), pp. 147–150, which is also hereby explicitly incorporated by reference. The nanotube is attached to the core material for use in making SPM measurements by bonding it to the core material. And, as described in this reference, the narrow diameter (e.g., 5–20 nanometers) of the nanotube enables it to provide sub nanometer resolution. And, its flexibility allows it to bend back into is original shape and position is case of inadvertent crashes in the object 102 or one of the calibration structures 128.

Figure 25:
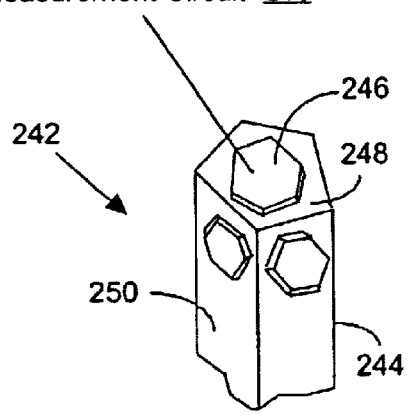

Turning to FIGS. 25, the tip 242 of each SPM tool 239 includes one or more crystals of an obdurate coating 246 on the nanotube 244. Since the ends of the nanotube 244 are closed when formed, as described in "Boron Nitride Nanotubes with Reduced Number of Layers Synthesized by Arc Discharge" just referenced, crystal of the obdurate material can be formed on the closed surface 248 at the free (or unattached) end of the nanotube. Moreover, crystals of the obdurate material may also be grown at the free end on the side walls 250 of the nanotube. As with the probes 122-1 and 122-2, the obdurate coating may comprise diamond, silicon carbide, carbon nitride, diamond like carbon, or some other suitable obdurate material and may be formed in the ways described earlier. Thus, as shown in FIG. 25, the obdurate coating could comprise a plate on the closed surface 248 and plates on the side walls 250 that are formed with a desired crystal orientation in the manner described earlier for the obdurate plate of each tip 238 of the second probe. And, these plates may be made conductive in the same was as was described earlier for the obdurate coating 146 so that it can be used with the STM measurement circuit 123-11 to make STM measurements.

Probe Loading and Unloading, Tip Activation and Deactivation, Calibration, Inspection and Modification Operation, and Operation of SPM Probe 122-3

Furthermore, referring back to FIG. 24, the third probe may be loaded onto and unloaded from one of the scanning heads 120 in the same ways as were described earlier for the first and second probes. Moreover, the hollow nanotube 244 may be used to capture light at or near a contact surface or guide light down it in the same manner as was described earlier for the SPM probe 122-1 to make radiation measurements. And, the tip of each tool of the third probe may be activated, deactivated, calibrated, and have its profile examined in the ways described earlier for the first probe, but without optical calibration of the position of each tip. Moreover, like the second probe, the activated tip of each tool of the third probe would be used to make SPM measurements in the ways described earlier for the first probe, except that it would not be used to make radiation measurements. Furthermore, optical images would be produced by the imaging optics 226 in the manner discussed earlier during operation and/or calibration of the third probe. And finally, during operation and/or calibration, a microvacuum chamber in the gap 198 between the third probe and the object 102 or calibration structure 128 may be established in any of the ways described earlier for the first probe with the apertures 132 and the gap sensors 164 of the third probe.

Structure of SPM Probe 1224

Figure 26:
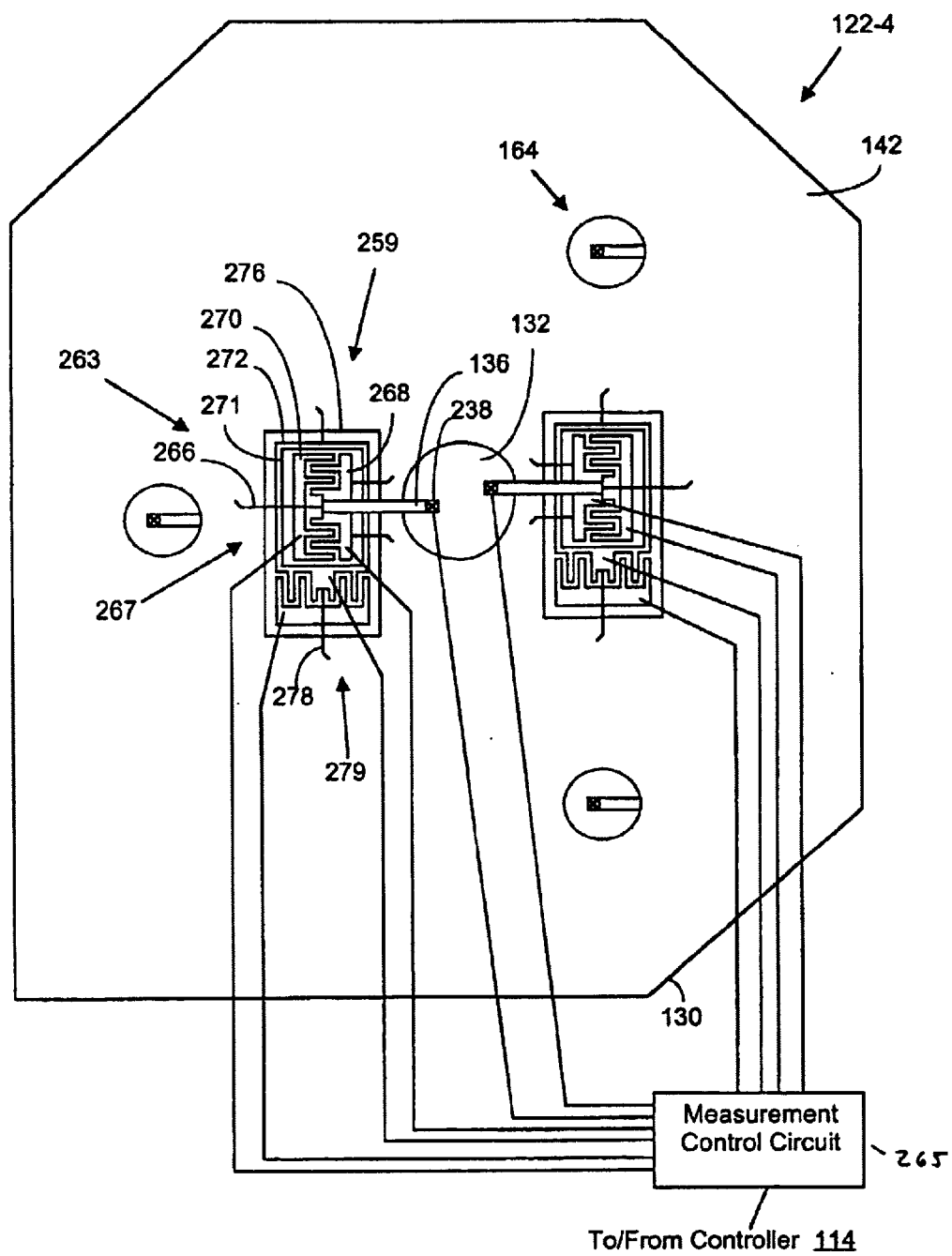
FIG. 26 shows a fourth SPM probe of the SPM system of FIG. 1.

Turning to FIG. 26, there is shown a fourth microstructured SPM probe 1224 for use in making SPM electrical measurements of the object 102. It has a pair of SPM electrical tools 259 for making such electrical measurements between two points on the object. Each of the tools includes a cantilever 136 and a corresponding conductive tip 238 on the cantilever like those discussed earlier for the first and second SPM probes 122-1 and 122-2. The tip of each tool may also be constructed like one of the tips 138 or 242 discussed earlier for the first and third SPM probes 122-1 and 122-3. In this probe, the cantilever of each tool is connected to a corresponding positioning system 263 for the tool instead of being directly connected to the base 130 of the probe. The base 130 has the same basic shape and construction as the base discussed for the first probe 122-1.

The positioning system 263 for each electrical tool 259 of the probe 1224 can position the corresponding cantilever 136, and therefore the corresponding tip 238, in the X and Y dimensions with respect to the object 102 or one of the calibration structures 128. A fixed end of the cantilever is connected to a first moveable comb structure 268 of the positioning system. The cantilever and the first moveable comb structure are moveably suspended by a first suspension system 267 over a second moveable comb structure 272 of the positioning system. The first suspension system comprises spring arms (or connectors) 266 which each have one end connected to the first moveable comb structure or the cantilever and another end connected to the second moveable comb structure. The fingers of the first moveable comb structure are interdigitized with (i.e., aligned between) the fingers of a corresponding first stationary comb structure 270 of the positioning system that is stationary with respect to the first moveable comb structure. This stationary comb structure is formed on a first insulating plate 271 that is on the second moveable comb structure. The fingers of this second moveable comb structure are interdigitized with the fingers of a corresponding second stationary comb structure 274 of the positioning system that is formed on a second insulating plate 276 on the base 130 of the probe. The second moveable comb structure is moveably suspended by a second suspension system 279 over the base. The second suspension system comprises spring arms 278 that each have one end connected to the second moveable comb structure and another end connected to the base.

The base 130, the moveable comb structures 268 and 270, and the spring arms 266 and 278 may be integrally formed together and comprise a semiconductor material, such as polysilicon, that is conductive. Similarly, the stationary comb structures may also comprise such a semiconductor material. And, the insulating plates 271 and 276 may comprise an insulating material, such as silicon dioxide.

The two moveable comb structures 268 and 272 of the positioning system 263 of each electrical tool 259 of the probe 1224 are respectively moveable in the X and Y dimensions to enable the tool to be positioned in the X and Y dimensions. Specifically, each pair of corresponding moveable and stationary comb structures forms an electrostatic (i.e., capacitive) comb drive of the type described earlier for the nanoforce balance 128-3. Thus, by applying a differential voltage across them, their comb fingers interact electrostatically (i.e., capacitively) with each other and the moveable comb structure moves linearly with respect to the stationary comb structure. Thus, since one end of the cantilever 260 of each tool is connected to the moveable comb structure 268, the cantilever may be moved so as to position the tip 262.

SPM Inspections with SPM Probe 122-4

The components of the SPM system 100 also include a measurement control circuit 265. The controller 114 can control the measurement control circuit to cause the positioning systems 263 of the electrical tools 259 of the probe 122-4 to position the tips 262 of the tools in the manner described earlier so that they are positioned at different scan points on the object 102 or calibration structure 128. Then, the controller can cause the measurement control circuit to make an SPM electrical measurement between these two points by applying a suitable voltage across the conductive tips 262. The measurement control circuit then provides the controller with an electrical measurement signal that represents the electrical measurement. These electrical measurements may then be used by the controller to generate an electrical analysis for performing a test, repair, and/or fabrication step of the object in the manner described earlier.

In fact, the SPM probe 1224 is particularly useful in testing, repairing, and/or performing fabrication steps on a semiconductor wafer. In particular, where an integrated circuit is being fabricated on the wafer, the SPM probe 122-4 may be used to analyze the electrical properties of the circuit when performing a test, repair, or fabrication step of the integrated circuit.

Probe Loading and Unloading, Tip Activation and Deactivation, Calibration, and Operation of SPM Probe 122-4

The fourth SPM probe 122-4 may be loaded onto and unloaded from one of the scanning heads 120 in the same ways as were described earlier for the first SPM probe 122-1, except that it would be loaded from one of the horizontal probe suppliers 125. The tip of each electrical tool 259 of the fourth probe may be calibrated and have its profile examined in the ways described earlier for the first probe, but without optical calibration of the positioning of each tip. Furthermore, optical images would be produced by the imaging optics 226 during operation and/or calibration of the fourth probe in the manner discussed earlier for the first probe. And finally, like the first SPM probe 122-1, the fourth probe has an aperture 132 and gap sensors 164 and may be operated and/or calibrated in a microvacuum chamber in the gap 198 between the fourth probe and the object 102 or calibration structure 128 in the same way as was described for the first probe.

Structure of SPM Probe 122-5

Figure 27:
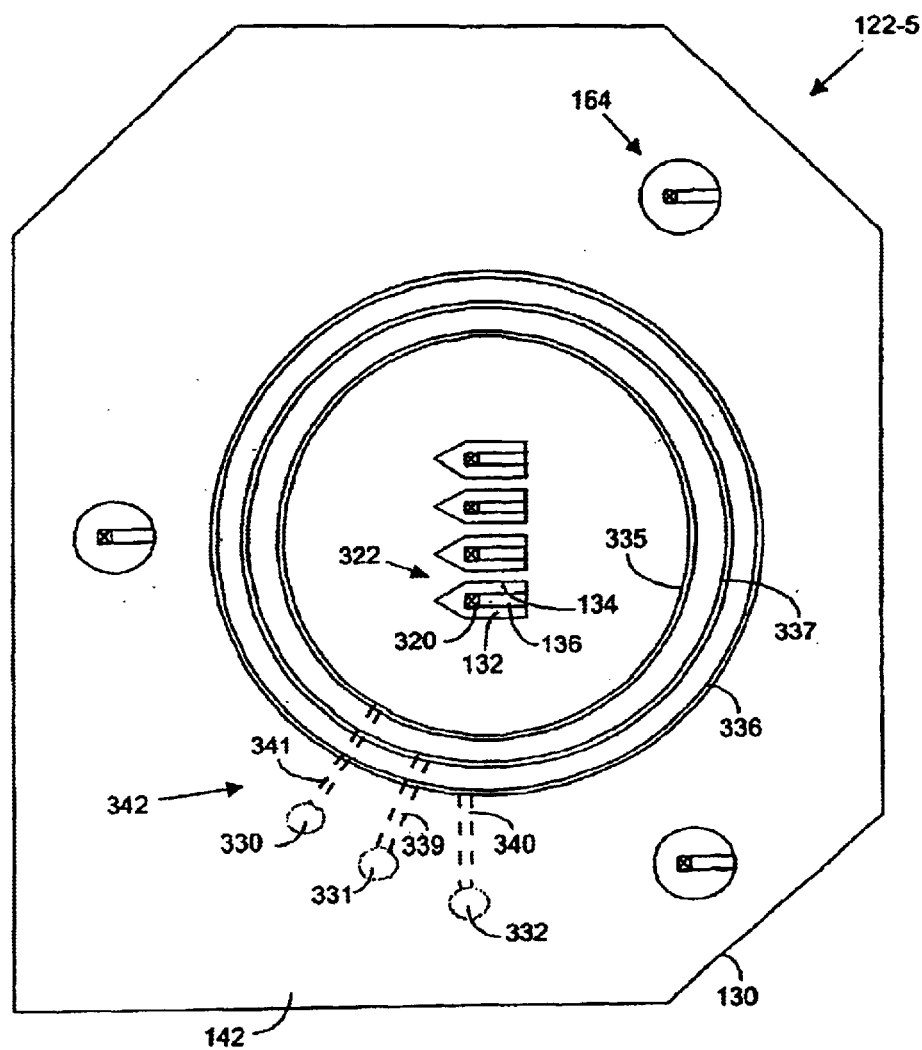
FIGS. 27 to 35, 82, 83, and 86 show different views of a fifth SPM probe of the SPM system of FIG. 1.

Referring now to FIG. 27, there is shown a fifth microstructured SPM probe 122-5 for modifying the object 102 by making cuts in its material. It is constructed like the first to third SPM probes 122-1 to 122-3 except for several differences. First, it has different tips 320 than the tips 138,238, and 242 of the first to third probes. Second, it does not have a lens 147 and a lens support 149 over each tip. Third, it has a particle removal structure 342 that is used to remove particles from the object.

Figure 28:
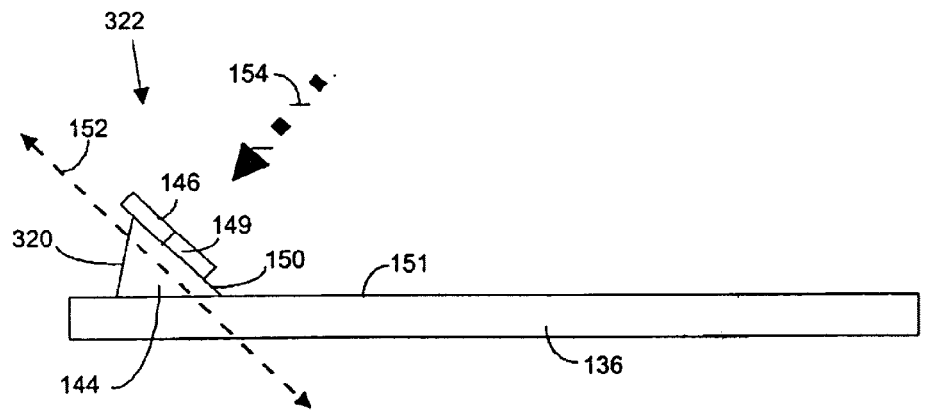
Figure 29:
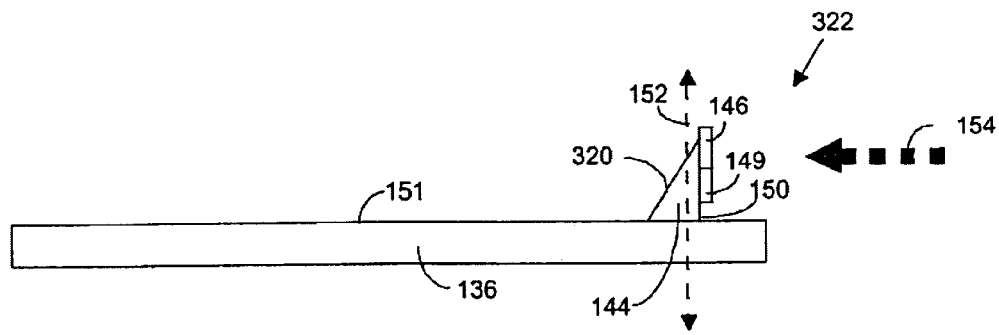

Referring to FIGS. 28 and 29, similar to each tip 238 of the second SPM probe 122-2, the tip 320 of each cutting tool 322 of the SPM probe 122-5 includes and is coated with an obdurate plate 146 at the sharp end of the tip along a tapered side of the core material 144 of the tip. This makes the tip resistant to frictional wear when being used to make cuts in the object 102. As with obdurate plate of each tip of the second probe, the obdurate plate of each tip of the fifth probe may comprise diamond, diamond like carbon, silicon carbide, carbon nitride, boron nitride or some other obdurate material and have a thickness in the range of approximately 1 Angstroms to 100 micrometers.

Furthermore, the tip 320 of each cutting tool 322 of the fifth SPM probe 122-5 is formed in a similar manner to that described earlier for the tip 238 of each SPM tool 237 of the second SPM probe 122-2 but with some modifications. Specifically, in constructing each cutting tool of the fifth probe, the target surface 150 for forming the obdurate plate 146 is formed so as to be oriented with respect to a particular crystal axis (or direction) 152 of the core material 144 with a desired orientation angle and with respect to the lower surface 151 of the cantilever with a desired cutting angle. Then, one or more crystals that comprise the obdurate plate are grown on the target surface of each tip in the manner discussed earlier for the second probe. Thus, by selecting the orientation, cutting, and crystal growth angles, the bias voltage, and the position of the target surface about the axis of the crystal growth vector 154, a tip with an obdurate plate having a desired cutting angle and a desired orientation of its crystal(s) can be produced. Then, the core material at each tip's sharp end may be etched away so that desired edges of the crystal(s) at the sharp end are exposed to form the cutting edges 149.

Figure 30:
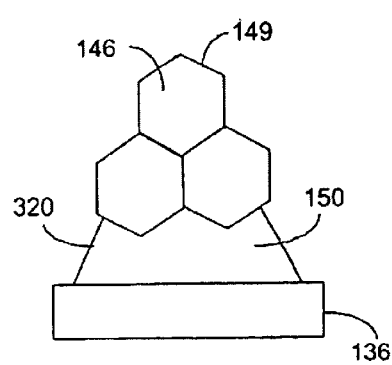
Figure 31:
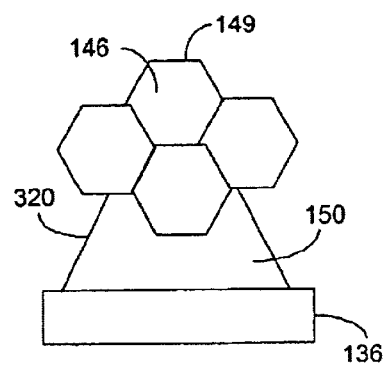

For example, in the case where the core material 144 is silicon, the target surface 150 of each tip 320 of the cutting probe 122-5 may be parallel to the [100] crystal axis of the silicon core material. Then, one or more crystals that comprise the obdurate plate are grown on the target surface of each tip with the crystal growth vector 154 perpendicular to the crystal axis of the core material. During crystal growth of the obdurate plate, a desired bias voltage can be applied to the core material to create an electrical field. By positioning the target surface in the electric field in different ways about the axis of the crystal growth vector, different crystal orientations of the obdurate plate can be formed on the target surface. In the case where multiple crystals are grown, they will all be symmetrically oriented on the target surface, as shown in FIGS. 30 and 31.

Furthermore, as with the first to third SPM probes 122-1 to 122-3, the fifth SPM probe 122-5 has multiple cutting tools 322. Thus, referring to FIGS. 28 and 29, the cutting tools may have tips 320 with different cutting angles and different crystal orientations from each other which are formed in the manner just discussed. As a result, these cutting tools can be used for performing different types of cuts in the object 102.

Figure 32:
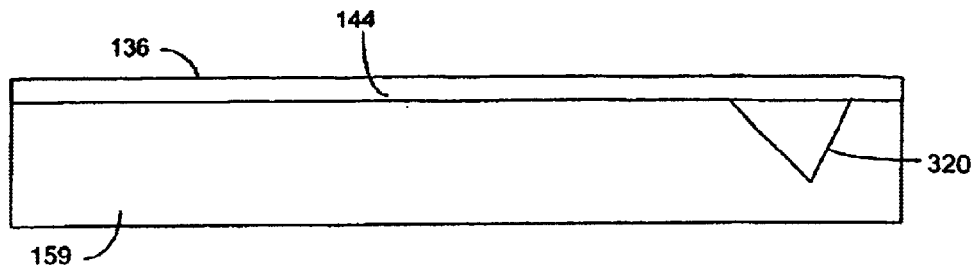
Figure 34:
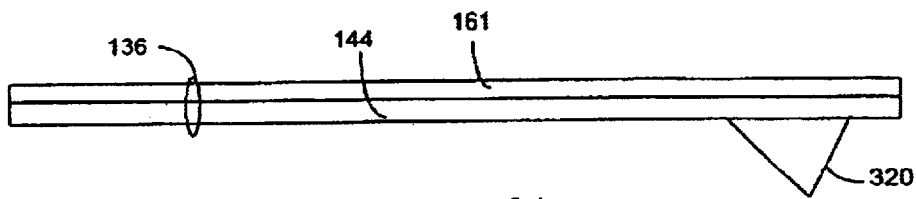

Alternatively, rather than forming an obdurate plate 146 on a core material 144 to form each cutting tool 322 of the cutting probe 122-5 as just described, the core material 144 of each cutting tool may in fact comprise diamond, silicon carbide, carbon nitride, boron nitride, or some other suitable obdurate material. Referring to FIG. 32, in order to do so, a mold 159 is used that comprises a semiconductor material, such as silicon. The obdurate material is then grown on the mold with a thickness sufficient to produce the cantilever 136 and tip 320 of the cutting tool. Then, the mold is etched away so as to leave the cutting tool, as shown in FIG. 33. As shown in FIG. 34, a material 161, such as polysilicon or tungsten, can be optionally deposited on top of the obdurate material to provide a reflective surface and mechanically strengthen the cantilever. Then, referring back to FIG. 27, the base 130 of the cutting probe is formed on and around each such cutting tool to produce the entire fifth SPM probe 122-5.

Figure 82:
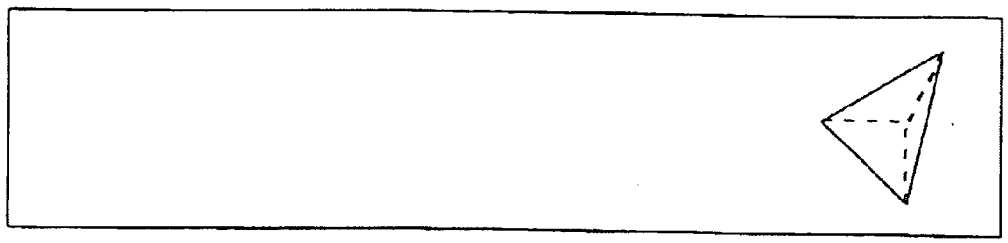
Figure 82:
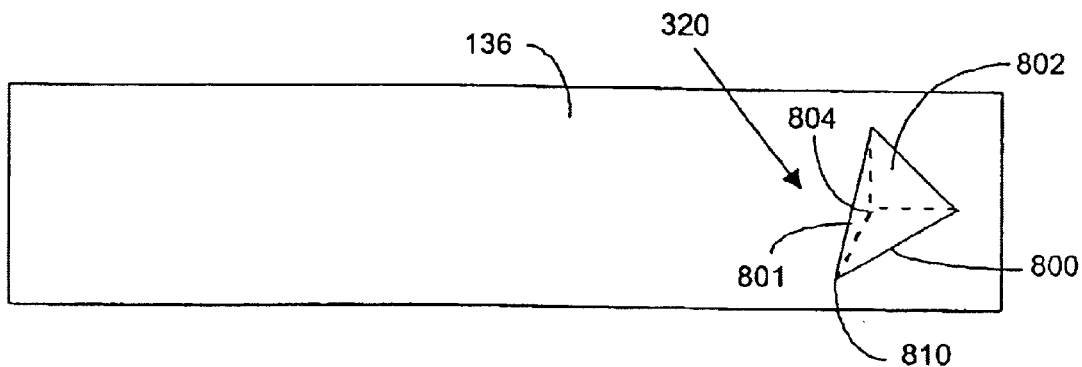
Figure 82:
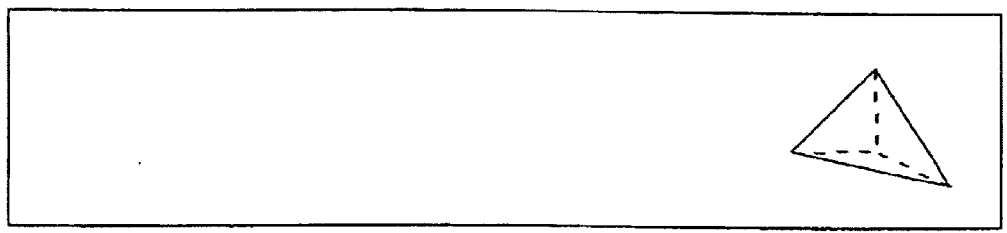
Figure 82:
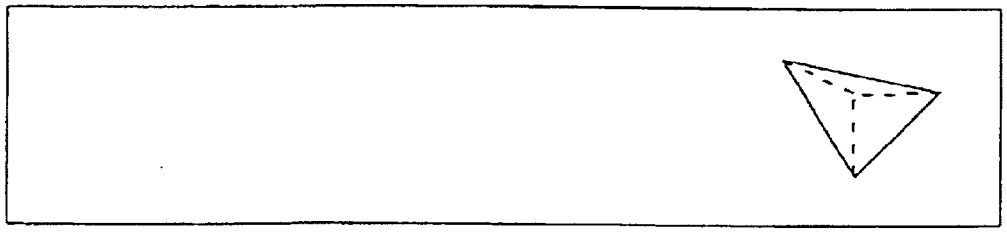
Figure 82:
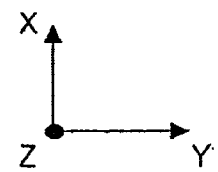
Figure 83:
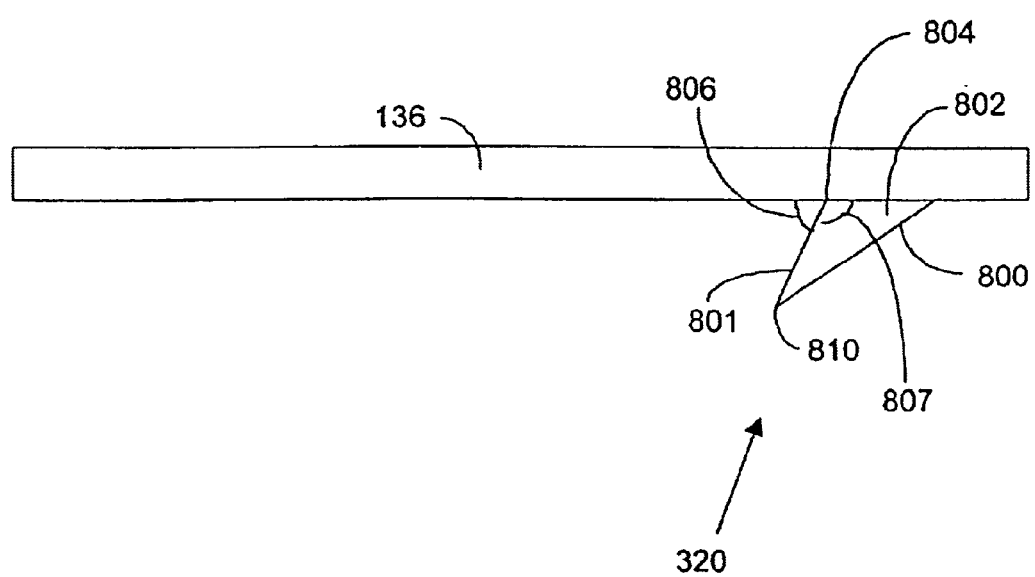

In another example, each tip 320 may be tetrahedronally shaped in the manner shown in FIGS. 82 and 83. Such a tip has three exposed surfaces 800, 801, and 802. Two of these surfaces meet at right angles at the base of the tip (i.e., where the tip is connected to the cantilever 136) to form a right angle corner 804 of the tip. For each of these two surfaces, the external angle 806 (i.e., external to the tip) formed between it and the lower surface 807 of the cantilever or the XY plane of motion of the cantilever is less than or equal to 90°. Conversely, the internal angle 808 (i.e., internal to the tip) formed between this surface and the lower surface of the cantilever and or the XY plane of motion is greater than or equal to 90°.

Here, each of the exposed surfaces 800 to 801 may be coated with an obdurate coating or plate 146 as described earlier for SPM probes 122-1, 122-2, and 122-5 or the entire tip 320 or cutting tool 322 may be formed of an obdurate material 146 as just described. As a result, the sharp end 810 of each tip may be used to make cuts in the object 102 so as to form a ledge in the object or cut below specific material of the object so as to remove other material below it but not remove this specific material.

Furthermore, as indicated earlier, the SPM probe 122-5 has multiple cutting tools 322. Thus, each tip 320 of the cutting tools 322 may have a different orientation on its corresponding cantilever 136 than any of the other tips. For example, as shown in FIG. 82, the SPM probe may have four cutting tools. In this case, the right angle corner 804 and sharp end 810 of each tip is rotated 90°, 180°, and 270° from the right angle corners and sharp ends of the other tips. As a result, these tips could be used to cut any material of the object 102 to leave a sharp corner at the ends of any cut series having common points.

Alternatively, the fine positioning system 104 of each scanning head 120 may be configured to rotate the scanning head. Thus, the controller 114 could cause the fine position system to rotate the scanning head so that a single tip 320 of the SPM probe 122-5 could be rotated so as to perform this same cut series without changing tips. Similarly, the rough positioning system 104 could be configured to rotate. Thus, under the control of the controller the object could be rotated by the rough positioning system so that a single tip 320 of the SPM probe 122-5 could perform this same cut series.

Those skilled in the art will recognize that this embodiment of tip 320 may be used to make AFM measurements in the manner described earlier for SPM probe 122-1. In fact, this embodiment is particularly useful for making AFM measurements of material below a ledge or overhang of the object 102 after the tip was used to perform the cut that created the ledge or overhang. Furthermore, those skilled in the art will recognize that similar shapes, such as pyramidal shapes, may be used for this embodiment as well.

Probe Loading and Unloading, Tip Activation and Deactivation, Calibration, and Vacuum Operation of SPM Probe 122-5

Figure 35:
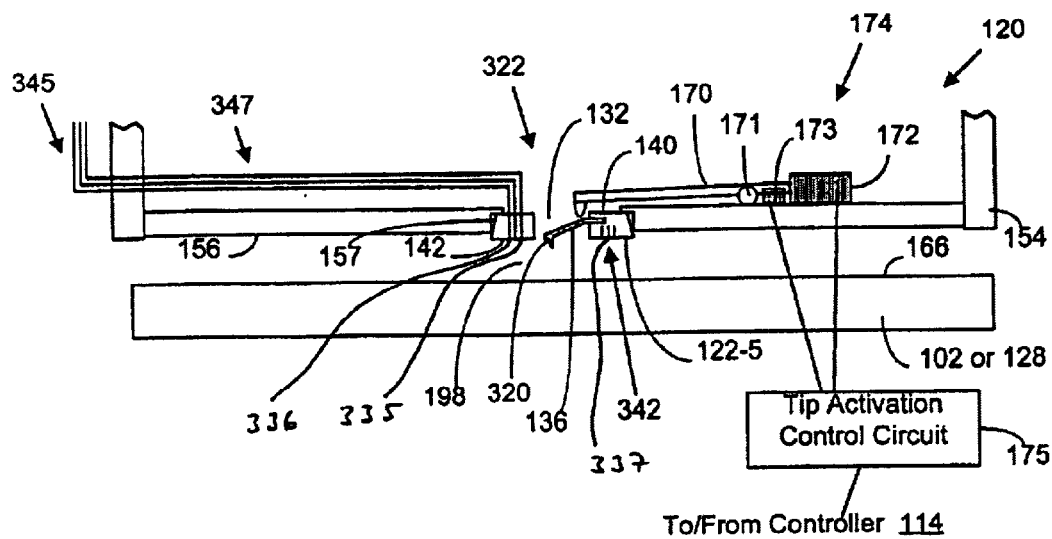

Referring to FIG. 35, the fifth SPM probe 122-5 may be loaded onto and unloaded from one of the scanning heads 120 in the same ways as were described earlier for the first SPM probe 122-1. In addition, the tip 320 of each cutting tool 322 of the fifth probe may be activated and deactivated, calibrated, and have its profile examined in the ways described earlier for the first probe, except that the positioning of the tip of the fifth probe would not be optically calibrated. Furthermore, optical images would be produced by the imaging optics 226 during operation and/or calibration of the fifth probe in the manner discussed earlier for the first probe. Finally, during operation and/or calibration, a microvacuum chamber in the gap 198 between the fifth probe and the object 102 or calibration structure 128 may be established in any of the ways described earlier for the first probe with the apertures 132 and the gap sensors 164 of the fifth probe.

SPM Modifications with SPM Probe 122-5

Referring again to FIG. 1, as mentioned earlier, the SPM probe 122-5 may be used to modify the object 102. This is done by performing a cut in the material of the object to remove material from the object. This is done when the user instructs the controller 114 with the user interface 116 to use the cutting probe to perform this operation. Referring to FIG. 35, in the manner described earlier, the controller controls loading of the cutting probe onto the scanning head 120 and the activation of the tip 320 of one of the cutting tools 322 of the probe. Then, the controller controls the positioning system 103 to lower the activated tip onto the target area of the object such that the activated tip pushes down on a target area of the object with sufficient force to make a desired cut in the material of the object when the tip is dragged across it. Then, the controller causes the positioning system to drag the tip in this way and make the desired cut. The controller then causes the positioning system to raise the tip from the cut or return it to the beginning of cut stroke without lowering it into the material.

As mentioned earlier, the fifth SPM probe 122-5 may have multiple cutting tools 322 with tips 320 with different cutting angles and crystal orientations. In this case, the controller 114 selects the cutting tool with the appropriate cutting angle and crystal orientation to perform the desired cut.

Moreover, the amount of force with which the activated tip 320 of the SPM probe 122-5 pushes down on the target area may be selected and selectively adjusted. Referring back to FIG. 35, the controller 114 causes the tip activation circuit 175 to control the tip actuator 174 in order to do this. Specifically, the tip activation circuit causes a change in the dimension of the adjustment transducer 173 so that it pushes or pulls against the end of the lever arm 170 to which it is fixed. In response, the lever arm is moved over the pivot 171 so that the pivot point of the lever arm (about which the lever arm pivots on the pivot) will change. This changes the point at which the rounded end of the lever arm contacts the cantilever 136 on which is located the activated tip. Since this contact point is also a pivot point for the deflection of the cantilever, the amount of force imparted on the target area depends on the location of this contact point. In this way, the amount of force imparted by the activated tip can be selected and selectively adjusted.

Moreover, the activated tip 320 the fifth SPM probe 122-5 can be calibrated using the force balance 128-3 in the manner described earlier for the first SPM probe 122-1. Thus, by using the force calibration table created for the tip during this calibration, a precise known force can be applied to the object 102 by the tip. As a result, a precise cut in the material of the object can be made to remove material from the object.

As was alluded to earlier, the first and second SPM probes 122-1 and 122-2 may also be used to make modifications to the material of the object 102. In particular, the first and second probes would be used to make cuts in and/or deform the material of the object. The cuts would be done in the same manner as was just described with a precise force applied to the material of the object while dragging the activated tips 136 and 238 of the first and second probes across the material of the object. Deformations would be similarly done by lowering the tips of the first and second probes onto, but not dragging across, the material of the object.

This is particularly useful in repairing and/or performing fabrication steps on a semiconductor wafer or fabrication mask. In particular, when excess material is on the wafer or mask, the SPM probes 122-1, 122-2, and 122-5 may be used to perform a precise cut to remove or etch away this material.

Moreover, this is also useful in performing precision repairs and/or fabrication steps of a magnetic microstructure. Specifically, a gap between magnetic elements of the magnetic microstructure can be precisely created and/or repaired by using the SPM probes 122-1, 122-2, and 122-5 to perform a precise cut in the magnetic material between the magnetic elements. This is particularly applicable to creating or repairing the gap between the write and read poles of the thin film magnetic material of a thin film magnetic read/write head.

Inspections with SPM Probe 122-5

Referring again to FIG. 27, the SPM probe 122-5 could also be used to inspect the object 102 by making SPM measurements of the object. This particularly true for the case when each cutting tool 322 of the probe is of the embodiment shown in FIGS. 32 to 34. As a result, AFM measurements could be made from the deflection of the cantilever 136 as the tip 320 is scanned over the surface 166 of the object in the manner discussed earlier for the first to third SPM probes 122-1 to 122-3. Furthermore, the obdurate material 146 could be made conductive in the manner discussed earlier for the first to third probes to make the tip of the fifth probe conductive. As a result, STM measurements could be made using this conductive tip in the manner discussed earlier for the first to third probes.

Particle Removal Structure

As mentioned earlier, the fifth SPM probe 122-5 includes a particle removal structure 342, as shown in FIGS. 27 and 35. As will be described shortly, the particle removal structure is used to remove particles from the object 102 or calibration structure 128 during operation and/or calibration of the probe. These particles may be contaminant particles from external sources or debris particles of particulate material removed from the object when cuts are made in the object with the tips 320 of the probe.

Referring to FIG. 1, in order to remove such particles, the fluid system 344 is used. As shown in FIG. 35, a flexible tube 346 for each scanning head is connected to a corresponding connector tube 347 of the scanning head.

Figure 86:
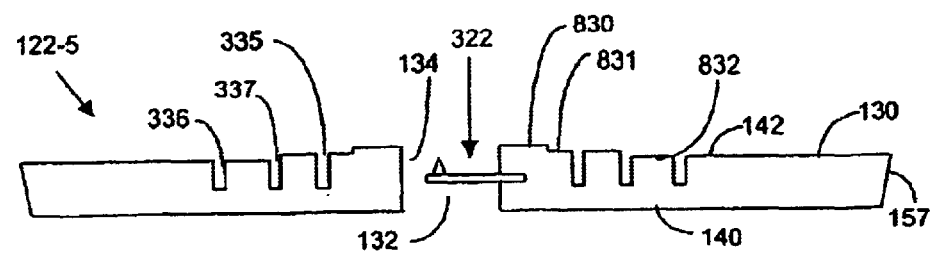

The particle removal structure 342 includes an inlet (i.e., input port) 332 on the upper surface 140 on the fifth SPM probe 122-5, a duct 340 formed in the base 130 of the probe, and an outer annular outlet (i.e., output port) 336 on the lower surface 142 of the probe, as shown in FIGS. 27 and 35. The duct connects the inlet and the outer annular outlet so that they are in fluid communication with each other. As shown in FIG. 86, the surface 142 of the base of the SPM probe 122-5 has steps 830 in it.

Referring now to FIGS. 1, 27, and 35, a corresponding connector tube 347 is connected to the inlet 337. Thus, when the controller 114 controls the corresponding valve 346 of the fluid system 344 to open, a gas source of the fluid system is in fluid communication with the inlet to provide it with a high pressure low viscosity gas, such as air, argon, helium, or other suitable gas. The gas travels through the duct 340 and exits at the outer annular outlet 336.

Similarly, as shown in FIGS. 27 and 35, the particle removal structure 342 includes an inlet 330 on the upper surface 140 of the fifth SPM probe 122-5, a duct 341 formed in the base 130 of the probe, and an inner annular outlet 335 on the lower surface 142 of the probe. The duct connects the inlet and the annular inner outlet so that they are in fluid communication with each other.

Turning now to FIGS. 1, 27, 35, and 86 a corresponding connector tube 347 is connected to the inlet 330. Thus, when the controller 114 controls the corresponding valve 346 of the fluid system 344 to open, a gas source of the fluid system is in fluid communication with the inlet to provide it with a low pressure high viscosity gas, such as carbon dioxide. The gas travels through the duct 341 and exits at the inner annular outlet 335.

The inner annular outlet 335 is at a step 831 lower than the step 830 at which the aperture opens out at. The low viscosity gas serves as seal to prevent the high viscosity gas discussed from entering the microvacuum chamber created in the gap between the step 831 and the surface 166 of the object 102. This microvacuum chamber is created in the manner discussed earlier for SPM probe 122-1. Moreover, a differential pressure chamber is created in the gap between the step 830 and the surface of the object. This is created in the same was as the microvacuum chamber just mentioned except that the high viscosity gas is introduced rather than a vacuum.

Additionally, the particle removal structure 342 includes an outlet 331 on the upper surface 140 of the fifth SPM probe 122-5, a duct 339 formed in the base 130 of the probe, and a middle annular inlet 337 on the lower surface 142 of the probe, as shown in FIGS. 27 and 35. The duct connects the outlet and the annular middle inlet so that they are in fluid communication with each other.

Referring again to FIGS. 1, 27, and 35, the outlet 331 of the particle removal structure 342 is connected to a corresponding connector tube 347. When the controller 114 controls the corresponding valve 346 of the fluid system 344 to open, a low pressure gas sink of the fluid system is in fluid communication with this outlet to draw the low pressure high viscosity and high pressure low viscosity gases in through the middle annular inlet 332 and the duct 339.

Specifically, the low pressure gas sink causes a high rate flow of the high pressure low viscosity gas from the outer annular outlet to the annular middle inlet. As a result, particles are swept up and removed from the upper surface 166 of the object 102 or calibration structure 128 by this high rate flow. Moreover, in order to increase the flow of the high viscosity gas, the step 832 is provided and is lower than the steps 831 and 830. This makes the gap 198 wider in this area so that the high viscosity gas can flow easier. An additional step could have been used for the middle annular inlet 337 to further increase the flow.

Furthermore, the low pressure gas sink causes a low rate of flow of the low pressure high viscosity gas from the inner annular outlet 335 to the middle annular inlet. As indicated earlier, this low rate flow acts as a buffer for the microvacuum chamber created in the gap 198 and prevents the high pressure low viscosity gas and the particles that it carries to enter this microvacuum chamber. Moreover, since the inner annular outlet is at a step 831 higher than the middle annular inlet 337, the flow of the high viscosity gas into the middle annular inlet is increased. And finally, the inner annular outlet 335 can serve as a gas bearing structure which operates like that of the gas bearing structure 402 discussed later.

In this way, the controller 114 can control the removal of particles from the upper surface 166 of the object 102 or calibration structure 128. This is done by selectively causing the valves 346 of the fluid system 344 to be opened during operation and/or calibration of the fifth SPM probe 122-5.

The particle removal structure 342 just described is particularly useful for performing repairs and/or fabrication steps on semiconductor wafers and fabrication masks and thin film magnetic microstructure. In this way, any particles that can potentially damage or effect the performance of the wafer, mask, or magnetic microstructure can be easily removed from its surface during a repair and/or fabrication step.

Finally, the particle removal structure 342 is particularly useful for performing repairs and/or fabrication steps in which material is removed from an object 102 when cuts are made with the fifth SPM probe 122-5. However, it can also be used when the fifth probe is simply used to make SPM measurements in the manner described earlier. Thus, those skilled in the art will recognize that the first to fourth SPM probes 122-1 to 122-4 described earlier may also be constructed with such a particle removal structure for removal of particles while making SPM measurements and/or SPM modifications.

Particle Removal with Sweeping Motion of SPM Probe 122-5

In addition, the SPM probe 122-5 may be used to sweep or collect debris particles resulting from a modification made with the probe to an area of the object 102 where they have no deleterious effect. Namely, they are swept to an area of the object where they do not obstruct inspection of the modification just made or further modification of the object in the area where the original modification was just made or in another area. Moreover, the collected debris particles may then be removed by a separate process, such as etching, or fixed in place by an adhesive or thermal fixing.

More specifically, after a modification is made with the SPM probe 122-5, the controller 114 controls the positioning system 103 so that sweeping motions of the SPM probe are made over the object 102. In doing so, the controller first controls the positioning system to position the tip 320 of the probe in the Z dimension so that it is just above or just contacts the surface 166 of the object while the sweeping motions are made. Then, the controller controls the positioning system so that the sweeping motions are made to remove the debris particles from the area where the modification was made. These motions include motions which follow a complex surface previously scanned or a surface calculated to be the result of the previous material removal activity. As discussed later, these sweeping motions can be made in 2-D (two dimensional) or 3-D (three dimensional).

The debris particles may be swept to an area where they will not obstruct further modifications to the object or inspection of the modification just made. These other modifications may be to the modification just made or in another area of the object. Moreover, they may be made using any of the SPM probes 122-1 to 122-18 in the manner discussed herein. Additionally, the inspections may be made with the other components 123 of the SPM system 100 separately or in conjunction with any of the SPM probes 122-1 to 122-18 also in the manner described herein.

The collected debris particles may be fixed to the object in an area where they will not affect the performance of the object as it is to be normally used. For example, the object 102 may be a semiconductor manufacturing mask. In this case, the SPM probe 122-5 may be used to perform a cut in some of the material of the mask, such as chrome. The resulting debris particles could then be swept to an area of the mask where the material can be fixed to the mask and not effect its performance when it is used in its normal environment. This may be done in several ways. For example, the other components 123 of the SPM system may include an adhesive mist source which sprays an adhesive mist onto the mask under the direction of the controller 114. The collected debris particles would then be adhesively fixed together on the mask. Alternatively, the other components of the SPM system may include a laser source that would under the control of the controller provide a laserbeam to heat the collected debris particles. These debris particles would then be fused together on the mask. This may also be done by heating the debris particles with the SPM probe 122-18 described later.

Furthermore, the debris particles may be removed from the object 102. In this case, the resulting debris particles would also be swept to an area of the mask where the material will not effect its performance when it is used in its normal environment. Then, the debris particles may be removed from this area. For example, in the case of a semiconductor manufacturing mask, the other components 123 of the SPM system 100 may include an acid bath station. The controller 114 would then control the object loader 115 described earlier to place the mask in the acid bath provided by the acid bath station. The concentration of the acid bath would be selected so that the acid bath dissolves the small debris particles but does not appreciably dissolve away the larger materials of the object. For example, the debris particles may be removed from chrome material on the mask. The acid bath would dissolve the small chrome debris particles away but would not appreciably dissolve the main chrome material of the mask.

As those skilled in the art will recognize, this sweeping technique may be used for any of the SPM probes 122-1 to 122-18 described herein.

Structure of SPM Probe 122-6

Figure 36:
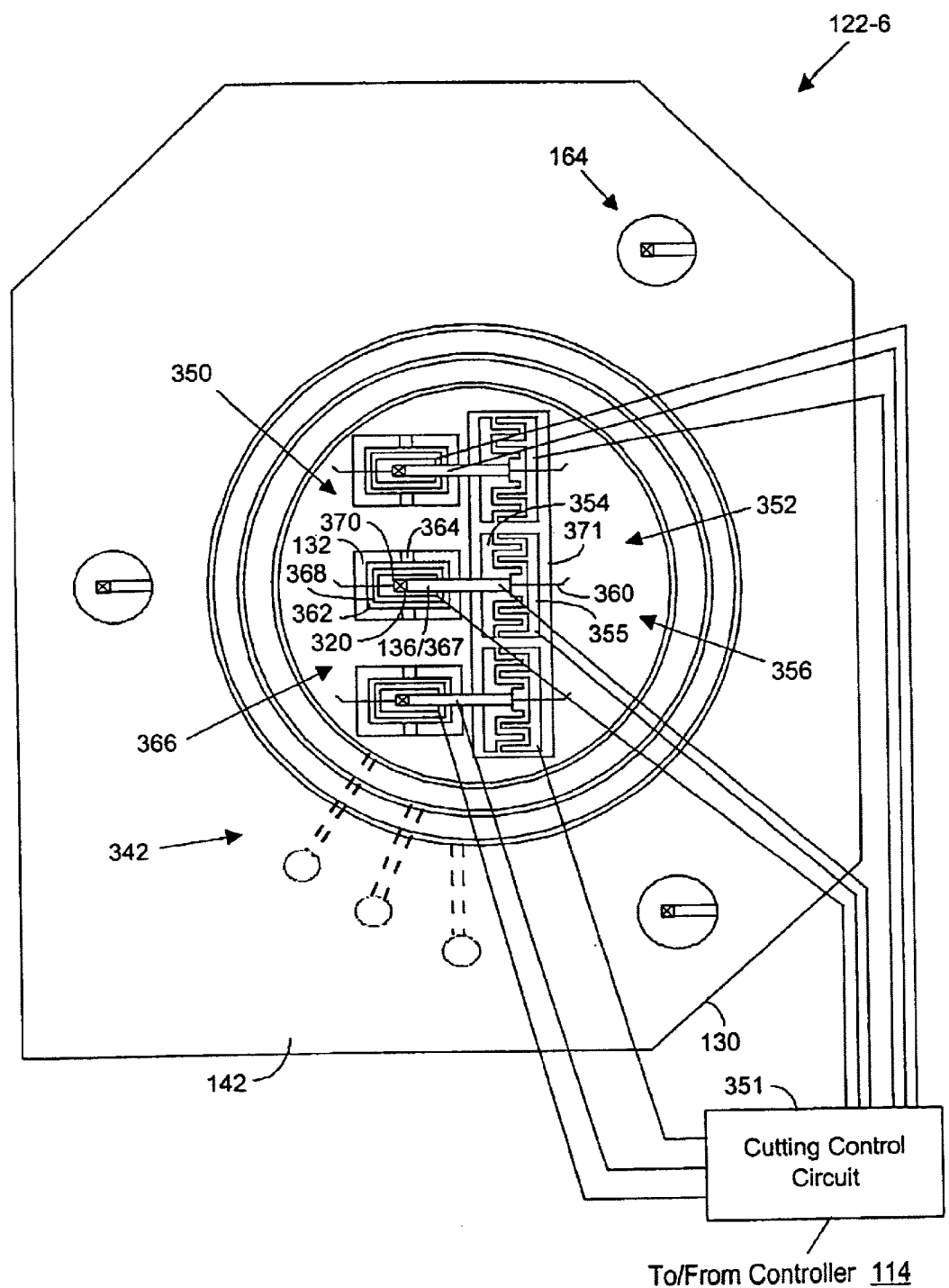
FIGS. 36 and 37 show different views of a sixth SPM probe of the SPM system of FIG. 1.
Figure 37:
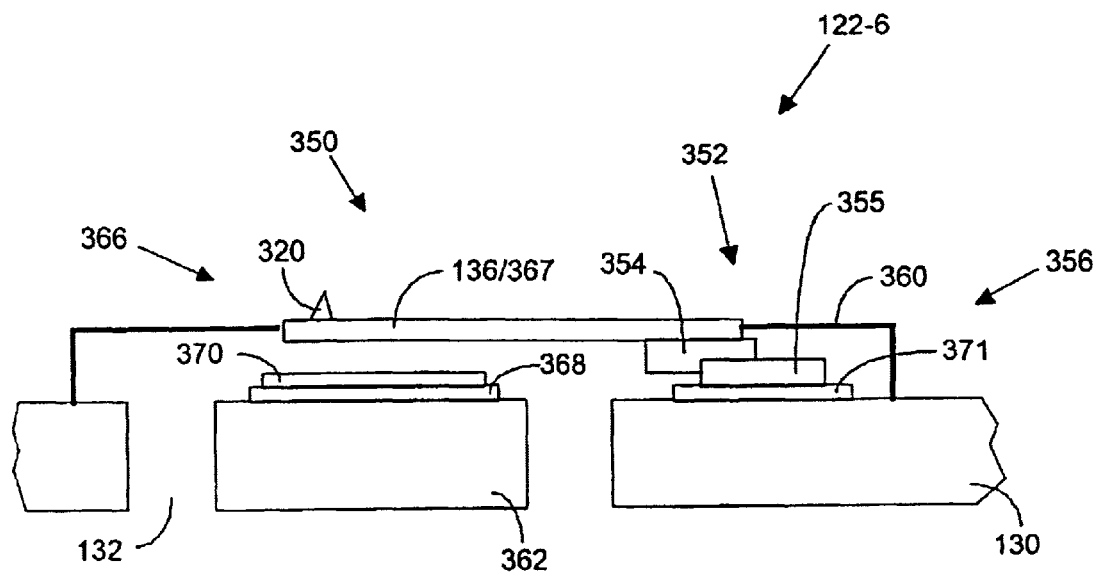

Referring now to FIGS. 36 and 37, there is shown a sixth microstructured SPM probe 122-6 for modifying the object 102 by making cuts in its material. The sixth probe includes several cutting tools 350. As with the fifth SPM probe 122-5, each cutting tool has a corresponding cantilever 136 and a corresponding tip 322 on one end of the cantilever. Alternatively, the tip may be one of the tips 138 and 238 of the first and second SPM probes 122-1 and 122-2. Furthermore, the base 130 and the particle removal structure 342 of the sixth probe are respectively constructed in the same manner as was described for the first and fifth probes.

However, the cantilever 136 of each cutting tool 350 is connected to a corresponding positioning system 352 for the tool instead of being directly connected to the base 130 of the probe. The positioning system for each cutting tool can position the corresponding cantilever, and therefore the corresponding tip 320, in one dimension with respect to the object 102 or one of the calibration structures 128. A fixed end of the cantilever is connected to a moveable comb structure 354 of the positioning system. The cantilever and the moveable comb structure are moveably suspended by a suspension system 356 under a stationary upper plate electrode 370. The suspension system comprises spring arms (or connectors) 360 that each have one end connected to the base 130. The other end of one of the spring arms is connected to the moveable comb structure or the fixed end of the cantilever and the other end of the other spring arm is connected to the free end of the cantilever. The fingers of the moveable comb structure are interdigitized with (i.e., aligned between) the fingers of a corresponding stationary comb structure 355. This stationary comb structure is formed on an insulating plate 371 and is therefore connected to the base via the insulating plate.

The moveable comb structure 354 of the positioning system 352 of each cutting tool 350 of the probe 122-6 is moveable in one dimension to enable the tool to be positioned in that dimension. The components of the SPM system 100 include a cutting control circuit 351 to do this. Specifically, the pair of corresponding moveable and stationary comb structures 354 and 355 of the cutting tool forms an electrostatic (i.e., capacitive) comb drive of the type described earlier for the nanoforce balance 128-3. Thus, when the cutting control circuit applies a differential voltage across the moveable and stationary comb structures, their comb fingers interact electrostatically (i.e., capacitively) with each other and the moveable comb structure moves linearly with respect to the stationary comb structure. Since one end of the cantilever 136 of each tool is connected to the moveable comb structure, the cantilever may be moved so as to position the tip 320.

Furthermore, each cutting tool 350 of the sixth SPM probe 122-6 has a tip deactuator 366 for removing the tip 320 from the object after a cut is made with the cutting tool. The tip deactuator includes an insulating plate 368 on a support platform 362 of the base 130, the upper plate electrode 370 on the insulating plate, and a moveable plate electrode 367. The support platform is suspended in a corresponding aperture 132 by corresponding bridges 364 of the base. In this embodiment, the cantilever comprises a conductive material, such as polysilicon which is made to be conductive, so that the cantilever actually comprises the moveable plate electrode. Alternatively, the tip deactuator may include an insulating plate formed on the cantilever with the moveable plate electrode being formed on the insulating plate. In either case, the moveable plate electrode and the upper plate electrode form a capacitor. Thus, when the cutting control circuit 351 applies an appropriate voltage is applied between the moveable plate electrode and the upper electrode plate, the cantilever can be electrostatically (i.e., capacitively) pulled toward the electrode plate.

The base 130, the moveable comb structure 354, the cantilever 136 and the spring arms 360 of each cutting tool 350 may be integrally formed together and comprise a semiconductor material, such as polysilicon, that is conductive. In this way, the moveable comb structure and the cantilever (i.e., the moveable plate electrode 367) may be electrically connected together for convenience. Similarly, the stationary comb structure 355 may also comprise such a semiconductor material. The plate electrodes may comprise a conductive material, such as polysilicon or tungsten. And, the insulating plates 371 and 368 may comprise an insulating material, such as silicon dioxide.

Probe Loading and Unloading, Tip Activation and Deactivation, Calibration, Vacuum Operation, and Particle Removal Operation of SPM Probe 122-6

The sixth SPM probe 122-6 may be loaded onto and unloaded from one of the scanning heads 120 in the same ways as were described earlier for the first probe. In addition, the tip 320 of each cutting tool 322 of the sixth probe may have its position calibrated and its profile examined in the ways described earlier for the first probe, except that the positioning of the tip of the sixth probe would not be optically calibrated. Furthermore, optical images would be produced during operation and/or calibration of the sixth probe by the imaging optics 226 in the manner discussed earlier for the first probe. During operation and/or calibration, a microvacuum chamber in the gap 198 between the sixth probe and the object 102 or calibration structure 128 may be established in any of the ways described earlier for the first probe with the apertures 132 and the gap sensors 164 of the sixth probe. Finally, particles can be removed during operation and/or calibration using the particle removal structure 342 of the sixth probe in the manner described earlier for the fifth SPM probe 122-5.

SPM Modifications with SPM Probe 122-6

Referring again to FIG. 1, the SPM probe 122-6 may be used to modify the object 102 by making a cut in the object to remove material from the object. This is done when the user instructs the controller 114 with the user interface 116 to use the probe to perform this operation. The controller controls loading of the probe onto the scanning head 120. Then, the controller controls the positioning system 103 to lower the activated tip onto the target area of the object such that the activated tip pushes down on the target area with sufficient force to make a desired cut in the material of the object when the tip is dragged across it. Then, referring to FIG. 36, the controller controls the cutting control circuit 351 to cause the positioning system 352 of the cutting tool to move the tip in the manner described earlier so that it is dragged across the object to make the desired cut The controller then controls the cutting control circuit to cause the tip deactuator 366 of the cutting tool to raise the tip from the cut in the manner described earlier.

Moreover, the activated tip 320 of the SPM probe 1226 may be calibrated for the amount of force with which it pushes down on the object 102 in performing a cut using the force balance 128-3 in the manner described earlier for the first SPM probe 122-1. Thus, by using the force calibration table created for the tip during this calibration, a precise known force can be applied to the object 102 by the tip. As a result, a precise cut in the material of the object can be made to remove material from the object.

As with the fifth SPM probe 122-5, the sixth SPM probe 122-6 may have multiple cutting tools 350 with tips 320 with different cutting angles and crystal orientations. In this case, the controller 114 selects the cutting tool with the appropriate cutting angle and crystal orientation to perform the desired cut. And, like the fifth SPM probe 122-5, the sixth SPM probe 122-6 is particularly useful in repairing and/or performing fabrication steps on a semiconductor wafer or fabrication mask or a magnetic microstructure.

Structure of SPM Probe 122-7

Figure 39:
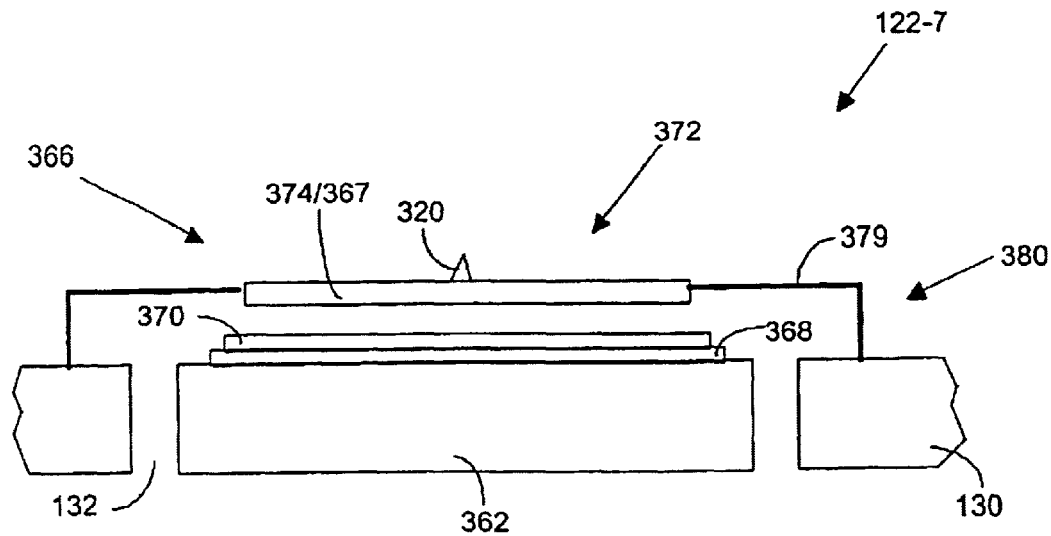
FIGS. 38 and 39 show different views of a seventh SPM probe of the SPM system of FIG. 1.
Figure 38:
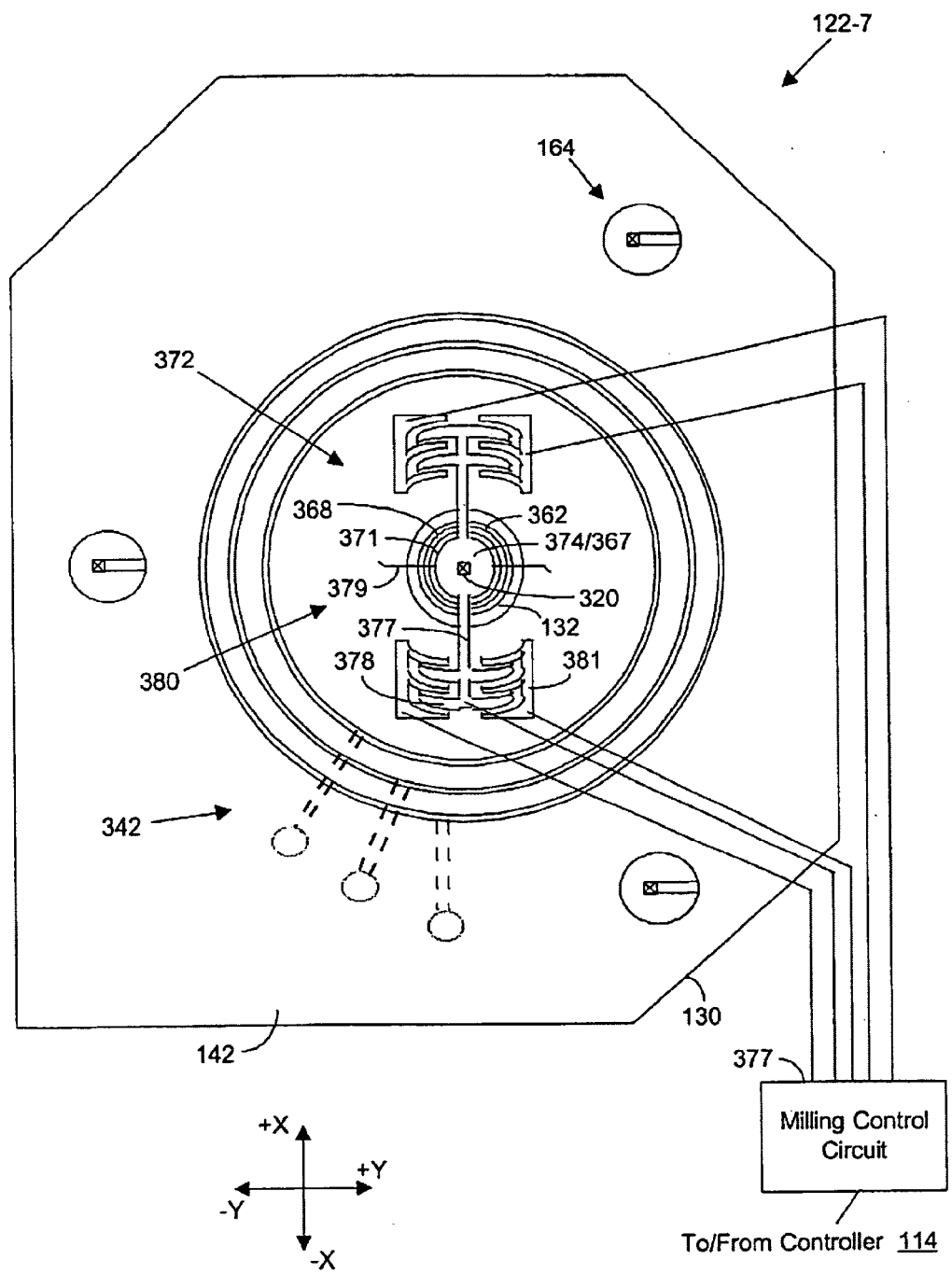

Referring now to FIGS. 38 and 39, there is shown a seventh microstructured SPM probe 122-7 for modifying the object 102 by milling the material of the object. The seventh probe includes a rotary milling tool 372. The milling tool has a tip 320 like that of each of the cutting tools 350 of the fifth SPM probe 122-5. Alternatively, the tip may be one of the tips 138 and 238 of the first and second SPM probes 122-1 and 122-2. Furthermore, the base 130 and the particle removal structure 342 of the seventh probe are respectively constructed in the same manner as was described for the first and fifth probes.

However, unlike the cutting tools 350 of the fifth SPM probe 122-5, the milling tool 372 has a milling platform 374. The tip 320 of the milling tool is centrally located on the milling platform. The milling platform is connected to a rotary movement system 376 of the milling tool.

The milling platform 376 has support arms 377 that extend in opposing directions (e.g., +Y and -Y) In the same dimension (e.g., Y). The rotary movement system 376 comprises two moveable comb structures 378 connected to each support arm of the milling platform. The milling platform and the moveable comb structures are moveably suspended by a suspension system 380 over a stationary upper plate electrode 370 on the base 130. The suspension system comprises spring arms (or connectors) 379 which each have one end connected to the milling platform and another end connected to the base 130.

Each of the moveable comb structures 378 has a set of curved fingers that extend out from the corresponding support arm 377 in two directions (e.g., +X or -X and -Y or +Y). For each moveable comb structure, the rotary movement system 376 has a corresponding stationary comb structure 381 with curved fingers that extend in the opposite directions (e.g., -X or +X and +Y or -Y). Each set of curved fingers of each moveable comb structure is interdigitized with (i.e., aligned between) the curved fingers of the corresponding stationary comb structure. The stationary comb structures are formed on insulating plates 386 and are therefore connected to the base via the insulating plates.

Each of the moveable comb structures 378 of the rotary movement system 376 is moveable in an arc to enable the milling platform 376 to be rotated. Specifically, each stationary comb structure 381 and the corresponding moveable comb structure 378 forms an electrostatic (i.e., capacitive) comb drive of the type described earlier for the nanoforce balance 128-3. Thus, by applying a differential voltage across this pair of corresponding moveable and stationary comb structures, their comb fingers interact electrostatically (i.e., capacitively) with each other and the moveable comb structure moves in one direction (e.g., clockwise or counter clockwise) in an arc with respect to the stationary comb structure.

Since the moveable comb structures 378 are connected to the support arms 377 of the milling platform 372, the milling platform may be rotated in this manner to perform milling operations with the tip 320 of the milling tool. In order to do so, the components of the SPM system 100 further include a milling control circuit 377. The controller 114 causes the milling control circuit to alternatingly apply voltages to the pairs of corresponding moveable and stationary comb structures that cause the milling platform to rotate in the counter clockwise direction and voltages to the pairs of corresponding moveable and stationary comb structures that cause the milling platform to rotate in the clockwise direction. As a result, the milling platform oscillatingly rotates back and forth in the clockwise and counter clockwise directions.

In an alternative embodiment, the milling tool 372 could include more than two moveable comb structures 378. In this case, the moveable comb structures would be disposed equidistant from one another around the milling platform 376.

Furthermore, the milling tool 372 has a tip deactuator 366 for removing the tip 320 from the object after a milling operation is performed. The tip deatuator is constructed and operates like the one described earlier for the each cutting tool 350 of the sixth SPM probe 122-6, except that the milling platform 376 comprises the moveable plate electrode 367. In an alternative embodiment, the tip deactuator may include an insulating plate formed on the milling platform with the moveable plate electrode being formed on the insulating plate.

The base 130, the milling platform 372, the moveable comb structures 378, and the spring arms 379 may be integrally formed together and comprise a semiconductor material, such as polysilicon, that is conductive. In this way, the moveable comb structures and the milling platform (i.e., the moveable plate electrode 367) may all be electrically connected together for convenience. Furthermore, the stationary comb structures 384 may also comprise such a semiconductor material. The upper plate electrode 370 may comprise a conductive material, such as polysilicon or tungsten. And, the insulating plates 368 and 386 may comprise an insulating material, such as silicon dioxide.

Probe Loading and Unloading, Calibration, Vacuum Operation, and Particle Removal Operation of SPM Probe 122-7

The seventh SPM probe 122-7 may be loaded onto and unloaded from one of the scanning heads 120 in the same ways as were described earlier for the first probe. In addition, the tip 320 of the milling tool of the seventh probe may have its position calibrated and its profile examined in the ways described earlier for the first probe, except that the positioning of the tip of the seventh probe would not be optically calibrated. Furthermore, optical images would be produced by the imaging optics 226 during operation and/or calibration of the seventh probe in the manner discussed earlier for the first probe. During operation and/or calibration, a microvacuum chamber in the gap 198 between the seventh probe and the object 102 or calibration structure 128 may be established in any of the ways described earlier for the first probe with the aperture 132 and the gap sensors 164 of the seventh probe. Finally, particles can be removed during operation and/or calibration using the particle removal structure 342 of the seventh probe in the manner described earlier for the fifth SPM probe 122-5.

SPM Modifications with SPM Probe 122-7

Referring again to FIG. 1, the seventh SPM probe 122-7 may be used to modify the object 102 by performing milling operations on the object to remove material from the object. This is done when the user instructs the controller 114 with the user interface 116 to use the probe to perform this operation. The controller controls loading of the probe onto the scanning head 120. Then, the controller controls the positioning system 103 to lower the activated tip onto the target area of the object such that the activated tip pushes down on the target area with sufficient force to perform the desired milling operation in the material of the object when the tip is rotated back and forth. Then, referring to FIG. 38, the controller controls the milling control circuit 377 to cause the rotary movement system 376 of the milling probe to oscillatingly rotate the milling platform back and forth (i.e., clockwise and counter clockwise) in the manner described earlier so that the tip is rotated back and forth and performs the desired milling operation. The controller then controls the milling control circuit to cause the tip deactuator 366 of the milling tool to raise the tip from the milled material of the object in the manner described earlier.

Moreover, the activated tip 320 of the SPM probe 122-6 may be calibrated for the amount of force with which it pushes down on the object 102 in performing a cut using the force balance 128-3 in the manner described earlier for the first SPM probe 122-1. Thus, by using the force calibration table created for the tip during this calibration, a precise known force can be applied to the object 102 by the tip. As a result, a precise cut in the material of the object can be made to remove material from the object.

Structure of SPM Probe 122-8

Figure 40:
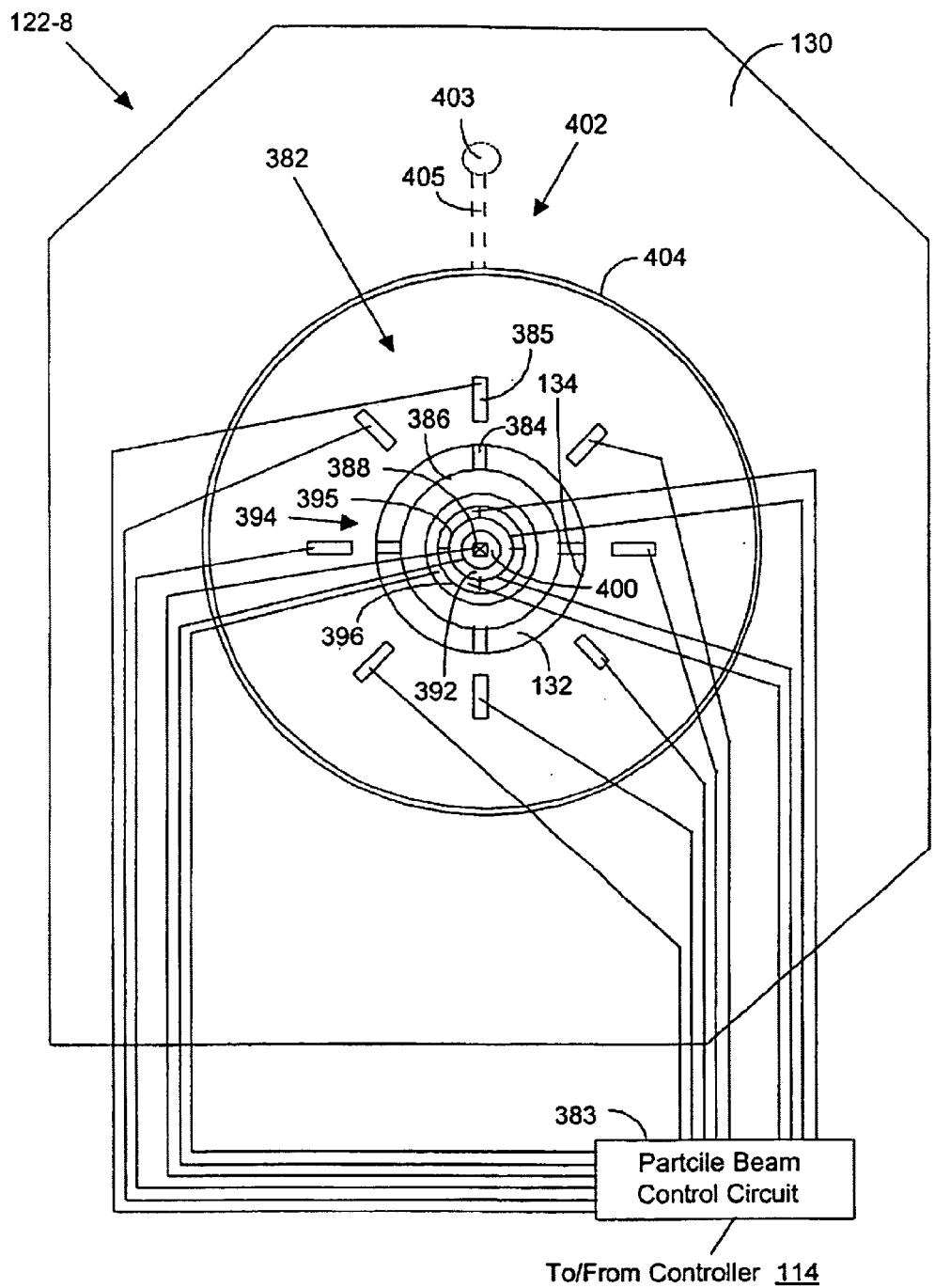

Turning now to FIG. 40, there is shown an eighth SPM probe 122-8 for use in making SPM measurements of the object 102 and/or SPM modifications of the object 102. In this case, the SPM measurements and the SPM modifications are made in response to radiation in the form of charged particles that are produced by the probe and directed at the object.

More specifically, the eighth SPM probe 122-8 has an e-beam tool 382 for generating an e-beam used in making the SPM measurements and the SPM modifications. The tool is suspended in the aperture 132 of the base 130 of the probe within the inner perimeter surface 134 so that the tool is between the lower and upper surfaces 142 and 140 of the base to prevent it from being damaged. Otherwise, the base has the same basic shape and construction as the base discussed for the first probe 122-1.

Figure 41:
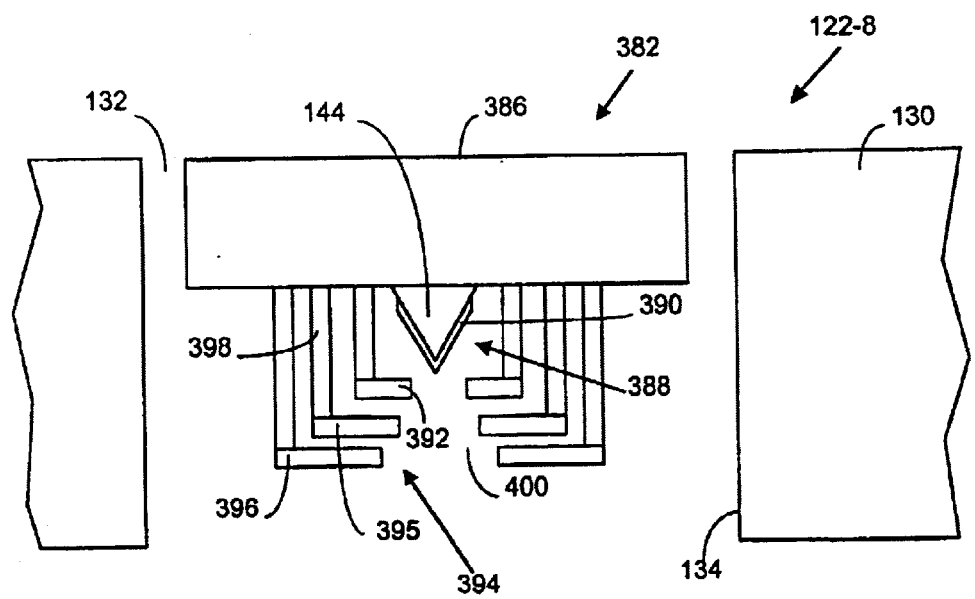
FIGS. 40 to 43 show different views and embodiments of an eight SPM probe of the SPM system of FIG. 1.

Referring to FIG. 41, the e-beam tool 382 includes a support platform 386 that is suspended in the aperture by the bridges 384 of the tool. The bridges connect the support platform to the inner perimeter surface 134 of the base 130 of the SPM probe 122-8. The support platform and the bridges may be separately formed or may be an integral portion of the base. A tip 388 is formed on the support platform and is constructed so as to emit an e-beam.

For example, the tip 388 may be made to be a field emissively conductive so that it can emit an e-beam. Thus, it may have a field emissive conductive coating 390 formed over the tip's core material 144. This coating may comprise conductive diamond, silicon carbide, carbon nitride, diamond like carbon, or other suitable conductive material and may be formed in the ways described earlier for the probes 122-1 to 122-3. In the case of diamond, this may be formed in the manner described in "Growth of Diamond Particles on Sharpened Silicon Tips for Field Emission", "Growth of Diamond Particles on Sharpened Silicon Tips", "Mold Growth of Polycrystalline Pyramidal-Shape Diamond for Field Emitters" referenced earlier. Thus, an e-beam is produced when an e-beam control circuit 383 applies a suitable voltage across the field emissive coating 390 and the accelerating electrode 392 of the e-beam tool 382. The e-beam control circuit is one of the other components of the SPM system 100.

The particle beam tool 382 also includes an accelerating electrode 392, a steering electrode assembly 394, and a collection electrode 396 that are all formed on insulating support structures 398 of the tool. The insulating support structures support the accelerating electrode, the steering electrodes 395 of the steering electrode assembly, and the collection electrode so that the accelerating electrode is disposed below the field emissive coating 390 of the tip 388, the steering electrodes are disposed below the accelerating electrode, and the collection electrode is disposed below the steering electrodes. The accelerating, steering, and collection electrodes may comprise a conductive material, such as polysilicon or tungsten, while the insulating support structures comprise an insulating material, such as silicon dioxide.

Turning back to FIG. 40, the steering electrodes 395 are electrically isolated from one another. In this way, the abeam can be steered (i.e., focused or directed) in selected directions by causing the e-beam control circuit 383 to selectively apply separate voltages to these steering electrodes. As those skilled in the art will recognize, a single steering electrode could also be used to steer the e-beam.

Furthermore, referring back to FIG. 41, there are apertures 400 in the accelerating, steering, and collection electrodes 392, 395, and 396 through which the e-beam passes to allow the e-beam to strike the object 102. In response, secondary electrons are reflected and/or emitted by the object and strike the collection electrode so as to be collected by the collection electrode.

Turning again to FIG. 40, the SPM probe 122-8 may also include steering magnets 385 that each comprise a coil around a magnetic material. The steering magnets are fixed to the lower surface 142 of the base 130 of the probe and are spaced equally apart. As a result, the e-beam can be further steered by selectively applying separate currents to the steering magnets to selectively recurve or bend the e-beam.

SPM Inspections with SPM Probe 122-8

Figure 42:
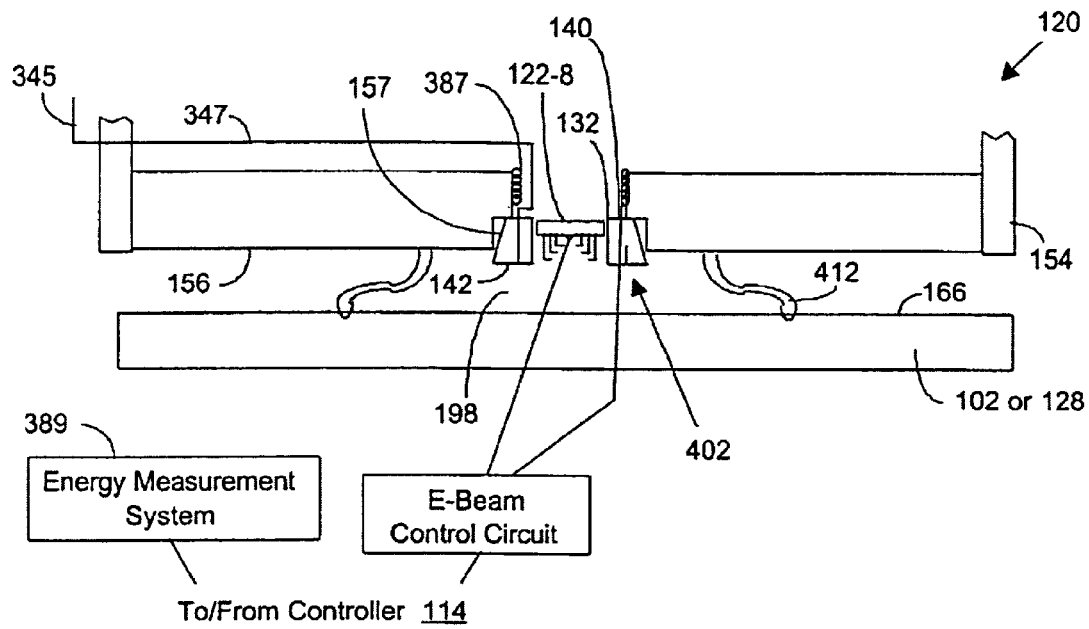

As mentioned earlier, the SPM probe 122-8 can be used to make radiation measurements in order to inspect the object 102. Referring to FIG. 42, in doing so, the controller 114 controls the loading and unloading of the probe from a scanning head 120 in the same way as was discussed for the first probe 122-1. However, the components of the SPM system 100 in this embodiment may also include a steering coil 387 fixed to the probe holder 156 of the scanning head. The steering coil is also used to selectively steer the e-beam by providing it with a selected current to cause the e-beam to have a spiral trajectory with a radius that is a function of the current.

Then, the controller 114 controls the positioning system 103 to position the probe 122-8 for a scan of the object 102. Referring back to FIGS. 40 to 42, at each scan point, the controller causes the e-beam control circuit 383 to produce an e-beam in the manner discussed earlier. At the same time, it causes the e-beam control circuit to apply suitable voltages and currents to the steering electrodes 394, the steering magnets 385, and the steering coil 387 to selectively steer the e-beam at the object 102. In this way, the e-beam can be steered at areas of the object 102, such as the sides and undersides of the object, that are difficult to reach. Then, when the e-beam interacts with the object 102, it causes secondary electrons to be reflected and/or emitted back to the collection electrode 396. This causes a current in the collection electrode which represents the electrons that contact the collection electrode. This current is measured by the e-beam control circuit as a radiation measurement of the electrons collected by the collection electrode. The radiation measurements made at all of the scan points may be collected and used by the controller to produce an image of the object like that made with a conventional scanning electron microscope.

Additionally, as discussed earlier, the SPM system 100 also include a radiation measurement system 389, as shown in FIG. 42. At each scan point, the radiation measurement system is used to detect and measure radiation, such as secondary charged particles or electromagnetic energy, reflected and/or emitted by the object 102 in response to the particle beam striking it. Specifically, the radiation measurement system makes a radiation measurement of the radiation it detects at the scan point. For example, this radiation measurement may be a spectrophotometric measurement of the spectrum of wavelengths of the detected radiation. In response, the radiation measurement system provides the radiation measurement to the controller 114 and the controller uses the radiation measurements collected over the scan to generate inspection data in the manner discussed earlier.

Figure 43:
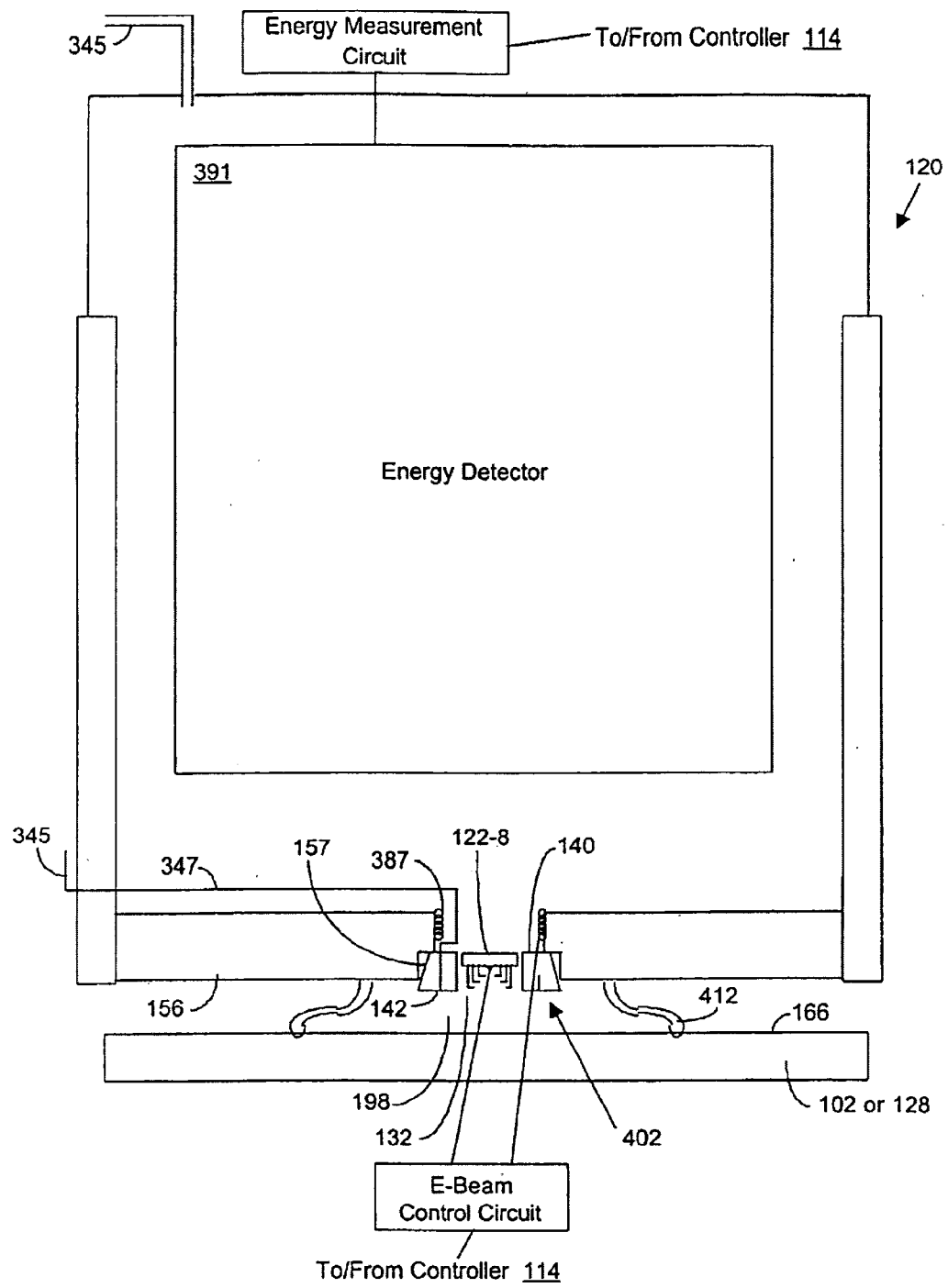

In an alternative embodiment shown in FIG. 43, the radiation measurement system 389 may comprise a radiation detector 391 that is located in the scanning head 120. In this case, the radiation detector may comprise a semiconductor radiation detector as described in "Semiconductor Detectors" referenced earlier. However, in this embodiment, the imaging optics 226 are replaced by the radiation detector and the radiation measurement system also includes a radiation measurement circuit 393. Thus, at each scan point, the radiation detector is used to detect radiation emitted by the object 102 in response to the e-beam striking it. The radiation measurement circuit than makes a radiation measurement of the detected radiation and provides it to the controller 114. The radiation measurements collected over the scan are then used by the controller to generate inspection data in the manner just discussed.

The radiation measurements made with the eighth SPM probe 122-8 and the radiation measurement system 398 are particularly useful for inspecting a lithographic structure, such as a semiconductor fabrication mask. Such a lithographic structure is used to expose only a certain portion of a replicable structure to electrons with which it is irradiated during fabrication. Thus, after a repair and/or fabrication step has been performed on the lithographic structure using any of the other SPM probes 122-1 to 122-8 to 122-18 discussed herein, the eighth probe can be used in conjunction with the radiation measurement system to emulate the way in which such a replicable structure would be exposed to electrons by the lithographic structure during actual fabrication.

Specifically, at each scan spot, the controller 114 causes the eighth SPM probe 122-8 to direct a e-beam at the lithographic structure. The radiation measurement system would then detect the resulting radiation that would be projected by the lithographic structure onto a replicable structure or that would be reflected and/or emitted by the lithographic structure. From the detected radiation, the controller 114 generates a patterned image of the detected radiation. Thus, this serves to emulate the way in which the lithographic structure would expose such a replicable structure to radiation during actual fabrication. The controller then compares the generated patterned image with a recorded target patterned image to generate repair and/or fabrication data that identifies any further repair and/or fabrication step to be performed on the lithographic structure. The entire process is then repeated until the generated patterned image has converged to the target patterned image within a specified tolerance level.

SPM Modifications with SPM Probe 122-8

The SPM probe 122-8 can also be used to make SPM modifications of the object 102 using the e-beam it generates. Specifically, the user instructs the controller 114 with the user interface 116 to use the probe to make an SPM modification to the object 102. In doing so, the controller controls the positioning system 103 and the e-beam control circuit 383 in causing the probe to generate an e-beam that strikes the object at a selected spot. This is done in the same way as described earlier. However, in this case, e-beam can then be used to heat the material of or remove material from the object. Or, it can be done to make chemical changes in the object. In this regard, an electron beam can provide the energy and/or free electrons necessary to cause chemical changes or induce chemical combinations in materials. For instance an electron beam can break bonds in proteins (including DNA and RNA) or polymers like plastics, oils or cause solid, liquid or gaseous material to change chemical states or go into combinations with materials much like heat or light can be used to make such changes. Typically an e-beam is more energetic and site specific then heating or electromagnetic exposure (even at x-ray energies because of the difficulty of focusing or controlling very energetic photons such as x or gamma radiation.

Calibration of SPM Probe 122-8

The position of the e-beam tool 382 of the SPM probe 122-8 may be calibrated and its profile examined using the AFM probe 131 and SEM probe 133 of the calibration structure 128-1 in the manner discussed earlier for the first SPM probe 122-1. Furthermore, the position of the e-beam tool 382 of the SPM probe 122-8 may be calibrated using the calibration structure 128-2 shown in FIG. 11. This calibration structure 128-2 may include one or more reference materials 188 on the insulating material 199 on the base 190 of the reference structure. Each reference material has a precisely known position with respect to the reference location. And, each reference material may comprise a material that has known radiation properties for when electrons strike it. For example, this may be a material, such as bismuth, which produces a known type of radiation, such as x-rays, in response to electrons striking it.

Turning again to FIG. 1, in this case, the controller 114 can calibrate the position of the e-beam tool 382 of the SPM probe 122-8 prior to making the radiation measurements just described. This is done by controlling the positioning system 103 to attempt to position the e-beam tool over one of the reference materials 188 of the calibration structure 128-2. Then, referring to FIGS. 40 to 43, the controller controls the making of an e-beam with the e-beam tool in the manner discussed earlier. From the radiation measurements made by the radiation measurement system 389, the controller generates a spectrum of the measured wavelengths (i.e., frequency spectrum) and compares the generated spectrum with a stored known reference spectrum of wavelengths for radiation that results when an e-beam strikes the reference material 188 If they match, this means that e-beam tool was positioned directly over the reference material. Alternatively, the controller may cause the e-beam to be chopped or modulated and lock on the results from the x-ray detector based on this chopping or modulation. This is done in the same manner discussed earlier for chopping or modulating the light emitted from the tip 138 of the SPM probe 122-1. When a peak in the intensity is detected by the controller, then the e-beam tool is positioned directly over the reference material. Thus, in a closed feedback loop, the e-beam tool is positioned, the e-beam is produced, the wavelengths or the intensity of the resulting radiation are measured, and the generated and reference spectrums are compared in the manner just described until it is determined by the controller that the e-beam tool is in fact positioned over the reference material. Once this occurs, the positional offset of the e-beam tool at the known position of the reference material is determined. Based on this positional offset, the precise positioning of the e-beam tool with respect to the reference location is then calibrated. If there are multiple reference materials, the results of the calibrations computed for all of the reference materials may be combined to provide a weighted or averaged calibration of the position of the e-beam tool.

Figure 52:
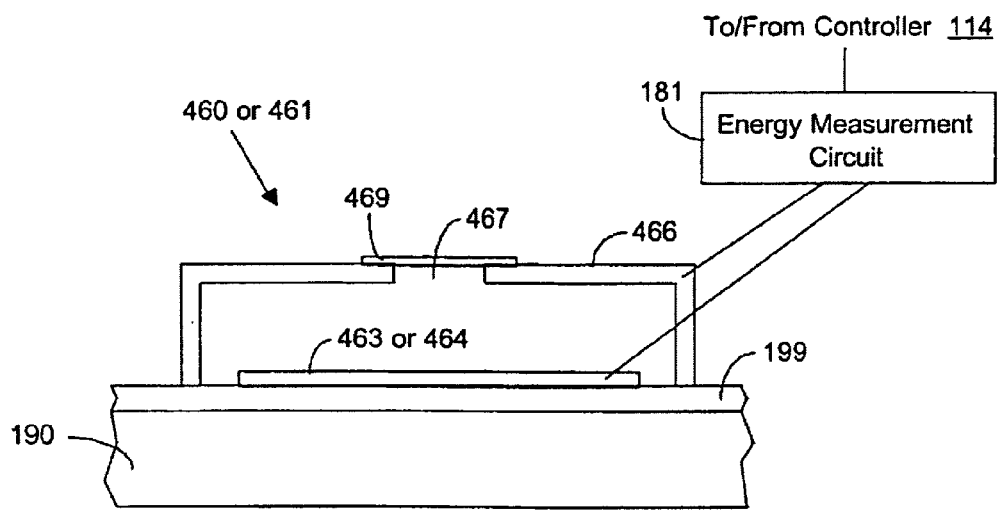

Referring to FIGS. 11 and 52, as mentioned earlier, the calibration structure 128-2 may include one or more radiation detection devices 460. Turning again to FIG. 1, in this case, the controller 114 calibrates the position of the e-beam tool 382 of the SPM probe 122-8 by controlling the positioning system 103 to attempt to position the e-beam tool over one of these radiation detection devices. Then, referring to FIG. 42, the controller causes the e-beam tool to produce an e-beam in the manner just discussed. The radiation detected by the radiation detector 464 of this radiation detection device is measured by the radiation measurement circuit 181. The controller analyses the measurement to determine if the radiation detection device in fact detected the electrons of the e-beam generated by the e-beam tool. Thus, in a closed feedback loop, the e-beam tool is positioned, the e-beam is produced, and the measurement from the radiation measurement circuit is analyzed in the manner just described until it is determined by the controller that the e-beam tool is in fact positioned over the radiation detection device. Once this occurs, a positional offset is computed and the precise positioning of the e-beam tool with respect to the reference location is then calibrated based on the positional offset in the manner described earlier. If there are multiple radiation detection devices 460, the results of the calibrations computed for all of these radiation detection devices may be combined to provide a weighted or averaged calibration of the position of the e-beam tool 382.

Referring to FIGS. 11 and 52, the calibration structure 128-2 may further include one or more radiation detection devices 461. Each of these radiation detection devices is constructed like each radiation detection device 460 described earlier, but includes instead a radiation detector 464 for detecting radiation in the form of charged particles, such as ions, electrons, protons, or alpha particles, that pass through the aperture 467 of the aperture structure 166. Thus, this radiation detector may simply comprise a collection electrode for collecting such charged particles. Then, the position of the e-beam tool is done in the same manner as just described for the radiation detectors 460, except that it is done with radiation measurements of the electrons of the e-beam that are collected by the collection electrode. These measurements are made by the radiation measurement circuit 181.

The radiation measurements of electrons collected with the collection electrode 396 of an e-beam tool 382 of the SPM probe 122-8 can also be used by the controller 114 to calibrate the e-beam tool for positioning. This is done by scanning the probe over the first calibration structure 128-1 to produce an image of the first calibration structure 128-1 from the radiation measurements made at the scan points. This produced image is then compared with a stored reference image of the calibration structure which was produced similarly using a reference particle beam tool that was precisely scanned (or positioned) over the calibration structure with respect to the reference location of the SPM system 100. The images are compared to determine the positional offset between them. Based on the determined positional offset, precise positioning of the e-beam tool with respect to the reference location is then calibrated.

Vacuum Operation with Gas Bearing Structure for Maintaining Gap

As shown in FIGS. 40 to 42, the eighth SPM probe 122-8 has an aperture 132. Thus, a microvacuum chamber in the gap 198 between the eighth probe and the object 102 or calibration structure 128 may be established during operation of the probe in a similar manner as described for the first SPM probe 122-1. Thus, the object 102 or calibration structure 128 can be effectively irradiated with the e-beam produced by the eighth probe without the danger of the e-beam colliding with other particles.

But, for the eighth SPM probe, the gap 198 may be set with a gas bearing structure 402 formed in the base 130 of the probe. As shown in FIG. 40, the gas bearing structure comprises an inlet 403, an annular outlet (or opening) 404, and a duct 405 for providing gas received at the inlet to the outlet.

Referring to FIG. 1, as mentioned earlier, the components of the SPM system 100 include a fluid supply/sink system 344 and corresponding flexible tubes 345 for each scanning head 120. The fluid supply/sink system includes a corresponding valve 346 for each flexible tube so that each flexible tube is connected to the fluid supply/sink system via the corresponding valve. As shown in FIG. 42, one of the flexible tubes is connected to a corresponding connector tube 347 of each of the scanning heads. Referring to FIG. 40, this connector tube is connected to the inlet 403 of the gas bearing structure 402 of the SPM probe 122-8.

Referring now to FIGS. 1, 40, and 42, when the controller 114 controls the corresponding valve 346 of the fluid supply/sink system 344 to open, a gas source of the fluid supply/sink system is in fluid communication with the gas bearing structure 402. This gas source provides a gas that enters the inlet 403, travels through the duct 405, and exits at the outlet 404. The pressure of the exiting gas establishes a gas bearing between the lower surface 142 of the base 130 of the probe and the upper surface 166 of the object 102 or calibration structure 128. This pressure may be approximately 1.1 atmospheres and is sufficient to maintain the width of the gap 198.

Furthermore, the object 102 may comprise a small free moving or partially constrained specimen, such as a micromachine or biological cell or material, and a flat specimen support structure, such as microscope slide, on which the specimen is located. In this case, the microvacuum chamber is created in the gap 198 between the SPM probe 122-8 and the specimen support structure. The annular outlet 404 of the gas bearing structure 402 and the aperture 132 can be selected so that the diameter of the specimen is smaller than the diameter of the annular outlet. In this way, the specimen is kept centered at a fixed position on the specimen support structure. Furthermore, in the case where the diameter of the specimen is larger than the diameter of the annular outlet, the specimen can still be kept centered and in a fixed position on the specimen support structure by the pressure of the gas exiting the outlet. Thus, the SPM system 100 may include multiple SPM probes 122-8 with annular outlets and apertures of different diameters for different types of objects that are to be inspected or modified.

In alternative embodiment, multiple outlets could be used rather than the single annular outlet 405. In this case, the multiple outlets could be arranged in a triangular fashion. In this way, the maintenance of the width of the gap 198 would be triangulated.

Referring back to FIG. 1, the components of the SPM system 100 also includes a valve 310 for each flexible tube 307 connected to a scanning head 120. Thus, by controlling the valve, the pressure of the gas that exits the outlets 304 of the gas bearing structure can be precisely controlled by the controller 114. In this way, the controller can precisely control the width of the gap 198.

As those skilled in the art will recognize, the SPM probes 122-1 to 122-7 described earlier could also be constructed with a gas bearing structure 402 in order to establish a microvacuum chamber in the gap 198. Conversely, the microvacuum chamber in the gap 198 for the eighth SPM probe 122-8 could be established instead in the manner described earlier for the first SPM probe 122-1. In this case, the eighth probe would include the gap sensors 164 discussed earlier. Furthermore, the eighth probe could have a particle removal structure 342 as described earlier for the fifth SPM probe 122-5. In this case, referring to FIG. 27, the inlet 332, the duct 340, and the outer annular outlet 336 or the inlet 330, the duct 341, and the inner annular outlet 335 could be used as the gas bearing structure 402.

Vacuum Operation with Conformal Seal

Referring to FIG. 42, in alternative embodiment, a conformal seal 412 could be used to establish the microvacuum chamber in the gap 198. The conformal seal could be attached to the probe holder 156 of the scanning head 120 or to the SPM probe 122-8 itself. The conformal seal would create a seal between the lower surface 142 of the base 130 of the probe and the upper surface 166 of the object 102 or calibration structure 128. This would enable the microvacuum chamber to be established in the gap without the need of maintaining the precise width of the gap as is done using the gap sensors 164 or the gas bearing structure 402 discussed earlier. As with the gas bearing structure, the conformal seal could also be used in order to establish a microvacuum chamber in the gap 198 for the SPM probes 122-1 to 122-7 described earlier.

Structure of SPM Probe 122-9

Figure 44:
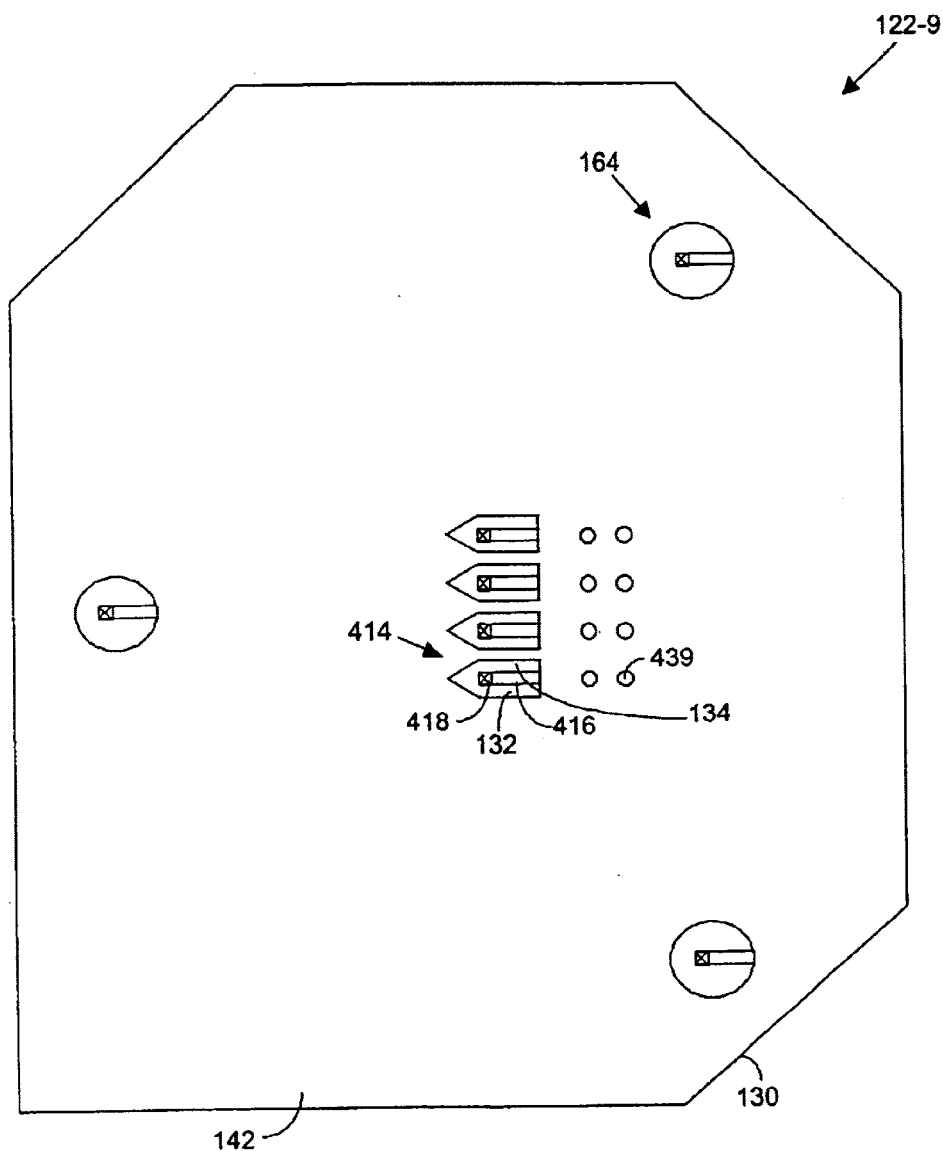
FIGS. 44 to 46 show different views of a ninth SPM probe of the SPM system of FIG. 1.

Turning now to FIG. 44, there is shown a ninth microstructured SPM probe 122-9 for use in making SPM modifications of the object 102. The probe has fluid material delivery tools 414 that each deliver fluid material to the object. This fluid material may simply comprise a fluid, such as a gas or liquid chemical, or it may comprise small microstructure, such as biological matter, and a carrier fluid, such as a gas or liquid biological agent, in which the small microstructure are carried.

Each fluid material delivery tool 414 has a support platform 416, such as a cantilever, and a tip 418 on the support platform. The support platform is connected to the base 130 of the SPM probe 122-9 and suspended in the aperture 132 of the base within the corresponding inner perimeter surface 134 of the base. This is done so that the tip is between the lower and upper surfaces 142 and 140 of the base to prevent it from being damaged. The support platform may be separately formed or may be an integral portion of the base. Otherwise, the base has the same basic shape and construction as the base discussed for the first probe 122-1.

Figure 45:
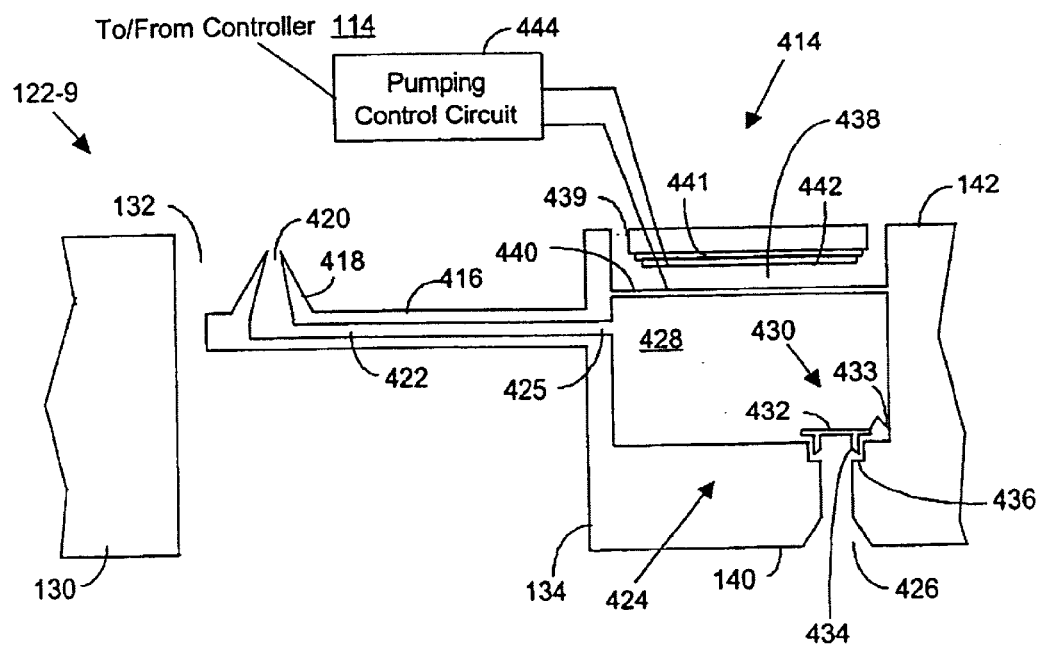

Turning now to FIG. 45, the tip 418 of each fluid material delivery tool 414 includes a capillary 420 in the core material 144 of the tip. The capillary is connected to and in fluid communication with a duct 422 in the support platform 416 of the tool. The duct is connected to and in fluid communication with the outlet 425 of a microstructured pump 424 of the fluid material delivery tool. In this embodiment, the pump is formed in the base 130 of the SPM probe 122-9.

The pump 424 has an inlet 426 on the upper surface 140 of the base for receiving fluid material to be delivered to the object 102. The inlet is connected to and in fluid communication with a pumping chamber 428 of the pump. Between the pumping chamber and the inlet of the pump is a check valve 430. The check valve includes a sealing plate 432 that extends across the inlet and is suspended in the inlet by a suspension mechanism 433 that comprises spring arms or a spring web. The check valve further includes sealing arms 434 that extend out from the sealing plate. The inlet includes sealing seats 436 for the sealing arms 434. The pump also includes a venting chamber 438 and a flexible membrane (or diaphragm) 440 between the pumping chamber and the venting chamber. The membrane serves as a displaceable lower wall of the pumping chamber and a displaceable upper wall of the venting chamber. One or more venting outlets 439 of the pump are located on the lower surface 142 of the base and are connected to and in fluid communication with the venting chamber. On the fixed lower wall of the venting chamber, the pump further includes an insulating plate 441 and a plate electrode 442 on the insulating plate.

The base 130, the tip 418, the support structure 416, the membrane 440, the suspension mechanism, the sealing plate 432, and the sealing arms 436 may be integrally formed together and comprise a semiconductor material, such as polysilicon, that is conductive. The plate electrode 442 may comprise a conductive material, such as polysilicon or tungsten. And, the insulating plate 441 may comprise an insulating material, such as silicon dioxide.

Probe Loading and Unloading, Vacuum Operation, and Particle Removal Operation of SPM Probe 122-9

Figure 46:
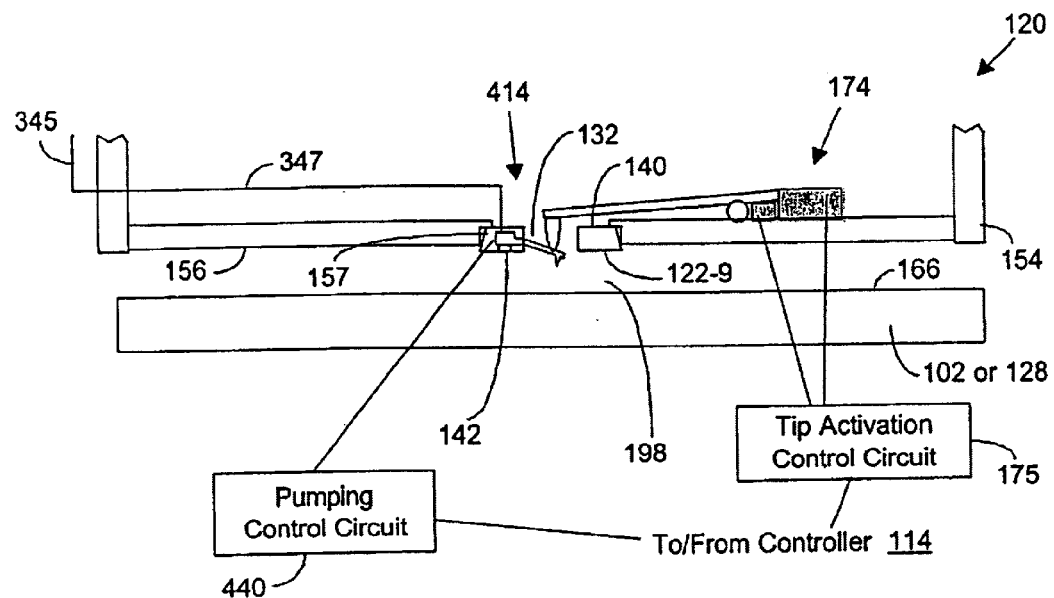

Referring to FIG. 46, the ninth SPM probe 122-9 may be loaded onto one of the scanning heads 120 in the same ways as were described earlier for the first probe. In addition, the tip 418 of each fluid material delivery tool 416 may have its profile examined in the manner discussed earlier for the first probe. The tip may be activated and deactivated in the ways described earlier for the first probe. Furthermore, optical images would be produced by the imaging optics 226 during operation and/or calibration of the ninth probe in the manner discussed earlier for the first probe. During operation and/or calibration, a microvacuum chamber in the gap 198 between the ninth probe and the object 102 or calibration structure 128 may be established in any of the ways described earlier for the first probe with the aperture 132 and the gap sensors 164 of the ninth probe. Or, the ninth probe may include instead a gas bearing structure 342 like that described earlier for the eighth SPM probe 122-8. Finally, the ninth probe could also include a particle removal structure 342 to remove particles during operation and/or calibration in the manner described earlier for the fifth SPM probe 122-5.

SPM Modifications with SPM Probe 122-9

Turning to FIG. 1, in order to make SPM modifications to the object 102 by delivering fluid material to the object 102 with the SPM probe 122-9, the fluid supply/sink system 344 includes a fluid material source for each of the fluid material delivery tools 414 of the probe. Each fluid material source is connected to a corresponding flexible tube 345 for each scanning head 120. As shown in FIG. 46, each of these flexible tubes is connected to a corresponding connector tube 347 of the scanning head. Each connector tube is in turn connected to a corresponding fluid material delivery tool 414.

The controller 114 then controls the positioning system 103 to position the probe for a scan of the object 102. Referring back to FIGS. 44 to 46, at each scan point, the controller causes the corresponding valve 346 to open so that the fluid source is in fluid communication with a selected fluid material delivery tool 414 of the probe whose tip 418 has been activated. As a result, the fluid material source provides the fluid material delivery tool with the fluid material.

Referring back to FIG. 45, at each scan point, the fluid material is received from the connector tube 347 at the inlet 426 of the pump 424 of the selected fluid material delivery tool 414 with a pressure sufficient to open the check valve 430. In doing so, the pressure of the fluid material on the sealing plate 432 of the check valve has a force larger than the spring force of the suspension mechanism 433. As a result, the sealing plate lifts the sealing arms 434 off of the sealing seats 436 of the inlet. The fluid material then travels through the inlet into the pumping chamber 428 of the pump.

The components of the SPM system 100 further include a pumping control circuit 444. At each scan point, while the fluid material is being provided to the pumping chamber 428 of the pump 424, a voltage is applied across the membrane 440 and the plate electrode 442 by the pumping control circuit 444 so that the membrane is displaced from its normal position toward the plate electrode and the pumping chamber is expanded. This is done in such a way that the pressure of the fluid material in the pumping chamber is kept below that which would cause the fluid material to be ejected by the capillary 420 of the activated tip 418. Furthermore, the ambient gas in the venting chamber 438 is vented out of the venting outlets 439 when this occurs so that the pressure of the ambient gas in the venting chamber is maintained at a constant level.

At each scan point, when the pumping chamber 428 contains the fluid material to be delivered to the object 102, the controller 114 causes the pumping control circuit 444 to apply a voltage across the membrane 440 and the plate electrode 442 which causes the spring restoring force of the membrane to restore the membrane to its normal position. This increases the pressure of the fluid material in the pumping chamber. This pressure on the sealing plate 432 of the check valve 430 causes the sealing plate to seat the sealing arms 433 on the sealing seats 436 of the inlet 426 so that the check valve is closed. Then, because of the increased pressure, the fluid material is pumped from the pumping chamber out through the outlet 425 of the pump 424 and into the duct 422. The fluid material travels through the duct and into the capillary 420 of the activated tip 418 and is ejected by the capillary. In this way, the fluid material is delivered to the object 102.

As shown in FIG. 46, the other components 123 of the SPM system 100 may include a electroresisitive material and a drive connection at the nozzle of the ion beam tool to heat the fluid. Or it may include a laser (or other electromagentic source such as a microwave genrator etc.) directed at the nozzle of the ion beam tool. Or, a catalytic substance may be placed on the outside of the nozzle or adjacent to it on the tool probe. Or, an ultrasonic source may induce a change in the ejected fluid by exciting the object with ultrasound from below or integrated in the probe 122-10. Finally, a magnetic field from a coil located on the probe can be used to induce the fluid to change.

Furthermore, as mentioned earlier and shown in FIG. 44, the SPM probe 122-9 includes multiple fluid material delivery tools 414. Thus, each fluid material delivery tool could be used to deliver a different fluid material from any of the other fluid material delivery tools.

Calibration of SPM Probe 122-9

The position of each fluid material delivery tool 414 of the SPM probe 122-9 may be calibrated and its profile examined using the AFM probe 131 and SEM probe 133 of the calibration structure 128-1 in the manner discussed earlier for the first SPM probe 122-1. Furthermore, the position of the each fluid material delivery tool may be calibrated using the calibration structure 128-2 shown in FIG. 11.

Structure of SPM Probe 122-10

Figure 48:
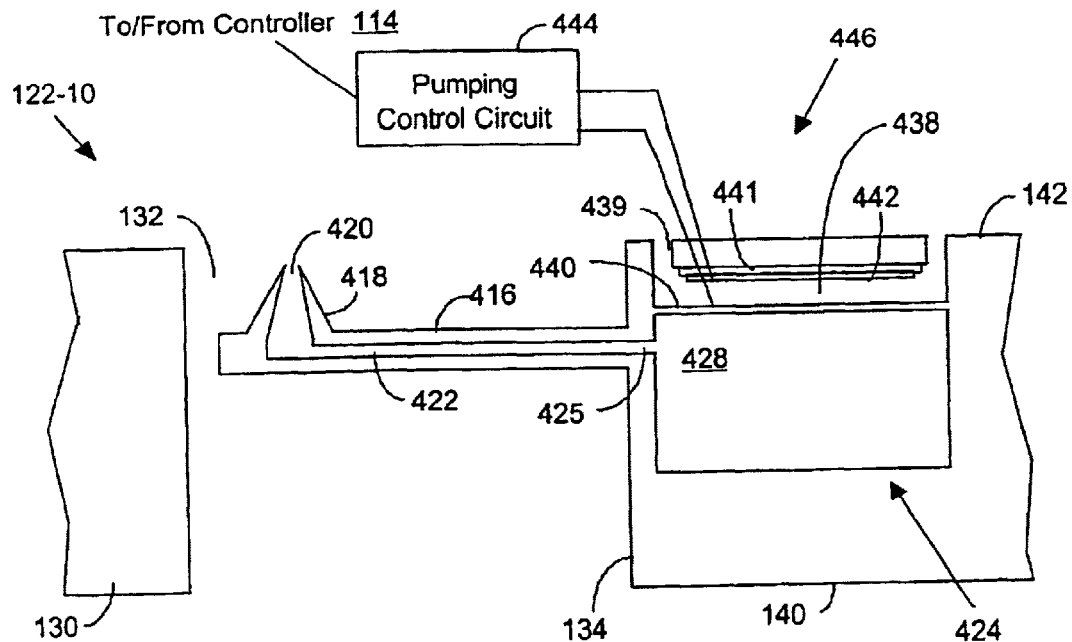
FIGS. 47 and 48 show different embodiments of a tenth SPM probe of the SPM system of FIG. 1.
Figure 47:
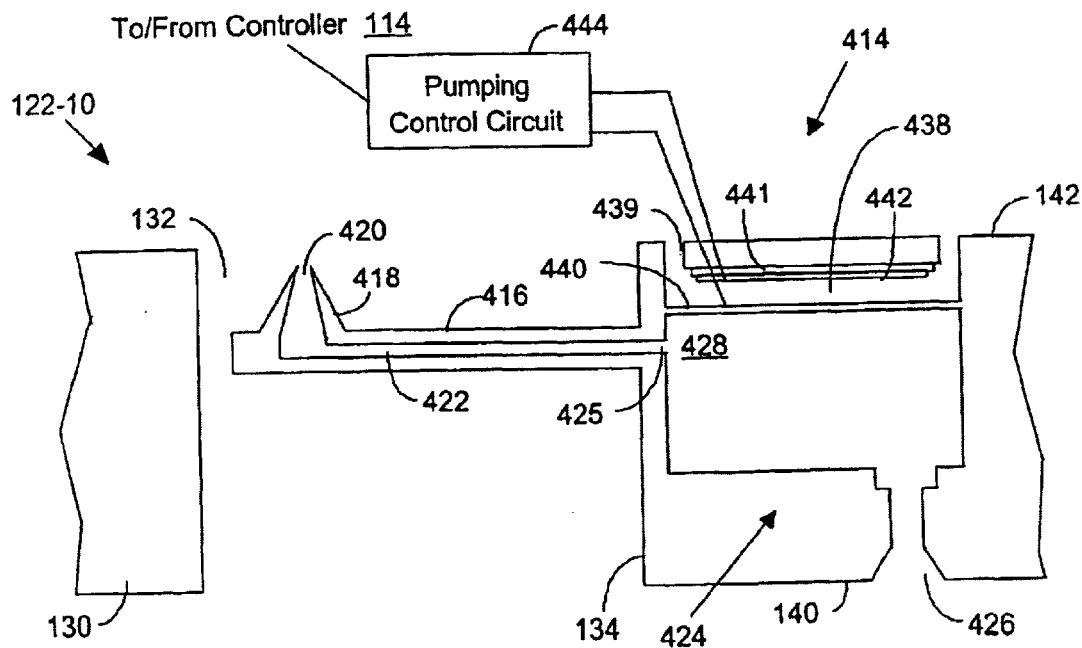

Turning now to FIGS. 47 and 48, there is shown a tenth microstructured SPM probe 122-10 for use in making SPM modifications of the object 102. The probe has pipette tools 446 that each can remove fluid material from and/or around the object. As with the fluid material delivery tools 414, this fluid material may simply comprise a fluid, such as a gas or liquid chemical, or it may comprise small microstructure, such as biological matter or contaminant particles on and/or around the object, and a carrier fluid, such as a gas or liquid biological agent or ambient gas, in which the small microstructure are carried. Furthermore, each pipette tool 446 is constructed like each fluid material delivery tool 414 of the SPM probe 122-10. However, in the embodiment of FIG. 47, the pump 424 does not have a check valve 430 and, in the embodiment of FIG. 48, the pump does not have the check valve and the inlet 426.

Probe Loading and Unloading, Tip Activation and Deactivation, Vacuum Operation, and Particle Removal Operation of SPM Probe 122-10

The tenth SPM probe 122-10 may be loaded onto and unloaded from one of the scanning heads 120 in the same ways as were described earlier for the first probe and similar to that shown for the ninth SPM probe 122-9 in FIG. 46. Thus, the tip 418 of each pipette tool 446 of the tenth probe may be activated and deactivated in the ways described earlier for the first probe. And, the tip may have its profile examined in the manner discussed earlier for the first probe. Furthermore, optical images would be produced by the imaging optics 226 during operation and/or calibration of the tenth probe in the manner discussed earlier for the first probe. During operation and/or calibration, a microvacuum chamber in the gap 198 between the tenth probe and the object 102 or calibration structure 128 may be established in any of the ways described earlier for the first probe with the aperture 132 and the gap sensors 164 of the tenth probe. Or, the tenth probe may include instead a gas bearing structure 342 like that described earlier for the eighth SPM probe 122-8. Finally, the tenth probe could also include a particle removal structure 342 to remove particles during operation and/or calibration in the manner described earlier for the fifth SPM probe 122-5.

SPM Modifications with SPM Probe 122-10

Turning to FIG. 1, in order to make SPM modifications to the object 102 by removing material from the object 102 with the SPM probe 122-10, the controller 114 controls the positioning system 103 to position the probe for a scan of the object 102. This is done at each scan point so that the capillary 420 of the activated tip 418 of a selected pipette tool 446 of the probe is positioned in or near the material of the object.

Referring to the embodiment of FIG. 47, in order to make SPM modifications to the object 102 by removing fluid material from the object 102 with the SPM probe 122-10, each pipette tool 446 of the probe is in fluid communication with the vacuum source 192 via the inlet 426 at each scan point. This is done in same manner as discussed earlier for the aperture 132 of the first SPM probe 122-1. Alternatively, the inlet may be directly connected to the vacuum source via one or more tubes. Or, as in the embodiment of FIG. 48, the inlet may be removed for each pipette tool 446 so that each pipette tool is self contained within the probe.

At each scan point, the controller causes the pumping control circuit 444 to apply a voltage across the membrane 440 and the plate electrode 442 of the pump 424 so that the membrane is displaced from its normal position toward the plate electrode and the pumping chamber is expanded. As a result, the fluid material to be removed from and/or around the object is drawn into the capillary of the tip, through the duct 422, and into the pumping chamber 428 via the inlet/outlet 425 of the pump. At the same time, the ambient gas in the venting chamber 438 is vented out of the venting outlets 439 when this occurs so that the pressure of the ambient gas in the venting chamber is maintained at a constant level. The material can then be ejected from the pumping chamber at a desired location or repository of the SPM system 100 in the manner described earlier for the SPM probe 122-9.

Calibration of SPM Probe 122-10

The position of each pipette tool 446 of the SPM probe 122-10 may be calibrated and its profile examined using the AFM probe 131 and SEM probe 133 of the calibration structure 128-1 in the manner discussed earlier for the first SPM probe 122-1. Furthermore, the position of each pipette tool may be calibrated using the calibration structure 128-2 shown in FIG. 11.

Structure of SPM Probe 122-11

Figure 49:
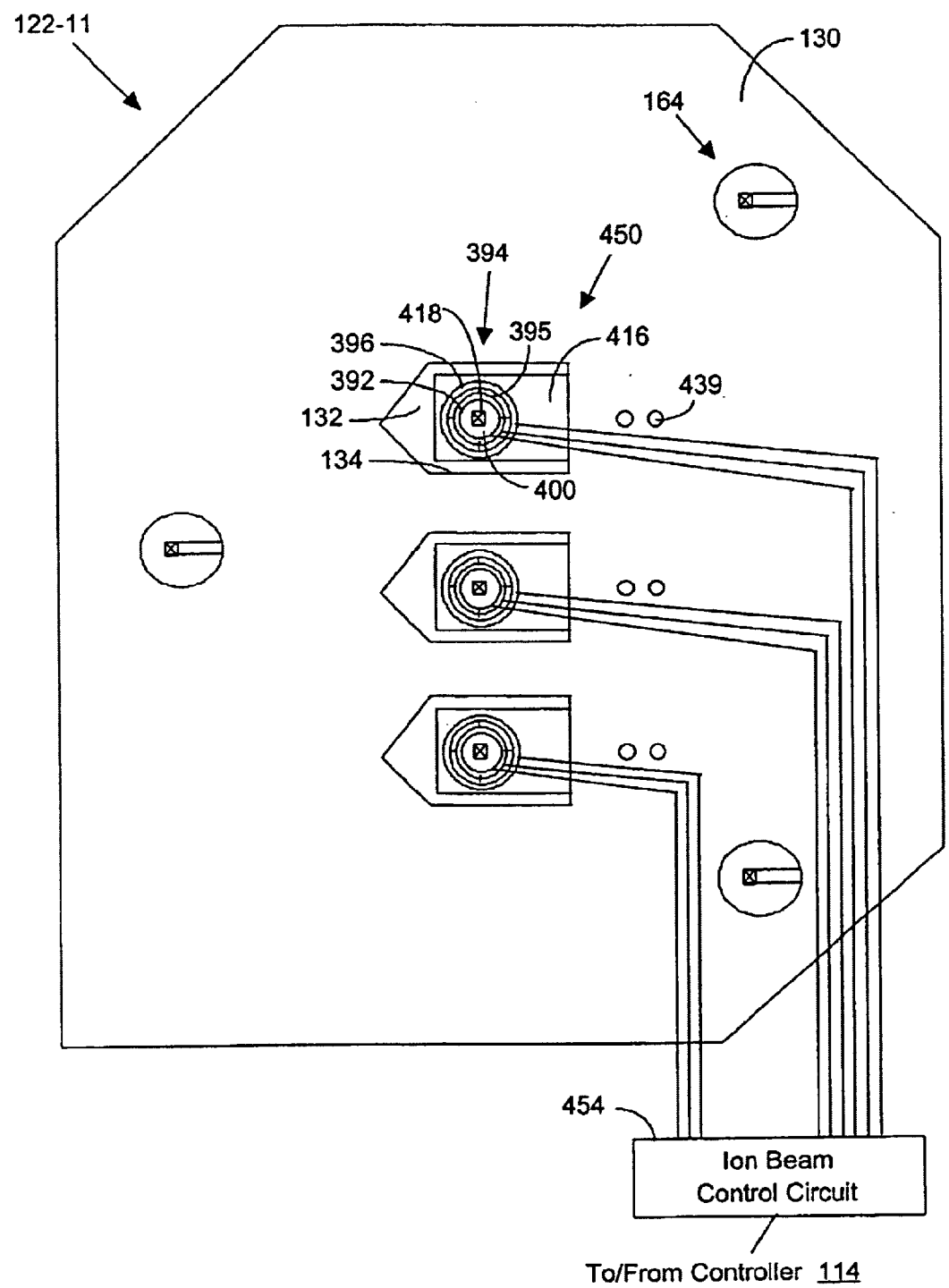
FIGS. 49 to 51 show different views of an eleventh SPM probe of the SPM system of FIG. 1.

Turning now to FIG. 49, there is shown an eleventh SPM probe 122-11 for use in making SPM measurements and/or SPM modifications of the object 102. Here, like the eighth SPM probe 122-8, the SPM measurements and the SPM modifications are made in response to radiation in the form of charged particles that are produced by the probe and directed at the object. But, in this case, the charged particles comprise an ion beam produced by one of the ion beam tools 450 of the eleventh probe.

Figure 50:
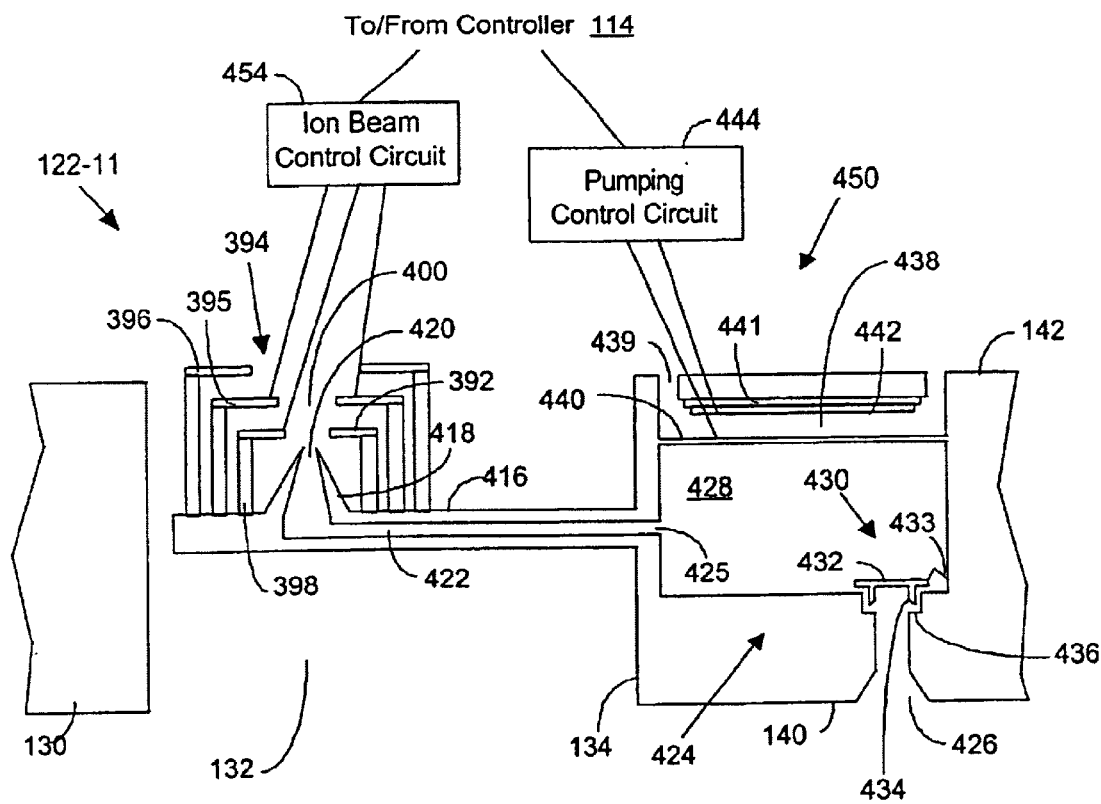

Referring to FIG. 50, each ion beam tool 450 is constructed like one of the fluid material delivery tools 414 of the ninth SPM probe 122-9, except for several differences. Namely, like each abeam tool of the eighth SPM probe 122-8, each ion beam tool includes an accelerating electrode 392, a steering electrode assembly 394, a collection electrode 396, and insulating support structures 398 on the support structure 416 of the tool. Here, the accelerating electrode is disposed below the opening of the capillary 420 of the tip 418. Otherwise, the base and the pump 424 formed in the base have the same basic shape and construction as that discussed for the ninth probe.

Probe Loading and Unloading, Tip Activation and Deactivation, Vacuum Operation, and Particle Removal Operation of SPM Probe 122-11

Figure 51:
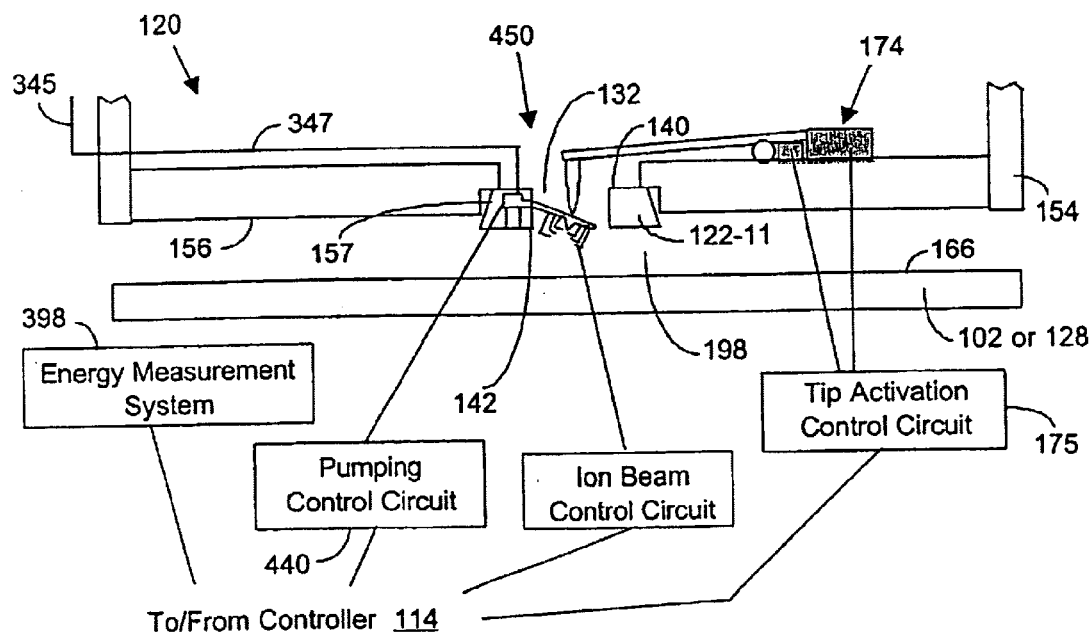

Referring to FIG. 51, the eleventh SPM probe 122-11 may be loaded onto and unloaded from one of the scanning heads 120 in the same ways as were described earlier for the first probe. Thus, the tip 418 of each ion beam tool 450 of the eleventh probe may be activated and deactivated in the ways described earlier for the first probe. And, the tip may have its profile examined in the manner discussed earlier for the first probe. Furthermore, optical images would be produced by the imaging optics 226 during operation and/or calibration of the eleventh probe in the manner discussed earlier for the first probe. During operation and/or calibration, a microvacuum chamber in the gap 198 between the eleventh probe and the object 102 or calibration structure 128 may be established in any of the ways described earlier for the first probe with the aperture 132 and the gap sensors 164 of the eleventh probe. Or, the eleventh probe may include instead a gas bearing structure 342 like that described earlier for the eighth SPM probe 122-8. Finally, the eleventh probe could also include a particle removal structure 342 to remove particles during operation and/or calibration in the manner described earlier for the fifth SPM probe 122-5.

SPM Modifications with SPM Probe 122-11

As mentioned earlier, the SPM probe 122-11 can be used to make SPM modifications of the object. Referring now to FIG. 1, in doing so, the controller 114 controls the positioning system 103 to position the probe for a scan of the object 102. Then, referring to FIGS. 1 and 49 to 51, at each scan point, the inlet 426 of each ion beam tool 450 is in fluid communication with a fluid source of the fluid supply/sink system 344 to receive fluid. This is done via a corresponding valve 346, flexible tube 345, and connector tube 347 in the same manner as was described for each fluid material delivery tool 414 of the SPM probe 122-9. Then, at each scan point, the controller 114 controls the pumping control circuit 444 to cause the pump 424 of the ion beam tool to pump the fluid out of the capillary 420 of the tip 418. This is done in the manner discussed earlier for each fluid material delivery tool.

The other components 123 of the SPM system 100 further include an ion beam control circuit 454. At the same time that the fluid is being ejected, the controller controls the ion beam control circuit to apply a voltage to the accelerating electrode 392 to ionize the ejected fluid. As a result, the ion beam tool 450 produces an ion beam that is directed at the object 102. As mentioned earlier for the first and eighth SPM probes 122-1 and 122-8, because of the microvacuum chamber, the object 102 can be effectively irradiated with the ion beam without colliding with other particles.

The ion beam can be steered by the steering electrodes 395 of the steering electrode assembly 394 in the same way as that described for the e-beam produced by the e-beam tool 382 of the eighth SPM probe 122-8. In addition, the SPM probe 122-11 could have steering magnets 385 and steering coil 387 like those of the SPM probe 122-8 in order to further steer the ion beam.

The ion beam can then used as a plasma torch to heat the material of or remove material from the object. Or, in the case where the object is a semiconductor material, it could be used to dope the object with ions. Moreover, the ion beam can be used to go in chemical recombination with the target. For example, this may be done to bombard silicon with carbon ions (by biasing the silicon substrate electrically with respect to the plasma) which go into the surface to form SiC (silicon carbide) chemical.

SPM Inspections with SPM Probe 122-11

As mentioned earlier, the SPM probe 122-11 can be used to make radiation measurements in order to inspect the object 102. To do so, the controller 114 controls the positioning system 103 to position the probe 122-8 for a scan of the object 102. At each scan point, the controller causes a selected ion beam tool 450 of the probe to direct an ion beam at the object in the manner discussed earlier.

Referring back to FIGS. 40 to 42, at each scan point, the controller causes the ion beam control circuit 454 to produce an ion beam in the manner just discussed. Then, when the ion beam interacts with the object 102, it causes secondary radiation to be reflected and/or emitted back to the collection electrode 396. This causes a current in the collection electrode which represents the ions that contact the collection electrode. This current is measured by the ion beam control circuit as a radiation measurement of the ions collected by the collection electrode. The radiation measurements made at all of the scan points may be collected and used by the controller to produce an image of the object like that made with a conventional electron microscope or other conventional particle microscope.

In addition, the radiation measurement system 389 may be used to detect and measure radiation, such as Optical, Radiofrequency or X-radiation (depending on the beam energy and the target), emitted by the object 102 in response to the ion beam striking it. This is done in the same manner as that discussed earlier for the e-beam tool 382 of the SPM probe 122-8, except that it is done in response to the Ion beam striking the object.

As with the eighth SPM probe 122-8, the radiation measurements made with the eleventh SPM probe 122-11 and the radiation measurement system 398 are particularly useful for inspecting a lithographic structure, such as a semiconductor fabrication mask. This would be done in the same manner as was described earlier using the e-beam produced by the eighth probe, except that an ion beam would be used.

Calibration of SPM Probe 122-11

The position of each ion beam tool 450 of the SPM probe 122-11 may be calibrated and its profile examined using the AFM probe 131 and SEM probe 133 of the calibration structure 128-1 in the manner discussed earlier for the first SPM probe 122-1. Furthermore, the position of each ion beam tool may be calibrated using the calibration structure 128-2 shown in FIG. 11 in the manner discussed next.

The calibration structure 128-2 may include one or more reference materials 458 on the insulating material 199 on the base 190 of the reference structure. Each reference material has a precisely known position with respect to the reference location. And, each reference material may comprise a material that has known radiation properties for when ions strike it. For example, this may be a material, such as tungsten, which produces specific wavelengths of radiation, such as x rays, in response to ions striking it. Then, the position of the ion beam tool is calibrated using these reference materials in the same way that the position of the e-beam tool 382 of the eighth SPM probe 122-8 is calibrated using the reference materials 191, except that an ion beam is used.

Furthermore, referring to FIGS. 11 and 52 and as discussed earlier for the eighth SPM probe 122-8, one or more of the radiation detection devices 461 of the calibration structure 128-2 may each have a radiation detector 464 that detects charged particles, such as ions. The controller 114 calibrates the position of the selected ion beam tool 450 of the SPM probe 122-11 using these radiation detection devices in a similar manner to that discussed for the e-beam tool 382 of the eighth probe. Here, however, the radiation measurements made by the radiation measurement circuit 181 are a measure of ions detected by the radiation detectors in response to an ion beam produced by the selected ion beam tool.

Structure of SPM Probe 122-12

Figure 53:
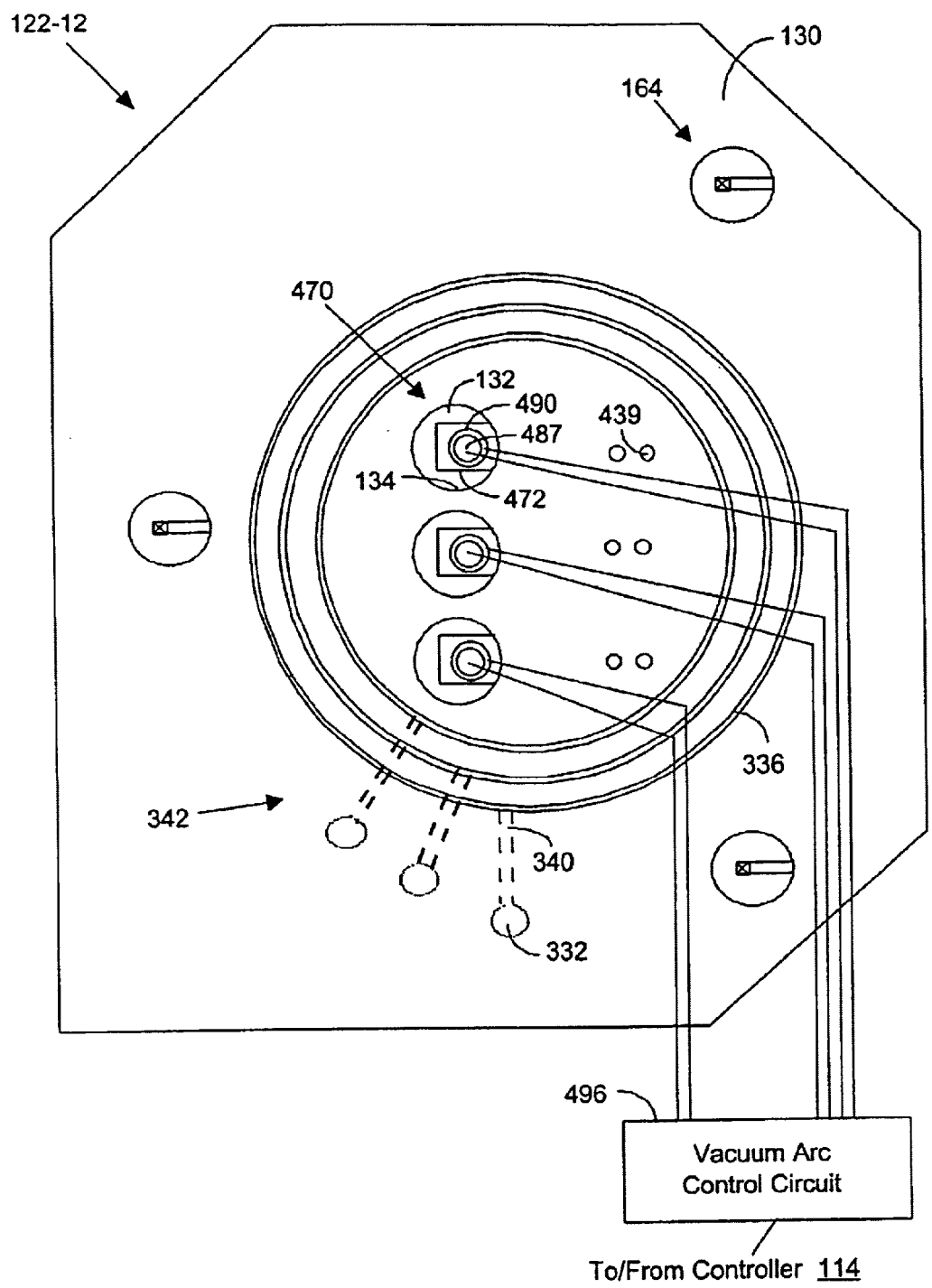
FIGS. 53 to 55 show different views of a twelfth SPM probe of the SPM system of FIG. 1.

Turning now to FIG. 53, there is shown a twelfth SPM probe 122-12 for use in making SPM modifications of the object 102 depositing material on and/or removing material from the object 102. The twelfth probe has vacuum arc tools 470 that are each suspended in a corresponding aperture 132 of the base 130 of the twelfth probe. And, like the eighth SPM probe 1228, the twelfth probe also has a particle removal structure 342 and gap sensors 164 formed in the base 130 of the probe. Otherwise, the base has the same basic shape and construction as that discussed for the first SPM probe 122-1.

Figure 54:
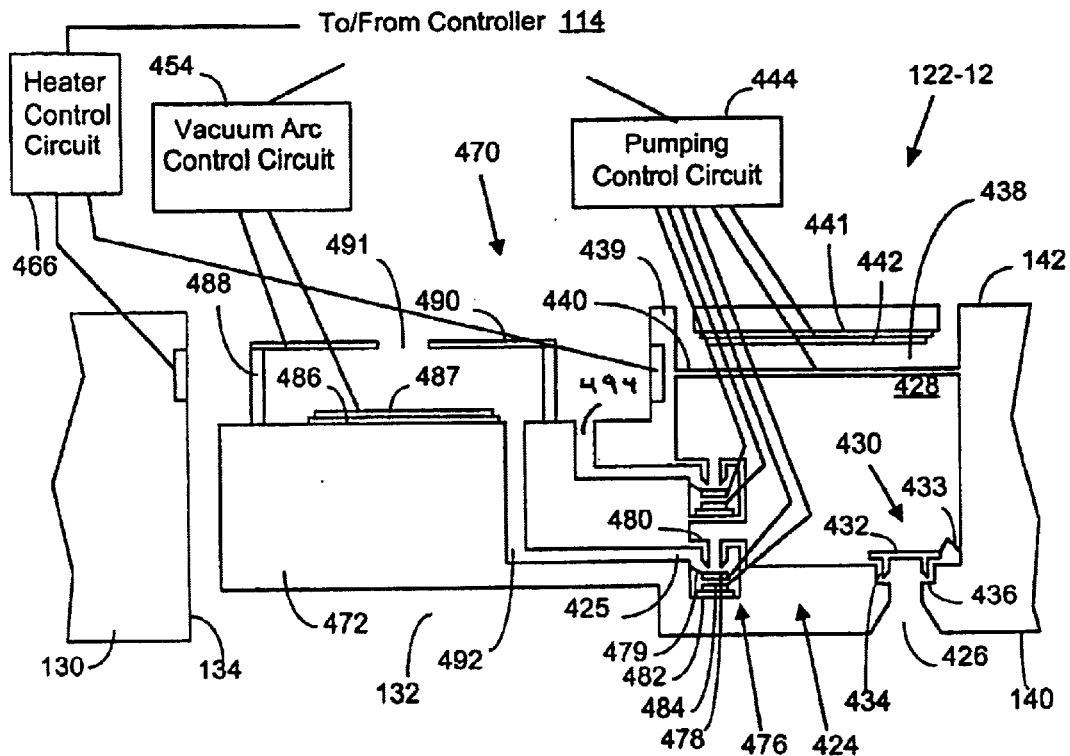

Referring to FIG. 54, each vacuum arc tool 470 includes a pump 424 that is formed in the base 130 like each fluid material delivery tool 414 of the ninth SPM probe 122-9. However, in this case, the pump includes two outlets 425. Between each outlet and the pumping chamber 428 is a corresponding outlet valve 476.

Each outlet valve 476 includes a sealing plate 478 that extends across the corresponding outlet and is suspended in the outlet by a suspension mechanism 479 that comprises spring arms or a spring web. The outlet valve further includes sealing arms 480 that extend out from the base. In its normal position, the sealing plate is seated against the sealing arms so as to form a tight seal that prevents any fluid from entering the outlet. This is due to the spring force of the suspension mechanism. The sealing plate, the sealing arms, and the suspension mechanism may integrally formed with the base. Thus, the sealing plate comprises a conductive semiconductor material. Each outlet valve also includes an insulating plate 482 on the inner surface of the outlet and a plate electrode 484 on the insulating plate. The plate electrode may comprise a conductive material, such as polysilicon or tungsten, and the insulating plate may comprise an insulating material, such as silicon dioxide.

In addition, each vacuum arc tool 470 has a support platform 472 that is connected to the base 130 of the SPM probe 122-12 and suspended in the aperture 132 of the base within the corresponding inner perimeter surface 134 of the base. This is done so that the tool is between the lower and upper surfaces 142 and 140 of the base to prevent it from being damaged. The support platform may be separately formed or may be an integral portion of the base. Each vacuum arc tool also includes an insulating plate 486 on the support platform and a cathode 487 on the insulating plate. And, each tool includes a support structure 488 and an anode 490 on the support structure. The support structure suspends the anode over the cathode. The anode has an aperture 491.

Each vacuum arc tool 470 further includes outlet ducts 492 and 494 formed in the support platform 472. Each of the outlet ducts is connected to a corresponding outlet 425 of the pump 424. The outlet duct 492 opens into the aperture 132 so that fluid can be pumped into the space between the anode 490 and the cathode 487. The other outlet duct opens into the aperture so that fluid may be pumped into the space between the anode and the object 102.

Probe Loading and Unloading, Calibration, Vacuum Operation, and Particle Removal Operation of SPM Probe 122-12

Figure 55:
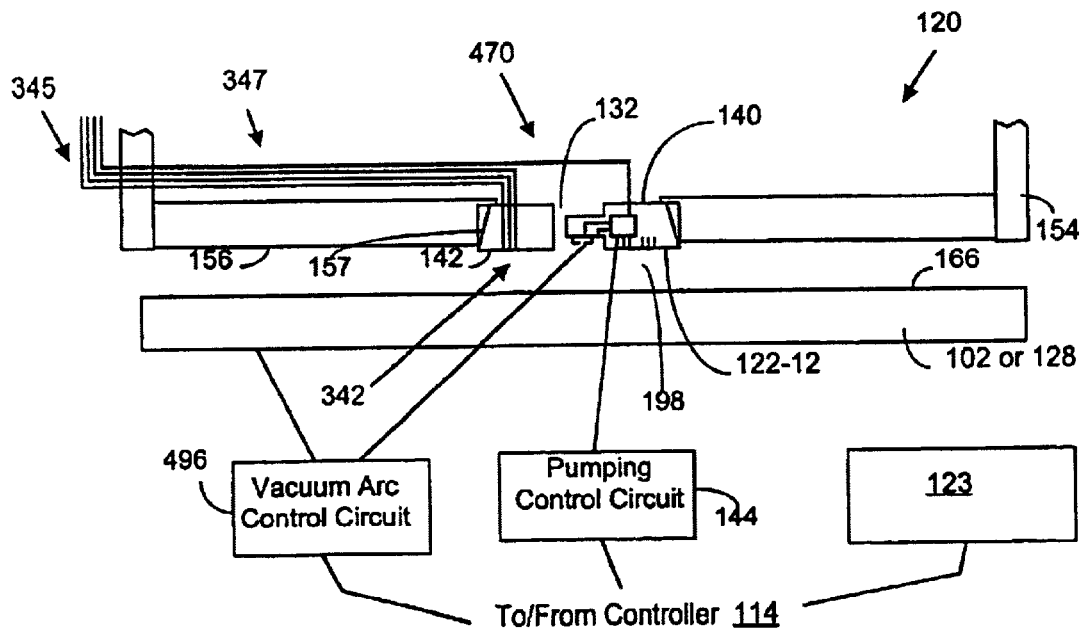

Referring to FIG. 55, the twelfth SPM probe 122-12 may be loaded onto and unloaded from one of the scanning heads 120 in the same ways as were described earlier for the first SPM probe 122-1. And, each vacuum arc tool 470 may have its profile examined in the manner discussed earlier for the first probe. And, optical images would be produced by the imaging optics 226 during operation and/or calibration of the twelfth probe in the manner discussed earlier for the first probe. During operation and/or calibration, a microvacuum chamber in the gap 198 between the twelfth probe and the object 102 or calibration structure 128 may be established in any of the ways described earlier for the first probe with the aperture 132 and the gap sensors 164 of the twelfth probe. Or, the twelfth probe may include instead a gas bearing structure 342 like that described earlier for the eighth SPM probe 122-8. Finally, the particle removal structure 342 removes particles during operation and/or calibration in the manner described earlier for the fifth SPM probe 122-5.

SPM Modifications with SPM Probe 122-12

The SPM probe 122-12 is used to make SPM modifications of the object by depositing material on the object or removing some of the material of the object. Referring now to FIG. 1, in doing so, the controller 114 controls the positioning system 103 to position the probe for a scan of the object 102.

Referring to FIGS. 1 and 53 to 55, at each scan point, the inlet 426 of each vacuum arc tool 470 is in fluid communication with a fluid source of the fluid supply/sink system 344 to receive fluid. This is done via a corresponding valve 346, flexible tube 345, and connector tube 347 in the same manner as was described for each fluid material delivery tool 414 of the SPM probe 122-9. Then, at each scan point, the controller 114 controls the pumping control circuit 444 to cause the pump 424 of the vacuum arc tool to pump the fluid out of one of the outlet ducts 492 and 494. This is done in the manner discussed earlier for each fluid material delivery tool except that the outlet valves 476 are used to control which outlet duct the fluid is ejected from. For example, if material is being deposited on the object 102, then the controller 114 causes the pumping control circuit to open the outlet valve that is connected to the outlet duct 492 while keeping the other outlet valve closed. As a result, the fluid is pumped into the space between the anode 490 and the cathode 487. Alternatively, if material is being removed from the object, then the controller causes the pumping control circuit to open the outlet valve connected to the outlet duct 494 while keeping the other outlet valve closed. In this case, the fluid is pumped into the into the space between the anode and the object 102.

In order to open one of the outlet valves 476, the pumping control circuit 444 applies a voltage across the sealing plate 478 of the outlet valve and the plate electrode 474. This causes the sealing plate to overcome the spring force of the suspension mechanism 479 of the outlet valve so that the sealing plate is displaced from its normal position of being seated against the sealing arms 480 of the outlet valve. Then, in order to close the outlet valve, the pumping control circuit applies an appropriate voltage across the sealing plate and the plate electrode so that the sealing plate moves back to its normal position. This is due to the spring force of the suspension mechanism. As those skilled in the art will recognize, the outlet valves just described could also be used in place of the check valves 430 of the SPM probes 122-9 and 122-11.

The other components 123 of the SPM system 100 further include a vacuum arc control circuit 496. In the case where material is being deposited on the object 102, the controller controls the vacuum arc control circuit at each scan point to apply a voltage to across the anode 490 and the cathode 487. Since a microvacuum chamber is created in the gap 198, a vacuum arc is created due to the presence of the fluid pumped into the space between the anode and the cathode. This vacuum arc causes material from the cathode to be ejected through the aperture of the anode and deposited on the object. The type of fluid, the material of the cathode 487, and some of the other components 123 of the SPM system 100 are appropriately selected in order to deposit a desired material on the object 102.

For example, it may be desire to deposit diamond like carbon on the object 102 to make the object harder. In this case, the fluid could be argon, the material of the cathode 487 would be carbon, and the other components 123 of the SPM system 100 would include a magnetic field source to create a magnetic field for deposition of the diamond like carbon. This may be done in the manner and under the conditions discussed in "Multilayer Hard Carbon Films with Low Wear Rates," by Joel W. Ager et. al., Surface and Coatings Technology, vol. 91, pp. 91–94, May 1997, "Properties of Vacuum Arc Deposited Amorphous Hard Carbon Films," by Simone Anders et al., Applications of Diamond Films and Related Materials: The Third International Conference, pp. 809–812, 1995, "Hardness, Elastic Modulus, and Structure of Very Hard Carbon Films Produces by Cathodic-Arc Deposition with Substrate Pulse Biasing," by George M. Pharr et al., Applied Phys. Left., vol. 68 (6), pp 779–781, Feb. 5, 1996, and "Development of Hard Carbon Coatings for Thin-Film Tape Heads," by Bharat Bhushan and B. K. Gupta, IEEE Trans. Magn., vol. 31, 2976–2978, 1995, which are all hereby incorporated by reference. Specifically, this may be done with multiple layers of the diamond like carbon to increase the overall strength of the deposited material.

Furthermore, it may also be desired to deposit metal on the object In this case, the fluid would be argon and the material of the cathode 487 would be a metal.

As mentioned earlier, the SPM probe 122-12 includes multiple vacuum arc tools 470. Thus, each vacuum arc tool could be used to deposit a different material on the object than the other vacuum arc tools. This means that each vacuum arc tool could include a cathode 487 with a different material and may be used with different other components 123 of the SPM system than any of the other vacuum arc tools of the probe.

Furthermore, in the case where material is being removed from the object 102, the controller controls the vacuum arc control circuit 496 at each scan point to apply a voltage across the anode 490 and the object. Here, a vacuum arc is created due to the presence of the fluid pumped into the space between the anode and the object and the micro-vacuum chamber in the gap 198. This vacuum arc causes material from the object to be ejected from the object toward the SPM probe 122-12. The type of fluid used would be argon.

As an additional note, the SPM probe 122-12 could be constructed without the pump 424. In this case, the gases used would be directly provided to the outlet ducts 492 and 494 formed in the support platform 472 under the control of the controller 114.

Calibration of SPM Probe 122-12

The position of each vacuum arc tool 470 of the SPM probe 122-12 may be calibrated and its profile examined using the AFM probe 131 and SEM probe 133 of the calibration structure 128-1 in the manner discussed earlier for the first SPM probe 122-1. Furthermore, the position of each vacuum arc tool may be calibrated using the calibration structure 128-2 shown in FIG. 11 in the manner discussed next.

Heating and Cooling with SPM Probe 122-12

Referring to FIGS. 53 and 55, as mentioned earlier, the twelfth SPM probe 122-12 includes a particle removal structure 342 to remove particles during operation and/or calibration in the manner described earlier for the fifth SPM probe 122-5. However, the particle removal structure could also be used to heat the object 102 to a target temperature during deposition of material on the object or removal of material from the object. In this case, the gas source of the fluid system 344 that provides the low viscosity high pressure gas to the inlet 332 of the particle removal structure would heat this gas to the target temperature. As a result, the heated gas travels through the duct 340 and exits the outlet 336 so that the object is heated to the target temperature. Similarly, the aperture 132 or the other outlets or inlets 337 and 336 could also be used to heat or cool the object 102 in the same way by introducing gas provided from the fluid system 344.

Similarly, the other components 123 of the SPM system 100 may include a local heating source to locally heat the object 102 under the control of the controller 114. This heating source may do so with inductive heating, flame heating, resistive heating, etc. Or, the SPM probe may itself have an integrated heater 467 that comprises resistive or inductive heating elements 471 located in the probe which are controller by the heater control circuit 466. Or, the heater source may comprise an external laser or flame source. Then, the gas source could cool the gas provided through the aperture 132 or one of the outlets or inlets 335 to 337 so that the cooled gas would be used to regulate the target temperature of the object for deposition or removal of material.

Deposition of Diamond

In the case where DLC is deposited on the object 102 using the SPM probe 122-12, the probe could also be used to grow diamond crystals at the DLC seed sites in the manner described earlier. In this case, the other components 123 of the system would include a magnetic field source.

Thus, referring again to FIG. 72, the controller causes a valve 345 that is 20 connected to a tube 346 which is connected to the internal chamber 135 of the scanning head 120 to be opened. As a result, the aperture 132 is in fluid communication with a gas source of the fluid system 344 that provides methane and hydrogen or methane and argon. These gases are introduced into the internal chamber and then flow through the aperture and into the differential pressure chamber caused in the gap 198. These gases may flow out of one of the outlets or inlets 335 to 337 to a gas sink of the fluid system via a corresponding tube 346.

The controller 114 then causes the heater 467 to heat the gases. As mentioned earlier, the heater may comprise resistive or inductive heating elements 471 located at the surfaces 142 of the probe or an external laser or flame source that is one of the other components 123 of the inspection and/or modification system. As a result, CVD deposition of diamond occurs on the object such that polycrystalline diamond is grown at the seed sites provided by the DLC.

Structure of Aperture Plate 122-13

Figure 56:
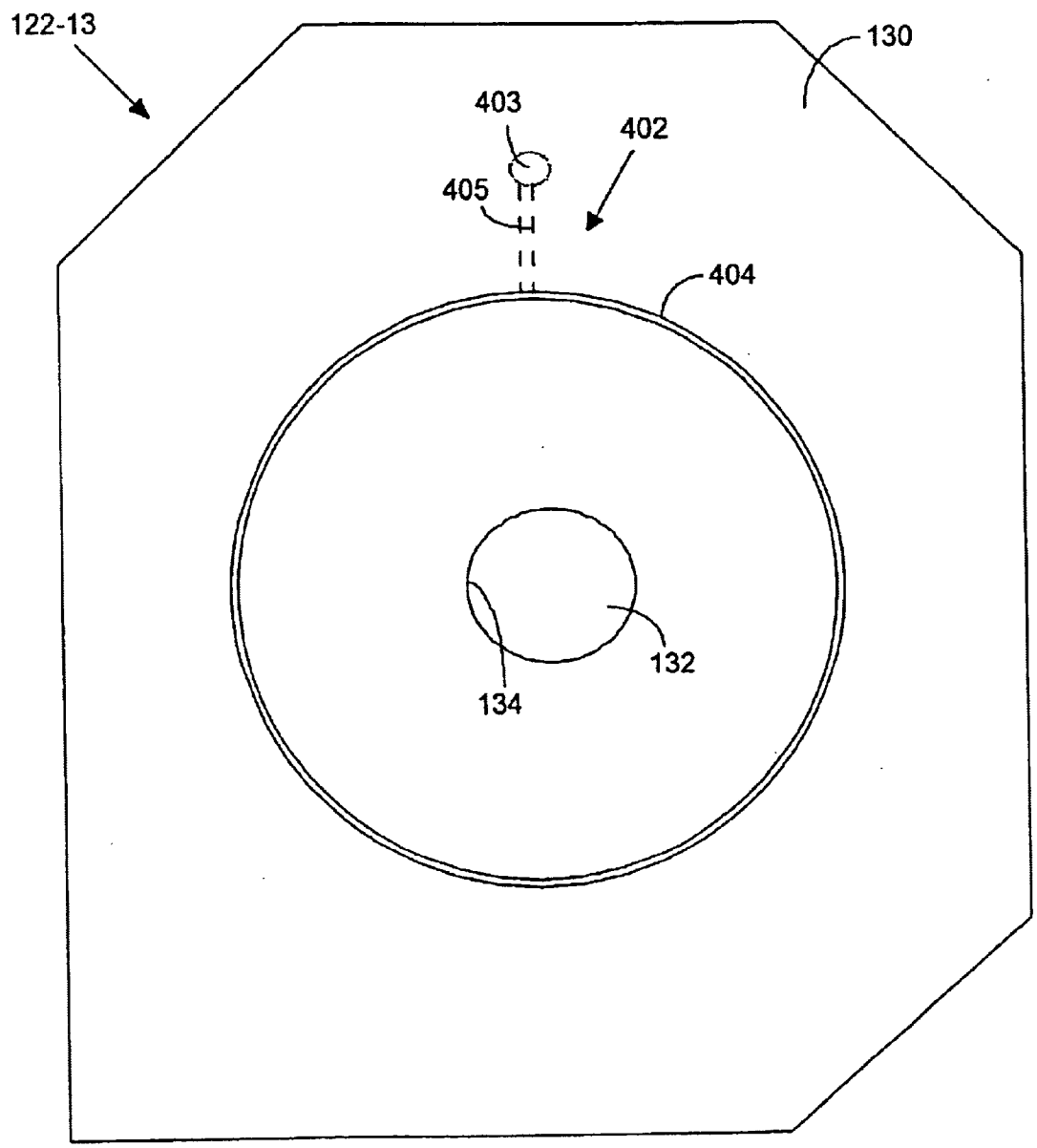
FIGS. 56 and 57 show different views of an aperture plate of the SPM system of FIG. 1.

Referring to FIG. 56, there is shown a microstructured aperture plate (or probe) 122-9 with an aperture 132 and a gas bearing structure 402 like the eighth SPM probe 122-8. In fact, the aperture plate is constructed like the eighth probe, except that it does not include an e-beam tool 382.

Modifications using Aperture Plate

Figure 57:
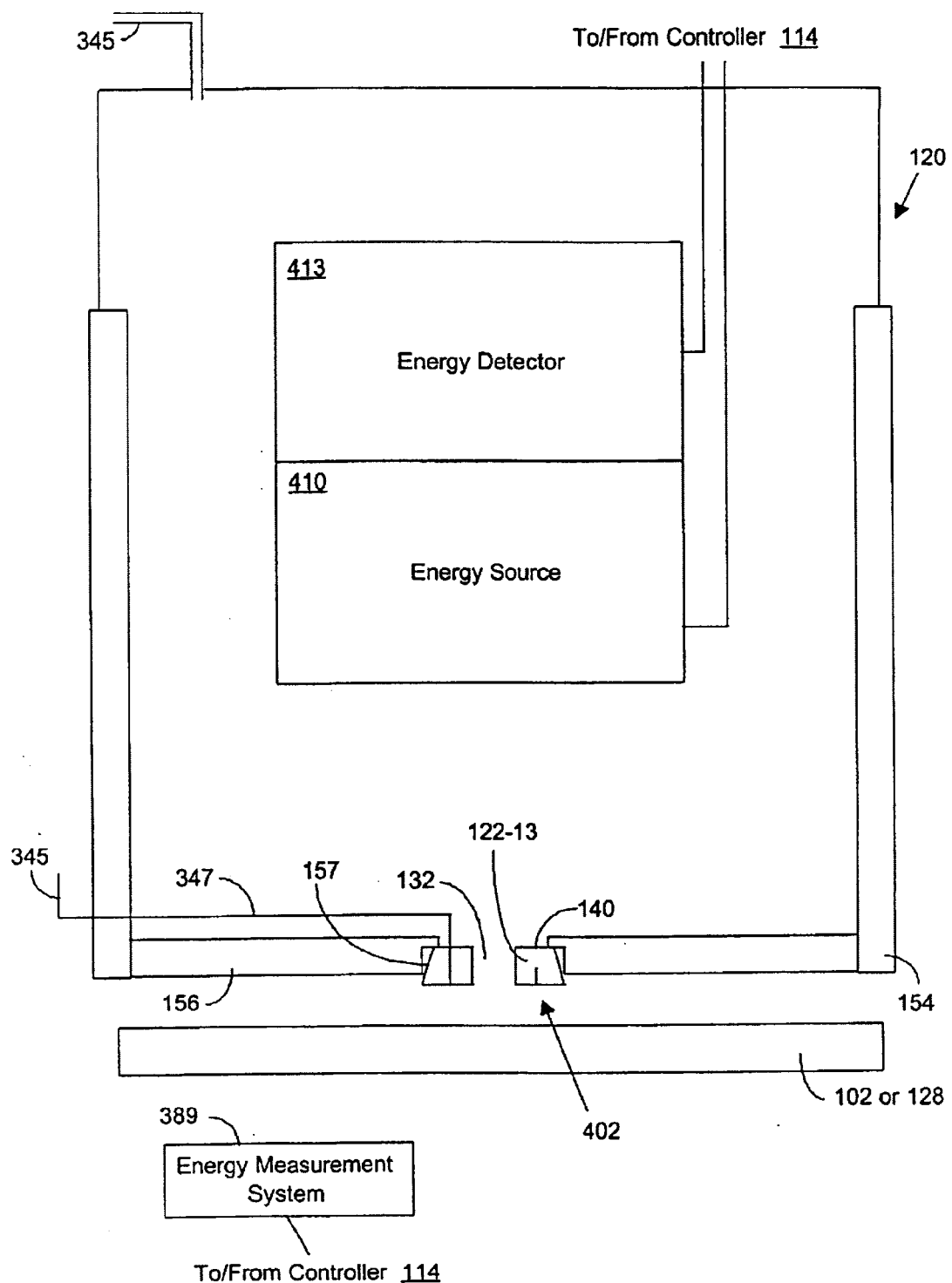

Still referring to FIG. 57, the aperture plate 122-13 may be loaded onto and unloaded from one of the scanning heads 120 in the same ways as were described earlier for the first SPM probe 122-1. Furthermore, the SPM system 100 may include a scanning head 120 that contains a conventional radiation source 410 within the housing 154 of the scanning head. The radiation source may comprise an ion beam source, e-beam source, other particle beam source, xray source, or light source.

Referring to FIG. 1, the controller 114 controls the positioning system 103 to position the probe 122-8 for a scan of the object 102. Turning to FIG. 57, at each scan point, the controller causes the radiation source 410 to produce a selected kind of radiation. Similar to the e-beam and ion beam produced by the SPM probes 122-8 and 122-11, the radiation in this case travels through the aperture 132 of the aperture plate 122-13 and strikes the object 102. In the case of an e-beam or an ion beam, the object may be modified in the manner discussed earlier for the eighth and eleventh probes. The radiation may be steered in the manner described earlier for the eighth SPM probe 122-8 with steering magnets 385 on the base 130 of the aperture plate and a steering coil 387 on the probe holder 156 of the scanning head.

Inspections with Aperture Plate 122-13

Referring to FIG. 57, a conventional radiation detector 413 may be integrated with the radiation source 410 to detect radiation reflected and/or emitted by the object in response to the radiation produced by the radiation source. For example, this radiation may be secondary electrons, ions, x-rays, gamma rays, alpha particles, visible, infrared light, and/or ultraviolet light.

Referring again to FIG. 1, in order to inspect the object 102 with radiation supplied by the radiation source 410, the controller 114 controls the positioning system 103 to position the probe 122-8 for a scan of the object 102. At each scan point, the controller causes the radiation source 410 to produce radiation that strikes the object in the manner described earlier. The resulting radiation that is reflected or emitted in response passes through the aperture 132 of the aperture plate 122-13 and is detected by the radiation detector 413. The radiation detector makes a measurement of the detected radiation at this scan point and provides this measurement to the controller. The controller collects all of the measurements over the scan and generates an image and/or analyses of the object.

As those skilled in the art will recognize, the radiation source 410 and the radiation detector 413 may be integrated to form a complete conventional SEM assembly that is housed by the housing 154 of the scanning head 120 and operated by the controller 114. In this case, the radiation source provides an e-beam and the radiation detector collects the resulting scattered electrons. Moreover, as will be discussed next, the SEM assembly can be operated with a microvacuum chamber created in the gap 198 between the object 102 being inspected and the aperture plate 122-13 of the housing.

Vacuum Operation, Calibration, and Particle Removal Operation with Aperture Plate 122-13

Referring to FIGS. 1 and 57, during operation and/or calibration, a microvacuum chamber in the gap 198 between the aperture plate and the object 102 or calibration structure 128 may be established in any of the ways described earlier for the eighth SPM probe 122-8 with the aperture 132 and the gas bearing structure 342. As mentioned earlier for the eighth and eleventh SPM probes 122-8 and 122-11, when a large vacuum chamber 194 and high capacity vacuum pump 193 are used the object 102 may be effectively irradiated with the radiation produced by the radiation source 410 without colliding with other particles in the gap.

Furthermore, as also discussed earlier, the object 102 may comprise a small free moving or partially constrained specimen, such as a micromachine or biological cell or material, and a flat specimen support structure, such as microscope slide, on which the specimen is located. Thus, the diameter of the aperture 132 and the annular outlet 404 of the gas bearing structure 402 can be selected for a particular specimen. As a result, the SPM system 100 may include multiple aperture plates with different diameter annular outlets and apertures for different types of objects that are to be inspected or modified. In this way, each aperture plate is a detachable portion of the housing 154 so that the housing can be fitted with different size annular outlets and apertures.

In addition, the particle removal structure 342 removes particles during operation and/or calibration in the manner described earlier for the fifth SPM probe 122-5. And, in an alternative embodiment, the aperture plate 122-13 may include gap sensors 164 like that described earlier for the eighth SPM probe 122-8 rather than the gas bearing structure 402.

Referring to FIGS. 11 and 52, in the case where the radiation source provides electromagnetic energy or charged particles, the position of the radiation source 410 can be calibrated using one or more of the radiation detection devices 460 in the same manner as that discussed for the first, eighth, eleventh, and seventeenth SPM probes 122-1, 122-8, 122-11, and 122-17. In the specific case where the radiation source provides x-rays, each of these radiation detection devices could include a thin metal window 469 on the aperture structure 466 and over the aperture. The metal window is used to block (or absorb) extraneous charged particles and to block very low energy electrons, x-rays and all other electromagnetic energy of lower wavelength far UV through radio waves.

Furthermore, In the case where the radiation source provides charged particles, its position can also be calibrated using one or more of the radiation detection devices 461 in the manner discussed earlier for the eighth and eleventh SPM probes. And, the reference materials 188, 189, and 458 could be used in the respective specific cases where the radiation source provides electrons, light, and ions.

Structure of SPM Probes 122-14 and 122-15

Figure 58:
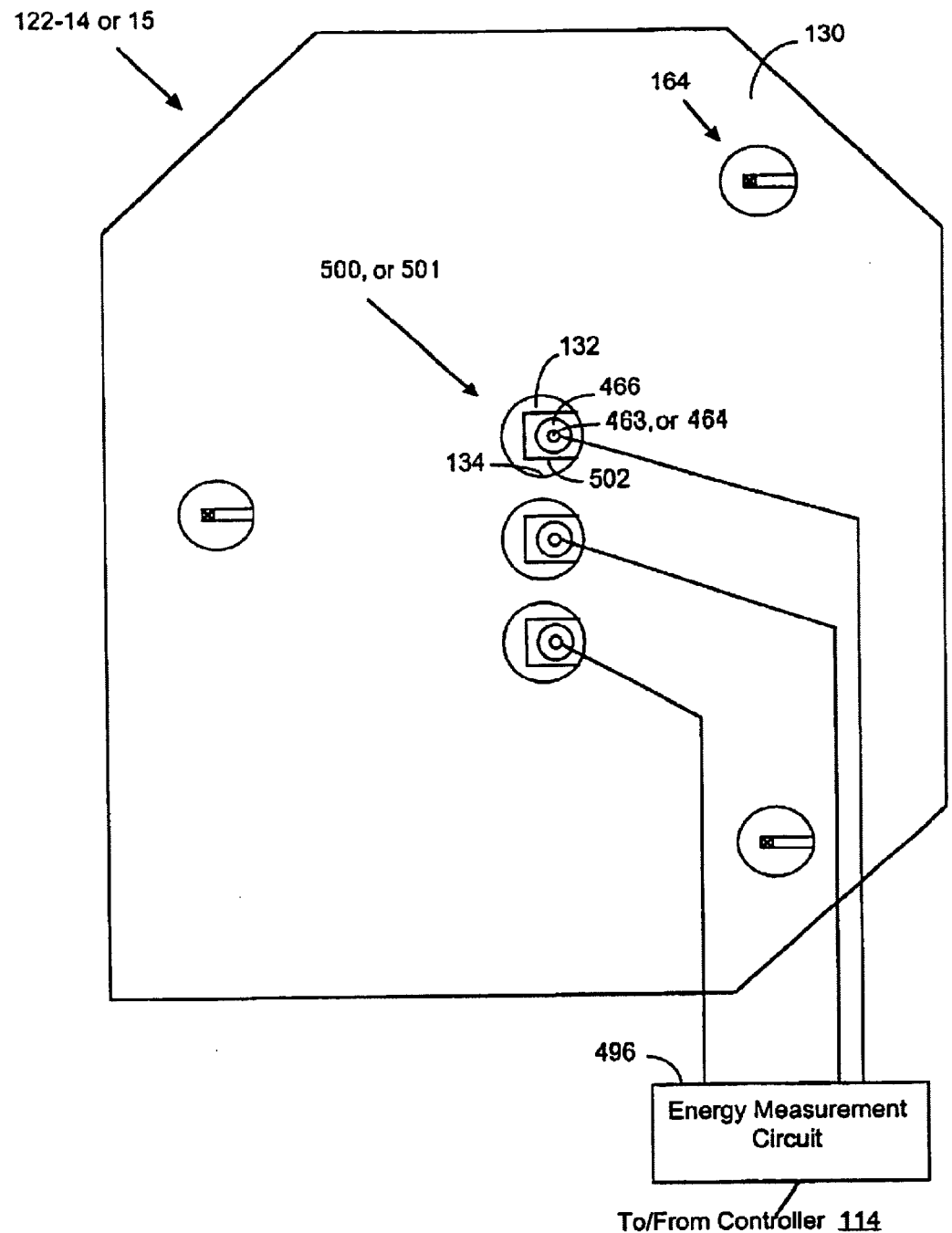
FIGS. 58 to 60 show different views of a fourteenth or fifteenth SPM probe of the SPM system of FIG. 1.

Turning now to FIG. 58, there is shown an embodiment for a fourteenth microstructured SPM probe 122-14 and a fifteenth microstructured SPM probe 122-15. These probes are used to make SPM measurements of the object 102 that are radiation measurements made with the radiation detection tools 500 and 501 of respectively the fourteenth and fifteenth probes. The fourteenth and fifteenth probes each include an aperture 132 and gap sensors 164 that are formed in the base 130 of the probe in the manner described earlier for the first SPM probe 122-1. The base 130 has the same basic shape and construction as was described earlier for the first probe.

Figure 59:
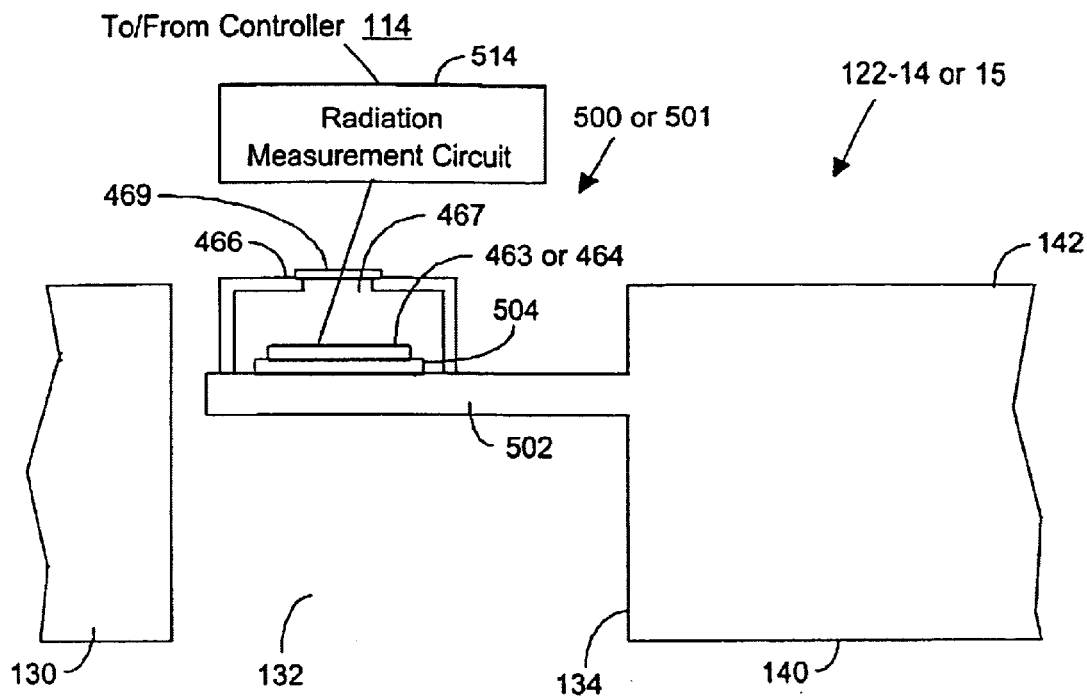

Referring to FIG. 59, each radiation detection tool 500 and 501 includes a support platform 502, such as a cantilever, that is suspended in the corresponding aperture 132 of the tool. The support platform is connected to the corresponding inner perimeter surface 134 of the base 130 of the SPM probe 122-14 or 122-15 so that the tool is between the upper and lower surfaces 140 and 142 of the probe. The support platform may be separately formed or may be an integral portion of the base. Each radiation detection tool further includes an insulating plate 504 on the support platform that comprises an insulating material, such as silicon dioxide. The radiation detection tools 500 and 501 are constructed like the radiation detection devices 460 and 461 of the calibration structure 128-2, except that their respective radiation detectors 463 and 464 are formed on the insulating plate and their aperture structure is formed on the support platform.

Probe Loading and Unloading, Calibration, Vacuum Operation, and Particle Removal Operation of SPM Probes 122-14 and 122-15

Figure 60:
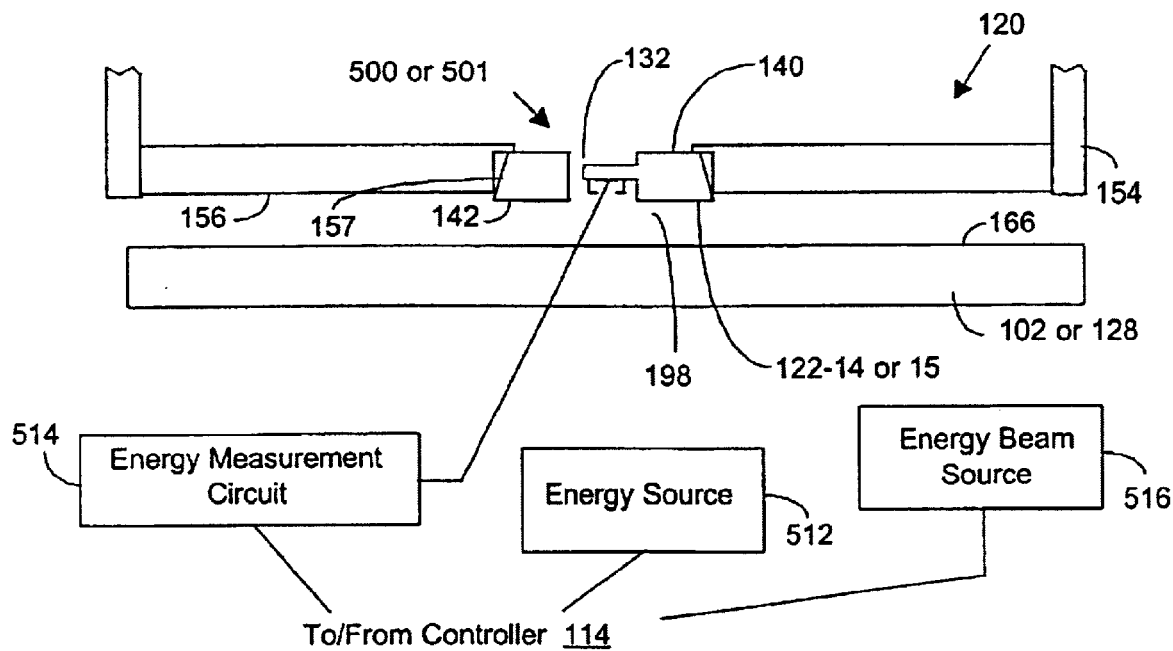

Referring to FIG. 60, the fourteenth and fifteenth SPM probes 122-14 and 122-15 may each be loaded onto and unloaded from one of the scanning heads 120 in the same ways as were described earlier for the first SPM probe 122-1. And, each radiation detection tool 500 and 501 may have its profile examined in the manner discussed earlier for the first probe. Furthermore, optical images would be produced by the imaging optics 226 during operation and/or calibration of each of the fourteenth, fifteenth, and sixteenth probes in the manner discussed earlier for the first probe. During operation and/or calibration of each of the fourteenth, fifteenth, and sixteenth probes, a microvacuum chamber in the gap 198 between the probe and the object 102 or calibration structure 128 may be established in any of the ways described earlier for the first probe with the aperture 132 and the gap sensors 164 of the probe. Or, the fourteenth, fifteenth, and sixteenth probes may each include instead a gas bearing structure 342 like that described earlier for the eighth SPM probe 122-8. Finally, the fourteenth, fifteenth, and sixteenth probes could each also include a particle removal structure 342 to remove particles during operation and/or calibration in the manner described earlier for the fifth SPM probe 122-5.

Inspections with SPM Probes 122-14 and 122-15

Referring to FIG. 60, the other components 123 of the SPM system 100 may include a radiation source 512 and a radiation measurement circuit 514. The radiation source provides radiation. This radiation may be electromagnetic energy, like visible light, ultraviolet light, infrared light, x-rays, gamma rays, and/or radio frequency waves, and/or charged particles, like ions, electrons, protons, and/or alpha particles. Alternatively, the radiation source may be in the form of light emitted by the SPM probe 122-17 in the manner discussed later.

Referring again to FIG. 1, in order to inspect the object 102 using one of the radiation detection tools 500 or 501 of one of the SPM probes 122-14 or 122-15, the controller 114 controls the positioning system 103 to position the probe for a scan of the object 102. Turning to FIGS. 58 to 60, at each scan point, the controller causes the radiation source 512 or the SPM probe 122-17 to produce radiation that is directed at the object. The resulting radiation that passes through the aperture 132 of the radiation detection tool is detected by the radiation detector 463 or 464 of the tool. The radiation measurement circuit makes a measurement of the detected radiation and provides it to the controller. This is done in the same manner as was described earlier for the radiation detection devices 460 or 461 depending on the kind of radiation that is detected. Furthermore, the radiation measurement circuit also grounds the aperture structure 466 to block extraneous radiation.

The selected radiation detection tool 500 or 501 of one of the SPM probes 122-14 or 122-15 may be used to detect radiation reflected and/or emitted by the object 102. In this case, the probe and the radiation source 512 or the SPM probe 122-17 would be positioned above the object. The controller 114 may then make an image and/or analysis of the object or a patterned image or analysis of the radiation reflected by the object with the measurements received from the radiation measurement circuit 514. This may be particularly useful for inspecting a lithographic structure, such as a semiconductor fabrication mask. In this case, the controller may generate a patterned image of the radiation reflected by it and to which a replicable structure being fabricated with the lithographic structure would not be exposed (i.e., would be masked from).

Alternatively, the selected radiation detection tool 500 or 501 may be used to detect radiation that passes through the object 102. In this case, the SPM probe 122-14 or 122-15 would be positioned above the object and the radiation source 512 or the SPM probe 122-17 would be positioned below it. The controller 114 would then make a patterned image or analysis of the radiation that the object projects (i.e., allows to pass through it) from the measurements received from the radiation measurement circuit 514. This also may be useful for inspecting a lithographic structure by generating a patterned image of the radiation which a replicable structure would be exposed to by the lithographic structure.

Calibration of SPM Probes 122-14 and 122-15

The position of the radiation detection tools 500 and 501 of the SPM probes 122-14 and 122-15 may be calibrated and their profiles examined using the AFM probe 131 and SEM probe 133 of the calibration structure 128-1. This would be done in the manner discussed earlier for the first SPM probe 122-1.

Referring to FIG. 60, the other components 123 of the SPM system 100 may further include a radiation beam source 516 that is located at precisely known location with respect to the reference location of the SPM system. This radiation beam source may also be used in calibrating the position of a selected radiation detection tool 500 or 501 of one of the SPM probes 122-14 or 122-15.

Specifically, referring again to FIG. 1, the controller 114 calibrates the position of the selected particle detection tool 500 or 501 by controlling the positioning system 103 to attempt to position the tool over the radiation beam source 516. Then, turning again to FIG. 60, the controller causes the radiation beam source to produce a radiation beam. The radiation beam may comprise a charged particle beam, such as an e-beam, ion beam, proton beam or alpha particle beam, or an electromagnetic energy beam, such as a visible light beam, ultraviolet light beam, infrared light beam, gamma ray beam, xray beam, or radio frequency beam. The controller analyses the measurement received from the radiation measurement circuit 514 to determine if the radiation beam is being detected by the radiation detection tool so that the radiation detection tool is positioned over the radiation beam source. Thus, in a closed feedback loop, the radiation detection tool is positioned, the radiation beam is produced, and the measurement from the energy measurement circuit is analyzed until it is determined by the controller that the radiation detection tool is in fact positioned over the radiation beam source. Once this occurs, a positional offset is computed and the precise positioning of the radiation detection tool with respect to the reference location is then calibrated based on the positional offset in the manner described earlier.

Structure of SPM Probe 122-16

Figure 61:
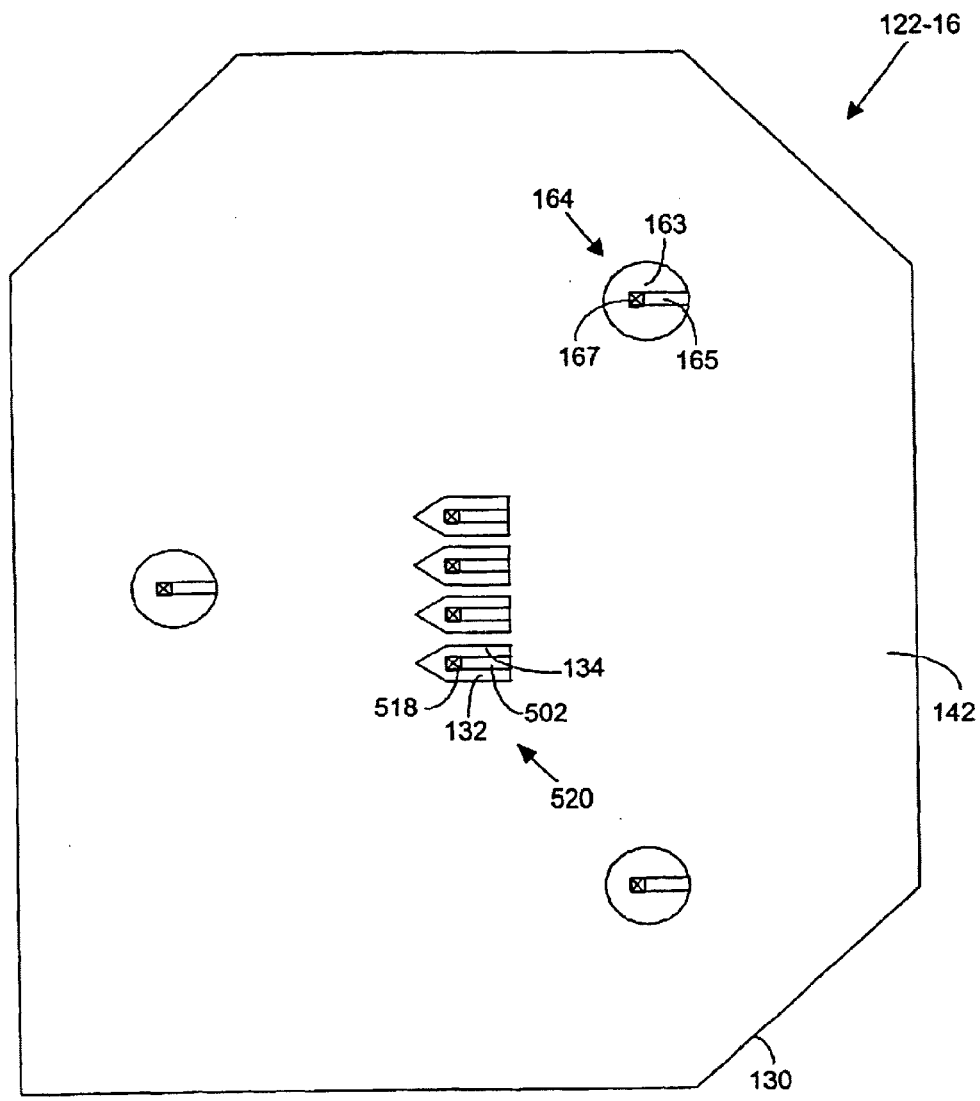
FIGS. 61 to 63 show different views and embodiments of a sixteenth SPM probe of the SPM system of FIG. 1.

Turning now to FIG. 61, there is shown an embodiment for a sixteenth microstructured SPM probe 122-16 for use in making SPM measurements of the object 102 which are radiation measurements. The sixteenth probe is constructed like the fourteenth SPM probe 122-14, except that the radiation detection tools 500 are replaced by the radiation detection tools 520.

Figure 62:
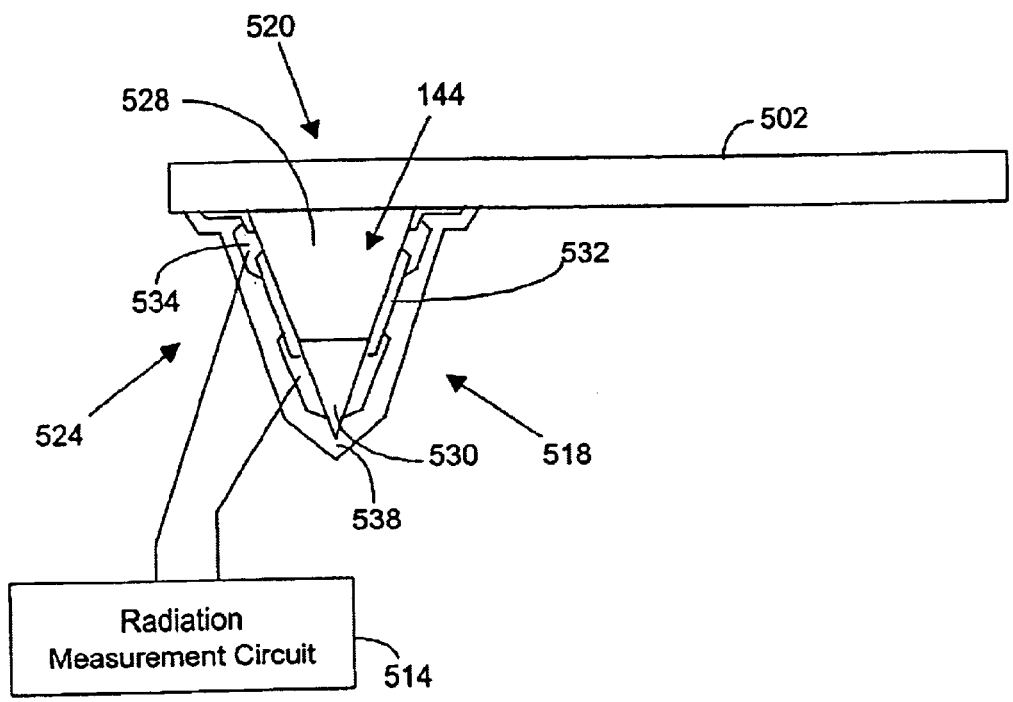
Figure 63:
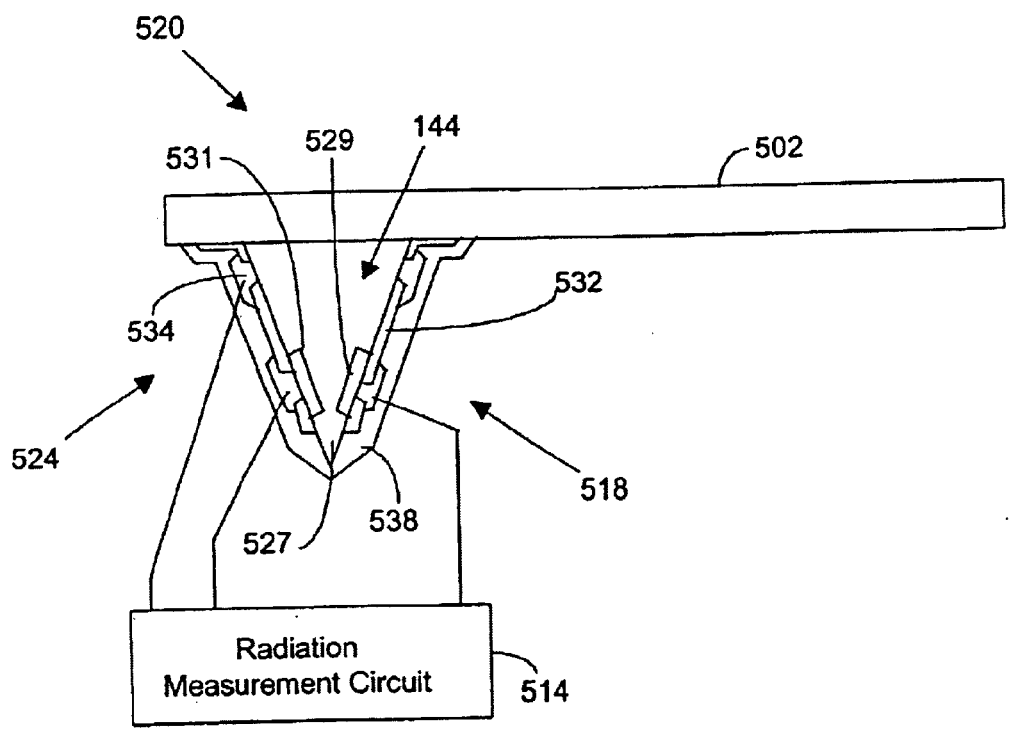

Referring to FIGS. 62 and 63, each radiation detection tool 520 includes a support platform 502 that is suspended in the corresponding aperture 132 of the tool, as was described for each radiation detection tool 500. However, here, each radiation detection tool includes a tip 518 on the support platform. Formed in the tip, is a semiconductor radiation detector 524.

In the embodiment of FIG. 62, the radiation detector comprises a radiation sensitive semiconductor junction diode that is formed in the tip 518. The core material 144 of the tip comprises a semiconductor material, such as silicon. The junction diode comprises an upper semiconductor region 528 in the core material that is doped to be N or P type. It also includes a lower semiconductor region 530 in the sharp end of the core material that is oppositely doped P or N type to that of the upper semiconductor region. The lower and upper semiconductor regions are doped using conventional techniques known to those skilled in the art and in the manner described in "Semiconductor Detectors" referenced earlier so that electromagnetic energy and/or charged particles can be detected by the radiation detector.

An insulating coating is formed over the core material and etched to provide the junction diode with insulating regions 532 and contact areas for conductive contact regions 534 of each radiation detector 524. The entire tip is coated with a conductive coating, such as tungsten, gold, aluminum, or indium tin oxide or silicon carbide, carbon nitride, or diamond that is doped to be conductive in the manner described earlier. This conductive coating is then etched to form the conductive contact regions which each contact a corresponding one of the upper and lower semiconductor regions. In doing so, the conductive coating may be removed or rubbed off from the sharp end of the tip. Or, if the conductive coating is a sufficiently light, it may pass an adequate amount of radiation without being removed. Moreover, if the conductive coating is transparent to radiation, such as silicon carbide, carbon nitride, or diamond, then it need not be removed at all and can also serve as an obdurate coating for the tip. And, in the case where the conductive coating is not an obdurate material, such as gold, aluminum, indium tin oxide, or tungsten, each radiation detector 524 may include an additional obdurate coating 538, like silicon carbide, carbon nitride, diamond like carbon, or diamond, that would be deposited over the entire tip. This is done in the manner described earlier for the first to third SPM probes 122-1 to 122-3. But, this obdurate coating is thin enough to be transparent to the radiation directed at the tip. As a result, a radiation sensitive PN or NP junction diode is formed. This type of radiation detector is further described in U.S. patent application Ser. Nos. 08/906,602 and 08/776,361 referenced earlier.

Referring to FIG. 63, in alternative embodiment, the semiconductor radiation detector 524 comprises a radiation sensitive junction transistor that is formed in the tip 518. In this case, the junction transistor includes a semiconductor base region 527, a semiconductor collector region 529, and a semiconductor emitter region 529 in the core material 144. The base, collector, and emitter regions respectively form the base, collector, and emitter of the junction transistor. The base region is oppositely doped N or P type from the P or N type doping of the collector and emitter regions. And, the base, collector, and emitter regions are each contacted by a corresponding one of the contact regions 534 that are formed between the insulating regions 532. This results in the tip having a radiation sensitive PNP or NPN junction transistor for detecting radiation directed at the tip. Otherwise, the radiation detector is constructed in the same manner as that described for the embodiment of FIG. 62.

Probe Loading and Unloading, Calibration, Inspection Operation, Vacuum Operation, and Particle Removal Operation of SPM Probe 122-16

The sixteenth SPM probe 122-16 may be loaded onto and unloaded from one of the scanning heads 120 in the same ways as were described earlier for the first SPM probe 122-1. And, the tip 518 of each of the radiation detection tool 520 may be activated, deactivated, and have its position calibrated and profile examined in the ways described earlier for the first probe, except that its position would not be calibrated using STM and radiation measurements. Moreover, these tools (and their tips) may have their positions calibrated and may be used to detect radiation in the same manner as was described earlier for the radiation detection tools 500 for the fourteenth SPM probe 122-14. And, optical images would be produced by the imaging optics 226 during operation and/or calibration of the sixteenth probe in the manner discussed earlier for the first probe. During operation and/or calibration of the sixteenth probe, a microvacuum chamber in the gap 198 between the probe and the object 102 or calibration structure 128 may be established in any of the ways described earlier for the first probe with the aperture 132 and the gap sensors 164 of the probe. Or, the sixteenth probe may include instead a gas bearing structure 342 like that described earlier for the eighth SPM probe 122-8. Finally, the sixteenth probe could also include a particle removal structure 342 to remove particles during operation and/or calibration in the manner described earlier for the fifth SPM probe 122-5.

SPM Modifications with SPM Probe 122-16

As mentioned earlier, the radiation detector 524 of each radiation detector tool 520 of the SPM Probe 122-16 may comprise an obdurate coating 534 or 538 on the tip 518 of the tool. Thus, such a radiation detector may be formed in the tips 138, 238, and 320 of the first, second, and fifth to seventh SPM probes 122-1, 122-2, and 122-5 to 122-7. In this case, these tips could be used not only to modify the object in the manner described earlier, but could also be used to inspect the object 102 and have their positions calibrated in the same manner as was just described. In addition, since this radiation detector is photosensitive (i.e., sensitive to visible light), they could be used to detect the buildup of opaque debri particles on the tips. These debri particles comprise particulate material removed from the object during the modifications performed with the tips.

Specifically, this would be done by monitoring the visible light detected by the radiation detector 524 in the tip 138, 238, or 320 with the energy measurement circuit 514. When, the radiation detector no loner detects a certain predefined threshold of visible light, this means too many debri particles have been accumulated on the surface of the tip. Then, another tip of the corresponding SPM probe 122-1, 122-2, 122-5, 122-6, or 122-7 is used, the tip is cleaned, or the probe is discarded in the manner discussed earlier.

Structure of SPM Probe 122-17

Figure 64:
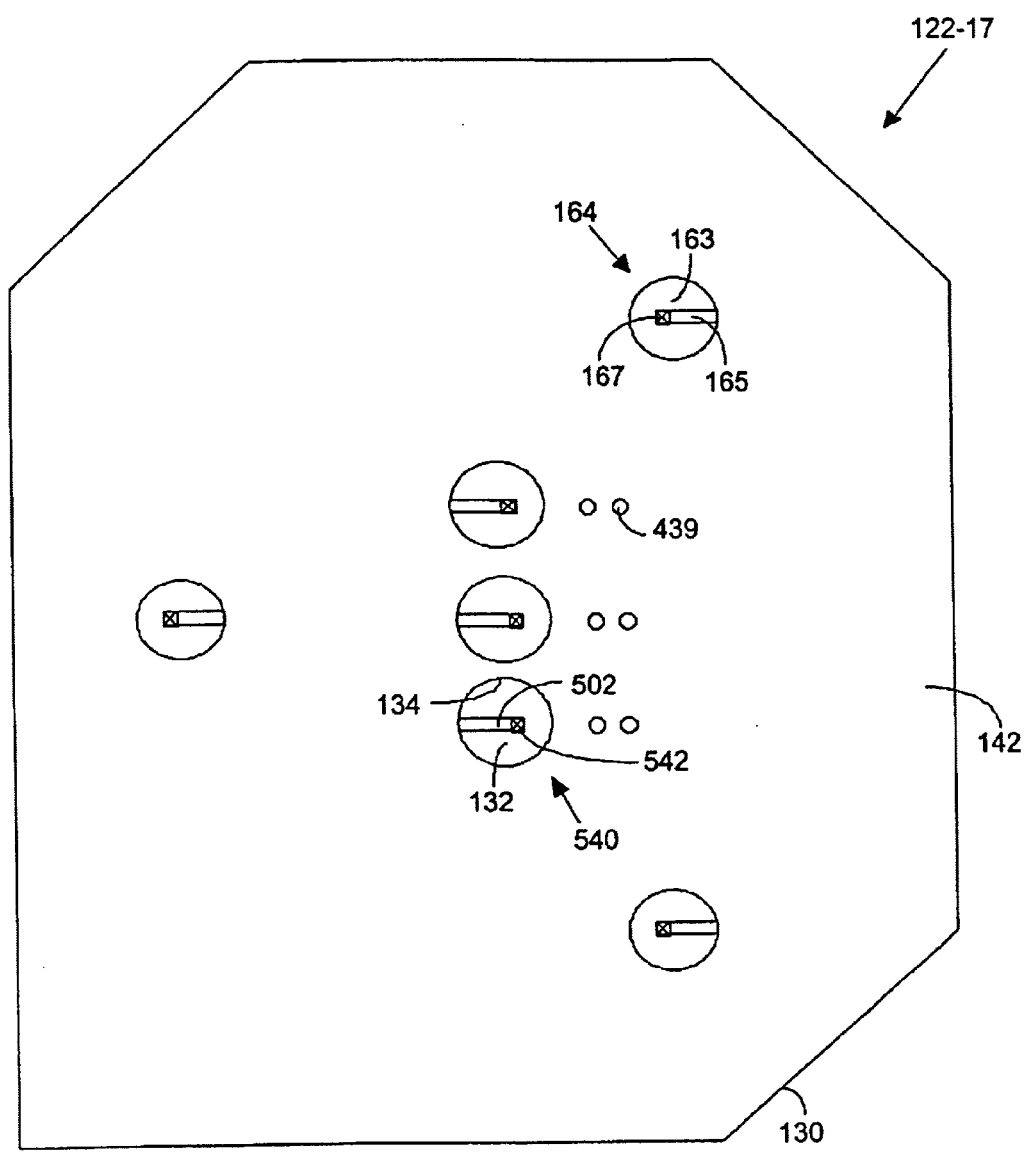
FIGS. 64 to 67 show different views and embodiments of a seventeenth SPM probe of the SPM system of FIG. 1.

Turning now to FIG. 64, there is shown a seventeenth microstructured SPM probe 122-17 for use in making SPM measurements of the object 102. Here, the SPM measurements are radiation measurements made in response to radiation directed at the object which is in the form of light. To do so, the seventeenth probe includes light emission tools 540 to direct the light at the object. Each light emission tool is suspended in a corresponding aperture 132. The seventeenth probe also has gap sensors 164 like the first SPM probe 122-1 and a base 130 that is constructed and has the same shape like that of the first probe.

Figure 65:
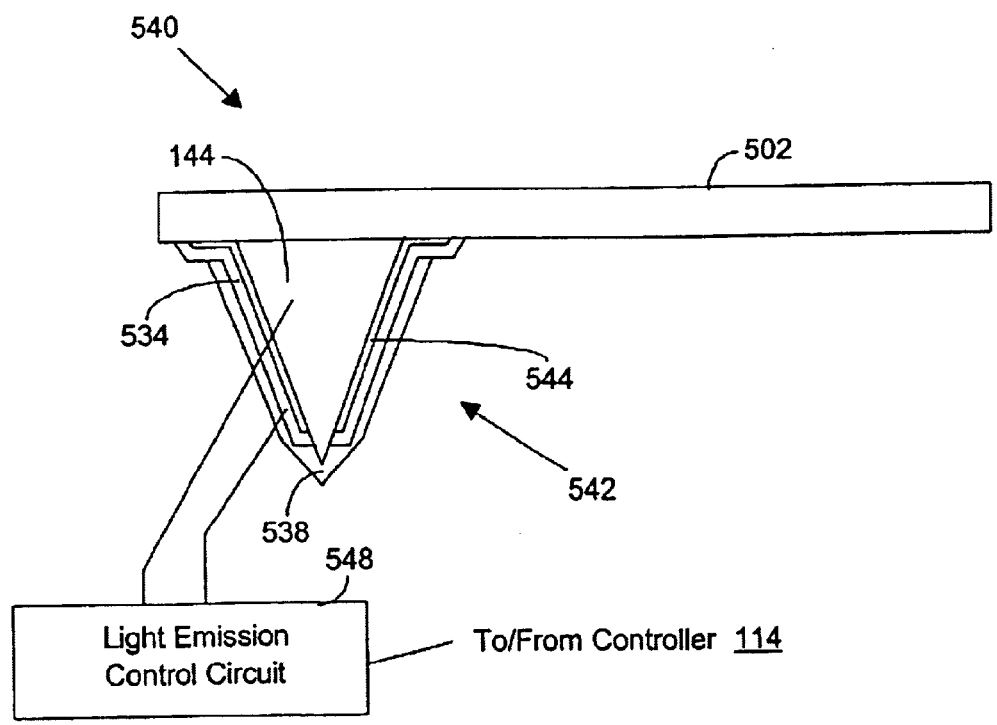

As shown in FIG. 65, each light emission tool 540 comprises a support platform 502 like each radiation detection tool 520. However, each light emission tool comprises a tip 542 that emits light. The core material 144 of the tip comprises a semiconductor material, such as silicon. The core material is coated with an emissive coating 544 at a thickness of approximately 10 to 200 nanometers. This emissive coating may comprise gallium nitride, gallium arsenide, or silicon carbide which is suitably doped to be emissive. A conductive coating 534 is deposited over the emissive coating and has a thickness of approximately 20 to 200 nanometers. This conductive coating may be tungsten, gold, aluminum, or indium tin oxide or silicon carbide, carbon nitride, or diamond that is doped to be conductive in the manner described earlier. About 5 to 10 nanometers of the conductive coating at the sharp end of the tip may be made sufficiently thin so that it is transparent to blue and/or UV light or can be removed or rubbed off from the sharp end of the write tip. This forms an aperture at the sharp end of the tip with a diameter in the range of approximately 5 to 100 nanometers.

The other components 123 of the SPM system 100 may include a light emission control circuit 548. When a voltage of about 4 volts is applied across the conductive coating and core material by the light emission control circuit, blue (e.g., 423 nanometer wavelength) and/or ultraviolet (UV) light (e.g., 372 nanometer wavelength) is emitted by the emissive coating as described in "Deposition, Characterization, and Device Development in Diamond, Silicon Carbide, and Gallium Nitride Thin Films" referenced earlier. The light propagates through the core material until it is emitted at the aperture. The aperture has a diameter substantially smaller than the wavelength of the light.

Additionally, in the case where the conductive coating is not an obdurate material, such as conductive diamond, silicon carbide, or carbon nitride, the tip may also include an obdurate coating 538 of the kind described earlier for the tip 518 of the radiation detection tool 520 of FIG. 62. Furthermore, the light emission tool 540 of the embodiment of FIG. 65 is further described in the U.S. patent application Ser. Nos. 08/906,602, 08/776,361, and 08/506,516 and PCT Patent Application No. PCT/US96/12255 referenced earlier.

Figure 66:
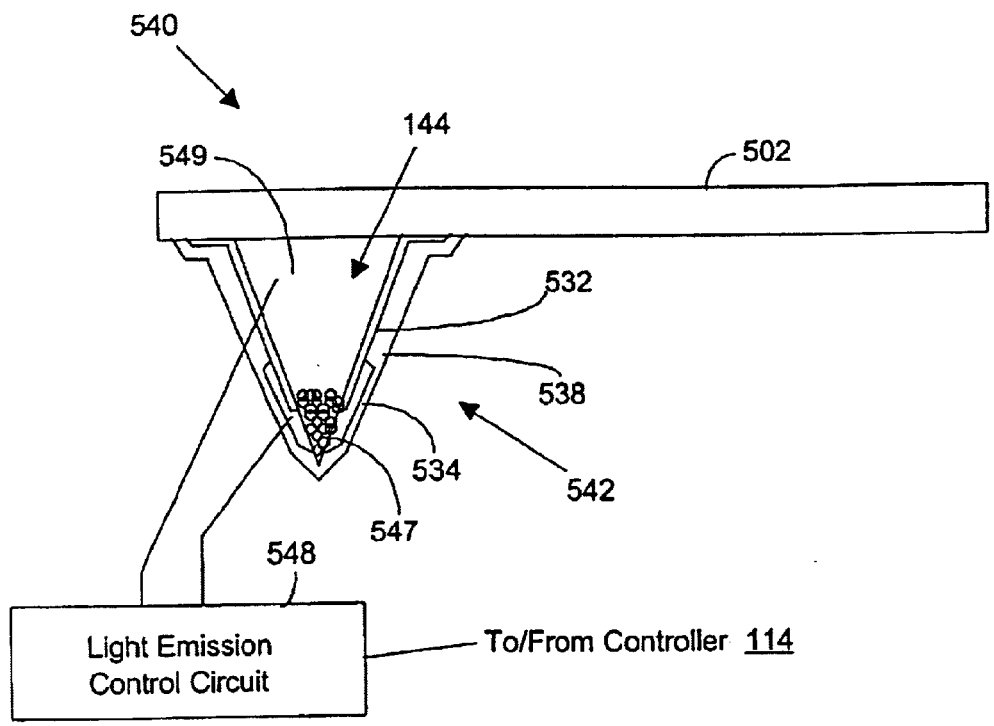

In an alternative embodiment shown in FIG. 66, the core material of each tip 542 of each light emission tool 540 is comprised of silicon. The lower region 547 of the core material at the sharp end of the tip is porous. This is accomplished by immersing the core material of the tip in a dilute solution of Hydrofluoric acid or a dilute solution Hydrofluoric and Nitric acid and operating the tip as an anode. In addition, a gold or platinum cathode is also immersed in the solution. A current is then produced between the anode and cathode which is sufficient to porously etch the lower region of the core material at the sharp end of the tip but leave the upper region 549 of the core material unetched. The insulating regions 532 and the contact regions 534 of the tip are then formed. This is done in the same manner as discussed earlier for the tip 518 of the embodiment of the radiation detection tool 520 of FIG. 62. To form an aperture at the sharp end of the tip, about 5 to 10 nanometers of the contact region at the sharp end may be made sufficiently thin so that it is transparent to light or can be removed or rubbed off from the sharp end of the tip. Thus, when a voltage is applied across the conductive coating and core material of each tip by the light emission light control circuit 548, a current is produced in the porous lower region which causes it to emit light through the aperture of the tip.

In the case where the conductive coating is not an obdurate material, such as conductive diamond, silicon carbide, or carbon nitride, the tip 542 may also include an obdurate coating 538 of the kind described earlier for the tip 518 of the radiation detection tool 520 of FIG. 62. The light emission tool 540 of the embodiment of FIG. 66 is further described in U.S. patent application Ser. No. 08/506,516 and PCT Patent Application No. PCT/US96/12255 referenced earlier. Furthermore, light emission by porous silicon is further described in *An Improved Fabrication Technique for Porous Silicon*, Review of Scientific Instruments, v64, m2 507–509 (1993), *Photoluminescence Properties of Porous Silicon Prepared by Electrochemical Etching of Si Epitaxial Layer*, Act. Physics Polonica A, v89, n4, 713–716 (1993), *Effects of Electrochemical Treatments on the Photoluminescence from Porous Silicon*, Journal of the Electrochemical Society, v139, n9, L86–L88 (1992), *Influence of the Formation Conditions on the Microstructure of Porous Silicon Layers studied by Spectroscopic Ellipsometry*. Thin Solid Films, v255, n1–2; 5–8 (1995), and *Formation Mechanism of Porous Si Layers Obtained by Anodization of Mono-Crystalline N-type Si in HF Solution and Photovoltaic Response in Electrochemically Prepared Porous Si*, Solar Energy Materials and Solar Cells, v26, n4, 277–283, which are hereby explicitly incorporated by reference.

Figure 67:
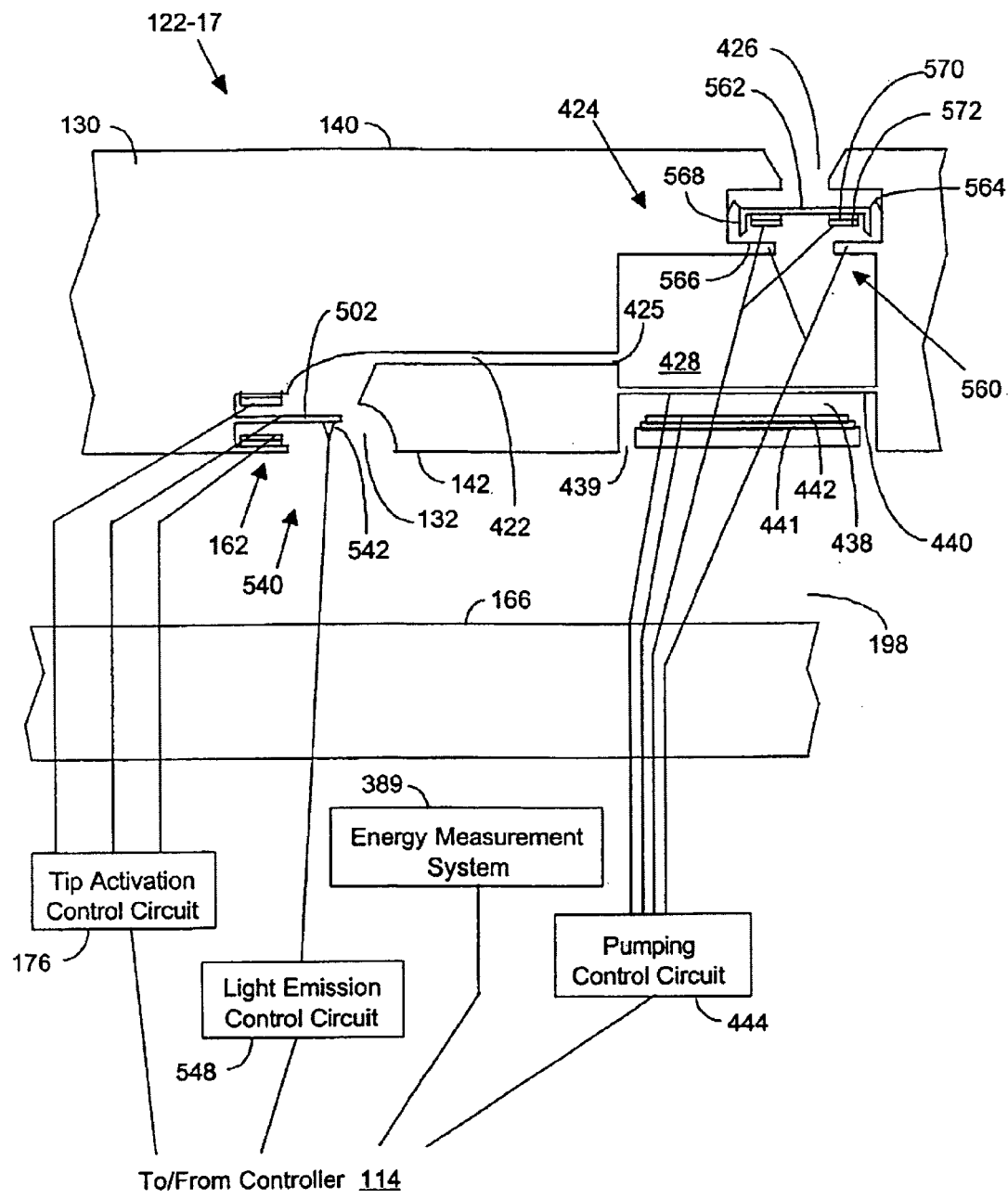

Additionally, referring to FIG. 67, the seventeenth probe includes a corresponding vacuum pump 424 formed in the base 130 of the probe for each light emission tool 540. This vacuum pump is formed like that described earlier for the fluid delivery tools 414 of the ninth SPM probe 122-9, except that it includes an outlet valve 560 instead of the check valve 430. As will be described in greater detail later, the vacuum pump is used to create a microvacuum chamber in the gap 198 between the upper surface 166 of the object 102 and the lower surface 142 of the base of the seventeenth probe. In an alternative embodiment, one vacuum pump could be used for all of the light emission tools.

The outlet valve 560 is disposed between the pumping chamber 428 and the outlet 426. The outlet valve includes a sealing plate 562 that extends across the outlet and floats between the stops 564 and the sealing seats 566 of the outlet valve that are formed in the base 130. The outlet valve further includes sealing arms 568 that extend out from the sealing plate. The sealing plate and the sealing arms may be integrally formed together. The outlet valve also includes an insulating plate 570 on the inner surface of the outlet and plate electrodes 572 on the insulating plate. The plate electrode may comprise a conductive material, such as polysilicon or tungsten, and the insulating plate may comprise an insulating material, such as silicon dioxide. The sealing plate may be integrally formed with the base and comprises a conductive semiconductor material. Thus, in order to close the outlet valve, the pumping control circuit 444 applies an appropriate voltage across the sealing seats and the plate electrodes. This causes the sealing plate to move toward the sealing seats so that the sealing arms are seated against the sealing seats. This seals the pumping chamber from the outlet. As those skilled in the art will recognize, the valve just described may be used in the SPM probes 122-9 to 122-12 in place of the check valve 430.

Each light emission tool 540 further includes an inlet duct 422 that connects the aperture 132 and the inlet 425 of the pump 424. In this way, the pump and the aperture are in fluid communication so that the pump can create a microvacuum chamber in the gap between the object and the base 130 of the seventeenth SPM probe 122-17.

In addition, the support platform 502 of each light emission tool 540 is connected to the base 130 of the SPM probe 122-12 and suspended in the aperture 132 of the base within the corresponding inner perimeter surface 134 of the base. This is done so that the tip 542 of the light emission tool is kept between the lower and upper surfaces 142 and 140 of the base while not in operation to prevent it from being damaged. The support platform may be separately formed or may be an integral portion of the base. Each light described earlier for the gap sensors 164 of the first SPM probe 122-1 to actuate the tip of the light emission tool for operation.

Probe Loading and Unloading, Tip Activation and Deactivation, Calibration, and Particle Removal Operation of SPM Probe 122-17

Referring to FIG. 67, the seventeenth SPM probe 122-17 may be loaded onto and unloaded from one of the scanning heads 120 in the same ways as were described earlier for the first SPM probe 122-1. And, the tip 542 of each of the light emission tools 540 may have its position calibrated and profile examined in the ways described earlier for the first probe, except that STM and radiation measurements would not be used to calibrate its position. The activation and deactivation of the tip may be done using the tip actuator 162 and deflection sensor 161 and the tip activation control circuit 176. The tip activation control circuit operates under the control of the controller 114 and like the gap control circuit 176 described earlier in activating the tip and sensing deflection of the cantilever 502. Moreover, the position of the tip may be calibrated using the radiation detectors 460 and the reference materials 189 of the calibration structure 128-2 in the same manner as was described earlier for the SPM tools 137 of the first SPM probe 122-8. Furthermore, optical images would be produced by the imaging optics 226 during operation and/or calibration of the sixteenth probe in the manner discussed earlier for the first probe. Finally, the seventeenth probe could also include a particle removal structure 342 to remove particles during operation and/or calibration in the manner described earlier for the fifth SPM probe 122-5.

Vacuum Operation of SPM Probe 122-17

Still referring to FIG. 67, during operation and/or calibration of the seventeenth SPM probe 122-7, a microvacuum chamber in the gap 198 between the lower surface 142 of the base 130 of the probe and the upper surface 166 of the object 102 or calibration structure 128 may be established using the vacuum pump 424 in the base. In order to do so, at each scan point, the controller 114 first controls the pumping control circuit 444 to close the outlet valve 560 in the manner described earlier. Then, the controller controls the pumping control circuit to cause the pump to pump the ambient gas that is in the gap into the pumping chamber 428. In doing so, the pumping chamber is expanded so that the ambient gas is drawn into the aperture 132, through the duct 422, and into the pumping chamber 428 via the inlet 425. This is done in the same way as was described earlier for pumping fluid material into the pumping chamber of a pipette tool 446 of the SPM probe 122-10.

Then, at each scan point after the pumping chamber 428 is filled with ambient gas, the controller 114 causes the ambient fluid in the pumping chamber to be pumped out of the outlet 426. This is done by first controlling the pumping control circuit 444 to open the outlet valve 560 in the manner discussed earlier. Then, the controller controls the pumping control circuit to cause the pumping chamber to contract back to its normal volume. In other words, a suitable voltage is applied across the membrane 440 and the plate electrode 442 so that the membrane is returned to its normal position. This increases the pressure of the ambient gas in the pumping chamber so that it travels through the outlet valve and out of the outlet 426.

Additionally, this is done under the same conditions and assumptions as was described earlier for the SPM probe 122-1 for creating such a microvacuum chamber. Moreover, referring to FIG. 64, the gap sensors 164 are used in the same manner as was described earlier in order to set the appropriate width of the gap.

Alternatively, the microvacuum chamber in the gap 198 may be established in any of the ways described earlier for the first SPM probe 122-1. Or, the seventeenth probe may include instead a gas bearing structure 342 like that described earlier for the eighth SPM probe 122-8. Conversely, the vacuum pump 424 could be used in any of the other SPM probes 122-1 to 122-16 and 122-18 described herein to create such a microvacuum chamber.

Inspections with SPM Probe 122-17

Referring again to FIG. 1, in order to inspect the object 102 using a selected light emission tool 540 of the SPM probe 122-17, the controller 114 controls the positioning system 103 to position the probe for a scan of the object 102. Turning to FIGS. 64 to 67, at each scan point, the controller controls the light emission control circuit 548 to cause the light emission tool to produce light that is directed at the object in the manner just discussed. The energy measurement system 389 or one of the SPM probes 122-14,122-15 and 122-16 then makes a measurement of the radiation that is reflected and/or emitted by the object or the light that is projected by the object in response to this produced light. This radiation measurement may be an NSOM measurement of the kind described earlier for the SPM probe 122-1. Moreover, the radiation measurements that are collected may be used to generate an analysis or a patterned image of the radiation reflected by the object or the light projected by the object in the manner discussed earlier for the radiation detection tools 500, 501, and 520 for the SPM probes 122-14,122-15 and 122-16.

SPM Inspections and Modifications with SPM Probe 122-17

As mentioned earlier, each light emission tool 540 of the SPM Probe 122-17 may comprise an obdurate coating 534 or 538 on the tip 542 of the tool. Thus, this tip could be used like one of the tips 138,238, and 320 of the SPM probes 122-1, 122-2, and 122-5 to 122-7 for modifying the object in the manner described earlier for the SPM probes 122-1, 122-2, and 122-5 to 122-7. But, it could also be used to inspect the object 102 in the manner described for the SPM probes 122-1 and 122-2. In this case, the deflection sensor 161 and the tip activation control circuit 176 would be used in the manner discussed earlier to sense deflection of the cantilever 502 or 136 of the tools of these probes. Moreover, the cantilever deflection measurement system 205 described earlier could be used if the light used is transparent to the base 130 of the probe and the cantilever includes a reflective material, such as gold, tungsten, or aluminum, to reflect the light.

Structure of SPM Probe 122-18

Figure 68:
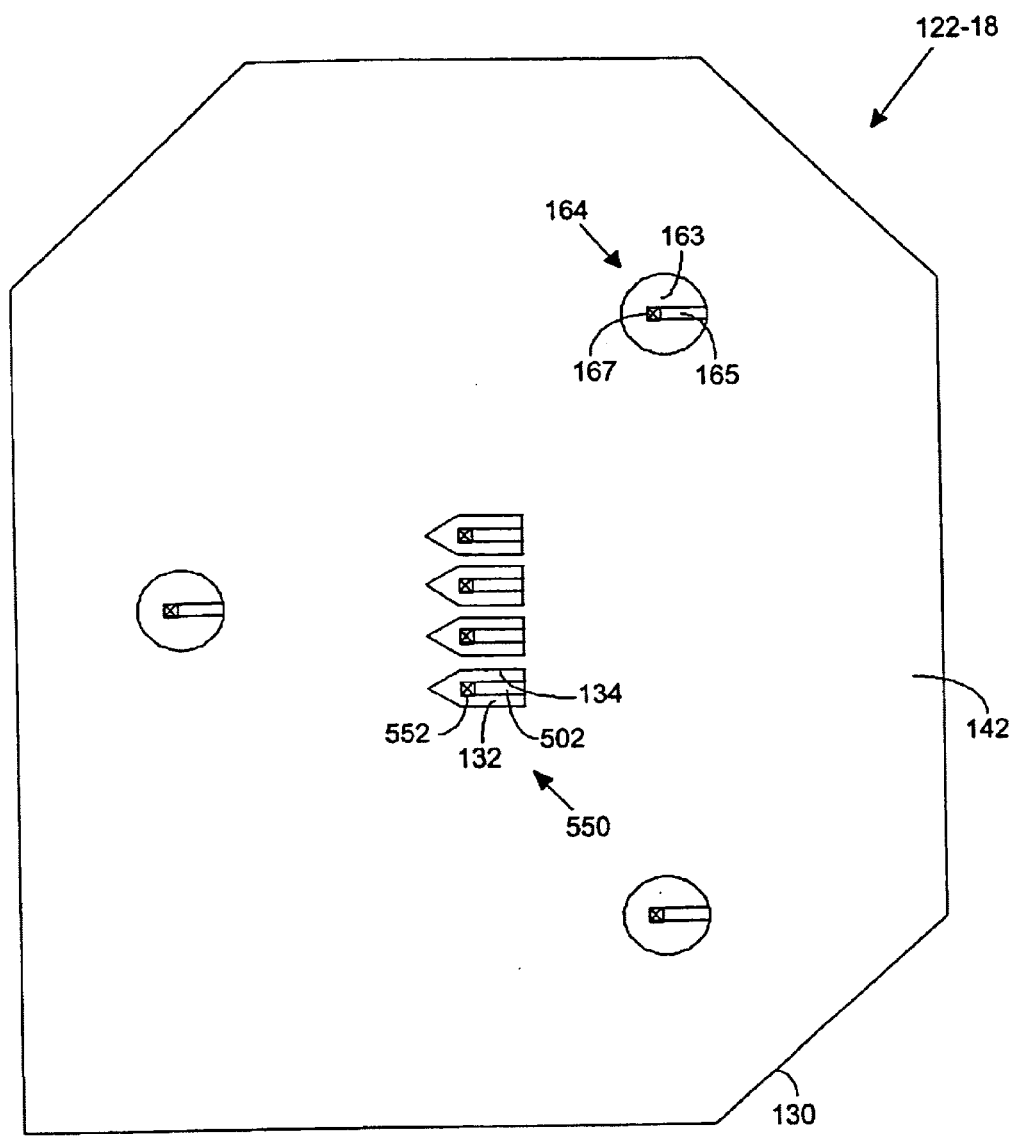
FIGS. 68 to 70 show different views of an eighteenth SPM probe of the SPM system of FIG. 1.

Turning now to FIG. 68, there is shown an eighteenth microstructured SPM probe 122-18 for use in making SPM modifications to the object 102. Here, the eighteenth probe includes heater tools 550 to heat the object. Each heater tool is suspended in a corresponding aperture 132. Otherwise, the eighteenth probe is constructed like the first SPM probe 122-1.

Figure 69:
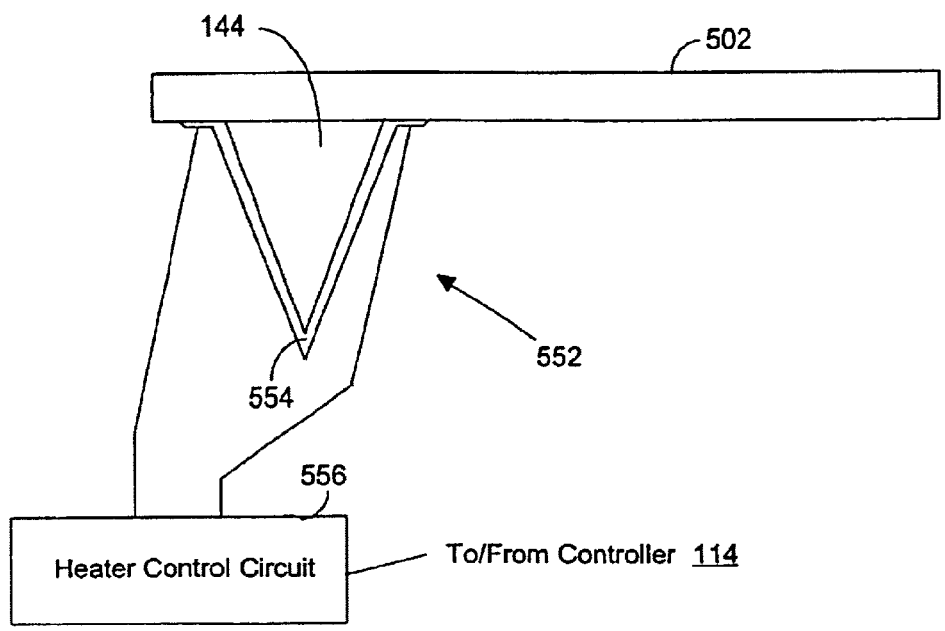

Referring to FIG. 69, each heater tool 550 includes a support platform 502, such as a cantilever, like the radiation detection tools 520 of the SPM probe 122-16. On the support platform is a tip 552. The core material 144 of the tip is coated with a resistive coating 554, such as Nichrome, Tungsten, or doped Silicon. Thus, when a voltage is applied across the resistive coating by the heater control circuit 556, the resistive coating generates heat which can be used to heat the object 102. The heater control circuit is one of the other components 123 of the SPM system 100.

Probe Loading and Unloading, Tip Activation and Deactivation, Calibration, Vacuum Operation, and Particle Removal Operation of SPM Probe 122-18

Figure 70:
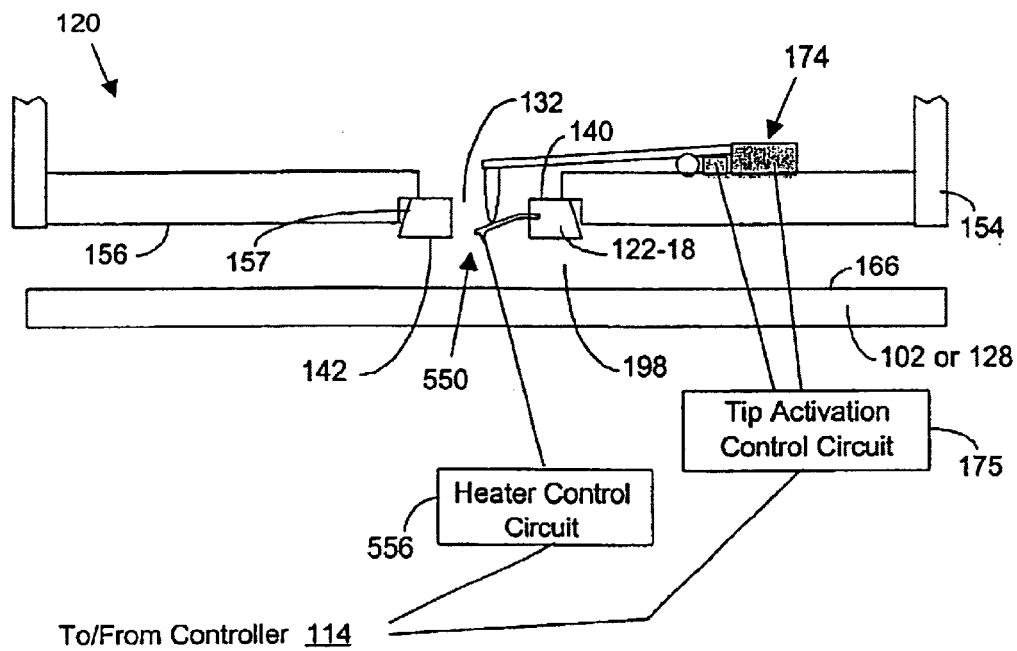

Referring to FIG. 70, the eighteenth SPM probe 122-18 may be loaded onto and unloaded from one of the scanning heads 120 in the same ways as were described earlier for the first SPM probe 122-1. And, the tip 552 of each of the heater tools 550 may be activated, deactivated, and have its position calibrated and profile examined in the ways described earlier for the first probe, except that radiation measurements would not be used to calibrate its position. Furthermore, optical images would be produced by the imaging optics 226 during operation and/or calibration of the eighteenth probe in the manner discussed earlier for the first probe. During operation and/or calibration, a microvacuum chamber in the gap 198 between the eighteenth probe and the object 102 or calibration structure 128 may be established in any of the ways described earlier for the first probe with the apertures 132 and the gap sensors 164 of the eighteenth probe or with the vacuum pump 424 of the seventeenth SPM probe 122-17. Finally, the eighteenth probe could also include a particle removal structure 342 to remove particles during operation and/or calibration in the manner described earlier for the fifth SPM probe 122-5.

SPM Modifications with SPM Probe 122-18

Referring again to FIG. 1, as mentioned earlier, the SPM probe 122-18 may be used to modify the object 102. This is done by heating the material of the object to plastically deform it, chemically change it change its crystalline state, or weld it and another material together. In doing so, the controller 114 controls the positioning system 103 to perform a scan of the object. At each scan point, the controller controls the positioning system to lower the activated tip 552 of a selected heating tool 550 of the probe to a target area of the object. Then, referring to FIG. 70, the controller controls the heating control circuit 556 to cause the tip 552 to heat the object in the manner discussed earlier.

Other SPM Probes 122

Referring back to FIG. 1, the SPM system 100 may also include other conventional SPM probes 122 to make SPM modifications and/or SPM measurements. For example, these probes may include a conventional MAFM (magnetic AFM) probe, a conventional LAFM (lateral AFM) probe, an electrical field strength probe used to respectively detect the magnetic field strength, the lateral force, and the electric field strength of the object at each scan point of a scan of the object controlled by the controller 114. In this case, the other components 123 of the SPM system would Include an MAFM measurement circuit, an LAFM measurement circuit, and an electric field measurement circuit that respectively provide MAFM, LAFM, and electric field strength measurements of the magnetic field strength, the lateral force, and the electric field strength to the controller at each scan point.

Such an SPM probe 122 would be constructed similar to that described for the first SPM probe 122-1 and may be loaded onto and unloaded from one of the scanning heads 120 in the same ways as were described earlier for the first probe. And, this probe may have its position calibrated and profile examined in the ways described earlier for the first probe. Furthermore, optical images would be produced by the imaging optics 226 during operation and/or calibration of this probe in the manner discussed earlier for the first probe. During operation and/or calibration, a microvacuum chamber in the gap 198 between this probe and the object 102 or calibration structure 128 may be established in any of the ways described earlier for the first probe with apertures 132 and gap sensors 164 or with the vacuum pump 424 of the seventeenth SPM probe 122-17. Finally, this probe could also include a particle removal structure 342 to remove particles during operation and/or calibration in the manner described earlier for the fifth SPM probe 122-5.

In addition, in the case of an MAFM probe, the probe would be particular useful in performing precision repairs and/or fabrication steps of a thin film magnetic read/write head or other magnetic structure. In particular, the magnetic properties of a gap (or groove) between the write and/or read poles of the thin film magnetic material can be precisely characterized (i.e., measured) using this probe. Thus, this gap may be formed and/or repaired in an iterative process using this SPM probe to measure the magnetic field strength of the gap at different scan points during each iteration and using the SPM probes 122-5 to 122-7 described earlier to physically form and/or modify the gap during each iteration. This is repeated until the desired magnetic properties of the gap are achieved.

Alternative Embodiments for SPM System 100

Figure 71:
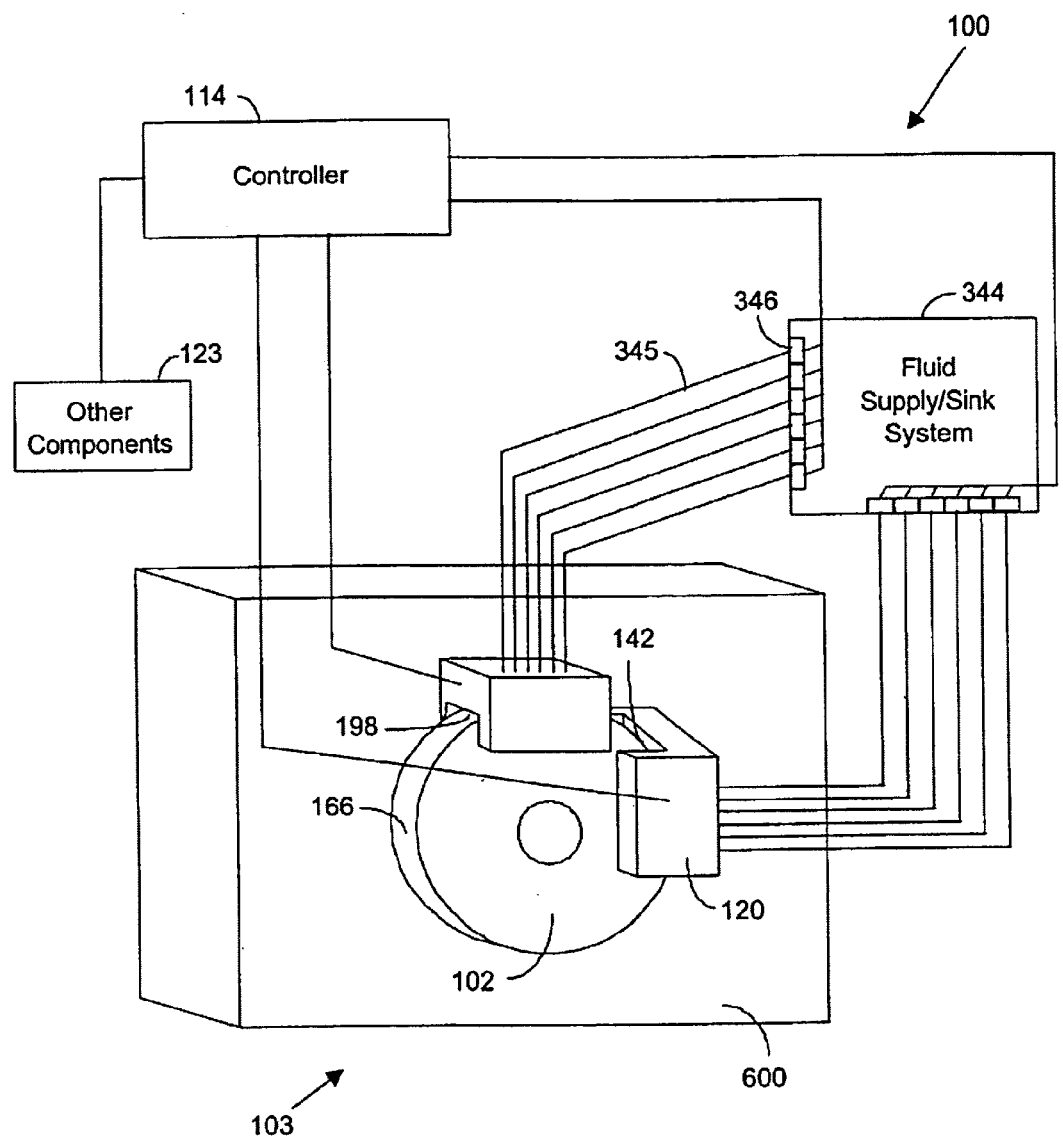
FIGS. 71 to 73 show different views of another embodiment of the SPM system of FIG. 1.

Referring to FIG. 71, there is shown another embodiment of the SPM inspection and/or modification system 100. As with the earlier embodiment of FIG. 1, the system includes a controller 114, one or more scanning heads 120, and a positioning or movement system 103 for moving the scanning heads and the object 102 with respect to each other.

Figure 72:
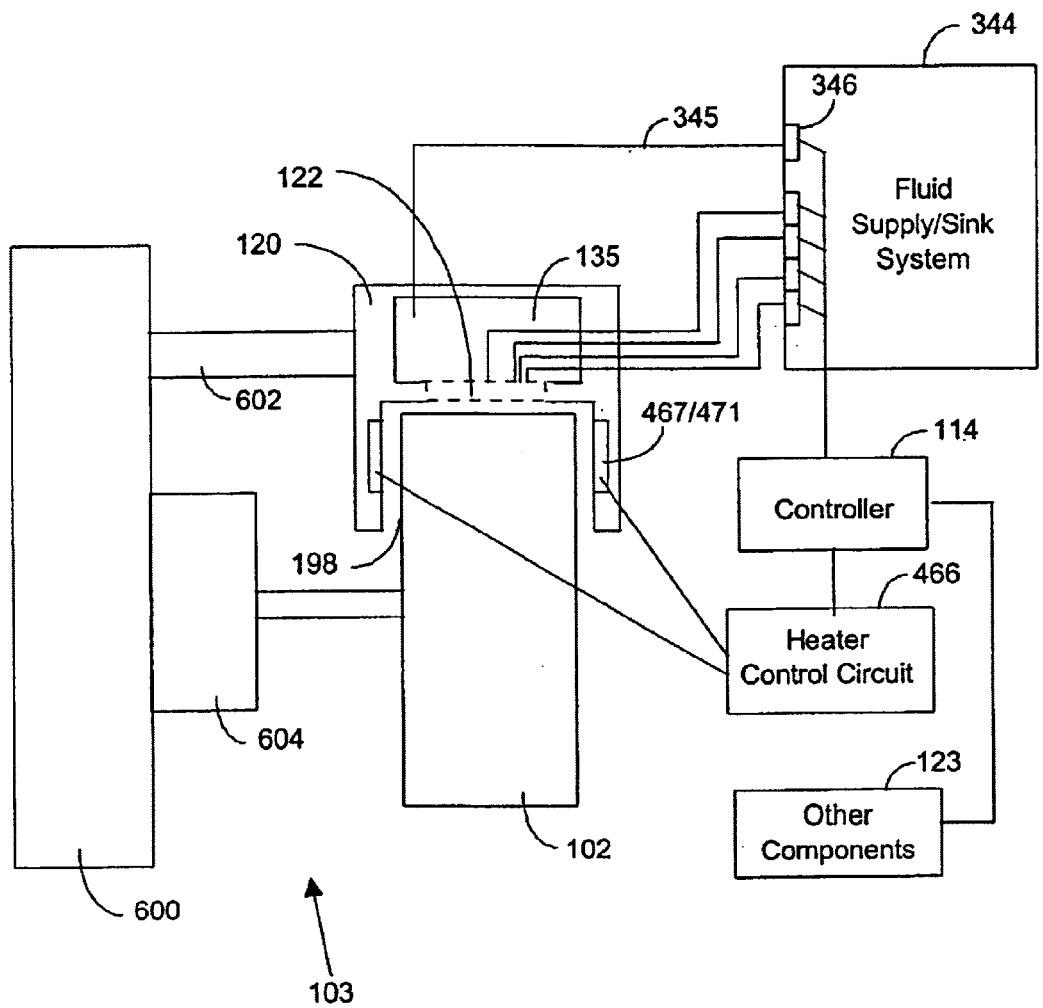

As shown in FIG. 72, the movement system 103 includes a support structure 600. Each scanning head 120 is fixed to the support structure with a corresponding support arm 602 of the movement system. The object 102 is mounted to a motor 604 of the movement system which is itself mounted to the support structure. The motor rotates the object 102 under the control of the controller 114 so that the object rotates through the scanning heads.

In this embodiment, each scanning head 120 includes one or more matching surfaces 142 that are correspondingly shaped to match the outer surfaces 166 of the object 102. Furthermore, each scanning head may include one of the SPM probes 122-1 to 122-18 described earlier. This probe is embedded, mounted, or loaded in the scanning head and provides at least one of the matching surfaces of the scanning head.

Each scanning head 120 also includes an internal chamber 135. As in the earlier embodiment of FIG. 1, the internal chamber is connected to the fluid system 344 of the inspection and/or modification system 100 via the corresponding tubes 345. Each tube is connected to a gas or vacuum source of the fluid system via a corresponding valve 345 of the fluid system.

As indicated previously, each of the SPM probes 122-1 to 122-18 includes an aperture 132. This aperture is connected to and in fluid communication with the internal chamber 135 of the scanning head 120. In addition, the aperture forms an aperture in one of the matching surfaces 142. Thus, a microdifferential pressure zone can be formed in the gap 198 between the outer surfaces 166 of the object 602 and the matching surfaces 142 of the scanning head in a similar manner to that described earlier for SPM probe 122-1.

Specifically, in order to do so, the controller 114 causes the valve 345 that is connected to a corresponding tube 346 which is connected to the internal pressure chamber 135 to be opened. As a result, the aperture 132 is in fluid communication with the gas or vacuum source of the fluid system 344 via the corresponding tube and the internal pressure chamber. This causes a microdifferential pressure chamber to be formed in the gap 198 in the manner discussed earlier for the SPM probe 122-1 under the conditions specified.

The inspection and/or modification system 100 may be used in a variety of applications. As mentioned earlier, this may be done in order to modify and/or inspect the object in any of the ways discussed earlier with the SPM probes 122-1 to 122-18. In order to do so, the system may include other components 123 like the embodiment of FIG. 1.

For example, material may be deposited on the object 102. In this case, one scanning head 120 may include the SPM probe 122-12. The controller 114 first causes a micro-vacuum chamber to be created in the gap 198 between the surfaces 166 and 142 of the object and the scanning head. This is done in the manner just described. Then, the controller 114 the causes the object to be rotated through the scanning head and causes the probe to deposit material on the object in a desired location in the manner discussed earlier using a vacuum arc tool 470 of the probe.

Referring back to FIG. 71, in the case where DLC is deposited on the object 102, an additional scanning head 120 could be used for CVD (i.e., chemical vapor deposition) deposition of diamond on the object. In this case, the scanning head simply includes the aperture plate 122-13 described earlier. The aperture plate would be used to grow diamond crsytals at the DLC seed sites in the manner described earlier for the SPM probe 122-12. In this case, the other components 123 of the system would include a magnetic macroparticle filter.

Thus, referring again to FIG. 72, the controller causes a valve 345 that is connected to a tube 346 which is connected to the internal chamber 135 of the scanning head 120 to be opened. As a result, the aperture 132 is in fluid communication with a gas source of the fluid system 344 that provides methane and hydrogen or methane and argon. These gases are introduced into the internal chamber and then flow through the aperture and into the differential pressure chamber caused in the gap 198. These gases flow out of the annular outlet 404 of the aperture plate to a gas sink of the fluid system via a corresponding tube 346. The controller 114 then causes the object to be rotated through the scanning head and controls the heater circuit 466 to cause the heater 467 to heat the gases. As mentioned earlier, the heater may comprise resistive or inductive heating elements 471 located at the surfaces 142 of the scanning head or an external laser or flame source that is one of the other components 123 of the inspection and/or modification system. As a result, CVD deposition of diamond occurs on the object such that poly-crystalline diamond is grown at the seed sites provided by the DLC.

Furthermore, referring again to FIG. 71, an additional scanning head 120 could be used for inspecting the object before or after the deposition of the material on the object 102. Referring to FIG. 72, for example, the scanning head 120 may include the SPM probe 122-8 discussed earlier. The controller 114 would then cause SEM measurements of the object to be made using the e-beam tool 382 of this probe in the manner discussed earlier. These SEM measurements would then be used by the controller to generate the kinds of inspection results mentioned earlier.

Then, referring again to FIG. 71, another scanning head 120 could be used to make modifications to the object 102 based on the inspection results. Turning to FIG. 72, this scanning head could include the SPM probe 122-5 mentioned earlier. The controller 114 would then cause cuts to be made in the object with a cutting tool 350 of the probe in order to remove portions of the unwanted material that was deposited.

Thus, in the embodiment shown in FIG. 72, a rotatable object 102, such as a circular saw blade or rock or concrete cutting blade, could be coated with material in the manner just discussed by rotating it through one or more scanning heads 120. Thus, the inspection and/or modification system 100 could be integrated into an entire saw or cutting system where the movement system 103 is also used to rotate the blade for normal operation in sawing or cutting another object. However, those skilled in the art will recognize that other embodiments also exist.

For example, the inspection and/or modification system 100 could be integrated into a band saw system. In this case, the movement system 103 would normally rotate the band saw blade for sawing an object and would also be used to move the band saw blade with respect to the scanning heads.

Alternatively, the movement system 103 may comprise a tape or disk on which knife or razor blades could be mounted. The movement system would then rotate the tape or disk so that the knife or razor blades pass through the scanning heads.

Figure 73:
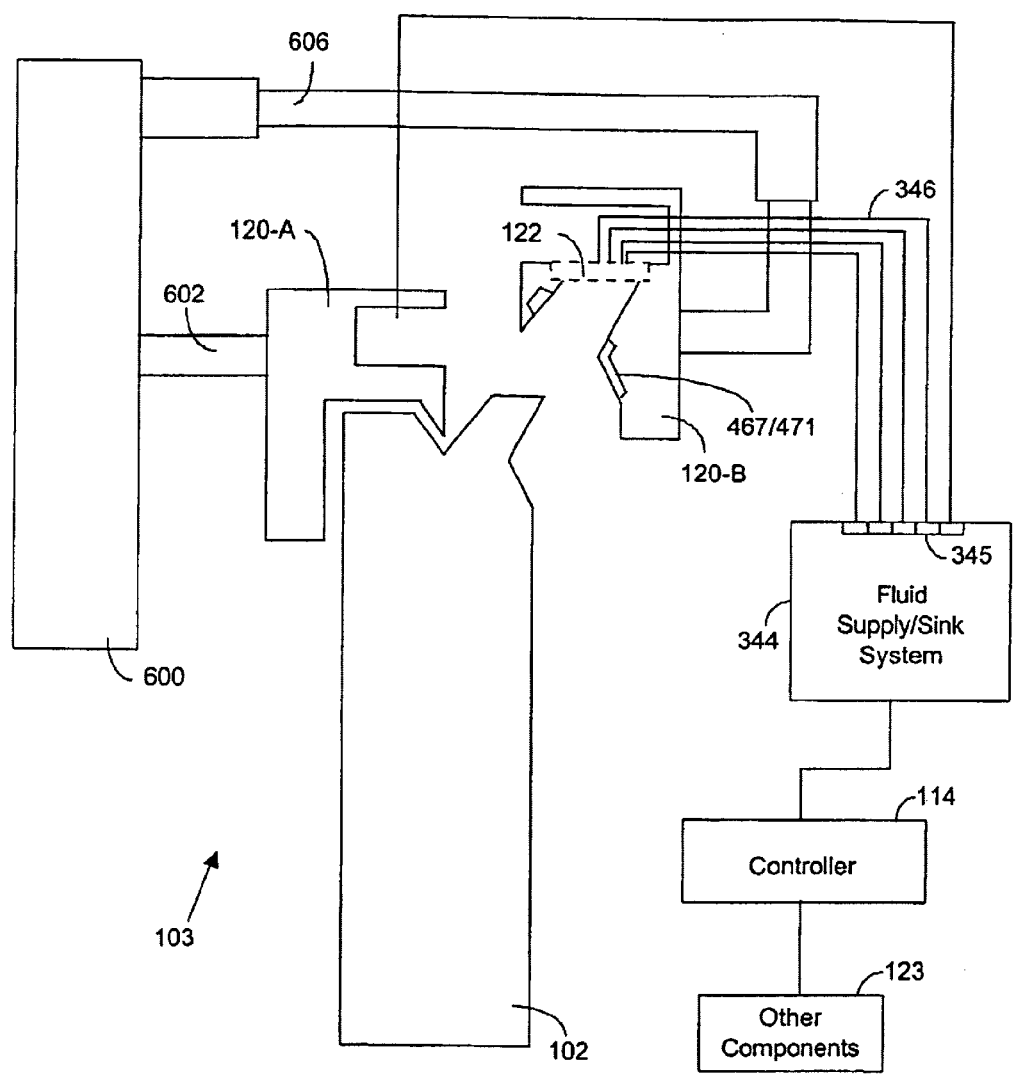

Referring to FIG. 73, each scanning head 120 could comprise separate stationary and moveable pieces 120-A and 120-B in order to provide a differential pressure chamber for a complex shaped object 102, such as a wood saw blade. In this case, the stationary piece 120-A is fixed to the support structure 600 with the support arm 602. The movement system further comprises an adjustable support arm 606. The controller 114 causes the movement system 103 to move the object 102 in place next to the stationary piece. It then causes the adjustable support arm to move the moveable piece 120-B so that it is locked in place with the stationary piece around the object.

Finally, in the embodiment of FIG. 71, the scanning heads 120 were shown as being separate. However, those skilled in the art will recognize that such scanning heads may be integrated into one large scanning head with separate sections for performing desired inspections and/or modifications.

Software and Hardware of Controller 114 of SPM System 100

Figure 74:
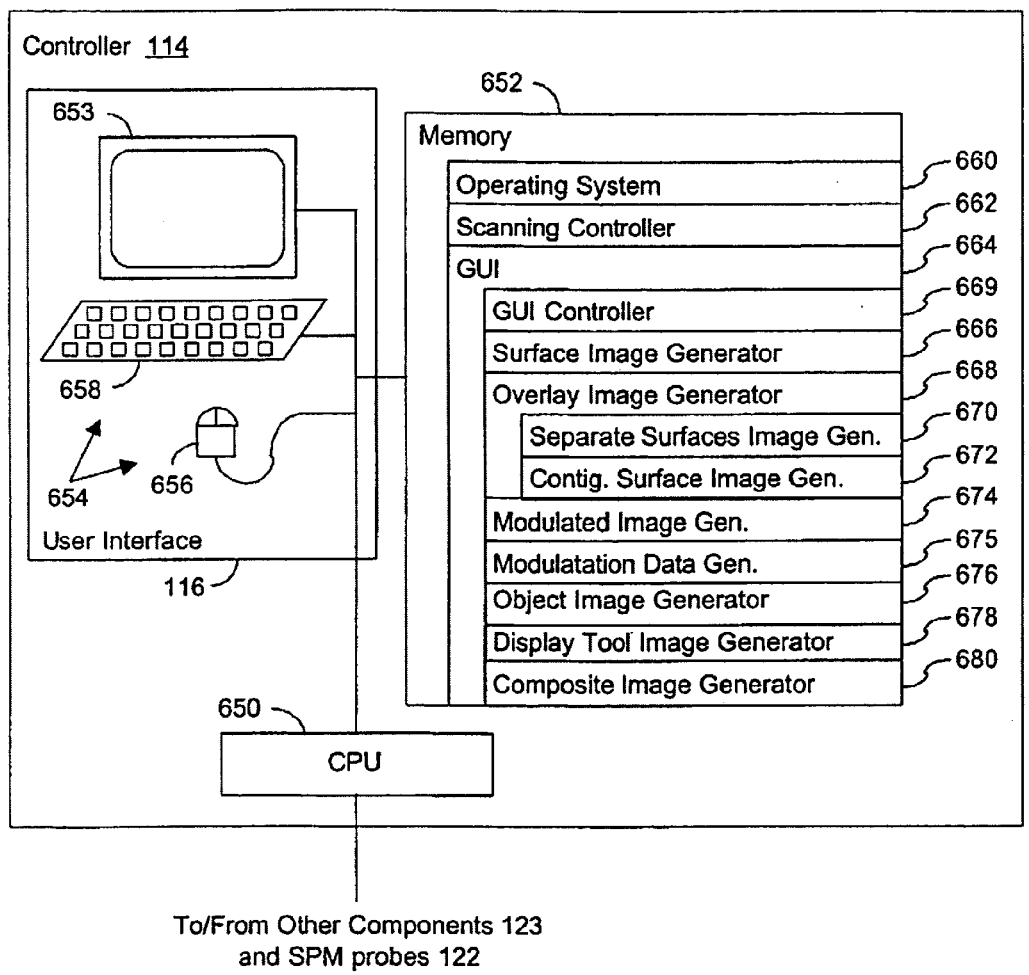
FIG. 74 shows a controller of the SPM system of FIG. 1.

Turning now to FIG. 74, the controller 114 of the SPM system 100 includes a CPU (central processing unit) 650, a memory 652, and the user interface 116 discussed earlier. The user interface includes a display 653, and user input devices 654, such as a mouse 656 and a keyboard 658. The memory stores an operating system 660, a scanning controller 662, and a GUI (graphical user interface) 664 that are all executed on the CPU. The operating system controls and coordinates execution of the scanning controller and the GUI in response to commands issued by a user with the user input devices 654.

The scanning controller 662 controls the operation of the SPM system 100 in the manner discussed earlier. Specifically, it controls the making of the earlier described SPM measurements and SPM modifications with the SPM probes 122 and the other components 123 of the SPM system. In doing so, the scanning controller collects the SPM measurements made and provides them as measurement data to the GUI 664 for display on the display 653.

Controlling Positioning System to Create Drive Vectors in X, Y, and Z Dimensions The scanning controller 662 controls the operation of the positioning system 103 shown in FIG. 1. In doing so, the scanning controller can individually drive the X, Y, and Z piezoelectric drives of the rough positioning system 104 and can individually drive the X, Y, and Z piezoelectric drives of each fine positioning system 106.

In order to perform the SPM measurements of the kind described earlier, the scanning controller 662 controls positioning of the SPM probes 122-1 to 1224 and 122-8 to 122-18 that are used to make SPM measurements in the conventional way. This involves moving such a probe from scan point to scan point with respect to the object 102 by only driving the positioning system 103 in one of the X, Y, and Z dimensions at a time during the scan. Specifically, in order to position the tip of such a probe, the positioning system is driven in only the X dimension or only in the Y dimension in order to move from one scan point to another scan point. Moreover, the positioning system is not driven in the Z dimension simultaneously while it is driven in the X or Y dimension. Instead, the positioning system is under the servo (i.e., feedback) control of the scanning controller in the Z dimension. As a result, positioning of such a probe in the Z dimension is done separately at each scan point. This is typically done in order to prevent the tip of the probe from crashing into the object 102.

However, in order to perform the SPM modifications of the kind described earlier where cutting or milling of the object is performed, the scanning controller 662 controls positioning of the SPM probes 122-1, 122-2, and 122-5 to 122-7 that are used to make SPM measurements in the conventional way. This involves moving such a probe with respect to the object 102 by driving the positioning system 103 in all three of the X, Y, and Z dimensions simultaneously to perform the cutting or milling operation. Thus, the motion of the tip of such a probe can be driven in a series of 3-D (three dimensional) vectors to pass through the loci of selected motion. This means that the entire cutting or positioning motion of the tip of the probe can be a series of 3-D vectors defining a larger 3-D vector, arc, curve, or surface.

This process is also applicable to performing the sweeping motions described earlier for SPM probe 122-5. In this way, 2-D or 3-D sweeping motions can be performed for sweeping away debris particles that are caused by modifications made with the SPM probes 122-1, 122-2, and 122-5 to 122-7.

Rendering Multiple Sets of Measurement Data as an Overlay Image

The GUI 664 may be used to render multiple sets of measurement data together as a 3-D (three dimensional) overlay image on the display 653. Each set of measurement data comprises SPM measurements of an object 102 made with the SPM system 100. Each measurement comprises a measurement data point that is three or more dimensional and includes a corresponding value for each dimension.

Specifically, each data point in the sets of measurement data includes X and Y coordinate values that represent respective locations in perpendicular X and Y dimensions. These coordinate values together represent a corresponding location in an XY plane. Thus, the sets of measurement data are related by the fact that they have data points with common coordinate values that represent common locations in the XY plane. Each data point in the sets of measurement data also includes a measurement value that represents a measurement for a predefined measurement parameter at the corresponding location in the XY plane. The measurement parameter is also considered as one of the dimensions of each data point.

The measurement parameter for the data points of one set of measurement data may be different from the measurement parameter for the data points of the other set of measurement data. For example, the measurement parameter for one set of measurement data may be the heighth of a selected object 102 while the measurement parameter for the other set of measurement data may be the magnetic field strength, the electrical field strength, or the material composition of the same object. Alternatively, the measurement parameter for the another set of measurement data could be the heighth of a comparable object, such as a modified version of the selected object.

More specifically, one set of measurement data may comprise AFM measurement data for a selected object 102. In this case, each data point in the AFM measurement data includes X and Y coordinate values that together represent a corresponding location in the XY plane of the object. Each data point of the AFM measurement data also includes a measurement value representing an AFM measurement of the heighth of the object at the corresponding location in the XY plane. This heighth is in the Z dimension that is perpendicular to the XY plane. Furthermore, these AFM measurements are made with one of the SPM probes 122-1 to 122-4 in the manner discussed earlier. As is evident here, the predefined measurement parameter for the data points of the AFM measurement data is the heighth of the object in the Z dimension.

Similarly, the another set of measurement data may comprise MAFM measurement data for the same object 102. Like the AFM measurement data, each data point in the MAFM measurement data includes X and Y coordinate values that together represent a corresponding location in the XY plane of the object. And, the measurement value of each data point of the AFM measurement data represents an MAFM measurement of the magnetic field strength of the object at the corresponding location in the XY plane. This MAFM measurement is made with one of the conventional SPM probes 122 in the manner discussed earlier. In this case, the predefined measurement parameter for the data points of the MAFM measurement data is the magnetic field strength of the object.

In order to render the two sets of measurement data as an overlay image on the display 653, the user first issues commands with one or more of the user input devices 654 in order to select the surface image generator 666 and the image overlay generator 668 of the GUI 664. These commands are received by the CPU 650 and the operating system 660 in response causes the surface image generator, the image overlay generator, and a GUI controller 669 to be executed.

Figure 75:
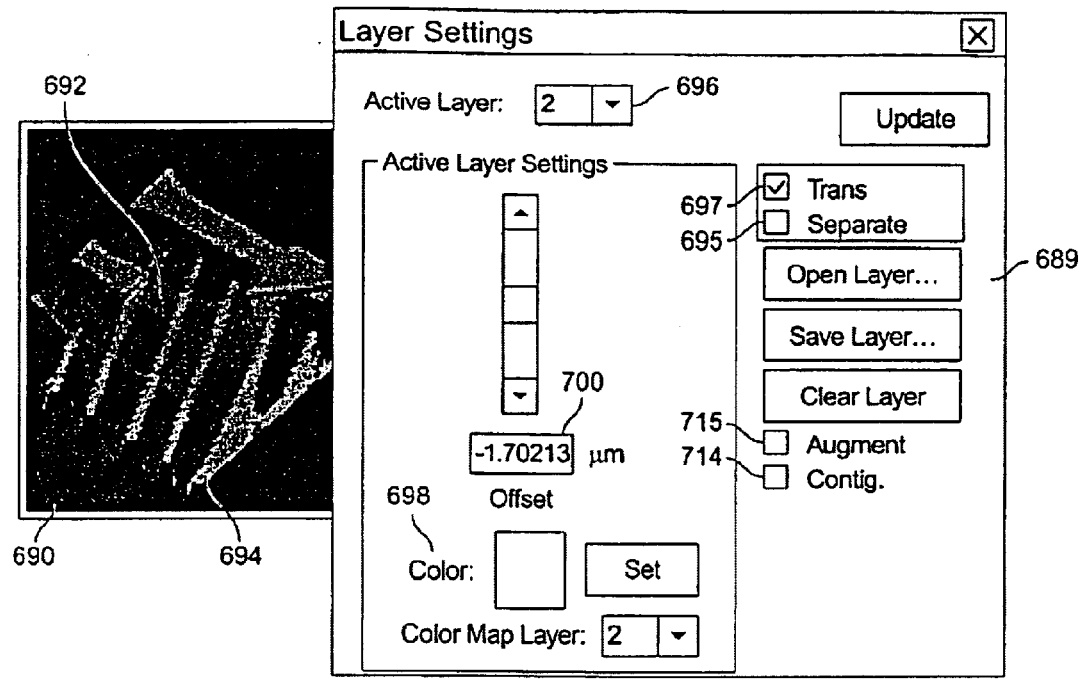
FIGS. 75 to 77 show different views of overlaid surfaces generated by an overlay image generator of the controller of FIG. 74.

The GUI controller 669 of the GUI 664 generates control image data representing an interactive image of a control dialog box 689, as shown in FIGS. 75. This interactive image is displayed by the display 653 in response to the control image data. The overlay image may be rendered in several ways by the image overlay generator. Each of these ways may be selected by the user with one or more of the user input devices 654 using the interactive image of the control dialog box.

Figure 76:
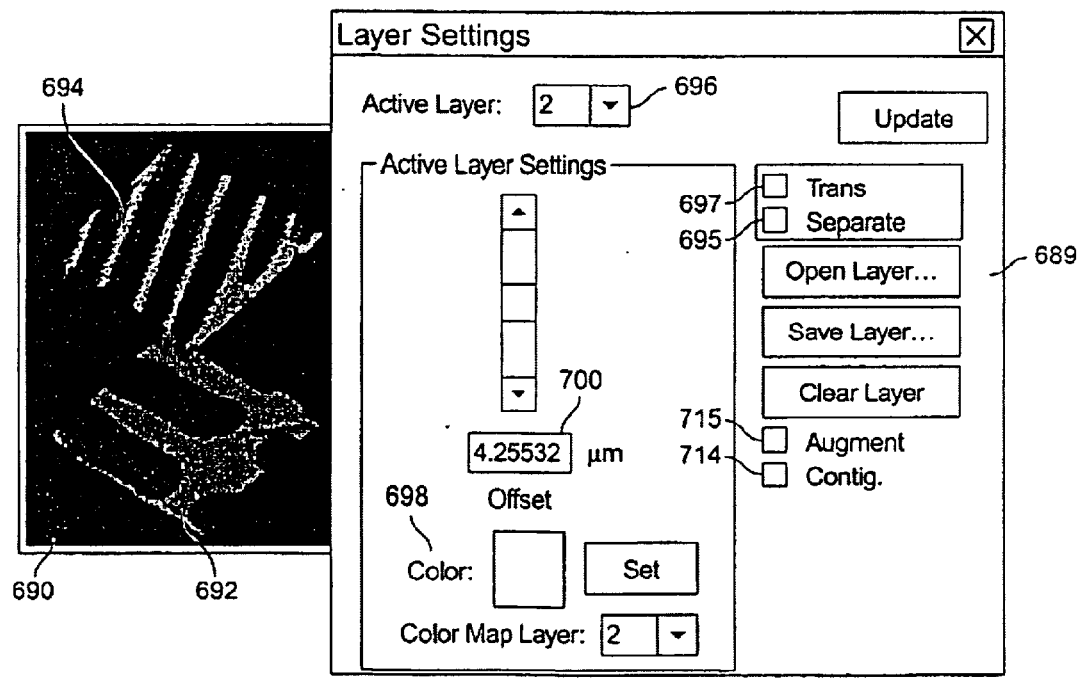

For example, the user may desire to have a first set of measurement data and a second set of measurement data rendered as an overlay image 690 as shown in FIGS. 75 and 76. Here, the overlay image is of a first surface 692 representing the first set of measurement data separately overlaid on a second surface 692 representing the second set of measurement data or vice versa. Referring also to FIG. 74, the user of the SPM system 100 may use one of the input devices 654 to select the separate surfaces image generator 670 of the image overlay generator 668 in order to display the two sets of measurement data together in this way.

The user does so by issuing corresponding commands with one or more of the user input devices 654 using the image of the control dialog box 689. For the each of the first and second surfaces 692 and 694, these commands include a command to select the surface in the active layer selection box 696 of the control dialog box, a command to select separate surfaces in the separate surfaces box 695 of the control dialog box, a command to select translucency or opacity (by not selecting translucency) for the surface in the translucency selection box 697 of the control dialog box, a command to select (or assigning) the surface's color mapping in the color map box 698 of the control dialog box, and a command to select the amount of offset between this surface and the other surface in the offset box 700 of the control dialog box. These commands are received by the CPU 650 and are in response provided to the GUI controller 669 which then passes them to the separate surfaces image generator. The two sets of measurement data are then rendered by the surface image generator 666 and the separate surfaces image generator for display on the display 653 in the manner shown in FIGS. 75 and 76.

In doing so, the surface image generator 666 generates a first set of image data from the first set of measurement data and a second set of image data from the second set of measurement data. The first and second sets of image data represent corresponding 3-D first and second surface images of the corresponding first and second surfaces 692 and 694. Each surface extends along the XY plane and is contoured based on and to reflect the measurement values for the data points of the corresponding measurement data that are perpendicular to the XY plane. Thus, each point of the corresponding surface is rendered from a corresponding data point of the measurement data.

For example, in the case where the first set of measurement data comprises AFM measurement data the first surface comprises the physical outer surface of the object 102. This physical outer surface extends along the XY plane and is contoured based on and to reflect the heights of the object perpendicular to the XY plane. Similarly, in the case where the second set of measurement data comprises MAFM data, the second surface comprises a surface of the magnetic field of the object. The magnetic field surface also extends along the XY plane but is contoured based on and to reflect the magnetic field strengths perpendicular to the XY plane.

In doing this, the surface image generator 666 identifies the data points of the first set of measurement data and the data points of the second set of measurement data that have common X and Y coordinate values (i.e., have common locations in the XY plane). This is done so that each data point in the first set of measurement data has a corresponding data point in the second set of measurement data and vice versa. Any data point in one set of measurement data that does not have such a corresponding data point in the other set of measurement data is removed by the surface image generator. Then the surface image generator generates the first and second sets of image data from the remaining (i.e., identified) measurement data points. For each set of image data, each data point in the corresponding set of image data is generated from a corresponding measurement data point in the corresponding measurement data.

In doing so, the surface image generator 666 first scales the first and second sets of measurement data to produce the first and second sets of image data so that they can be display together in a meaningful manner and with a meaningful relationship. This may be done in several ways which can be selected by the user by issuing appropriate commands with one of the user input devices 654. The commands are received by the GUI controller 669 which passes them onto the surface image generator.

For example, this may be done for each set of measurement data according to the following relationship $m \times Z/K = c$. Here, m is a multiplier and c is a constant. Furthermore, Z is the largest range (i.e., difference) between any of the measurement values of the data points of the measurement data. And, K is the largest of (1) the largest range (i.e., difference) between any of the X coordinate values of the data points of the measurement data, and (2) the largest range between any of the Y coordinate values of the data points of the measurement data.

In order to render a qualitative relationship between the first and second surfaces of the overlay image 690, the scaling may be done so that the same constant c is used for both sets of measurement data. As a result, two different multipliers $m_1$ and $m_2$ will be used for the two sets of measurement data. Then, for each set of measurement data, the measurement value for each measurement data point of the measurement data is scaled by the corresponding multiplier $m_1$ or $m_2$ to form a Z coordinate value in the Z dimension.

As indicated previously, each image data point in one of the sets of image data is generated from the corresponding measurement data point in the corresponding set of measurement data. This is done so that each image data point includes the X and Y coordinate values of the measurement data point and the corresponding Z coordinate value computed by the surface image generator 666. Thus, in the case where the Z coordinate values of the first and second sets of image data are computed in the manner just described, they are qualitatively comparable so that the first and second surfaces that are formed from the Z coordinate values are also qualitatively comparable.

Alternatively, the scaling may be done so as to render a quantitative relationship between the first and second surfaces 692 and 694. This is done in the same manner as just described, except that the multiplier m obtained for one set of measurement data is also used for the other set of measurement data. Then, for each set of measurement data, the measurement value in the measurement data is scaled by this multiplier m to create a Z coordinate value for the corresponding image data point of the corresponding image data. As a result, the Z coordinate values of the first and second image data are quantitatively comparable. This makes the first and second surfaces that are formed from the Z coordinate values also quantitatively comparable.

Each image data point in each set of image data also includes a color coordinate value. This color coordinate value is assigned by the surface image generator 666 in response to the coloring mapping selected by the user in the color map box 698. For example, the color coordinate value of each image data point may be based on and correspond to the Z coordinate value of the data point. The coloring of the surfaces 692 and 694 may also be selected so as to distinguish them from each other.

The separate surfaces image generator 670 then generates overlay image data by overlaying the first and second sets of image data it receives from the surface image generator 666. This is done based on the selections made by the user using the control dialog box 689. The display 653 then displays the overlay image 690 in response to the overlay image data, as shown in FIG. 75 or 76.

The separate surfaces image generator 670 generates the overlay image data by overlaying the data points of the first and second sets of image data based upon the users selection of translucency or opacity in the translucency selection box 697 for the first and second surfaces. If translucency was selected for the first surface 692 and opacity for the second surface 694, the separate surfaces image generator generates the overlay image data so that the first surface is translucently overlaid on the opaque second surface in the overlay image 690, as shown in FIG. 75. In contrast, if opacity was selected for both the first and second surfaces, the separate surfaces image generator generates the overlay image data so that the second surface is opaquely overlaid on the opaque first surface in the overlay image, as shown in FIG. 76. As those skilled in the art will recognize, both surfaces could be translucent or the second surface could be opaquely overlaid on the translucent first surface. Moreover, standard 3-D rendering techniques are used in overlaying the data points of the first and second sets of image data to make the first and second surfaces appear translucent and opaque.

As also indicated earlier, for each of the first and second surfaces 692 and 694, the user may issue a command to select the amount of offset between this surface and the other surface using the offset box 700 of the control dialog box 689. The GUI controller 669 receives the command and provides an offset value specifying the selected amount of offset to the separate surfaces image generator 666. The separate surfaces image generator then adds the offset value to each Z coordinate value of the image data for this surface. The separate surfaces image generator 670 then generates the overlay image data so that this surface appears offset from the other surface in the overlay image by the amount of offset specified by the offset value, as shown in FIGS. 75 and 76.

Figure 77:
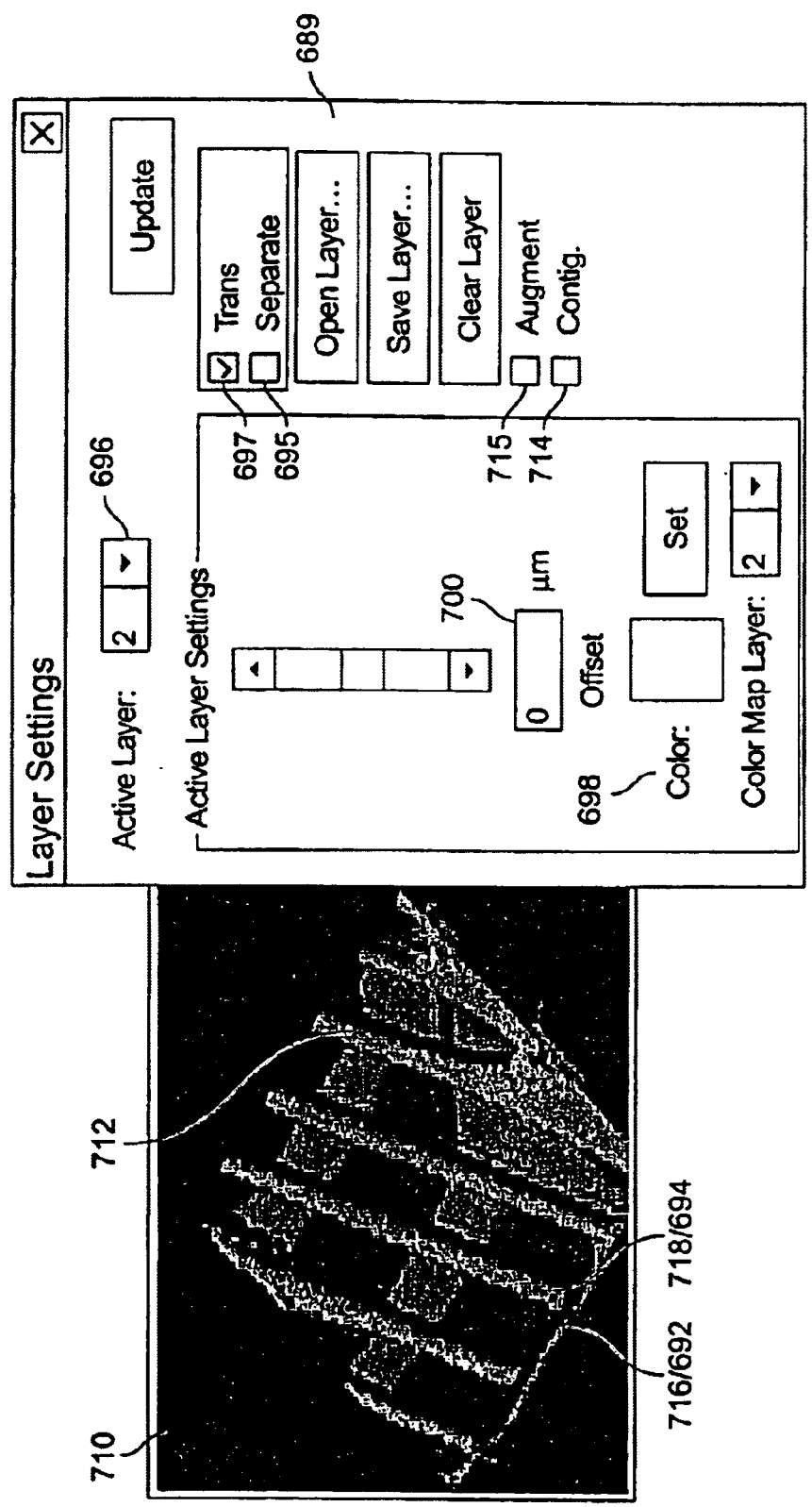

Alternatively, the user may desire to have the two sets of measurement data rendered as an overlay image 710 of a single contiguous surface 712, as shown in FIG. 77. Referring also to FIG. 74, the user of the SPM system 100 may use one of the input devices 654 to select the contiguous surface image generator 672 of the image overlay generator 668 in order to display the two sets of measurement data together in this way. In a similar manner to that discussed earlier for the rendering the overlay image 690 of FIGS. 75 and 76, the user does so by issuing corresponding commands with one or more of the user input devices using the control dialog box 689. However, for each of the first and second surfaces 692 and 694 in this case, these commands include a command to select the surface in the active layer selection box 696 of the control dialog box, a command to select a contiguous surface in the contiguous surface box 714 of the control dialog box, a command to select (or assign) the surface's coloring mapping in the color map box 698 of the control dialog box, and a command to select the amount of offset between this surface and the other surface in the offset box 700 of the control dialog box. These commands are received by the CPU 650 and are in response provided to the GUI controller 669 which then passes them to the contiguous surface image generator. The two sets of measurement data are then rendered by the surface image generator 666 and the contiguous surface image generator for display on the display 653 in the manner shown in FIG. 77.

In doing so, the surface image generator 666 generates the first and second sets of image data from the first and second sets of measurement data in the manner discussed earlier. The contiguous surface image generator 672 then generates overlay image data by overlaying the first and second sets of image data based on the selections made by the user using the control dialog box 689. The display 653 then displays the overlay image 710 in response to the overlay image data in the manner shown in FIG. 77.

In this case, the contiguous surface image generator 672 generates the overlay image data by overlaying the data points of the first and second sets of image data so that a single contiguous surface 712 is rendered when the overlay image data is displayed by the display 635. In doing so, the contiguous surface image generator identifies the data points of the first image data that have larger Z coordinate values than the corresponding data points of the second image data (i.e., those with the same X and Y coordinate values) and identifies the data points of the second image data that have larger Z coordinate values than the corresponding data points of the first image data. The data points of the first image data that have larger Z coordinate values than the corresponding data points of the second image data represent the portions 716 of the first surface 692 that overlap (i.e., extend over) the second surface 694. Similarly, the data points of the second image data that have larger Z coordinate values than the corresponding data points of the first image data represent the portions 718 of the second surface that overlap (i.e., extend over) the first surface.

These identified data points are then used by the contiguous surface image generator 672 as the overlay image data. As a result, the contiguous surface 712 comprises only the portions 716 of the first surface 692 that overlap the second surface 694 and only the portions 718 of the second surface that overlap the first surface. These portions of the first and second surfaces are connected so as to form the contiguous surface.

As with the overlay image 690 of FIG. 75 or 76, the user may issue a command to select the coloring mapping of each of the surfaces 692 and 694 using the color map box 698 of the control dialog box 689. This coloring mapping is done in the same manner as was described earlier and may be selected so as to distinguish the portions 716 and 718 of these surfaces in the contiguous surface 712 from each other.

As also with the overlay image 690, for each of the first and second surfaces 692 and 694, the user may issue a command to select the amount of offset between this surface and the other surface using the offset box 700 of the control dialog box 689. The GUI controller 669 receives the command and provides an offset value specifying the selected amount of offset to the contiguous surface image generator 672. The contiguous surface generator then adds the offset value to each Z coordinate value of the image data for the surface. The contiguous surface image generator generates the overlay image data in the same way as just described. But, the portions 716 of the first surface that overlap the second surface and the portions 718 of the second surface that overlap the first surface have changed in the contiguous surface 712.

The GUI 664 is not limited to use in the SPM system 100 described herein. For example, the GUI may be used for rendering an overlay image in any of the ways just described in a geographical mapping system. In this case, the GUI could be used to generate the overlay image where one of the surfaces represents the annual rainfall in an area and the other surface is the topographical surface of the same area.

Rendering and Augmenting a Surface with Multiple Sets of Measurement Data

Figure 78:
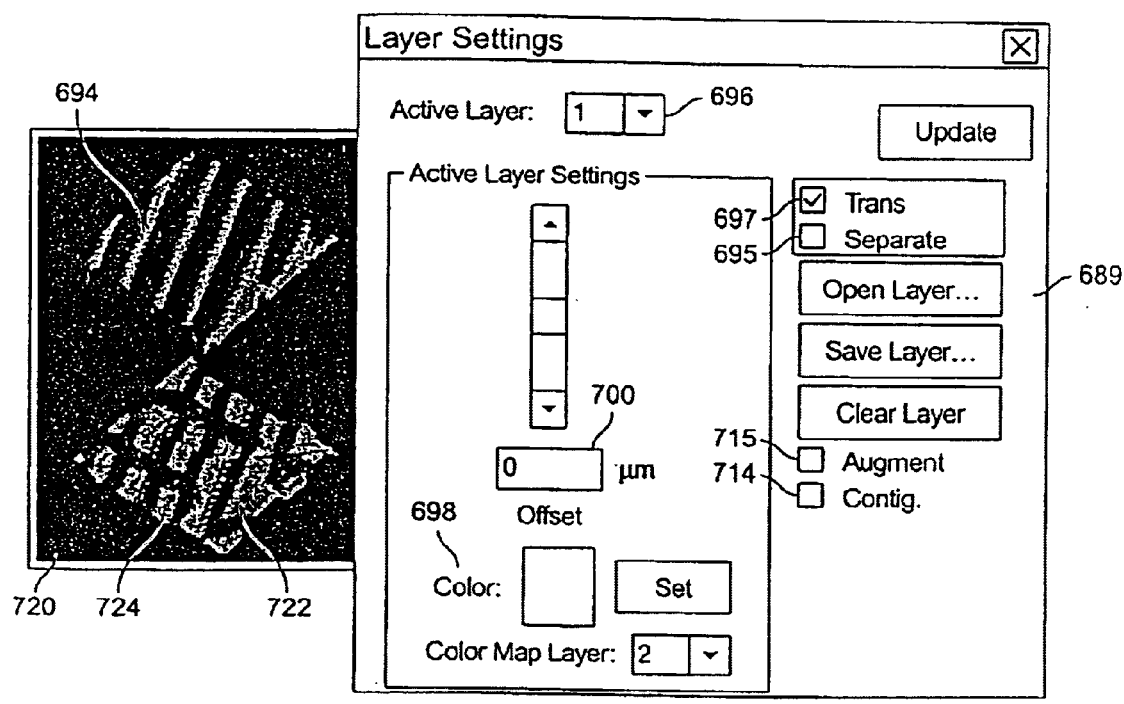
FIG. 78 shows a modulated surface image generated by a modulated image generator of the controller of FIG. 74.

Referring to FIG. 78, the GUI 664 may also be used to render the multiple sets of measurement data together as a 3-D (three dimensional) surface image 720 of an augmented surface 722 on the display 653. In this case, a primary set of measurement data for a predefined primary measurement parameter is used to render the basic contour of the surface and one or more secondary sets of measurement data for one or more corresponding secondary measurement parameters are used to provide augmentation of various aspects of this surface. For example, the secondary sets of measurement data may be used to texture and/or color the surface.

Referring also to FIG. 74, the user of the SPM system 100 may use one of the input devices 654 to select the augmented surface image generator 674 of the GUI 664 in order to display the sets of measurement data together in this way. Here, the user also issues commands with one or more of the user input devices using the control dialog box 689. These commands include a command to select the first surface in the active layer selection box 696 of the control dialog box, a command to select augmentation in the augmentation box 715 of the control dialog box, and a command to select (or assign) the coloring mapping of augmented surface 722 in the color map box 698 of the control dialog box. These commands are received by the CPU 650 and are in response provided to the GUI controller 669 which then passes them to the surface image generator 666, the augmentation data generator 675, and the augmented image generator 674. The sets of measurement data are then rendered by the surface image generator, the augmentation data generator, and the augmented image generator for display on the display 653 in the manner shown in FIG. 78.

In doing so, the surface image generator 666 generates base image data from a primary set of measurement data for a predefined primary measurement parameter in the manner discussed earlier. Specifically, this base image data represents a base surface, such as surface 692 as shown in FIGS. 75 and 76. Each image data point of the base image data includes the X, Y, and Z coordinate values. The Z coordinate value is derived from the measurement value of the corresponding measurement data point. This measurement value is for the predefined primary measurement parameter.

The one or more secondary sets of measurement are then used to augment the base image data. As discussed earlier, each measurement data point of such a set of measurement data includes X and Y coordinate values and a measurement value. The measurement value represents a measurement of a predefined secondary measurement parameter made at the location in the XY plane corresponding to the XY coordinate values.

The augmentation data generator 675 uses each of the one or more secondary sets of measurement data to generate augmentation data. For each secondary set of measurement data, the augmentation data includes augmentation data points. Each augmentation data point includes X and Y coordinate values and a corresponding augmentation value for each secondary set of measurement data. Each augmentation value is generated based on the measurement value of the measurement data point in the corresponding secondary set of measurement data that has the same X and Y coordinate values.

The augmented image generator 674 then generates the augmented image data by augmenting the base image data received from the surface image generator 666 with the augmentation data received from the augmentation data generator 675. This may be done by including the augmentation value in each augmentation data point of the augmentation data as another coordinate value of the corresponding image data point of the base image data. Or, this may be done by substituting the augmentation data value for or adding the augmentation value to the corresponding Z coordinate value in the corresponding image data point of the base image data.

The augmentation image data is then displayed by the display 653 as a 3-D augmented image of an augmented surface 722. Thus, the basic contour of this surface is like that of the surface 692 of FIGS. 75 and 76 and is based on the primary measurement data set. However, this surface is augmented based on the one or more secondary sets of measurement data.

In one example, the basic contour of the augmented surface 722 may be generated from AFM measurement data of the object 102. Then, the coloring of the augmented AFM surface 722 could be based on MAFM measurement data for the object.

In this case, the base image data is generated by the surface image generator 666 from the AFM measurement data in the manner discussed earlier for the overlay image generator 668. Then, the augmentation data generator 675 may cause the surface image generator to generated a second set of image data from the MAFM measurement data also in the manner discussed earlier for the overlay image generator.

Then, the augmentation data generator 675 uses the color mapping selected by the user in the color map box 689 to generate augmentation data for coloring the surface 722 based on the Z coordinate values for the image data points of the second set of image data. Thus, the augmentation value for each augmentation data point is a color coordinate value that is based on the Z coordinate value for the image data point in the second set of image data that has the same X and Y coordinate values.

The augmented image generator 674 then uses the color coordinate value in each augmentation data point of the augmentation data as another coordinate value of the corresponding image data point of the base image data. Referring again to FIG. 78, the basic contour of the augmented AFM surface is like that of the surface 692 of FIGS. 75 and 76 and is based on the AFM measurement data. Moreover, the augmented AFM surface is colored based on the MAFM measurement data.

Additionally, as shown in FIG. 78, the augmented image data for the augmented AFM surface 722 can be overlaid with the second image data for the magnetic field surface 694. This is done in the manner discussed earlier for the overlay image generator 668.

In another example, the basic contour of the augmented surface 722 may also be generated from AFM measurement data of the object 102. Then, the texturing (i.e., stippling) of the augmented AFM surface 722 could be based on LAFM measurement data for the object.

In this case, the base image data for the augmented AFM surface 722 is again generated by the surface image generator 666 from the AFM measurement data in the manner discussed earlier for the overlay image generator 668. Moreover, the augmentation data generator 675 generates augmentation data from the LAFM measurement data.

The LAFM measurement data may be generated using one of the conventional SPM probes 122 described earlier. Each measurement data point of the LAFM measurement data includes X and Y coordinate values and an LAFM measurement value for the lateral force at the location in the XY plane corresponding to the XY coordinate values.

The augmentation value for each augmentation data point of the augmentation data is a texture coordinate value. The texture coordinate value is based on the LAFM measurement value for the measurement data point in the LAFM measurement data that has the same X and Y coordinate values. Here, the texture coordinate value represents a texture density (stipples per unit area) that corresponds to the LAFM measurement value.

The augmented image generator 674 then uses the texture coordinate value in each augmentation data point of the augmentation data as another coordinate value of the corresponding image data point of the base image data. Referring again to FIG. 78, the basic contour of the augmented AFM surface is like that of the surface 692 of FIGS. 75 and 76 and is based on the AFM measurement data. Moreover, the augmented AFM surface is textured based on the MAFM measurement data.

Furthermore, as described earlier, the GUI 664 is not limited to use in the SPM system 100 described herein. Similar to the example given earlier, the GUI may be used in a geographical mapping system for modulating a surface in any of the ways just described. In this case, the GUI could be used to generate the modulated image where a surface representing the topography of an area would be modulated by a color corresponding to the rainfall and by texture (i.e., stippling) whose density (stipples per unit area) corresponds to the amount of annual biomass produced in the area.

Rendering a 3-D Embedded Display Tool Image

Figure 79:
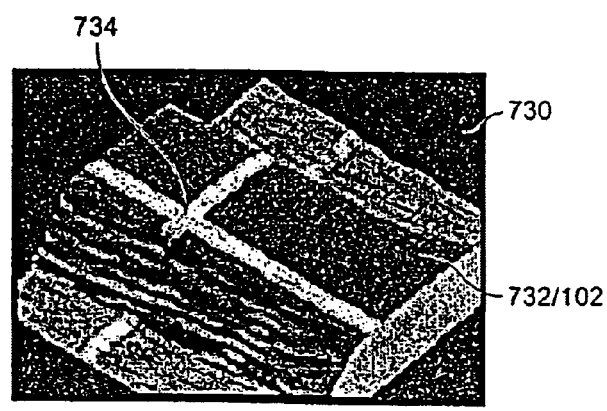
FIGS. 79 to 81 show different composite images of measuring tools embedded in objects generated by the composite image generator of the controller of FIG. 74.
Figure 80:
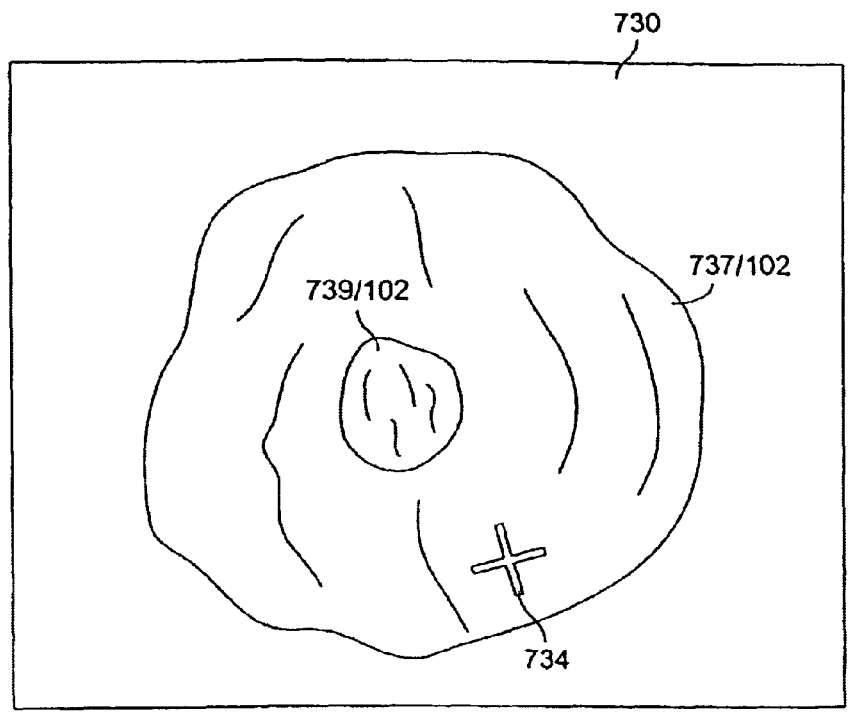
Figure 81:
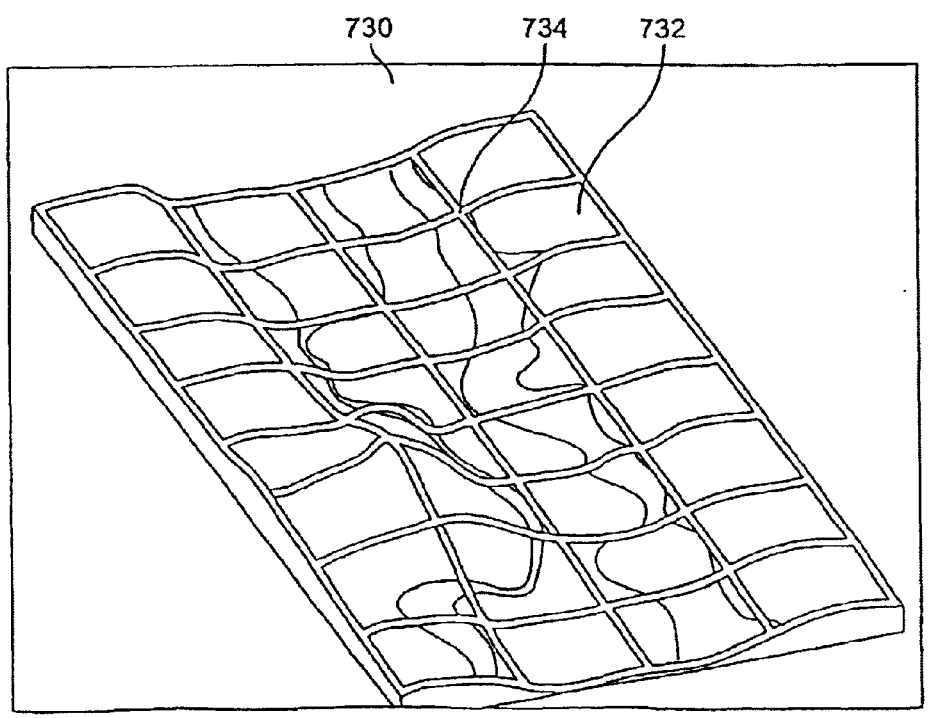

The GUI 664 may also be used to render a 3-D composite image 730 on the display 653, as shown in FIGS. 79, 80, and 81. The composite image is of an object 102 and a display tool 734 embedded in the object. The user can adjustably locate the display tool in the object with one or more of the user input devices 654.

In order to render the composite image 730 on the display 653, the user first issues commands with one or more of the user input devices 654 in order to select an object image generator 676, a display tool image generator 678, and a composite image generator 780 of the GUI 664. These commands are received by the CPU 650 and the operating system 660 in response causes the object image generator, the display tool image generator, and the composite image generator to be executed on the CPU or in or with specialized display resources.

The object image generator 676 generates object image data that represents a 3-D object image of the object 102. The object image generator generates the object image data from one or more sets of measurement data. For example, the object image generator may comprise the surface image generator 666 to generate surface image data of the object from a set of measurement data in the manner discussed earlier. Or, the object image generator may comprise both the surface image generator and the overlay image generator 668 to generate together overlay image data from two sets of measurement data in the manner discussed earlier.

As mentioned earlier, the display tool 734 is embedded in the object 102 of the composite image 730 and can be adjustably located in the object using one or more of the user input devices 654 in the manner described shortly. The display tool image generator 678 determines the location of the display tool in response to a command issued by the user with one or more of the input devices. The display tool image generator also receives the object image data from the object image generator 676. In response, the display tool image generator determines the location and sizing in 3-D that the display tool would have in the object of the object image. Based on this determination, the display tool image generator generates display tool image data representing a 3-D display tool image of the display tool as it would otherwise appear in the object of the object image.

Referring to FIG. 79, the display tool 734 may comprise an embedded cursor defined by cross hairs or arrows. In the case where the composite image 730 is of the outer surface 732 of the object, the embedded cursor is embedded in and adjustably locatable in this surface, as shown in FIG. 79. As is evident in FIG. 79, the cross hairs of the cursor extend perpendicular to each other across the surface. The user locates the embedded cursor in the surface with one or more of the user input devices 654 by issuing corresponding commands. For example, the user may use a mouse to first position a mouse cursor at the intersection of the cross hairs. Then, the user may activate the movement of the embedded cursor by clicking and holding one of the control buttons of the mouse at this intersection. Then, while still holding down this control button, the user may move the mouse so as to drag the embedded cursor and its cross hairs across the surface of the object to a desired location on the object specified by the intersection of the cross hairs.

In this case, the display tool image generator 678 determines the surface of the object 102 from the object image data. Then, it translates the position of the mouse cursor into a location on the surface of the object in the object image. In response, the display tool image generator then determines the location and sizing in 3-D that the display tool would have on this surface and generates the display tool image data based on this.

Alternatively, the composite image 730 may be of the volume of the object 102 including the surfaces 737 and 739 of volume elements of the object. In this case, the display tool 734 may also comprise an embedded cursor that is embedded and positionable in this volume, as shown in FIG. 80. In this case, the cross hairs of the cursor extend perpendicular to each other across the surface 737 of a first volume element of the object. Here, the user may position the embedded cursor on this surface with one or more of the user input devices 654 by issuing corresponding commands. This is done in the same manner as described earlier for the case where the composite image is of the outer surface 732 of the object.

But, in this case, the user may also position the embedded cursor so as to move it from the surface 737 of a first volume element to the surface 739 of a second volume element of the object. This also done by issuing corresponding commands with one or more of the user input devices 654. For example, the user may use a mouse to first position a mouse cursor at the intersection of the cross hairs. Then, the user may activate the movement of the embedded cursor by clicking and holding a different control button on the mouse than the one used to position across a surface. Then, while still holding down this control button, the user may move the mouse so as to drag the embedded cursor and its cross hairs from the surface of the first volume element to the surface of the second volume element. In order to indicate to the user when the embedded cursor is on the new surface, the shading of the cross hairs changes when this occurs. Then, the embedded cursor can be positioned across the surface of this new volume element in the same manner as that described earlier for the first volume element.

Moreover, the volume of the object 102 may either be homogeneous or contain distinct interior surfaces, such as surface 739, of volume elements that may also contain volume information or be mainly surface like (i.e., very thin homogeneous in cross section). Thus, the user could cause the embedded cursor to move between the surfaces and cause it to adopt the surface tracking behavior just described when it encounters these interior surfaces. Thus, the user can cause the embedded cursor to move throughout a volume of distinct surfaces alternatingly sticking to the surfaces and being pushed in or pulled out of the surfaces.

In this case, the display tool image generator 678 determines the surfaces 737 and 739 of the volume elements of the object 102 from the object image data. Then, it translates the position of the mouse cursor into a position in the volume of the object in the object image. In response, the display toot image generator then determines the positioning and sizing in 3-D that the display tool would have in this volume and generates the display tool image data based on this.

As those skilled in the art will recognize, the display tool 734 in the examples just described may comprise a measurement tool of the kind described in PCT Application No. PCT/US96/12255 referenced earlier. This kind of measurement tool includes one or more embedded cursors of the type just described for making various types of measurements in an image of an object. Additionally, those skilled in the art will recognize that the user input devices 654 could include a three axis pointing device. This would be particularly useful in positioning the display tool 734 in 3-D in the composite image 730 of the volume of the object 102 shown in FIG. 80 in a similar manner to that described earlier.

In another example shown in FIG. 81, the display tool 734 may comprise a measurement grid embedded in the outer surface 732 of the object 102. Here as well, the embedded measurement grid is adjustably locatable in this surface. For example, the user may adjust the spacing and/or coloring of the X grid lines and/or the Y grid lines by issuing corresponding commands with one or more of the user input devices 654.

In all of the cases just described, the composite image generator 680 then generates composite image data by combining the object image data and display tool image data it receives from the object image generator 676 and the display tool image generator 678. The display 653 then displays the composite image 690 in response to the composite image data, as shown in FIGS. 79 to 81.

The composite image generator 676 generates the composite image data by overlaying the data points of the display tool image data on the data points of the object image data. This is done so that the display tool is embedded in the object and appears in 3-D as an element of the object, as shown in FIGS. 79 to 81. In doing so, the composite image generator 676 assigns sizing, texture, coloring, shading, opacity, and translucency to the various elements, including the display tool 734, of the object 102 so that they can be distinguished from each other and their positions with respect to each other can be discerned. This is all done using standard 3-D rendering techniques.

While the present invention has been described with reference to a few specific embodiments, the description is illustrative of the invention and is not to be construed as limiting the invention. Various modifications may occur to those skilled in the art without departing from the true spirit and scope of the invention as defined by the appended claims.

What is claimed is:

1. A scanning probe microscopy system for working with an object having a work surface, comprising:

a movable scanning head having a seat therein;

a probe mounted in the seat, the probe comprising:

a probe base having a probe surface oriented toward the work surface of the object, the probe surface having a first aperture therein; and a probe tool mounted in the first aperture and configured to interact with the object; and means for restricting gas flow into a region between the probe surface and the work surface of the object so that when the first aperture is placed in fluid communication with a vacuum source, a microvacuum chamber is formed in a gap region surrounding the first aperture and extending between the probe surface and the work surface of the object.

2. The system of claim 1, wherein the means for restricting gas flow comprises a conformal seal mounted on the probe surface with an edge of the conformal seal surrounding the first aperture.

3. The system of claim 1, wherein the means for restricting gas flow comprises a conformal seal mounted on the scanning head with the conformal seal surrounding the seat.

4. The system of claim 1, wherein the means for restricting gas flow comprises:

a gap sensor system configured to determine a gap width between the probe surface and the work surface; and a gap adjustment mechanism, responsive to the gap sensor system, configured to maintain the gap width at a value sufficient to allow a zone of substantially reduced pressure to be formed in a gap region centered on the first aperture and extending between the probe surface and the work surface when a vacuum source is operated in fluid communication with the first aperture.

5. The system of claim 4, wherein the probe tool comprises a cantilever and the cantilever is used in the gap sensor system to determine the gap width.

6. The system of claim 4, wherein the gap sensor system comprises:

a cantilevered tip mounted in a recess in the probe surface and configured to be deflected by an amount that varies with a distance between the cantilevered tip and the work surface of the object; and an electrostatic sensor configured to detect an amount of deflection of the cantilevered tip.

7. The system of claim 4, wherein the object is a conductive object and the gap sensor system comprises:

an insulating plate mounted on the probe surface; and a plate electrode mounted on the insulating plate, wherein a voltage between the plate electrode and the conductive object is detected and used to determine the gap distance.

8. The system of claim 4, wherein the gap adjustment mechanism comprises:

an annular outlet in the probe surface;

an inlet in a surface of the probe base other than the probe surface; and a duct connecting the annular outlet to the inlet, wherein the gap distance is adjusted by controlling a pressure of a gas flowing into the inlet, through the duct, and out of the annular outlet.

9. The system of claim 4, wherein the gap adjustment mechanism comprises:

a plurality of outlets in the probe surface surrounding the first aperture;

a corresponding plurality of inlets in a surface of the probe base other than the probe surface; and a corresponding plurality of ducts, each duct connecting one of the outlets to a respective one of the inlets, wherein the gap distance is adjusted by independently adjusting a pressure of a gas flowing into each of the inlets, through the respective duct, and out through the respective outlet.

10. The system of claim 4, wherein the gap adjustment mechanism comprises:
- a first annular outlet in the probe surface surrounding the first aperture;
- an annular inlet in the probe surface surrounding and substantially concentric with the first annular outlet;
- a second annular outlet in the probe surface surrounding and substantially concentric with the annular inlet;
- a first remote inlet in a surface of the probe base other than the probe surface, the first remote inlet connected to the first annular outlet by a first duct;
- a second remote inlet in a surface of the probe base other than the probe surface, the second remote inlet connected to the second annular outlet by a first duct; and
- a remote outlet in a surface of the probe base other than the probe surface, the remote outlet connected to the annular inlet by a third duct,
- wherein the probe surface is stepped such that a distance between the first annular outlet and the work surface is less than a distance between the annular inlet and the work surface, and the distance between the annular inlet and the work surface is less than a distance between the second annular outlet and the work surface,
- wherein adjustment of the gap width is provided by regulating the flow of a low pressure, high viscosity first gas through the first remote inlet to the first annular outlet,
- wherein loose material is removed from the object by the flow of a high pressure low viscosity second gas through the second remote inlet the second annular outlet, and
- wherein the annular inlet draws both the first gas and the second gas away from the work surface when the remote outlet is connected to a vacuum source.

11. The system of claim 4, wherein the gap adjustment mechanism comprises a plurality of displacement transducers in the seat of the scanning head for moving the probe surface relative to the seat along a line substantially normal to the work surface of the object, thereby adjusting the gap width.

12. The system of claim 1, further comprising a vacuum source in fluid communication with the first aperture.

13. The system of claim 12, wherein the vacuum source comprises:
- a vacuum pump; and
- a large vacuum chamber in fluid communication with the vacuum pump and with the first aperture.

14. The system of claim 6, wherein the vacuum source comprises a vacuum pump within the probe base.

15. The system of claim 14, wherein the vacuum pump comprises:
- a pumping control circuit;
- a pumping chamber within the probe base, the pumping chamber having a movable membrane wall and an inlet in a wall other than the membrane wall;
- an outlet in a surface of the probe base other than the probe surface, the outlet connected to the pumping chamber;
- an outlet valve controlled by the pumping control circuit, the outlet valve disposed between the pumping chamber and the outlet; and
- a plate electrode located in the probe base outside the pumping chamber and oriented toward the membrane wall, the plate electrode controlled by the pumping control circuit,
- wherein at a first time, the outlet valve is closed and the plate electrode moves the membrane wall to expand the pumping chamber, and at a second time, the outlet valve is opened and the plate electrode moves the membrane wall to contract the pumping chamber.

16. The system of claim 1, wherein when the first aperture is placed in fluid communication with a gas source, a microdifferential pressure chamber is formed in the gap region.

17. The system of claim 1, wherein the probe tool comprises a particle beam tool.

18. The system of claim 17, wherein the particle beam is an electron beam.

19. The system of claim 17, wherein the particle beam is an ion beam.

20. The system of claim 1, wherein the probe tool comprises a vacuum arc tool.

21. A particle beam tool for measuring and modifying an object, comprising:
- a probe base having a probe surface oriented toward a work surface of the object, the probe surface having a first aperture therein;
- a particle beam emitter suspended in the first aperture;
- an accelerating electrode located within the first aperture and below the particle beam emitter, the accelerating electrode having an aperture allowing a particle beam from the particle beam emitter to pass;
- a plurality of steering electrodes located within the aperture and below the accelerating electrode, the steering electrodes operable to control a direction of the particle beam and arranged to provide an aperture allowing the particle beam to pass;
- a collecting electrode within the aperture and below the steering electrode, the collecting electrode having an aperture allowing the particle beam to pass;
- a control circuit configured to operate the particle beam emitter to emit a particle beam, to operate the plurality of steering electrodes to direct the particle beam, and to operate the collecting electrode to collect particles reflected from the object; and
- means for restricting gas flow into a region between the probe surface and the work surface of the object so that when the first aperture is placed in fluid communication with a vacuum source, a microvacuum chamber is formed in a gap region centered on the first aperture and extending between the probe surface and the work surface of the object.

22. The system of claim 21, wherein the particle beam is an electron beam.

23. The system of claim 21, wherein the particle beam is an ion beam.

24. The system of claim 21, further comprising:
- a plurality of steering magnets fixed to the probe surface and disposed around the first aperture, wherein selectively applying currents to the plurality of steering magnets causes the particle beam to be steered in a selected direction.

25. The system of claim 21, further comprising:
- a steering coil surrounding the first aperture, wherein selectively applying a current causes the particle beam to be steered in a spiral trajectory.

26. The system of claim 25, wherein the steering electrodes, steering magnets, and steering coil together are operable to steer the particle beam into a surface of the object not substantially parallel to the work surface.

* * * * *